(12) United States Patent
Niwa et al.

(10) Patent No.: US 10,494,437 B2
(45) Date of Patent: Dec. 3, 2019

(54) HETERODIMER PROTEIN COMPOSITION

(71) Applicant: KYOWA HAKKO KIRIN CO., LTD, Tokyo (JP)

(72) Inventors: Rinpei Niwa, Tokyo (JP); Mami Tsuchiya, Tokyo (JP); Takuya Murakami, Tokyo (JP); Yuta Tezuka, Tokyo (JP)

(73) Assignee: KYOWA KIRIN CO., LTD, Tokyo (JP)

( * ) Notice: Subject to any disclaimer, the term of this patent is extended or adjusted under 35 U.S.C. 154(b) by 65 days.

(21) Appl. No.: 15/624,581

(22) Filed: Jun. 15, 2017

(65) Prior Publication Data

US 2017/0362323 A1    Dec. 21, 2017

Related U.S. Application Data

(62) Division of application No. 14/046,478, filed on Oct. 4, 2013, now Pat. No. 9,714,291.

(60) Provisional application No. 61/710,221, filed on Oct. 5, 2012.

(51) Int. Cl.
| | |
|---|---|
| *C07K 16/46* | (2006.01) |
| *C07K 16/28* | (2006.01) |
| *C12N 15/62* | (2006.01) |
| *C12N 15/63* | (2006.01) |
| *C07K 16/32* | (2006.01) |

(52) U.S. Cl.
CPC ...... *C07K 16/2833* (2013.01); *C07K 16/2887* (2013.01); *C07K 16/32* (2013.01); *C07K 16/468* (2013.01); *C07K 2317/41* (2013.01); *C07K 2317/64* (2013.01); *C07K 2317/72* (2013.01); *C07K 2317/732* (2013.01); *C07K 2317/734* (2013.01)

(58) Field of Classification Search
CPC ........ C12N 15/62; C12N 15/63; C12N 15/70; C12N 15/79; C12N 2330/00; C07K 16/2833; C07K 16/468; C07K 16/32; C07K 16/2887; C07K 2317/734; C07K 2317/732; C07K 2317/72; C07K 2317/64; C07K 2317/41
See application file for complete search history.

(56) References Cited

U.S. PATENT DOCUMENTS

| | | |
|---|---|---|
| 6,992,174 B2 | 1/2006 | Gillies et al. |
| 7,183,076 B2 | 2/2007 | Arathoon et al. |
| 8,193,322 B2 | 6/2012 | Yan et al. |
| 2004/0132101 A1 | 7/2004 | Lazar et al. |
| 2006/0134105 A1 | 6/2006 | Lazar et al. |
| 2007/0105199 A1 | 5/2007 | Yan et al. |
| 2009/0162360 A1 | 6/2009 | Klein et al. |
| 2009/0226421 A1 | 9/2009 | Parren et al. |
| 2009/0232811 A1 | 9/2009 | Klein et al. |
| 2010/0226925 A1 | 9/2010 | Dillon et al. |
| 2010/0322934 A1 | 12/2010 | Imhof-Jung et al. |
| 2010/0322935 A1 | 12/2010 | Croasdale et al. |
| 2010/0331527 A1 | 12/2010 | Davis et al. |
| 2012/0237507 A1 | 9/2012 | Bossenmaier et al. |

FOREIGN PATENT DOCUMENTS

| | | |
|---|---|---|
| WO | 02/056910 A1 | 7/2002 |
| WO | 2004/029207 A2 | 4/2004 |
| WO | 2004/058820 A2 | 7/2004 |
| WO | 2005/000899 A2 | 1/2005 |
| WO | 2005/063816 A2 | 7/2005 |
| WO | 2007/048037 A2 | 4/2007 |
| WO | 2007/059782 A1 | 5/2007 |
| WO | 2007/110205 A2 | 10/2007 |
| WO | 2009/080251 A1 | 7/2009 |
| WO | 2009/080253 A1 | 7/2009 |
| WO | 2009/089004 A1 | 7/2009 |
| WO | 2010/082136 A1 | 7/2010 |
| WO | 2010/136172 A1 | 12/2010 |
| WO | 2010/145793 A1 | 12/2010 |
| WO | 2010/151792 A1 | 12/2010 |
| WO | 2011/090754 A1 | 7/2011 |
| WO | 2011/090762 A1 | 7/2011 |
| WO | 2012/116927 A1 | 9/2012 |
| WO | 2012/125850 A1 | 9/2012 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Carter, "Bispecific human IgG by design", Journal of Immunological Methods, Elsevier Science B.V., Feb. 1, 2001, vol. 248, Issues 1-2, pp. 7-15.
Carter, "Potent antibody therapeutics by design", Focus on Translational Immunology, Nature Reviews Immunology, Nature Publishing Group, May 1, 2006, vol. 6, pp. 343-357.
Elkabetz et al., "Alternative pathways of disulfide bond formation yield secretion-competent stable and functional immunoglobulins", Molecular Immunology, Elsevier Ltd., Aug. 9, 2008, vol. 46, pp. 97-105.

(Continued)

*Primary Examiner* — Phuong Huynh
(74) *Attorney, Agent, or Firm* — Sughrue Mion, PLLC

(57) ABSTRACT

According to the present invention, a heterodimer protein composition that is composed of a first polypeptide comprising an immunoglobulin heavy chain constant region and a second polypeptide comprising CL-Fc prepared by fusion of an immunoglobulin light chain constant region (CL) and Fc region, and also has a deletion or substitution of Cys residues involved in disulfide bonds between CL and CH1, a purification method of the protein composition thereof, a preparation method of the protein composition thereof, a DNA and a vector encoding the protein composition thereof are provided.

19 Claims, 28 Drawing Sheets

Specification includes a Sequence Listing.

(56) References Cited

OTHER PUBLICATIONS

Elkabetz et al., "Cysteines in CH1 Underlie Retention of Unassembled Ig Heavy Chains", The Journal of Biological Chemistry, The American Society for Biochemistry and Molecular Biology, Inc., Feb. 10, 2005, vol. 280, No. 15, pp. 14402-14412.

Gunasekaran et al., "Enhancing Antibody Fc Heterodimer Formation through Electrostatic Steering Effects: Applications to Bispecific Molecules and Monovalent IgG", The Journal of Biological Chemistry, The American Society for Biochemistry and Molecular Biology, Inc., Jun. 18, 2010, vol. 285, No. 25, pp. 19637-19646.

Jackman et al., "Development of a Two-part Strategy to Identify a Therapeutic Human Bispecific Antibody That Inhibits IgE Receptor Signaling", The Journal of Biological Chemistry, The American Society for Biochemistry and Molecular Biology, Inc., Jul. 2, 2010, vol. 285, No. 27, pp. 20850-20859.

Kufer et al., "A revival of bispecific antibodies", TRENDS in Biotechnology, Elsevier Ltd., May 1, 2004, vol. 22, No. 5, pp. 238-244.

Labrjin et al., "When binding is enough: nonactivating antibody formats", Current Opinion in Immunology, Elsevier Ltd., Aug. 2008, vol. 20, Issue 4, pp. 479-485.

Lindhofer et al., "Preferential Species-Restricted Heavy/Light Chain Pairing in Rat/Mouse Quadromas: Implications for a Single-Step Purification of Bispecific Antibodies", The Journal of Immunology, The American Association of Immunologists, Jul. 1, 1995, vol. 155, No. 1, pp. 219-225.

Merchant et al., "An efficient route to human bispecific IgG", Nature Biotechnology, Nature Publishing Group, Jul. 1998, vol. 16, pp. 677-681.

Müller et al., "The first constant domain (CH1 and CL) of an antibody used as heterodimerization domain for bispecific miniantibodies", FEBS Letters, Jan. 30, 1998, vol. 422, No. 2, pp. 259-264.

Ridgway et al., "'Knobs-into-holes' engineering of antibody CH3 domains for heavy chain heterodimerization", Protein Engineering, Oxford University Press, Jul. 1996, vol. 9, No. 7, pp. 617-621.

Wolf et al., "BiTEs: bispecific antibody constructs with unique anti-tumor activity", Reviews Drug Discovery Today, Elsevier Ltd., Sep. 15, 2015, vol. 10, No. 18, pp. 1237-1244.

Search Report dated Jan. 7, 2014, issued by the International Searching Authority in counterpart International Application No. PCT/JP2013/077172.

European Patent Office, Communication dated Apr. 21, 2016, issued in counterpart European Patent Application No. 13843485.7.

Dufner, et al.; "Harnessing phage and ribosome display for antibody optimisation"; TRENDS in Biotechnology; vol. 24, No. 11; pp. 523-529.

\* cited by examiner

FIG. 4A

```
RTVAAPSVFIFPPSDEQLKSGTASVVCLLNNFYPREAKVQWKVDNALQSGNSQESVTEQD
→
Cκ
                                              214
SKDSTYSLSSTLTLSKADYEKHKVYACEVTHQGLSSPVTKSFNRGEC DKTHTCPPCPAPE
                                               →              →
                                              ΔHinge          CH2

LLGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPP
                                                →
                                                CH3
SRDELTKNQVSLTCLVKGFYPSDIAVEWESNGQPENNYKTTPPVLSDGSFFLYSKLTVD
                435 436
KSRWQQGNVFSCSVMHEALHNHYTQKSLSLSPGK
```

FIG. 4B

```
RTVAAPSVFIFPPSDEQLKSGTASVVCLLNNFYPREAKVQWKVDNALQSGNSQESVTEQD
→
Cκ
                                              214          228
SKDSTYSLSSTLTLSKADYEKHKVYACEVTHQGLSSPVTKSFNRGEC ESKYGPPCPSCPA
                                                →            →
                                                Hinge        CH2
  235
PEFLGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTL
                                                  →
                                                  CH3
                                                              409
PPSQEEMTKNQVSLTCLVKGFYPSDIAVEWESNGQPENNYKTTPPVLSDGSFFLYSRLT
                435 436
VDKSRWQEGNVFSCSVMHEALHNHYTQKSLSLSLGK
```

(1) 4D5/mvG4-4 F
(2) hLL1/mvG4-4 F
(3) hLL1-4D5/mvG4-4 F
(4) hLL1-2F2/mvG4-4 F

HER2

RTVAAPSVFIFPPSDEQLKSGTASVVCLLNNFYPREAKVQW
→
C *kappa*

KVDNALQSGNSQESVTEQDSKDSTYSLSSTLTLSKADYEK

C214S
                            ★
HKVYACEVTHQGLSSPVTKSFNRGES|DKTHTCPPC|APEL
                                →       CH2
                              Hinge
                                          K274Q
LGGPSVFLFPPKPKDTLMISRTPEVTCVVVDVSHEDPEVQF
                                            •
N276K                 Y296F Y300F
•                             •    •
KWYVDGVEVHNAKTKPREEQFNSTFRVVSVLTVLHQDWL
                        A339T
                         •
NGKEYKCKVSNKALPAPIEKTISKTKGQPREPQVYTLPPSR
D356E  L358M                 CH3
•     •
EEMTKNQVSLTCLVKGFYPSDIAVEWESSGQPENNYKTTP
V397M                        V422I            H435R
•                            •             ★
PMLDSDGSFFLYSKLTVDKSRWQQGNIFSCSVMHEALHNR
Y436F
★
FTQKSLSLSPGK ● High CDC activity-amino acid residue substitution
★ Amino acid residue substitution in heterodimer protein

HETERODIMER PROTEIN COMPOSITION

CROSS-REFERENCE TO RELATED APPLICATIONS

This is a Divisional of U.S. application Ser. No. 14/046,478, which is now U.S. Pat. No. 9,714,291, filed Oct. 4, 2013, claiming priority based on Provisional Application No. 61/710,221 filed Oct. 5, 2012, the contents of all of which are incorporated herein by reference in their entirety.

BACKGROUND OF THE INVENTION

1. Field of the Invention

The present invention relates to a heterodimer protein composition that is efficiently and stably separated and purified.

2. Brief Description of the Background Art

Monoclonal antibodies are biological polymers having high binding affinity and specificity for antigens, and applied as molecular targeted therapeutics for the treatment of cancer, immune disorders or the like. The known action mechanisms of immunoglobulin G (hereinafter, abbreviated to IgG) which is widely used as a therapeutic monoclonal antibody include neutralization of antigens, receptor agonist or antagonist action, induction of apoptosis, phagocytosis, induction of complement or effector cell-dependent cytotoxicity, delivery of chemotherapeutic agents, toxins, and radioactive isotopes, or the like.

IgG antibodies are tetrameric molecules composed of two antibody heavy chains (hereinafter, abbreviated to H chain) and two antibody light chains (hereinafter, abbreviated to L chain), consisting of a variable region as an antigen-binding site and a constant region having a constant amino acid sequence (FIG. 1).

Each structure of an antibody is known to be involved in the various roles. The antigen-binding site is formed by a heavy chain variable region (hereinafter, abbreviated to VH) and a light chain variable region (hereinafter, abbreviated to VL), and various antigen specificities and binding affinities are caused by variability in primary sequence and higher-order structure.

Each constant region of IgG H chain (hereinafter, abbreviated to CH) is composed of CH1, hinge, CH2, and CH3 domains, and among them, hinge, CH2, and CH3 constitute the Fc region (hereinafter, also simply referred to as Fc). Fc binds to the Fcγ receptor (hereinafter, abbreviated to FcγR) present on leukocytes to be involved in release of inflammatory mediators, phagocytosis, and antibody-dependent cellular cytotoxicity (hereinafter, abbreviated to ADCC), and also binds to complement components to be involved in complement-dependent cytotoxicity (hereinafter, abbreviated to CDC).

Further, Fc of IgG antibody binds to the neonatal Fc receptor (hereinafter, abbreviated to FcRn) in the endosome under low pH conditions, and avoids lysosomal degradation to be involved in extension of the blood half-life. The primary sequence of Fc region varies depending on its subclasses (IgG1, IgG2, IgG3, IgG4), and its binding activity for FcγR, FcRn and complement components also differs, for this reason, they cause differences in biological properties (Non-Patent Document 1).

IgG antibody molecule has two fragments called as Fab, which is composed of VH, CH1, VL, and L chain constant region (hereinafter, abbreviated to CL), and these two Fabs form the bivalent binding with antigen molecules. This bivalent binding activity increases avidity for antigens, as well as induces intracellular signaling by cross-linking antigens when the antibodies bind to antigen molecules such as receptors present on the surface of cell membrane.

In order to avoid the bivalent antigen-binding activity of IgG antibody, antibody engineering consideration has been made, such as preparation of monovalent antibodies having a single antigen-binding site or antibody variants having an Fc variant containing substitution of amino acid residues for removing the FcγR binding activity. Meanwhile, Fab fragment including an antigen-binding site shows a monovalent binding activity for antigens, but shows a short blood half-life and is not useful as a therapeutic agent because there is no Fc (Non-Patent Document 2).

Meanwhile, bispecific antibodies are allowed to have the action mechanisms that cannot be achieved by the conventional IgG monoclonal antibodies, because of their bispecificity. For example, bispecific T cell engager [BiTE (registered trade name)] binds with both CD3 and a cancer antigen to recruit T cells and to efficiently damage cancer cells (Non-Patent Document 3). In addition, bispecific antibodies have a possibility of inhibiting activated intracellular signaling by crosslinking the inhibitory Fcγ receptor FcγRIIb with the receptor (Non-Patent Documents 4 and 5).

The first technology of producing bispecific antibodies is a production method using a fusion cell of two hybridomas, called quadroma. Theoretically, tetramers composed of two different H chains and two different L chains are produced as a mixture of up to 10 assemblies, of which only one is the desired antibody having bispecific activity. It is difficult to separate the desired bispecific antibodies from by-products that are similar in physicochemical properties (Non-Patent Document 6).

The known methods for reducing the kind of by-products of the bispecific antibody are a method of introducing a substitution of amino acid residues stabilizing a "heterologous assembly" of the different H chains into CH3 domain (Non-Patent Documents 7, 8, and 9, and Patent Document 4), and a method of stabilizing heterologous assembly of H chains by using chimeric CH3 domains of IgG1 antibody and IgA antibody (Patent Document 1).

In this regard, a method of removing the undesirable by-products generated by "homologous assembly" of homologous H chains during expression of the bispecific antibodies in a purification step has been reported, and a purification method using a difference in binding affinity of IgG antibody subclasses for Protein A has also been known.

Lindhofer et al. have disclosed a purification method of bispecific antibodies consisting of rat IgG2b and mouse IgG2a, based on the properties of rat IgG2b binds to Protein A and mouse IgG2a doesn't bind to Protein A. That is, it is known that a heterodimer of rat IgG2b and mouse IgG2a and a homodimer of mouse IgG2a bind to Protein A, and heterodimeric bispecific antibody can be isolated by pH control during elution (Non-Patent Document 10).

Further, Samuel et al. have proposed a method of specifically purifying human IgG type bispecific antibody by using a difference in the affinity for Protein A. It has been also disclosed that of the two different H chains constituting the bispecific antibody, the CH3 domain of one H chain is subjected to modification of amino acid residues of Arg at position 435 and Phe at position 436 of the EU index, thereby reducing the binding affinity for Protein A, and as a result, heterodimeric IgG type bispecific antibody can be separated and purified from three molecules having different Protein A affinities by pH control during elution (Patent Document 2).

A heterodimeric monovalent antibody consisting of a human IgG1 antibody H chain and a fusion protein of a human κ light chain and an Fc molecule of human IgG1 has been reported as one of the antibody molecules prepared by application of a heterodimeric structure (Patent Document 3).

However, it has been known that when this molecule is expressed, homodimers of H chain-H chain are not secreted, but heterodimers of H chain-fusion protein, homodimers of fusion protein, and multimers are secreted into the culture supernatant, and conjugation of a tag sequence to H chain is required in order to obtain the specific heterodimeric monovalent antibody from the secreted proteins, and this tag should be used for purification. For the use of this monovalent antibody molecule as a drug, side effects caused by possible multimers having unexpected biological activities and a cumbersome and expensive affinity purification using a tag sequence are challenging problems.

CITATION LIST

Patent Documents

[Patent Document 1] WO 2007/110205
[Patent Document 2] WO 2010/151792
[Patent Document 3] WO 2007/048037
[Patent Document 4] WO 2009/089004

Non-Patent Documents

[Non-Patent Document 1] Cater et al, Nature Review, 2006; 6: 343.
[Non-Patent Document 2] Labrjin A F et al, Current Opinion in Immunology, 2008; 20: 1
[Non-Patent Document 3] Wolf et al, Drug Discovery Today, 2005; 10: 1237
[Non-Patent Document 4] Kufer et al, TRENDS in Biotech., 2004; 22: 238
[Non-Patent Document 5] Jackman et al., J. Biol. Chem., 2010; 285: 20850
[Non-Patent Document 6] Cater et al. J. Immunol. Methods, 2001; 248: 7
[Non-Patent Document 7] Ridway et al. Protein Eng., 1996; 9: 617
[Non-Patent Document 8] Merchant et al., Nature Biotech., 1998; 16: 677
[Non-Patent Document 9] Gunasekaran et al., J. Biol. Chem., 2010; 285: 19637
[Non-Patent Document 10] Lindhofer H et al., J. Immunol., 1995; 155: 219

SUMMARY OF THE INVENTION

With respect to the previously known heterodimer proteins, their production efficiency was low and unstable, and specific production, separation and purification of heterodimer protein molecules were difficult. Accordingly, there is a need for a heterodimer protein composition that can be efficiently and stably produced, a purification method and a preparation method of the protein composition.

The heterodimer protein of the present invention is composed of a first polypeptide comprising an immunoglobulin heavy chain constant region (CH) and a second polypeptide comprising CL-Fc prepared by fusion of an immunoglobulin light chain constant region (CL) and Fc region, and it can be efficiently and stably produced by inhibiting the amounts of multimers, halfmers and multimer/halfmer produced during production of the heterodimer proteins, resulting from deletion or substitution of Cys residues involved in disulfide bonds between L chain-H chain molecules in the IgG antibody.

BRIEF DESCRIPTION OF THE DRAWINGS

FIG. 4A shows the amino acid sequence (IgG1-L) of CL-Fc of IgG1 type monovalent antibody (SEQ ID NO: 22). The amino acid residues underlined represent amino acid residue substitution-introduced region (Table 2), and the numbers represent those defined by the EU index.
FIG. 4B shows the amino acid sequence (IgG4-L) of CL-Fc of IgG4 type monovalent antibody (SEQ ID NO: 26). The amino acid residues underlined represent amino acid residue substitution-introduced region (Table 2), and the numbers represent those defined by the EU index.

DF sample (FIG. 9) fractionated by cation exchange chromatography. Anti-kappa chain antibody was used for L chain detection, anti-His tag antibody was used for H chain detection, and anti-human IgG antibody was used for IgG detection. Peaks (2), (4), (5), (6), (7) and (10) were below the detection limits.

Figure 11:
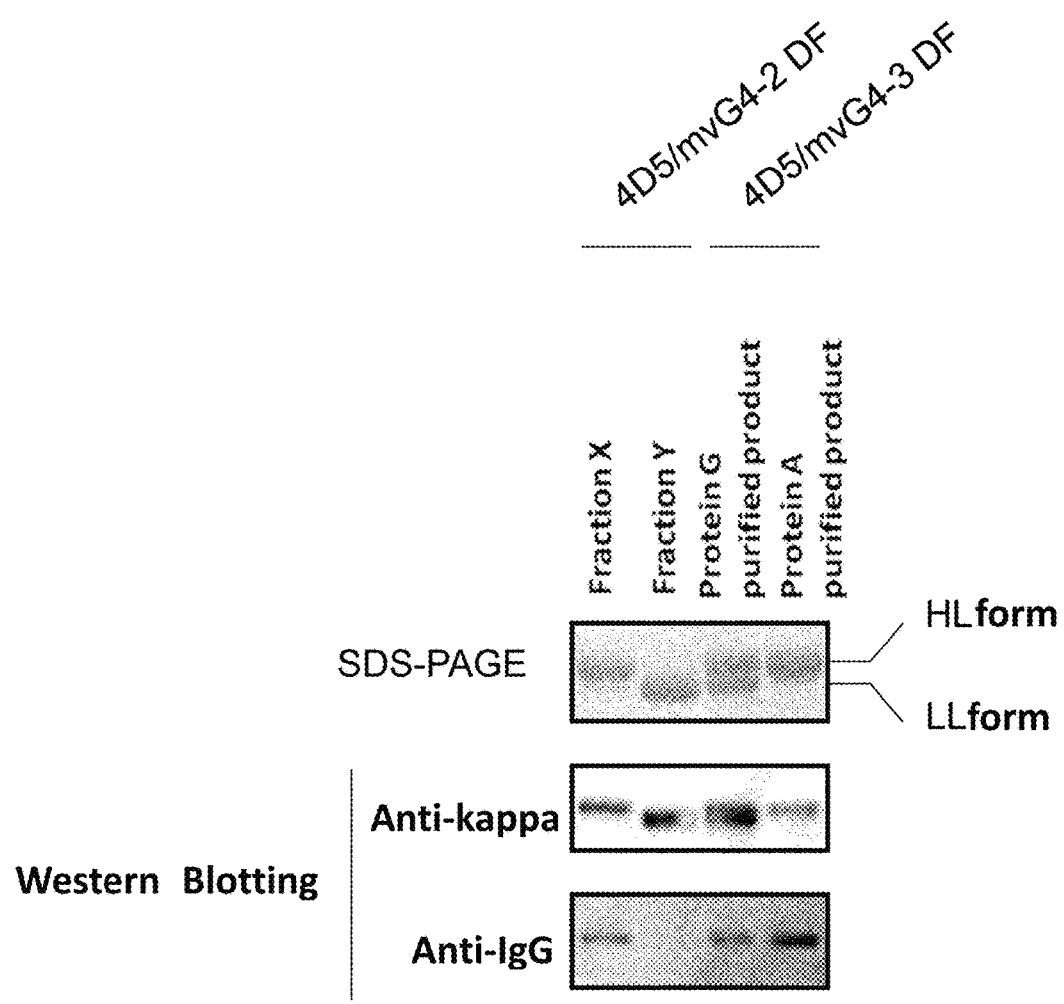

FIG. 11 shows the results of SDS-PAGE, L chain-specific western blot, and H chain-specific western blot of fraction X which is one of the fractions eluted at pH 3.5 and fraction Y eluted at pH 5.0 in Protein A purification of anti-HER2 IgG4 type monovalent antibody 4D5/mvG4-2 DF, and 4D5/mvG4-3 DF purified by use of Protein A or Protein G. As shown in Table 5, the fractions X and Y of 4D5/mvG4-2 DF are an elution fraction having HL form as a main component and an elution fraction having LL form as a main component, respectively. Protein G-purified product and Protein A-purified product of 4D5/mvG4-3 DF were obtained by performing Protein G or Protein A purification of the cell culture supernatant obtained at the same time and then by eluting them collectively.

Figure 12:
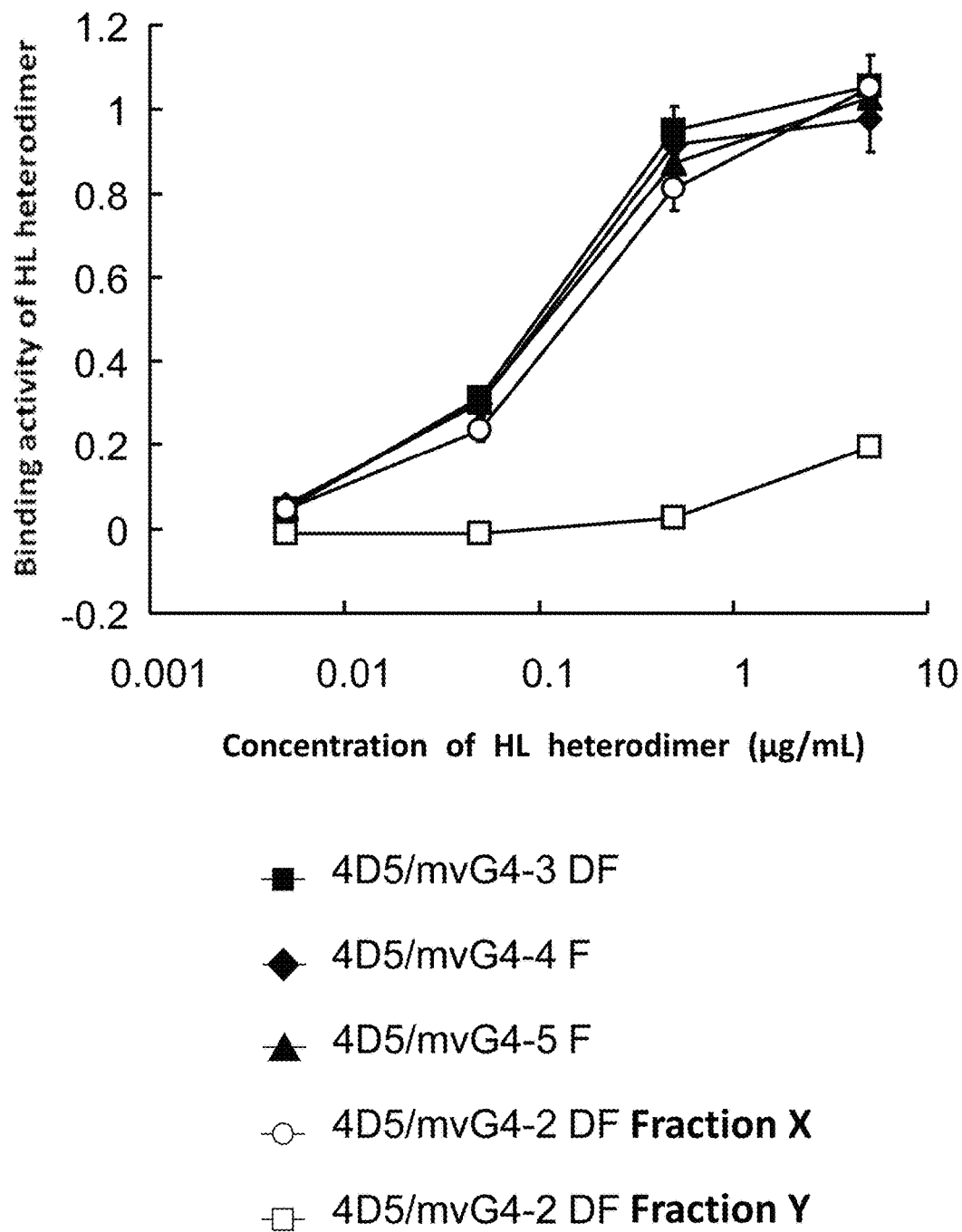

FIG. 12 shows the amount of HL heterodimer of IgG4 type monovalent antibody by sandwich ELISA. The experiment was performed at N=3. The vertical axis represents the binding activity of HL heterodimer, and the horizontal axis represents the HL heterodimer concentration (μg/mL).

Figure 13A:
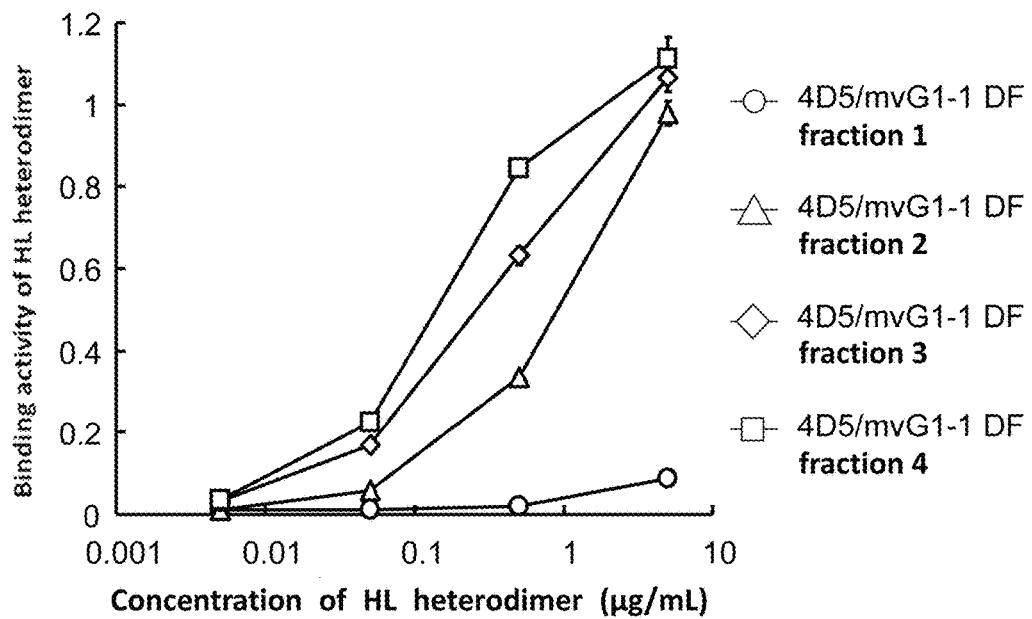

FIG. 13A shows the amount of IgG4 type monovalent antibody HL heterodimer in each protein A purification fraction by sandwich ELISA. The experiment was performed at N=3. The vertical axis represents the binding activity of HL heterodimer, and the horizontal axis represents the HL heterodimer concentration (μg/mL).

Figure 13B:
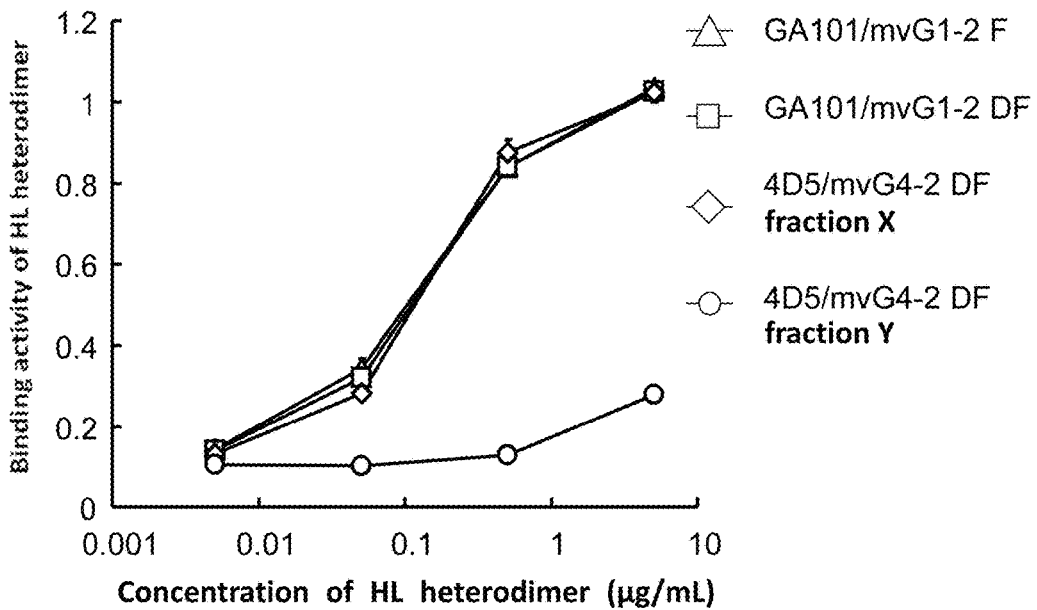

FIG. 13B shows the amount of IgG4 type monovalent antibody HL heterodimer in each protein A purification fraction by sandwich ELISA. The experiment was performed at N=3. The vertical axis represents the binding activity of HL heterodimer, and the horizontal axis represents the HL heterodimer concentration (μg/mL).

Figure 14A:
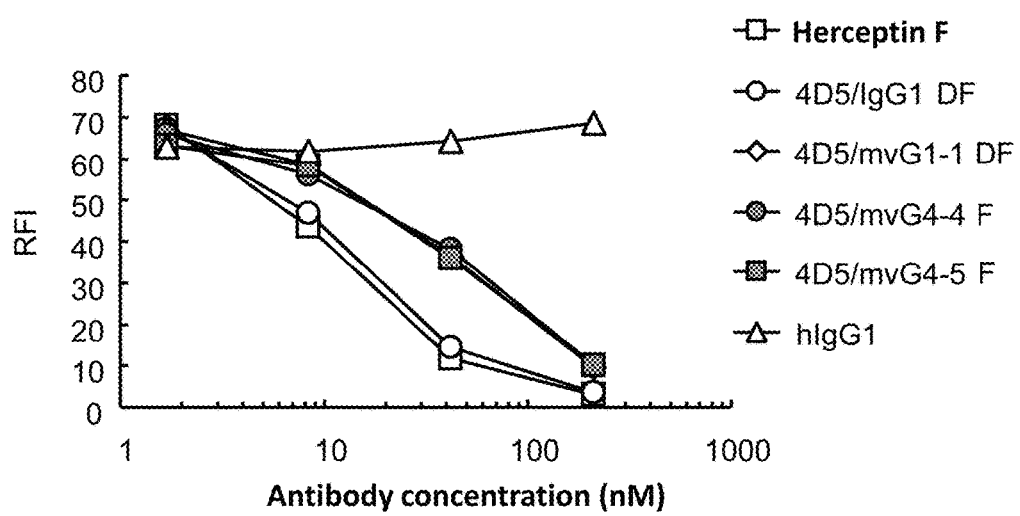

FIG. 14A shows the results of flow cytometry for evaluating competitive binding inhibition of various monovalent antibodies in the binding assay of anti-HER2 humanized antibody Herceptin, in which the binding activity for HER2 positive human breast cancer cell line SK-BR-3 is shown. Relative fluorescence intensity in the figure was calculated by (average fluorescence intensity of sample)/(average fluorescence intensity of hIgG1 Alx). The experiment was performed at N=2. In all figures, the vertical axis represents relative fluorescence intensity (RFI), and the horizontal axis represents the concentrations (nM) of IgG1 antibody and monovalent antibody competitively reacted.

Figure 14B:
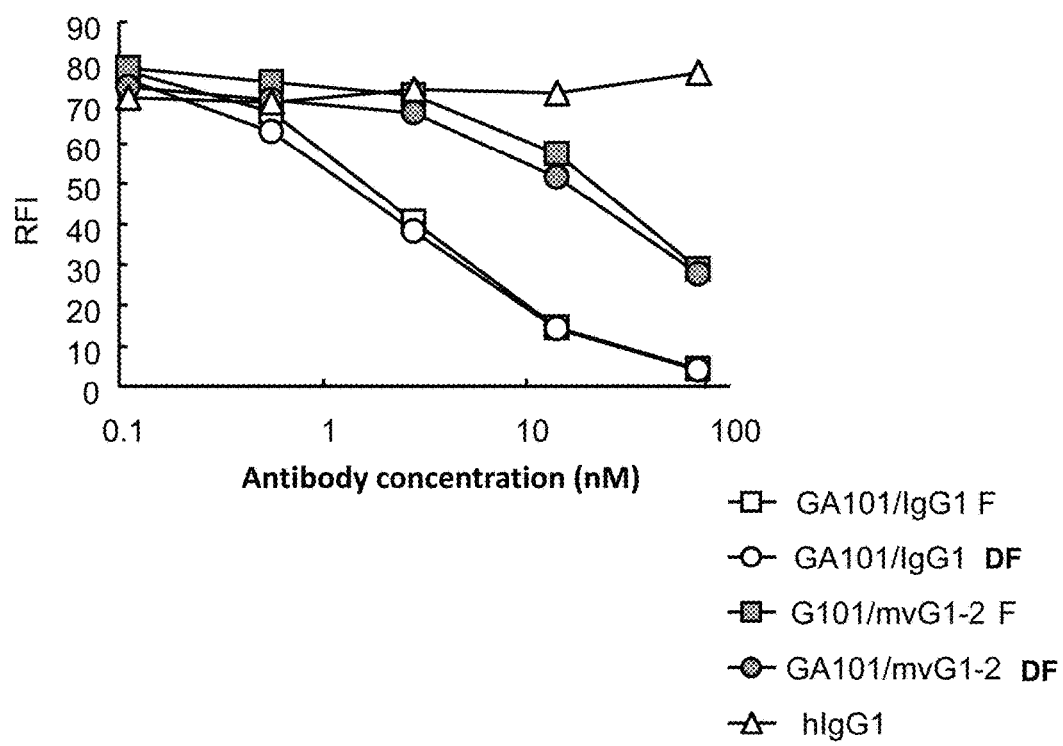

FIG. 14B shows the results of flow cytometry for evaluating competitive binding inhibition of various monovalent antibodies in the binding assay of anti-CD20 humanized antibody GA101, in which the binding activity for CD20 positive human lymphoma cell line Raji is shown. Relative fluorescence intensity in the figure was calculated by (average fluorescence intensity of sample)/(average fluorescence intensity of hIgG1$_{13}$Alx). The experiment was performed at N=2. In all figures, the vertical axis represents relative fluorescence intensity (RFI), and the horizontal axis represents the concentrations (nM) of IgG1 antibody and monovalent antibody competitively reacted.

Figure 15A:
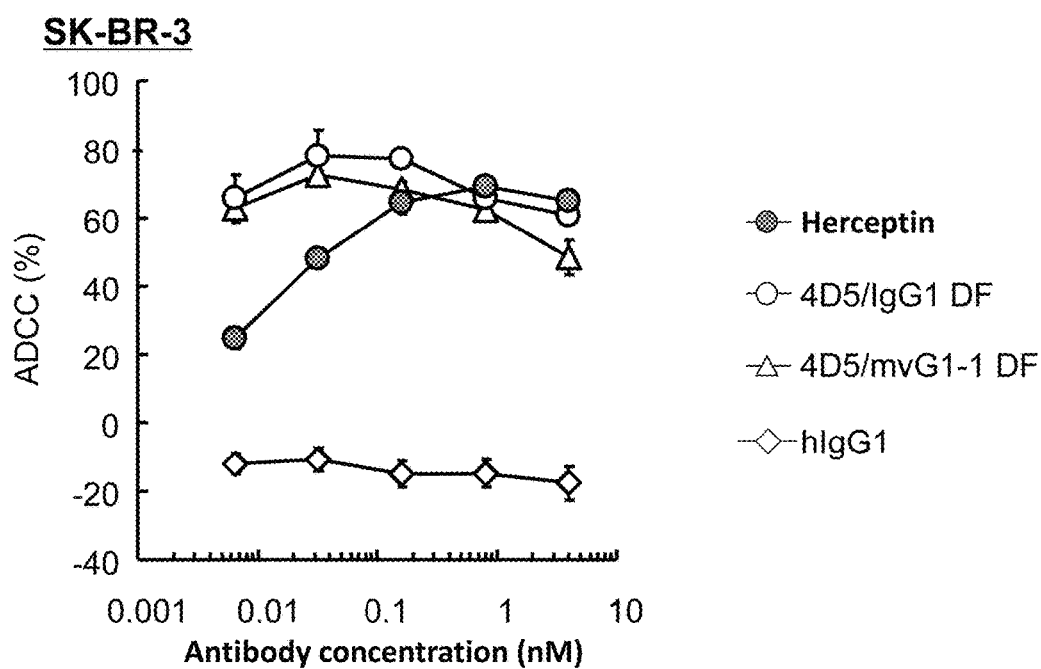
Figure 15B:
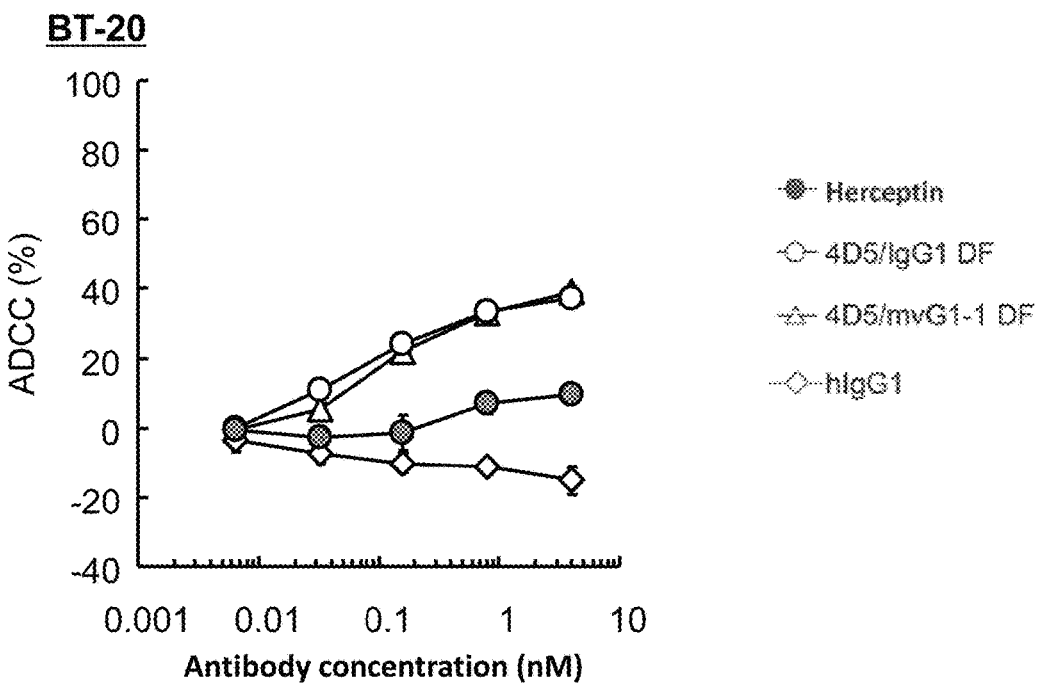

FIGS. 15A and 15B show antibody dependent cellular cytotoxicity (ADCC) activity for human breast cancer cell line SK-BR-3 and BT-20 by the IgG1 type anti-HER2 monovalent antibodies, in which fraction (FIGS. 13A and 13B) showing the highest content of HL heterodimer was used as 4D5/mvG1-1 DF. In the experiment, PBMC obtained from another donor was used. The experiment was performed at N=3. The vertical axis represents the ADCC activity, and the horizontal axis represents the antibody concentration (nM).

Figure 15C:
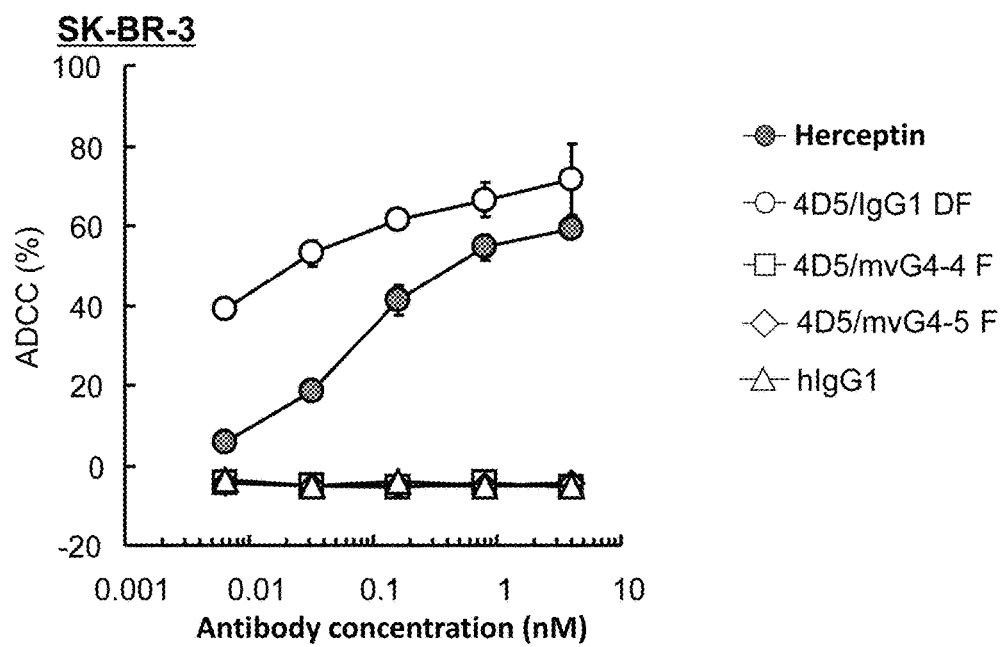
Figure 15D:
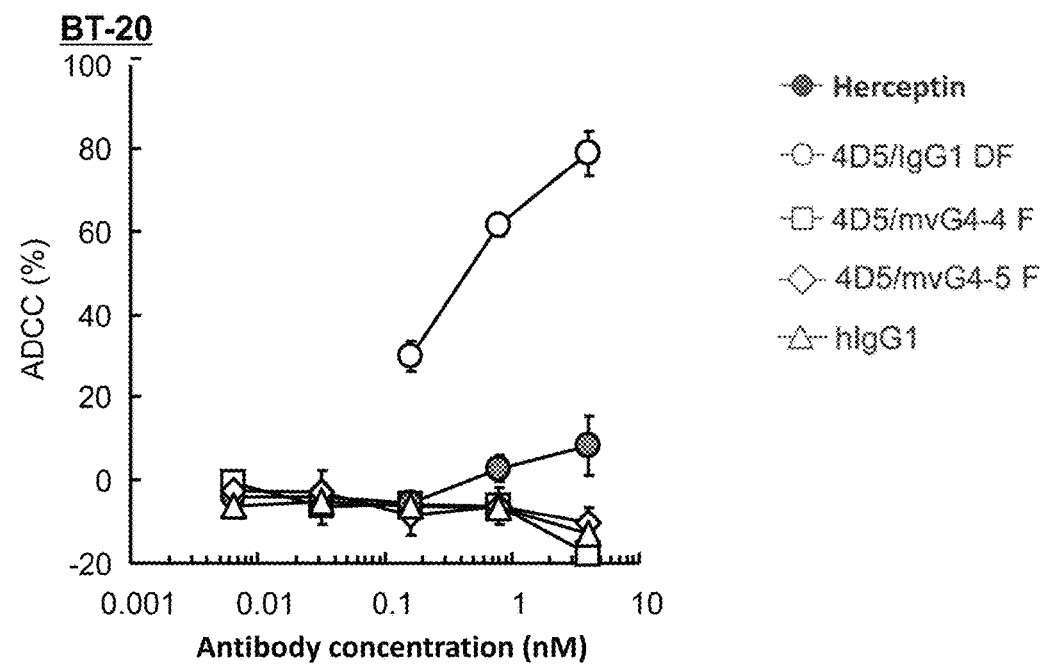

FIGS. 15C and 15D show ADCC activity for human breast cancer cell line BT-20 by the IgG1 type and IgG4 type anti-HER2 monovalent antibodies. In the experiment, PBMC obtained from another donor was used. The experiment was performed at N=3. The vertical axis represents the ADCC activity, and the horizontal axis represents the antibody concentration (nM).

Figure 16A:
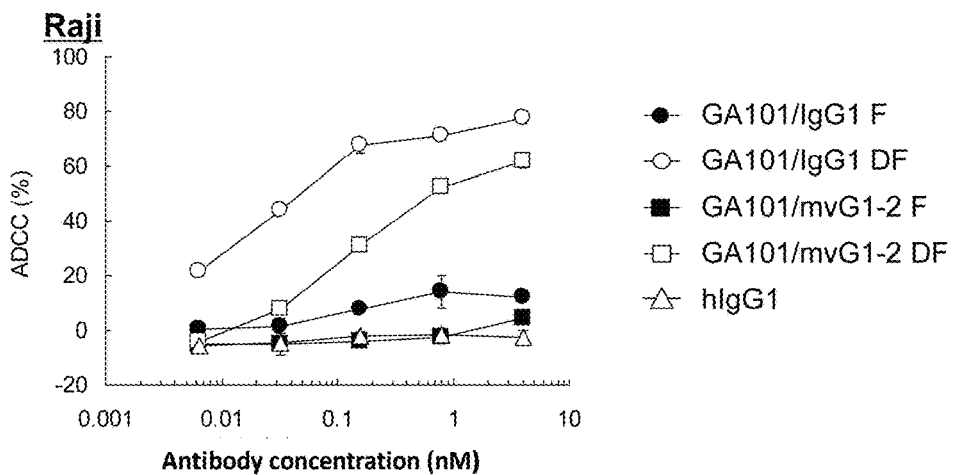
Figure 16B:
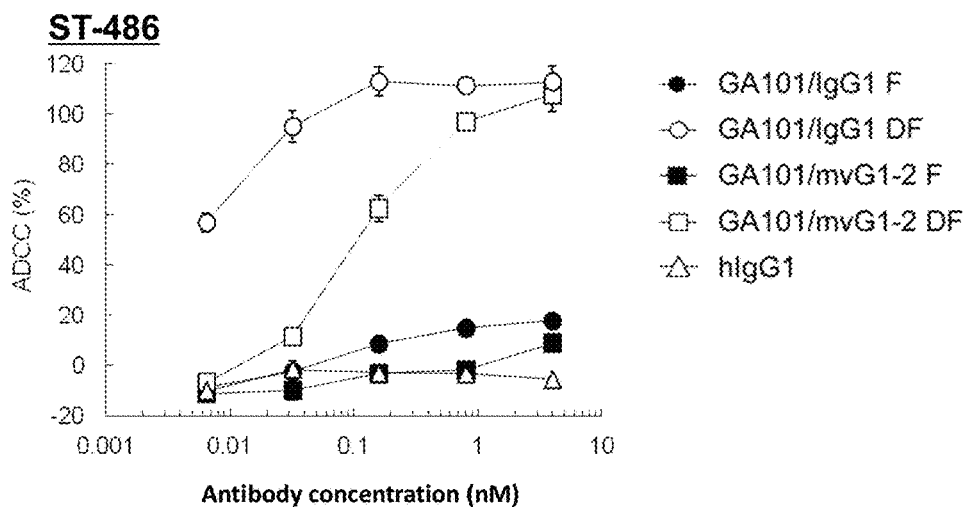
Figure 16C:
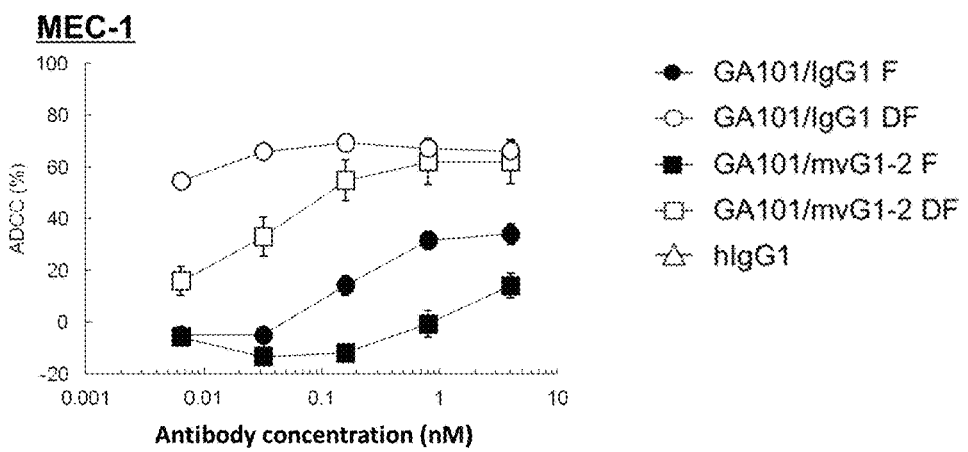

FIGS. 16(a) to (c) show ADCC activity of anti-CD20 IgG1 type monovalent antibody for Burkitt lymphoma cell lines Raji and ST-486 and chronic B cell leukemia cell line MEC-1. The vertical axis represents the ADCC activity (%), and the horizontal axis represents the antibody concentration (nM).

Figure 17:
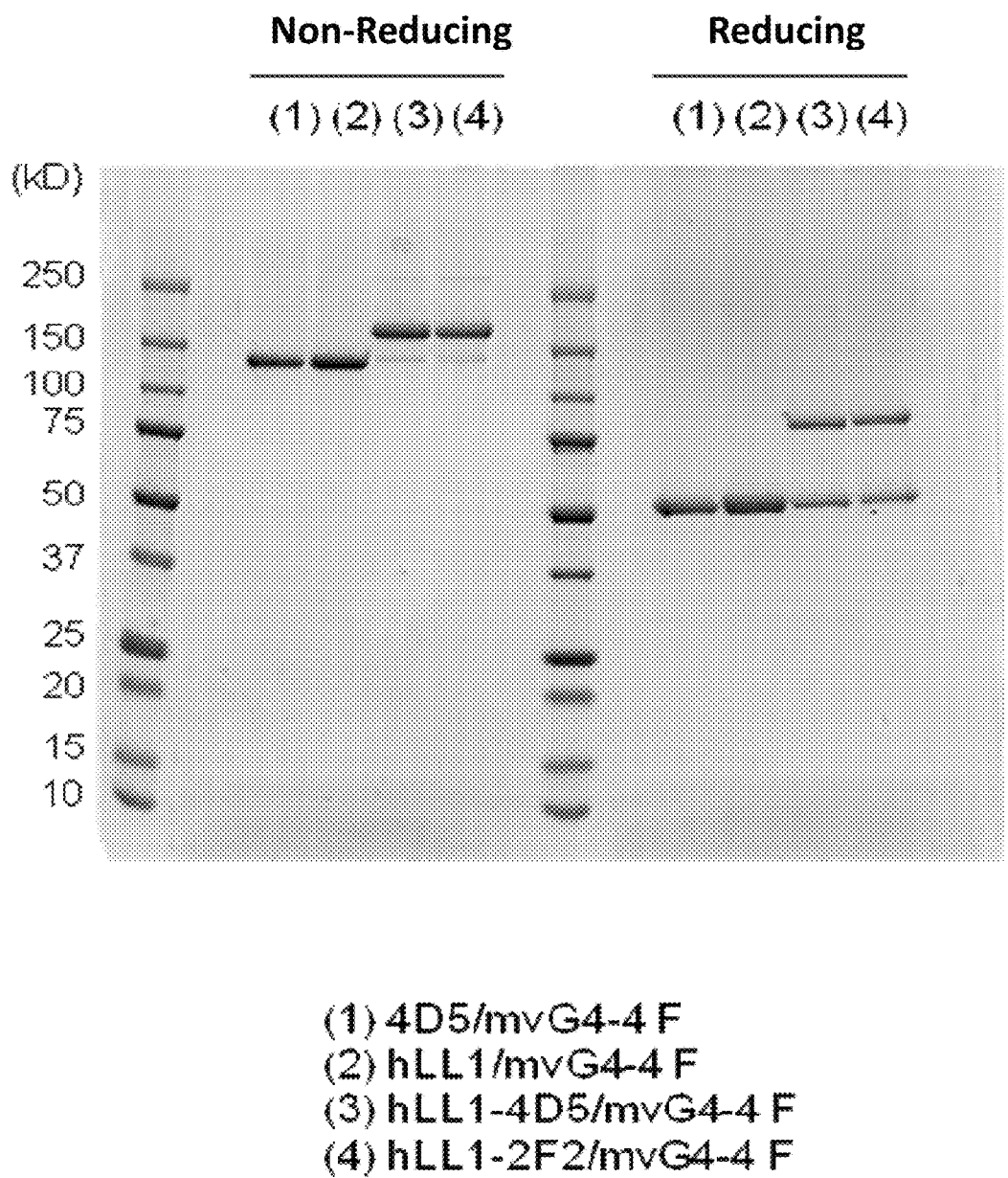

FIG. 17 shows the results of SDS-PAGE analysis of anti-HER2 IgG4 type monovalent antibody 4D5/mvG4-4F, anti-CD74 IgG4 type monovalent antibody hLL1/mvG4-4F, HER2-CD74 bispecific antibody hLL1-4D5/mvG4-4F and CD74-CD20 bispecific antibody hLL1-2F2/mvG4-4F under non-reducing and reducing conditions.

Figure 18A:
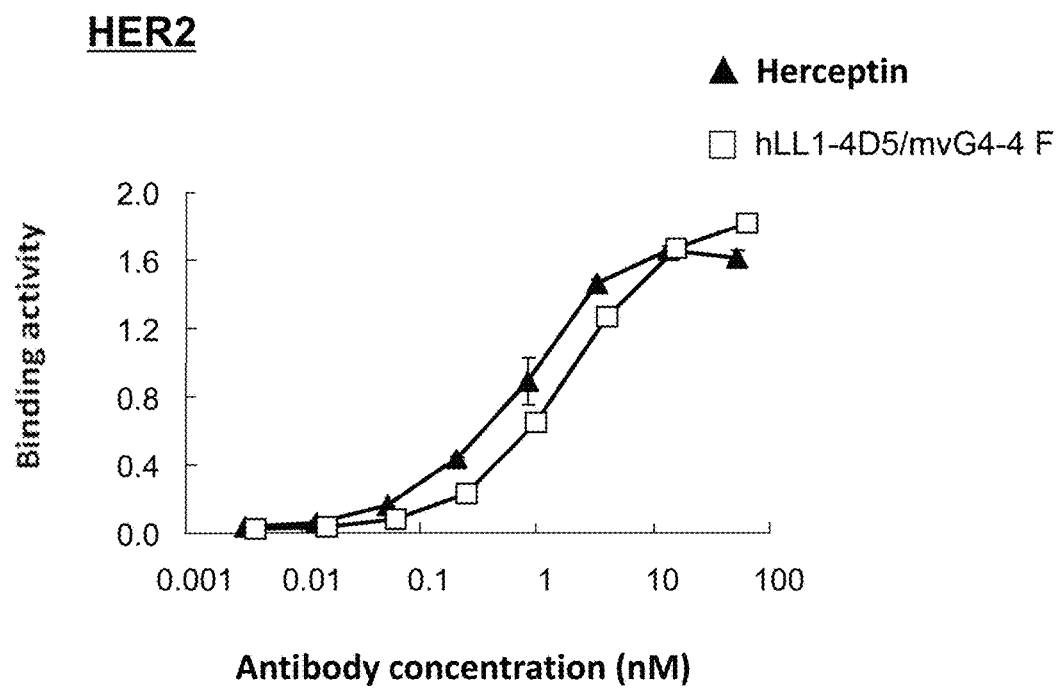

FIGS. 18(a) and (b) show the binding activity of HER2-CD74 bispecific antibody hLL14D5/mvG4-4F for recombinant HER2 protein and recombinant CD74 protein by ELISA. The vertical axis represents the antigen-binding activity (0D415-490) and the horizontal axis represents the bispecific antibody concentration (nM). Anti-HER2 humanized antibody Herceptin and anti-CD74 antibody hLL1 antibody were used as a positive control IgG1 antibody for each antigen.

Figure 19:
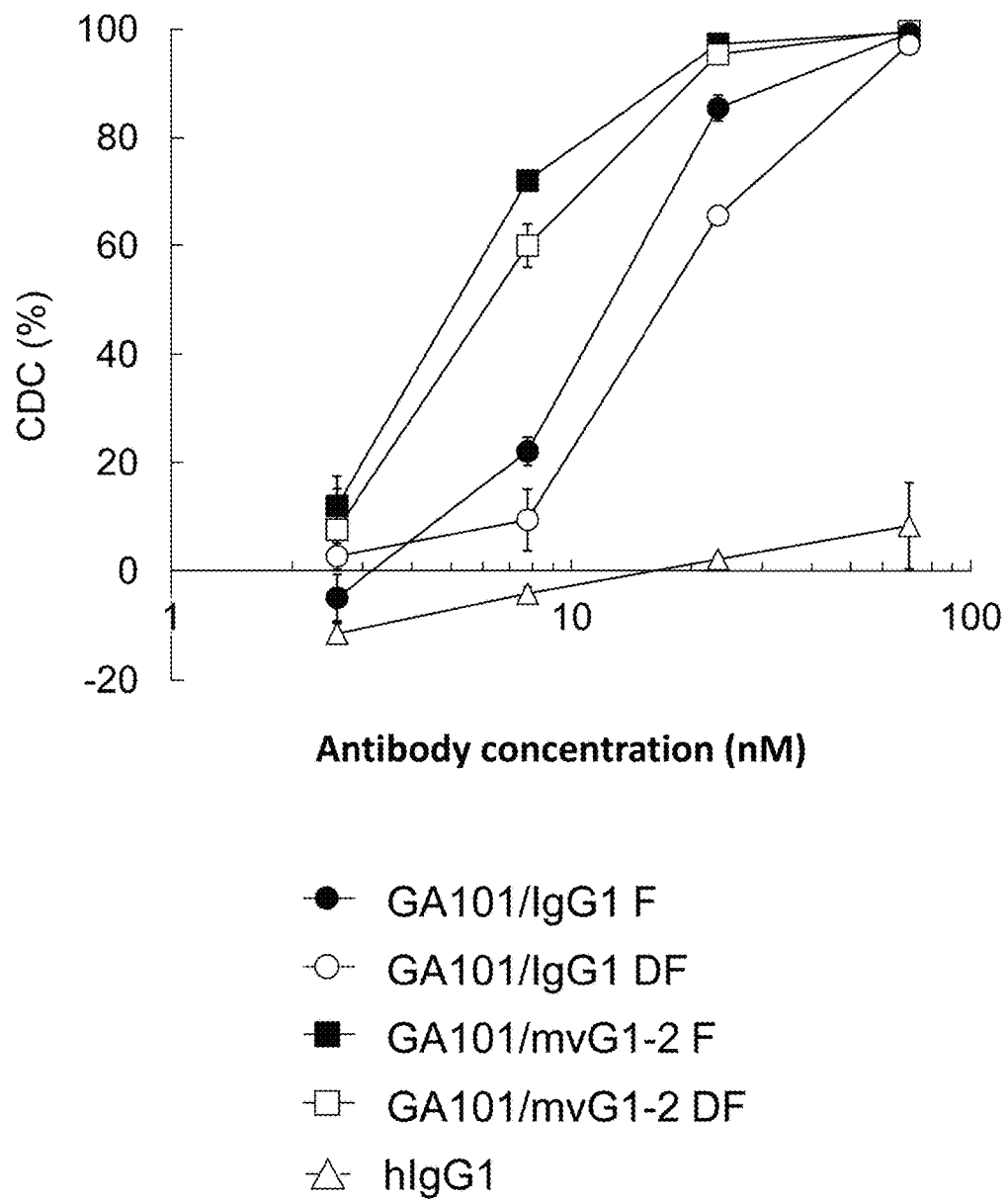

FIG. 19 shows complement-dependent cytotoxicity (CDC activity) of anti-CD20 IgG1type monovalent antibody GA101/mvG1-2 and anti-CD20 IgG1 antibody GA101/IgG1 for Burkitt lymphoma cell line ST-486. The vertical axis represents the CDC activity (%) and the horizontal axis represents the mol concentration (nM) of each monovalent antibody and IgG1antibody.

Figure 20A:
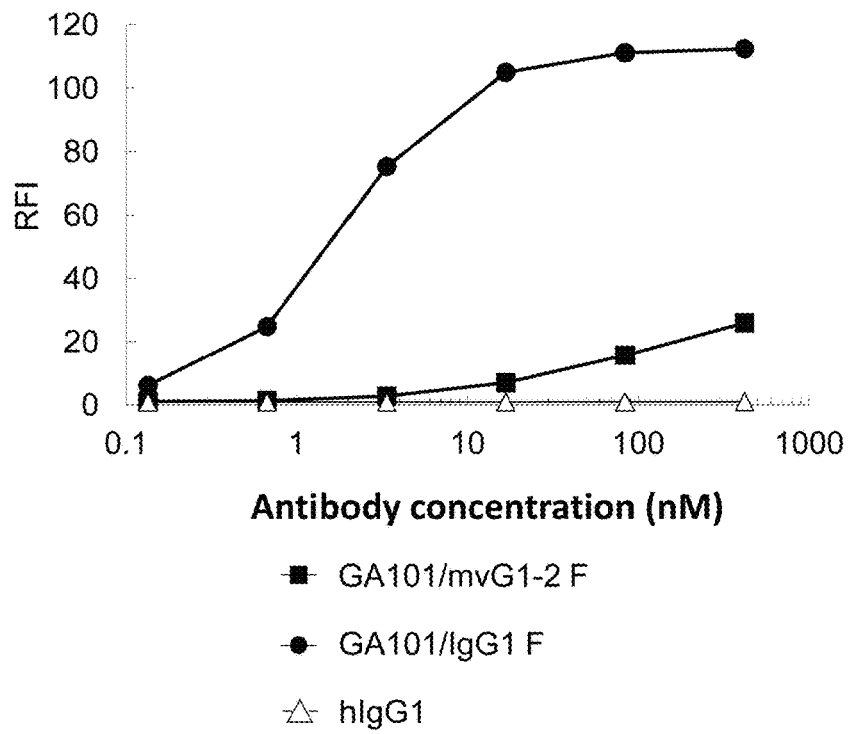
Figure 20B:
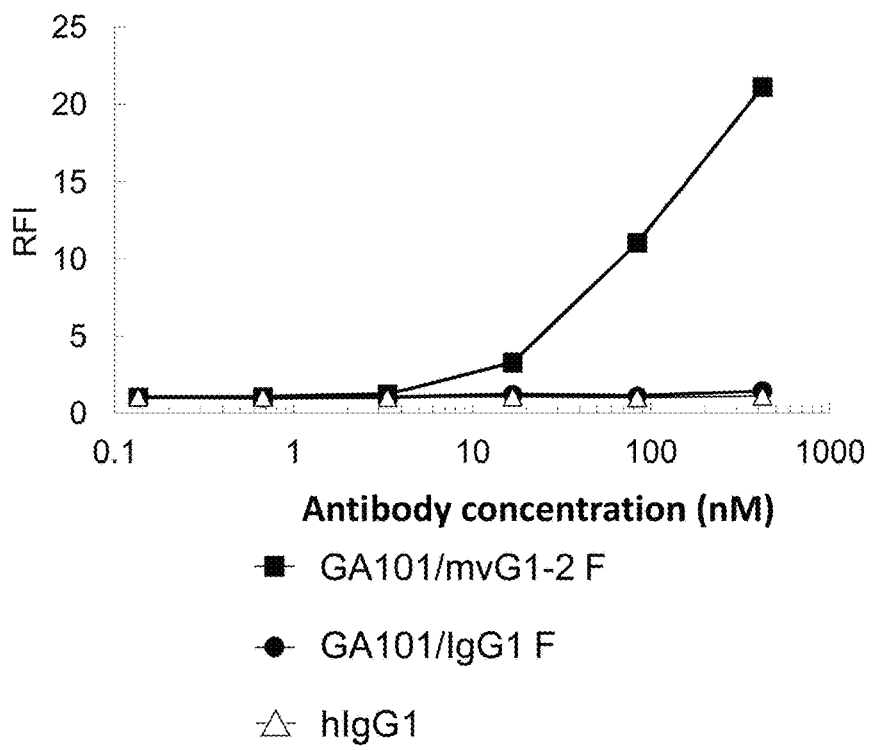

FIG. 20(a) shows the binding amounts of anti-CD20 IgG1 type monovalent antibody GA101/mvG1-2 and anti-CD20 IgG1 antibody GA101/IgG1 to Burkitt lymphoma cell line Raji. FIG. 20(b) shows the binding amount of complement factor C1q. In both figures, the vertical axis represents relative fluorescence intensity (RFI) value, and the horizontal axis represents the mol concentration (nM) of each monovalent antibody and IgG1 antibody.

Figure 21A:
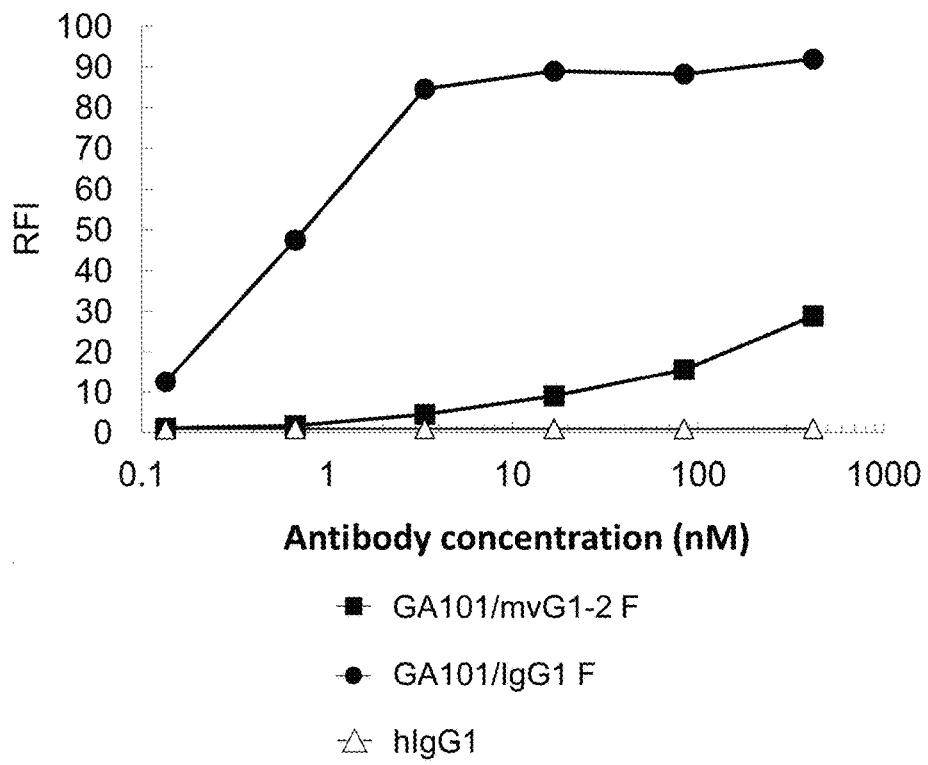
Figure 21B:
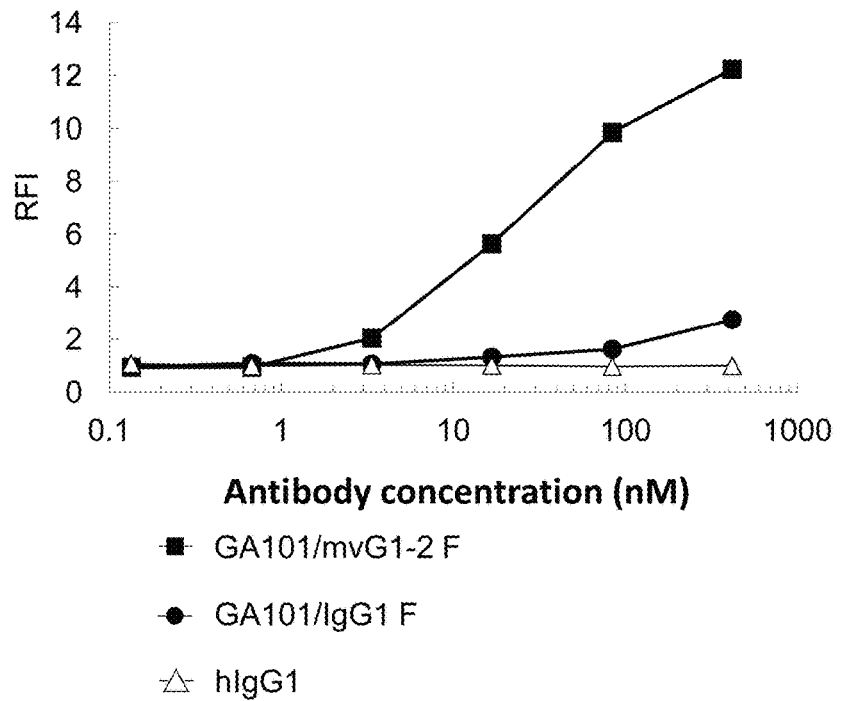

FIG. 21(a) shows the binding amounts of anti-CD20 IgG1 type monovalent antibody GA101/mvG1-2 and anti-CD20 IgG1 antibody GA101/IgG1 to Burkitt lymphoma cell line ST-486. FIG. 21(b) shows the binding amount of complement factor C1q. In both figures, the vertical axis represents relative fluorescence intensity (RFI) value, and the horizontal axis represents the mol concentration (nM) of each monovalent antibody and IgG1 antibody.

Figure 22A:

FIG. 22A shows the amino acid sequence of H chain constant region domain of the heterodimer protein including the CDC enhanced-constant region (SEQ ID NO: 59). The amino acid numbers are represented according to the EU index defined by Kabat et al., and ● represents the CDC enhanced-amino acid substitution sites of the IgG1 type and ★ represents the amino acid substitution sites for the heterodimer protein.

FIG. 22B shows the amino acid sequence of CL-Fc chain of the heterodimer protein including the CDC enhanced-constant region (SEQ ID NO: 60). The amino acid numbers are represented according to the EU index defined by Kabat et al., and ● represents the CDC enhanced-amino acid substitution sites of the IgG1 type and ★ represents the amino acid substitution sites for the heterodimer protein.

Figure 23:
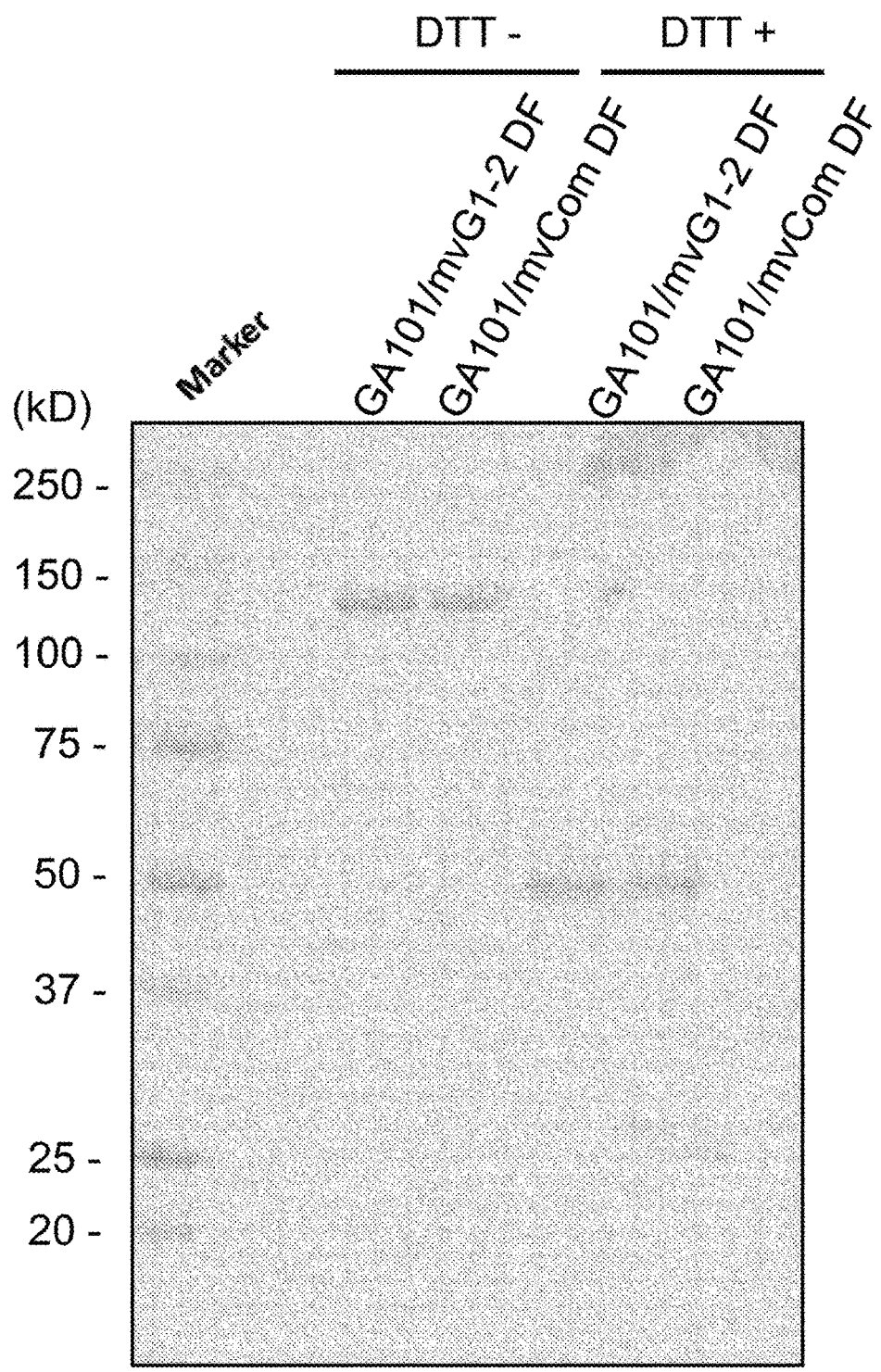

FIG. 23 shows the results of SDS-PAGE using the purified proteins of anti-CD20 IgG1type monovalent antibody GA101/mvG1-2 and anti-CD20 CDC enhanced-monovalent antibody GA101/mvCom. DTT- represents a non-reduced state and DTT+ represents a reduced state.

Figure 24A:
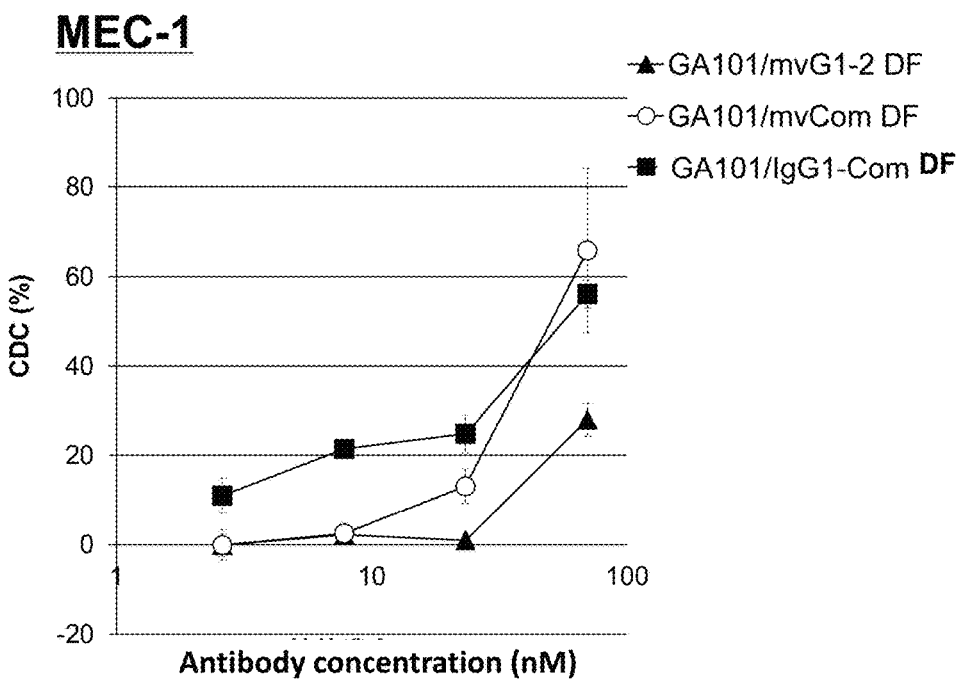

FIGS. 24(a) and (b) show CDC activity of anti-CD20 IgG1 type monovalent antibody GA101/mvG1-2 and CDC enhanced anti-CD20 high monovalent antibody GA101/mvCom for Burkitt lymphoma cell line Raji or chronic B cell leukemia cell MEC-1. The vertical axis represents the CDC activity (%), and the horizontal axis represents the mol concentration (nM) of each monovalent antibody and IgG1 antibody.

Figure 25A:
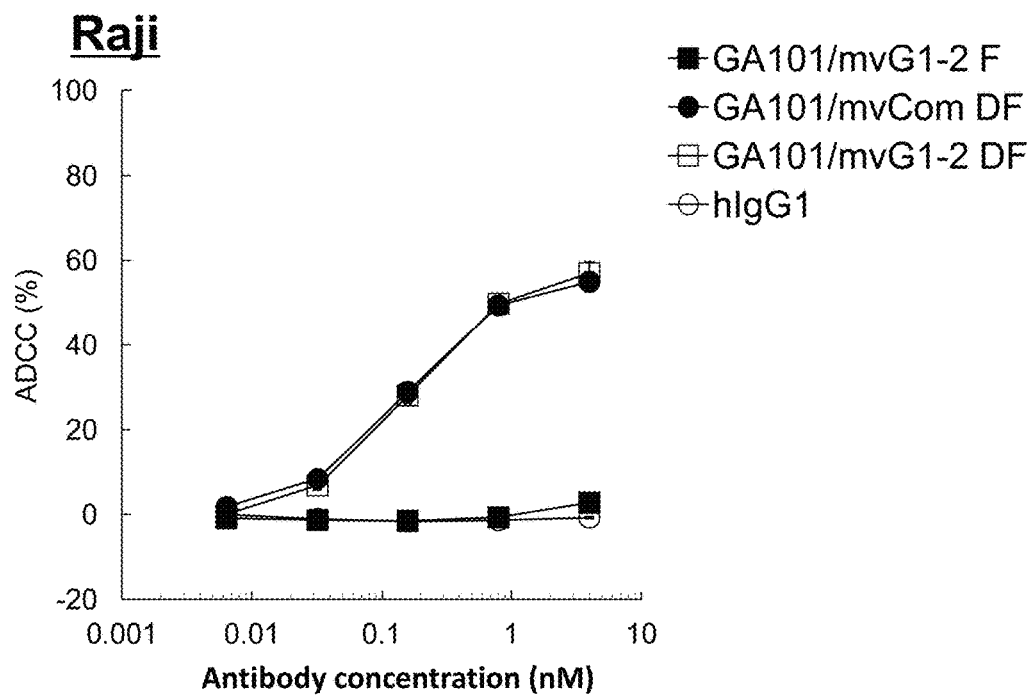

FIGS. 25(a) and (b) show ADCC activity of anti-CD20 IgG1 type monovalent antibody GA101/mvG1-2 and CDC enhanced anti-CD20 monovalent antibody GA101/mvCom for Burkitt lymphoma cell line Raji or chronic B cell leukemia cell MEC-1. The vertical axis represents the ADCC activity (%), and the horizontal axis represents the mol concentration (nM) of each monovalent antibody and IgG1 antibody.

DETAILED DESCRIPTION OF THE INVENTION

The present invention relates to the following (1) to (25).

(1) A heterodimer protein that is composed of a first polypeptide comprising an immunoglobulin CH and a second polypeptide comprising CL-Fc prepared by fusion of an immunoglobulin CL and Fc region, and also has a deletion or substitution of Cys residues involved in disulfide bonds between L chain-H chain molecules in the IgG antibody.

(2) A heterodimer protein that is composed of a first polypeptide comprising an immunoglobulin CH and a second polypeptide comprising CL-Fc prepared by fusion of an immunoglobulin CL and Fc region, in which the second polypeptide is a polypeptide having a reduced binding activity for a CH binder.

(3) The heterodimer protein described in (1) or (2), in which the second polypeptide is a polypeptide having a substitution of the amino acid residue at position 214 of the EU index of Kabat et al. (hereinafter, referred to as EU index) with Ser.

(4) The heterodimer protein described in any one of (1) to (3), in which the first polypeptide is a polypeptide including CH1 domain, hinge domain, CH2 domain and CH3 domain, and the second polypeptide is a polypeptide including CL domain, hinge domain, CH2 domain and CH3 domain.

(5) The heterodimer protein described in any one of (2) to (4), in which the CH binder is any one selected from anti-CH1 domain antibody, anti-hinge antibody, anti-CH2 domain antibody, anti-CH3 domain antibody, Fc receptor protein, Protein A and Protein G.

(6) The heterodimer protein described in any one of (1) to (5), in which the immunoglobulin subclass is any one selected from IgG1, IgG2 and IgG4.

(7) The heterodimer protein described in any one of (1) to (6), in which the second polypeptide is a polypeptide having a substitution of the amino acid residue at position 435 of the EU index with Arg.

(8) The heterodimer protein described in any one of (1) to (7), in which the immunoglobulin subclass is IgG4.

(9) The heterodimer protein described in (8), in which the first polypeptide is a polypeptide having a substitution of the amino acid residue at position 131 of the EU index with Ser.

(10) The heterodimer protein described in (9), in which the first polypeptide and the second polypeptide are polypeptides having a substitution of the amino acid residue at position 228 of the EU index with Pro.

(11) The heterodimer protein described in (10), in which the first polypeptide and the second polypeptide are polypeptides having a substitution of the amino acid residue at position 409 of the EU index with Lys.

(12) The heterodimer protein described in (11), in which the first polypeptide and the second polypeptide are polypeptides having a substitution of the amino acid residue at position 235 of the EU index with Glu.

(13) The heterodimer protein described in any one of (1) to (7), in which the immunoglobulin subclass is IgG1.

(14) The heterodimer protein described in (13), in which the first polypeptide is a polypeptide having a substitution of the amino acid residue at position 220 of the EU index with Ser.

(15) The heterodimer protein described in (14), in which the second polypeptide is a polypeptide including a hinge domain having a deletion of the amino acid residues at positions 216 to 220 of the EU index or a polypeptide having a substitution of the amino acid residue at position 220 of the EU index with Ser.

(16) The heterodimer protein described in (15), in which the sugar chain with no fucose bound to N-acetylglucosamine at the reducing end of the sugar chain among the total N-glycoside linked sugar chains binding to the Fc region included in the heterodimer protein is 20% or more.

(17) The heterodimer protein described in (15) or (16), in which the first polypeptide and/or the second polypeptide are(is) a polypeptide including at least one amino acid residue substitution selected from P247I, F243L, R292P, Y300L, Y300F, P396L, T393A, H433P, S239D, S298A, A330L, I332E, E333A, K334A, L235E, P238A, N297A, K322A, P331S, K326A, S267E, H268F, S324T, K274Q, N276K, Y296F, K326W, K326Y, E333A, E333S, A339T, A339D, D356E, L358M, N384S, K392N, T394F, T394Y, V397M and V422I.

(18) The heterodimer protein described in any one of (1) to (17), in which the first polypeptide and/or the second polypeptide are(is) a polypeptide having at least one binding protein bound to the N-terminus and/or the C-terminus of CH and CL-Fc.

(19) The heterodimer protein described in (18), in which the binding protein is any one selected from an antibody variable region, a single chain Fv(scFv), a single variable domain (VHH), a ligand protein, and a receptor protein.

(20) The heterodimer protein described in any one of (1) to (19), selected from (i) a heterodimer protein, in which the first polypeptide is a polypeptide having an immunoglobulin VH bound to the N-terminus of CH and the second polypeptide is a polypeptide having an immunoglobulin VL bound to the N-terminus of CL-Fc, and (ii) a heterodimer protein, in which the first polypeptide is a polypeptide having VL bound to the N-terminus of CH and the second polypeptide is a polypeptide having VH bound to the N-terminus of CL-Fc.

(21) The heterodimer protein described in any one of (1) to (20), selected from (i) a heterodimer protein, in which the first polypeptide is a polypeptide having VH bound to the C-terminus of CH and the second polypeptide is a polypeptide having VL bound to the C-terminus of C-Fc, and (ii) a heterodimer protein, in which the first polypeptide is a polypeptide having VL bound to the C-terminus of CH and the second polypeptide is a polypeptide having VH bound to the C-terminus of CL-Fc.

(22) The heterodimer protein described in any one of (1) to (21), which is any one selected from a monovalent antibody, a divalent antibody, a trivalent antibody, and a tetravalent antibody.

(23) DNA encoding the heterodimer protein described in any one of (1) to (22).

(24) A cell expressing the heterodimer protein, which includes a protein expression vector containing the DNA described in (23).

(25) A method for preparing a heterodimer protein, including the processes of culturing the cell expressing the heterodimer protein described in (24) and purifying the heterodimer protein from the culture supernatant.

The present invention relates to a heterodimer protein that is composed of a first polypeptide comprising an immunoglobulin heavy chain constant region (CH) and a second polypeptide comprising CL-Fc prepared by fusion of an immunoglobulin light chain constant region (CL) and Fc region, and also has a deletion or substitution of Cys residues involved in disulfide bonds between L chain-H chain molecules in the IgG antibody, a purification method of the protein, a preparation method of the protein, a DNA and a vector encoding the protein.

1. Structure of Heterodimer Protein

The heterodimer protein of the present invention may be a heterodimer protein that is composed of a first polypeptide comprising an immunoglobulin CH and a second polypeptide comprising CL-Fc prepared by fusion of an immunoglobulin CL and antibody Fc region, and also has a deletion or substitution of Cys residues involved in disulfide bonds between L chain-H chain molecules in the typical IgG antibody.

Hereinafter, unless otherwise particularly mentioned, the amino acid numbering is based on the EU index numbering as in Kabat et al. [Sequences of Proteins of Immunological Interest, US Dept. Health and Human Services (1991)] (hereinafter, referred to as only EU index). In addition, the amino acid residue before substitution was described before a number, and the amino acid residue after substitution was described after the number.

In the present invention, the Cys residues involved in disulfide bonds between CL and CH typically refer to Cys residues that are needed to form intermolecular disulfide bonds between H chain and L chain of an antibody.

Therefore, the heterodimer protein of the present invention has a deletion or substitution of Cys residues that are included in CH of the first polypeptide and/or CL-Fc of the second polypeptide and also involved in disulfide bonds between L chain-H chain molecules in IgG antibody. Formation of unnecessary multimers can be reduced by the deletion or substitution of the Cys residues.

Examples of the Cys residues in L chain that are involved in disulfide bonds between CL and CH1 can include the Cys residue at position 214 of the EU index of human κ and λ chains.

Further, examples of the Cys residues in H chain that are involved in disulfide bonds between CL and CH1 can include the Cys residue at position 220 of human IgG1 and the Cys residue at position 131 of IgG4 antibody.

Further, deletion or substitution of amino acid residues is also possible. Therefore, substitution or deletion of the Cys residues of CH1 domain or hinge domain is also possible, together with substitution or deletion of the Cys residues included in CL.

In the heterodimer protein of the present invention, therefore, CH of the first polypeptide and CL-Fc of the second polypeptide are connected by disulfide bonds only in the hinge domain.

Further, the heterodimer protein of the present invention is a protein that is composed of the first polypeptide comprising CH and the second polypeptide comprising CL-Fc prepared by fusion of CL and Fc, in which the second polypeptide is a polypeptide having a reduced binding activity for a CH binder.

In the present invention, the second polypeptide having a reduced or no binding activity for the CH binder and/or the Fc-binding protein refers to the second polypeptide having a reduced or no binding activity for the CH binder and/or the Fc binder by addition, deletion and/or substitution of amino acid sequence of CL-Fc of the second polypeptide.

The CH binder may be any one as long as it specifically binds to the antibody H chain constant region, such as proteins, chemicals, resins or the like, and examples thereof can include Fc-binding protein, antibody H chain constant region (CH)-binding antibody or the like.

Specific example of the Fc-binding protein can include *Staphylococcus Aureus*-derived Protein A, hemolytic *Streptococcus*-derived Protein G, Fc receptor, subclasses (FcγRI, IIA, IIB, IIIA, IIIB) thereof, binding fragments of the above proteins or the like.

The CH-binding antibody can be any antibody as long as it binds to at least one selected from CH1 domain, hinge domain, CH2 domain and CH3 domain, and it can be a monoclonal antibody or a polyclonal antibody.

CH1 domain is not included in the second polypeptide constituting the heterodimer of the present invention and CH1 domain is included in the first polypeptide. Therefore, the heterodimer protein of the present invention can be purified by using anti-CH1 antibody as the CH binder.

In the present invention, the second polypeptide having a reduced or no binding activity for the CH binder means that the binding activity is substantially reduced or depleted by a reduction in the affinity for the CH binder. The second polypeptide having a reduced or defective binding activity is a second polypeptide, of which binding activity for the CH binder is reduced or depleted by addition, deletion or substitution of amino acid residues in the second polypeptide having the binding activity for the CH binder, compared to the original second polypeptide having no addition, deletion or substitution of amino acid residues. The binding activity for the CH binder can be examined by using a measurement system such as binding ELISA, surface plasmon resonance method (SPR) or the like, described below.

Therefore, in the heterodimer protein of the present invention, the first polypeptide comprising CH specifically binds to the above described CH binder and the second polypeptide comprising g CL-Fc has a reduced or no binding activity for the CH binder, and thus only the heterodimer protein composed of the first polypeptide and the second polypeptide binds to the CH binder, and can be specifically separated and purified.

Herein, when the heterodimer protein of the present invention is expressed in cells, homodimers of the first polypeptide comprising CH are not secreted out of the cells. Monomers and homodimers of the second polypeptide comprising CL-Fc are secreted out of the cells, but since all of them have a reduced or no binding activity for the CH binder, by purification based on the specific binding activity for the CH binder, the heterodimer protein composed of the first polypeptide and the second polypeptide can be specifically separated and purified.

As the method for specifically expressing, separating, and purifying the heterodimer protein of the present invention without use of a CH binder, a fusion protein prepared by fusion of a proper tag with the N- or C-terminus of the first polypeptide of the present invention can be used.

Specific examples of the tag can include a histidine tag (hereinafter, abbreviated to His tag), a myc tag, a FLAG tag, a hemagglutinin (HA) tag, a glutathione-S transferase (GST) tag or the like. The above described method can be applied in combinations with separation and purification of the heterodimer protein of the present invention.

In the present invention, the second polypeptide having a reduced or no binding activity for the CH binder is prepared by performing addition, deletion and substitution of amino acid sequences of CL-Fc included in the second polypeptide.

Example of the CL-Fc having a reduced or no binding activity for Protein A can include CL-Fc having a deletion or substitution of at least one amino acid residue selected from positions 253, 310, 433, 435, and 436 of the EU index, preferably, CL-Fc having a substitution of the amino acid residue at position 435 of the EU index, and CL-Fc having a substitution of the amino acid residues at positions 435 and 436 of the EU index, and more preferably, CL-Fc having a substitution of His at position 435 with Arg and a substitution of Tyr at position 436 with Phe, and CL-Fc having a substitution of His at position 435 with Arg.

With respect to other CH-binding proteins, the binding activity for the CH-binding protein can be reduced by performing addition, deletion and substitution of amino acid sequence of CL-Fc of the heterodimer protein of the invention bound to the binding protein. For example, the second polypeptide having a reduced binding activity for each CH-binding protein or antibody can be prepared by performing substitution and/or deletion of at least one amino acid residue included in the epitope that is present on CL-Fc of the heterodimer protein of the present invention, such as the binding site in the Fc bound by Protein G, an epitope bound by anti-Fc antibody, and an epitope bound by anti-hinge domain antibody.

The antibody can be a polyclonal antibody or a monoclonal antibody. If the epitope is clearly specified by each antibody, amino acid residues included in the epitope of any antibody can be substituted.

Further, the heterodimer protein of the present invention is a protein that is composed of a first polypeptide comprising CH and a second polypeptide comprising CL-Fc prepared by fusion of CL and Fc, in which the second polypeptide is a polypeptide having a reduced binding activity for the CH binder, and also has a deletion or substitution of Cys residues involved in disulfide bonds between L chain-H chain molecules in the IgG antibody.

The heterodimer protein of the present invention is a protein composed of a first polypeptide comprising CH and a second polypeptide comprising CL-Fc prepared by fusion of CL and Fc, in which the second polypeptide is a polypeptide having a reduced binding activity for the CH binder and CH and CL-Fc are connected by disulfide bonds only in the hinge domain.

Specifically, the heterodimer protein of the present invention is a protein that is composed of a first polypeptide comprising CH and a second polypeptide comprising CL-Fc, in which the second polypeptide is any one polypeptide selected from the group consisting of (i) a polypeptide having a substitution of the amino acid residue at position 214 with other amino acid residue, (ii) a polypeptide having a substitution of the amino acid residue at position 220 with other amino acid residue, (iii) a polypeptide having a substitution of the amino acid residue at position 214 with Ser, (iv) a polypeptide having a substitution of the amino acid residue at position 220 with Ser, (v) a polypeptide having a substitution of the amino acid residue at position 435 with Arg, (vi) a polypeptide having substitutions of the amino acid residues at positions 214 and 435 with Ser and Arg, (vii) a polypeptide having substitutions of the amino acid residues at positions 220 and 435 with Ser and Arg, and (viii) a polypeptide having substitutions of the amino acid residues at positions 214, 435 and 436 with Ser, Arg and Phe, numbered of the EU index.

Further, the heterodimer protein of the present invention is a protein that is composed of the first polypeptide and the second polypeptide having a binding domain bound to at least one selected from the N-terminus and the C-terminus of CH and CL-Fc, in which the second polypeptide is a polypeptide having a reduced or no binding activity for the CH binder.

In the present invention, the binding domain can be any protein as long as it is a protein having a binding activity for other molecule, and specifically, it can include an antibody fragment, an antibody variable region (hereinafter, abbreviated to V), single chain Fv (scFv), Fab, Fab', F(ab')$_2$, diabody, disulfide-stabilized Fv (dsFv) and a peptide comprising CDR, a single variable domain (VHH), a ligand protein, a receptor protein or the like.

CH included in the first polypeptide of the heterodimer protein of the present invention is composed of CH1 domain, hinge domain, CH2 domain and CH3 domain which constitute an antibody constant region. Any isotype is available, but IgG isotype is preferred.

The IgG subclass may be any subclass of IgG1, IgG2 and IgG4. Further, the first polypeptide can include a hinge domain of each immunoglobulin isotype/subclass, or a hinge domain having addition, deletion or substitution of a part of its amino acid sequence. A hinge domain of isotype/subclass identical to Fc and a hinge domain having substitution of the amino acid residue can be preferred. Further, the hinge domain can be extended or shortened to be suitable for the production of the heterodimer protein of the present invention.

In the present invention, the CH comprised in the first polypeptide can be a CH having any amino acid sequence as long as it is suitable for the efficient and stable production of the heterodimer protein, and preferably, a CH including addition, deletion and substitution of amino acid sequence.

Specifically, it can include CH including at least one amino acid residue substitution selected from substitutions of the amino acid residue at position 131 with S, the amino acid residue at position 133 with K, the amino acid residue at position 220 with S, the amino acid residue at position 228 with P, and the amino acid residue at position 409 with K, numbered of the EU index.

The number of the amino acid residue to be substituted is 1 to 15, preferably 1 to 10, more preferably 1 to several, and most preferably 1 to 5 amino acid residues. In the case of IgG1 subclass, CH including a substitution of C220S of the hinge domain can be exemplified.

The amino acid residue at position 220 of the EU index is known to be involved in the disulfide bond with L chain in IgG1, and the substitution or deletion of this amino acid residue can cause a defect in the disulfide bond of CL-hinge domain.

In the case of IgG4 subclass, CH including at least one amino acid residue substitution selected from C131S and R133K of CH1 domain, S228P of hinge domain, and R409K, R409T, R409M and R409L of CH3 domain, preferably CH including amino acid residue substitutions of C131S and R409K, more preferably, CH including amino acid residue substitutions of C131S, R133K and R409K, and CH including amino acid residue substitutions of C131S, R133K, S228P and R409K can be exemplified.

The amino acid residue at position 409 of the EU index is known to be involved in the stable interaction between CH3-CH3 domains of antibody Fc region, and thus the effect of improving stability of Fc-Fc interaction and the effects of inhibiting Fab-arm exchange and aggregation under low pH can be obtained by amino acid modifications of R409K, R409T, R409M and R409L.

Further, for the purpose of increasing the formation ability of CH3/CH3 heterodimers included in the heterodimer protein, amino acid residue modifications of K409D/K392D and D399K/E356K (WO 2009/089004) or SEED technology using immunoglobulin subclasses (WO 2007/110205) can be also combined in the heterodimer of the present invention.

The Ser residue at position 228 of the EU index is known to be involved in instability of disulfide bonds between hinge domains, and the amino acid modification of S228P is involved in stabilization of hinge domain.

CL included in the second polypeptide of the heterodimer protein of the present invention can be any one of κ chain and λ chain. Further, Fc included in the second polypeptide is composed of hinge domain, CH2 domain and CH3 domain. Any isotype is available, but IgG isotype is preferred. IgG subclass can be any subclass of IgG1, IgG2 and IgG4.

Further, the second polypeptide can include a hinge domain of each immunoglobulin isotype/subclass, or a hinge domain having addition, deletion or substitution of a part of its amino acid sequence. A hinge domain of isotype/subclass identical to Fc and a hinge domain having the amino acid residue substitution can be preferred. Further, the hinge domain can be extended or shortened to be suitable for the production of the heterodimer protein of the present invention.

In the present invention, the CL-Fc included in the second polypeptide can be CL-Fc having any amino acid sequence as long as it is suitable for the efficient and stable production of the heterodimer protein, and preferably, CL-Fc including addition, deletion and substitution in the amino acid sequence.

Specifically, it can include CL-Fc including at least one amino acid residue substitution selected from substitutions of the amino acid residue at position 214 with S, the amino acid residue at position 220 with S, the amino acid residue at position 228 with P, the amino acid residue at position 409 with K, the amino acid residue at position 435 with R, and the amino acid residue at position 436 with F, numbered of the EU index.

The number of the amino acid residue to be substituted is 1 to 15, preferably 1 to 10, more preferably 1 to several, and most preferably 1 to 5 amino acid residues.

In the case of IgG1 subclass, CL-Fc including at least one amino acid residue substitution selected from C214S, C220S, H435R and Y436F, CL-Fc including an amino acid residue substitution of C220S at position 220 of the EU index, CL-Fc including a deletion of EPKSC at positions 216-220 of the EU index, preferably, CL-Fc including amino acid residue substitutions of C214S and H435R and CL-Fc including amino acid residue substitutions of C214S, C220S and H435R, and more preferably, CL-Fc including amino acid residue substitutions of C214S, H435R and Y436F and CL-Fc including amino acid residue substitutions of C214S, C220S, H435R and Y436F can be exemplified.

In the case of IgG4 subclass, CL-Fc including at least one amino acid residue substitution selected from C214S, S228P, L235E, R409K, H435R and Y436F, preferably, CL-Fc including amino acid residue substitutions of C214S and H435R and CL-Fc including amino acid residue substitutions of C214S, R409K and H435R, more preferably, CL-Fc including amino acid residue substitutions of C214S, R409K, H435R and Y436F, and most preferably, CL-Fc including amino acid residue substitutions of C214S, S228P, L235E, R409K, H435R and Y436F can be exemplified.

In the present invention, the monoclonal antibody is an antibody secreted by antibody-producing cells of a single clone. The monoclonal antibody recognizes only a single epitope (also called antigenic determinant), and the amino acid sequence (primary structure) constituting the monoclonal antibody is same.

Examples of the epitope can include a single amino acid sequence recognized and bound by a monoclonal antibody, a conformation of the amino acid sequence, an amino acid sequence bound with a modification residue such as a sugar chain, an amino group, a carboxyl group, phosphate, sulfate or the like, and a conformation of the amino acid sequence bound with the modification residue. The conformation is a naturally occurring three-dimensional structure of a protein, and it refers to a conformation of proteins that are expressed within cells or on cell membrane.

In the present invention, the antibody molecule is also called immunoglobulin (hereinafter, referred to as Ig) and human antibody is classified into the isotypes of IgA1, IgA2, IgD, IgE, IgG1, IgG2, IgG3, IgG4 and IgM, based on the difference in its molecular structure. IgG1, IgG2, IgG3 and IgG4 having relatively high homology in amino acid sequences are generically called IgG.

The antibody molecule is composed of polypeptides, called a heavy chain (hereinafter, referred to as H chain) and a light chain (hereinafter, referred to as L chain).

Further, the H chain is constituted by regions of an H chain variable region (also referred to as VH) and an H chain constant region (also referred to as CH) from its N-terminus, and the L chain is constituted by regions of an L chain variable region (also referred to as VL) and an L chain constant region (also referred to as CL) from its N-terminus. Regarding CH, α, δ, ε, γ and μ chains are known for each subclasses. Regarding CL, λ and κ are known.

A domain refers to a functional structural unit constituting each polypeptide of antibody molecules. Further, Fc and Fc region of the present invention refers to a partial sequence and a partial structure of H chain constant region composed of hinge domain, CH2 domain and CH3 domain.

Further, CH is composed of CH1 domain, hinge domain, CH2 domain and CH3 domain from the N-terminus. The CH1 domain, hinge domain, CH2 domain, CH3 domain, and Fc region in the present invention can be identified by the number of amino acid residues from the N-terminus according to the EU index [Kabat et al., Sequences of Proteins of Immunological Interest, US Dept. Health and Human Services (1991)].

Specifically, CH1 is identified by the amino acid sequence from positions 118 to 215 of the EU index, the hinge is identified by the amino acid sequence from positions 216 to 230 of the EU index, CH2 is identified by the amino acid sequence from positions 231 to 340 of the EU index, and CH3 is identified by the amino acid sequence from positions 341 to 447 of the EU index, respectively.

CL-Fc is composed of CL domain, hinge domain, CH2 domain and CH3 domain from the N-terminus. CL-Fc in the present invention can be identified by the number of amino acid residues from the N-terminus according to the EU index [Kabat et al., Sequences of Proteins of Immunological Interest, US Dept. Health and Human Services (1991)].

Specifically, CL of CL-Fc is identified by the amino acid sequence from positions 108 to 214 of L chain defined by Kabat et al., Fc of CL-Fc is identified as the hinge of the amino acid sequence from positions 216 to 230 of the EU index, CH2 of the amino acid sequence from positions 231 to 340 of the EU index, and CH3 of the amino acid sequence from positions 341 to 447 of the EU index, respectively.

In the present invention, the antibody includes recombinant antibodies produced by a recombination technology as well as monoclonal antibodies obtained from hybridomas. The recombinant antibodies include a chimeric antibody that is prepared by binding a human antibody constant region to a non-human antibody variable region, a humanized antibody (or CDR-grafted antibody) that is prepared by grafting the complementarity determining region (hereinafter, abbreviated to CDR) of H chain and L chain of a non-human antibody variable region into a framework region (hereinafter, abbreviated to FR) of a human antibody variable region, and a human antibody that is prepared by using a human antibody-producing animal, or the like.

The chimeric antibody can be produced by obtaining cDNAs encoding VH and VL from a monoclonal antibody-producing hybridoma derived from a non-human animal, inserting them into an expression vector for animal cell having DNA encoding CH and CL of human antibody so as to construct a human chimeric antibody expression vector, and then introducing the vector into an animal cell so as to express the antibody.

The humanized antibody refers to an antibody in which the amino acid sequence of CDRs of VH and VL of a non-human animal antibody are grafted into the corresponding CDRs of VH and VL of a human antibody. The region other than CDRs of VH and VL is referred to as a framework region (hereinafter, referred to as FR).

The humanized antibody can be produced in the following manner: cDNA encoding an amino acid sequence of VH which consists of an amino acid sequence of CDR of VH of a non-human antibody and an amino acid sequence of FR of VH of any human antibody, and cDNA encoding an amino acid sequence of VL which consists of an amino acid sequence of CDR of VL of a non-human animal antibody and an amino acid sequence of FR of VL of any human antibody are constructed, these cDNAs are inserted respectively into expression vectors for animal cells having DNA encoding CH and CL of a human antibody so as to construct a humanized antibody expression vector, and this vector is introduced into animal cells so as to express the antibody.

The human antibody originally refers to an antibody naturally existing in the human body. However, the human antibody also includes antibodies that are obtained from a human antibody phage library, cloning of immortalized human peripheral blood lymphocytes, or human antibody-producing transgenic animals prepared according to the technical advancement in genetic engineering, cell engineering, and development engineering in recent years.

The human antibody can be obtained by immunizing a mouse having human immunoglobulin genes (Tomizuka K. et al., Proc Natl Acad Sci USA. 97, 722-7, 2000) with a desired antigen. In addition, by selecting a human antibody having a desired binding activity using a phage display library which is formed by antibody gene amplification from human B cells, it is possible to obtain human antibodies without performing immunization (Winter G. et al., Annu Rev Immunol. 12: 433-55. 1994).

Moreover, by immortalizing human B cells using an EB virus to prepare human antibody-producing cells having a desired binding activity, it is possible to obtain human antibodies (Rosen A. et al., Nature 267, 52-54. 1977).

The antibody existing in the human body can be purified in the following manner, for example; lymphocytes isolated from the human peripheral blood are immortalized by infection with the EB virus or the like, followed by cloning, whereby lymphocytes producing the antibody can be cultured and the antibody can be purified from the culture.

The human antibody phage library is a library of phages which are caused to express antibody fragments such as Fab and scFv on the surface thereof by insertion of antibody genes prepared from the human B cells into the gene of the phage. From this library, it is possible to recover phages which express antibody fragments having a desired antigen binding activity, by using binding activity with respect to an antigen-immobilized substrate as an index. The antibody fragments can be also converted into a human antibody molecule consisting of two complete H chains and two complete L chains by genetic engineering technique.

The human antibody-producing transgenic animal refers to an animal obtained by integration of the human antibody gene into chromosomes of a host animal. Specifically, the human antibody gene is introduced to mouse ES cells, the ES cells are grafted to the early embryo of another mouse, and then the embryo is developed, whereby the human antibody-producing transgenic animal can be prepared.

As a method of preparing human antibodies from the human antibody-producing transgenic animal, a human antibody-producing hybridoma is obtained by a normal hybridoma preparation method which is implemented using a mammal other than a human being, followed by culture, whereby human antibodies can be produced and accumulated in the culture.

The amino acid sequences of VH and VL bound to the heterodimer protein of the present invention can be any one of amino acid sequences of VH and VL of a human antibody, amino acid sequences of VH and VL of a non-human animal antibody, amino acid sequence of a humanized antibody that is prepared by grafting CDR of a non-human animal antibody into the framework of a human antibody, and amino acid sequences of VH and VL derived from a human antibody.

Specifically, it can include amino acid sequences of VH and VL of a non-human animal antibody, a humanized antibody, and a human antibody that are produced by hybridomas or antibody-producing cells.

The amino acid sequence of CL in the heterodimer protein of the present invention can be any one of the amino acid sequence of human antibody or the amino acid sequence of non-human animal antibody. The amino acid sequence of Cκ or Cλ of human antibody is preferred.

CH in the heterodimer protein of the present invention can be any one belonging to immunoglobulin. Preferably, any of γ1(IgG1), γ2(IgG2), and γ4(IgG4) belongs to human IgG class can be used.

In the present invention, the antibody fragment can include Fab, Fab', F(ab')$_2$, scFv, diabody, dsFv, a peptide comprising plural CDRs, and preferably, a peptide comprising 6 CDRs of an antibody, or the like.

Fab refers to an antibody fragment having about a half H-chain of the N-terminus and a full L-chain which are bound to each other via a disulfide bond (S—S bond), a molecular weight of about 50000 and an antigen binding activity, among fragments (cleaved at position 224 of the amino acid residue of the H-chain) which are obtained by treating the IgG antibody with a protease papain.

F(ab')$_2$ refers to an antibody fragment which is slightly longer than Fab bound to each other via a S—S bond of the hinge region and has a molecular weight of about 100,000 and an antigen binding activity, among fragments (cleaved at position 234 of the amino acid residue of the H-chain) which are obtained by treating IgG with a protease pepsin.

Fab' is an antibody fragment which is obtained by cleaving the S—S bond of the hinge region of the F(ab')$_2$ and has a molecular weight of about 50,000 and an antigen binding activity.

scFv is an antibody fragment having an antigen binding activity, which is a VH-P-VL or VL-P-VH polypeptide obtained by linking one VH to one VL by using an appropriate peptide linker (P), such as a linker peptide prepared by linking an arbitrary number of linker (G4S) consisting of 4 Gly residues and 1 Ser residue.

Diabody is an antibody fragment as a dimer formed of scFVs showing the same or different antigen binding specificity, and this antibody fragment has a divalent antigen binding activity with respect to the same antigen or has 2 types of specific antigen binding activity with respect to different types of antigens.

dsFv is one in which 1 amino acid residue in each of VH and VL is substituted with a cystine residue, and the polypeptides are linked through a S—S bond between these cysteine residues.

The peptide comprising CDR is constituted with at least one or more regions of CDR of VH or VL. In the peptide comprising plural CDRs, the CDRs can be bound to each other directly or via an appropriate peptide linker.

It can be prepared by constructing DNAs encoding CDRs of VH and VL of the heterodimer protein of the present invention, inserting these DNAs into an expression vector for prokaryote or eukaryote, and introducing this expression vector into prokaryote or eukaryote for expression. The peptide comprising CDR can be also prepared by chemical synthesis method such as an Fmoc method or a tBoc method.

The heterodimer protein of the present invention can be any one of a heterodimer protein, in which two antibody variable regions formed by the first polypeptide and the second polypeptide bind to two different epitopes, and a heterodimer protein, in which two antibody variable regions bind to the same epitope, respectively.

Further, a heterodimer protein comprising a binding protein that is further bound at least one of the C-terminus of the above described CH and CL-Fc and binding to two or more epitopes is also included in the present invention.

2. Control of Heterodimer Protein Activity
(1) Control of Effector Activity

Since the heterodimer of the present invention has Fc region composed of hinge domain, CH2 domain and CH3 domain, an effector activity depending on the Fc region of the heterodimer protein can be also provided. The effector activity of the heterodimer of the present invention can be controlled by various methods.

The effector activity refers to an antibody-dependent activity that is mediated by the Fc region of an antibody. As the effector activity, antibody-dependent cellular cytotoxicity activity (ADCC activity), complement-dependent cytotoxicity activity (CDC activity), and antibody-dependent phagocytosis (ADP activity) caused by phagocytes such as macrophages, dendritic cells or the like are known. In the present invention, the ADCC and CDC activities can be measured using known measurement methods [Cancer Immunol. Immunother., 36, 373 (1933)].

The ADCC activity refers to an activity in which an antibody bound to an antigen on a target cell binds to an Fc receptor of an immunocyte via the Fc region of the antibody, thereby activating the immunocyte (a natural killer cell or the like) and damaging the target cell.

The Fc receptor (hereinafter, referred to as FcR in some cases) refers to a receptor binding to the Fc region of an antibody, and induces various types of effector activity due to the binding of an antibody.

FcR corresponds to antibody subclasses, and IgG, IgE, IgA, and IgM specifically bind to FcγR, FcεR, FcαR, and FcμR respectively. FcγR has subtypes including FcγRI (CD64), FcγRII(CD32) and FcγRIII(CD16), and the subtypes respectively have isoforms including FcγRIA, FcγRIB, FcγRIC, FcγRIIA, FcγRIIB, FcγRIIC, FcγRIIIA, FcγRIIIB These different types of FcγR exist on different cells [Annu Rev. Immunol. 9:457-492 (1991)].

In human beings, FcγRIIIB is specifically expressed in neutrophils, and FcγRIIIA is expressed in monocytes, Natural Killer cells (NK cells), and a portion of T cells. The antibody binding caused via FcγRIIIA induces NK cell-dependent ADCC activity.

The CDC activity refers to an activity in which an antibody bound to an antigen on a target cell activates a series of cascades (complement activation pathways) consisting of a group of complement-related proteins in the blood, thereby damaging the target cell. By the protein fragments generated due to the complement activation, it is possible to induce migration and activation of immunocytes.

When C1q having a binding domain for the Fc region of an antibody binds to the Fc region, and C1r and C1s as two serine proteases bind thereto, a C1 complex is formed, whereby the cascade of CDC activity begins.

The method for controlling the effector activity of the heterodimer protein of the present invention can be exemplified as follows.

Examples of methods of controlling the effector activity of the heterodimer protein can include a method of controlling the amount of fucose (also referred to as core fucose) which forms α1,6-bound to N-acetylglucosamine (GlcNAc) present in a reducing end of a complex type N-linked sugar chain (hereinafter, simply abbreviated to complex sugar chain in some cases) bound to Asn at position 297 of the EU index using the amino acid sequence of Fc of IgG1 subclass as Fc of the heterodimer protein of the present invention (WO 2005/035586, WO 2002/31140, WO 00/61739), or a method of controlling the activity by substituting amino acid residues of Fc region of the antibody.

1) Control of Effector Activity by Modification of Sugar Chains

The effector activity of the heterodimer protein can be increased or decreased by controlling the content of fucose that is added to N-acetylglucosamine in the reducing end of the complex sugar chain bound to the Fc region of the heterodimer protein.

The method for decreasing the content of fucose binding to the complex-type N-linked sugar chain bound to the Fc region of the heterodimer protein can be the method to obtain the heterodimer protein with no fucose binding thereto by expressing an antibody using CHO cell from which α1,6-fucosyltransferase gene (FUT8) is deleted. The heterodimer protein with no fucose binding thereto has high ADCC activity.

On the other hand, the method for increasing the content of fucose binding to the complex-type N-linked sugar chain bound to the Fc region of the heterodimer protein can be the method to obtain the heterodimer protein with fucose binding thereto by expressing the heterodimer protein using a host cell in which α1,6-fucosyltransferase gene is introduced. The heterodimer protein with fucose binding thereto has lower ADCC activity than the heterodimer protein with no fucose binding thereto.

In the Fc region of the heterodimer protein of the present invention, the N-linked sugar chain is bound to the Asn residue at position 297 of the EU index, but there is no report that sugar chain is bound to the Asn residue of other Fc region. Therefore, two N-glycoside linked sugar chains are typically bound to one molecule of the heterodimer protein.

The known N-linked sugar chains are high mannose type, complex type and hybrid type sugar chains. As long as the N-linked sugar chain has no fucose binding thereto, it has higher ADCC activity than the sugar chain with fucose binding thereto.

The complex-type sugar chain bound to the Fc region of the heterodimer protein of the present invention can include a sugar chain in which one or more of N-acetylglucosamine (GlcNAc) or galactose-N-acetylglucosamine (hereinafter, referred to as Gal-GlcNAc) are α1-2- or α1-4-linked to mannose (Man) at the non-reducing end of the core structure (tri-mannosyl core structure).

It can also include a complex-type sugar chain having sialic acid, bisecting N-acetylglucosamine (hereinafter, referred to as bisecting GlcNAc), or the like at the non-reducing end of Gal-GlcNAc.

In the present invention, the core-fucose or α1,6-fucose refers to a sugar chain structure in which the 1-position of fucose (hereinafter, referred to as Fuc in some cases) is bound to the 6-position of N-acetylglucosamine (hereinafter, referred to as GlcNAc in some cases) in the reducing end through α-bond of a complex type N-glycoside-linked sugar chain. Further, those having no core fucose bound to N-acetylglucosamine in the reducing end of the complex type N-glycoside-linked sugar chain are simply referred to as sugar chains with no fucose or no core fucose.

In the present invention, the core structure or the tri-mannosyl core structure refers to a Manα1-6(Manα1-3)Manβ1-4GlcNAcβ1-4GlcNAc structure.

As the sugar chain bound to the heterodimer protein of the present invention, a biantennary N-glycoside linked complex sugar chain (also called biantennary complex sugar chain) is represented by the following Chemical Formula.

composed of heterodimer protein molecules having a single or plural different sugar chains.

In other words, the heterodimer protein composition of the present invention means a composition that is composed of heterodimer protein molecules having a single or plural different sugar chains, and specifically, a heterodimer protein, in which the sugar chain with no fucose bound to N-acetylglucosamine at the reducing end of the sugar chain among the total N-glycoside linked sugar chains bound to the Fc region included in the heterodimer protein is 20% or more.

The ratio of the sugar chain with no core fucose can be any ratio in the heterodimer protein composition, as long as ADCC activity of the heterodimer protein is increased. The ratio can be preferably 20% or more, more preferably 51%-100%, much more preferably 80%-100%, particularly preferably 90%, 91%, 92%, 93%, 94%, 95%, 96%, 97%, 98%, 99%, and most preferably 100%.

The heterodimer protein composition having 50% of the ratio of the sugar chain with no core fucose can be any of a heterodimer protein composition comprising 100% of molecules with no fucose at one sugar chain of the N-glycoside linked sugar chains bound to the first and second polypeptides of the heterodimer protein molecule, and a heterodimer protein composition comprising 50% of molecules with no fucose at both sugar chains of the N-glycoside linked sugar chains bound to the first and second polypeptides of the heterodimer protein molecule and 50% of molecules with fucose at both sugar chains of the N-glycoside linked sugar chains bound to the first and second polypeptides of the heterodimer protein molecule.

In the present invention, the sugar chain with no fucose can have any structure of the sugar chain at the non-reducing end, as long as fucose does not bind to N-acetylglucosamine at the reducing end in the above Chemical Formula.

In the present invention, no fucose (no core fucose) bound to N-acetylglucosamine at the reducing end of the sugar chain means that fucose is not substantially bound. The heterodimer protein composition in which "fucose is not substantially bound" means a heterodimer protein composition in which fucose cannot be substantially detected in the sugar chain analysis described below. The "fucose cannot be substantially detected" means that it is below the detection limit. The heterodimer protein composition with no core fucose in all of the sugar chains has the highest ADCC activity.

[Chemical Formula 1]

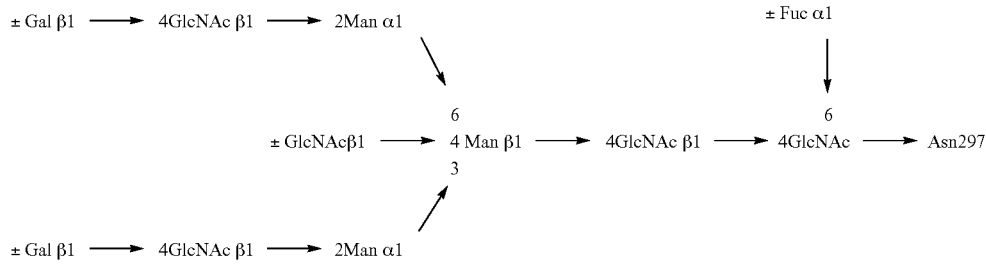

The heterodimer protein composition of the present invention is a heterodimer protein molecule having the Fc region in which the complex-type sugar chain is bound to Asn at position 297 of the heterodimer protein molecule, and as long as it has the above sugar structure, it can be The ratio of heterodimer protein molecules having sugar chains with no fucose contained in the composition which is composed of a heterodimer protein molecule having the Fc region bound with complex-type N-glycoside-linked sugar chains can be determined by releasing the sugar chains from the heterodimer protein molecule using a known method such as hydrazinolysis or enzyme digestion [Biochemical Experimentation Methods 23—Method for Studying Glycoprotein Sugar Chain (Japan Scientific Societies Press), edited by Reiko Takahashi (1989)], carrying out fluorescence labeling or radioisotope labeling of the released sugar chains and then separating the labeled sugar chains by chromatography.

Also, the ratio of heterodimer protein molecules bound with sugar chains with no fucose contained in the composition which is composed of a heterodimer protein molecule having the Fc region bound with complex-type sugar chains can be determined by analyzing the released sugar chains with the HPAED-PAD method [J. Liq. Chromatogr., 6, 1577 (1983)].

2) Control of Effector Activity by Substitution of Amino Acid Residues

The ADCC, ADCP, and CDC activities of the heterodimer protein of the present invention can be increased or decreased by changing antibody subclass of Fc constituting the heterodimer protein or by substituting the amino acid residues of Fc.

For example, CDC activity of the antibody can be increased by using the amino acid sequence of the Fc region, which is described in US Patent Application Publication No. 2007/0148165. Also, ADCC activity or CDC activity of the heterodimer protein can be increased or decreased by carrying out substitution of the amino acid residues, which is described in U.S. Pat. Nos. 6,737,056, 7,297,775, and 7,317,091.

Specific amino acid residue substitution for increasing ADCC activity may include P247I, A339D, F243L, R292P, Y300L, P396L, T393A, H433P, S239D, S298A, A330L, I332E, E333A, K334A or the like. Meanwhile, specific amino acid residue substitution for reducing ADCC activity can include L235E, P238A, N297A, K322A, P331S or the like.

Specific amino acid residue substitution for increasing CDC activity can include at least one amino acid residue substitution selected from K326A, S267E, H268F, S324T, K274Q, N276K, Y296F, Y300F, K326W, K326Y, E333A, E333S, A339T, D356E, L358M, N384S, K392N, T394F, T394Y, V397M and V422I.

CDC activity can be increased in combinations of two or more of amino acid residue substitutions, and amino acid residues to be substituted can be increased depending on the purpose. Preferably, the amino acid residue substitution for increasing CDC activity can include at least one amino acid residue substitution selected from N276K, A339T, T394F and T394Y, amino acid residue substitutions of N276K and A339T, and amino acid residue substitutions of K274Q, N276K, Y296F, Y300F, A339T, D356E, L358M, N384S, V397M and V422I, or the like. Meanwhile, specific amino acid residue substitution for reducing CDC activity can include L235E, N297A, K322A, P329A and P331S or the like.

The blood half-life can be also prolonged by introduction of amino acid mutations of T250Q, M428L, M252Y, S254T, T256E, or the like. into Fc of human IgG1 subclass. Cell cytotoxicity such as ADCC activity, ADCP activity, CDC activity can be also reduced by using Fc in which N-linked sugar chain is removed by introduction of amino acid mutation at position N297, Fc of human IgG2 or IgG4 subclass, chimeric Fc of IgG2 and IgG4, or the like.

Further, binding activity for the inhibitory Fc receptor FcγRIIb can be increased by introduction of amino acid mutation of G236D, L328F, S239D, S267E, or the like into human IgG1.

The heterodimer protein of the present invention includes any of the heterodimer proteins having increased or reduced effector activity described above.

Specifically, the IgG1-type heterodimer protein of the present invention can be a heterodimer protein composed of the first polypeptide comprising CH of IgG1 antibody and the second polypeptide comprising Fc and CL of IgG1, and also any one of IgG1-type heterodimer proteins of the following (1) to (9).

(1) a heterodimer protein, in which the first polypeptide includes a substitution of C220S of the EU index and the second polypeptide includes a substitution of H435R (2) a heterodimer protein, in which the first polypeptide includes no amino acid substitution and the second polypeptide includes substitutions of C214S and H435R of the EU index (3) a heterodimer protein, in which the first polypeptide includes a substitution of C220S of the EU index and the second polypeptide includes substitutions of C214S and H435R (4) a heterodimer protein, in which the first polypeptide includes a substitution of C220S of the EU index and the second polypeptide includes substitutions of C220S, C214S and H435R (5) a heterodimer protein, in which the first polypeptide includes a substitution of C220S of the EU index and the second polypeptide includes substitutions of C214S and H435R and a deletion of EPKSC of 216-220 of the EU index (6) a heterodimer protein, in which the first polypeptide includes a substitution of C220S of the EU index and the second polypeptide includes substitutions of C214S, H435R and Y436F (7) a heterodimer protein, in which the first polypeptide includes a substitution of C220S of the EU index and the second polypeptide includes substitutions of C214S, H435R, Y436F and a deletion of EPKSC of 216-220 of the EU index (8) a heterodimer protein, in which the first polypeptide includes substitutions of C220S, K322A and P331S of the EU index and the second polypeptide includes substitutions of C214S, K322A, P331S, H435R, Y436F and a deletion of EPKSC of 216-220 of the EU index (9) a heterodimer protein, in which the first polypeptide includes substitutions of C220S and I332E of the EU index and the second polypeptide includes substitutions of C214S, I332E, H435R and Y436F and a deletion of EPKSC of 216-220 of the EU index Specifically, the IgG4-type heterodimer protein of the present invention can be a heterodimer protein composed of the first polypeptide comprising CH of IgG4 antibody and the second polypeptide comprising Fc and CL of IgG4 and also any one of IgG4-type heterodimer proteins of the following (1) to (10).

(1) a heterodimer protein, in which the first polypeptide includes a substitution of C131S of the EU index and the second polypeptide includes substitutions of C214S and H435R (2) a heterodimer protein, in which the first polypeptide includes a substitution of C131S of the EU index and the second polypeptide includes substitutions of C214S, H435R and Y436F (3) a heterodimer protein, in which the first polypeptide includes substitutions of C131S and R409K of the EU index and the second polypeptide includes substitutions of C214S, R409K, H435R and Y436F (4) a heterodimer protein, in which the first polypeptide includes substitutions of C131S, S228P and R409K of the EU index and the second polypeptide includes substitutions of C214S, S228P, R409K, H435R and Y436F (5) a heterodimer protein, in which the first polypeptide includes substitutions of C131S, S228P, L235E and R409K of the EU index and the second polypeptide includes substitutions of C214S, S228P, L235E, R409K, H435R and Y436F (6) a heterodimer protein, in which the first polypeptide includes substitutions of C131S and R133K of the EU index and the second polypeptide includes substitutions of C214S and H435R (7) a heterodimer protein, in which the first polypeptide includes substitutions of C131S and R133K of the EU index and the second polypeptide includes substitutions of C214S, H435R and Y436F (8) a heterodimer protein, in which the first polypeptide includes substitutions of C131S, R133K and R409K of the EU index and the second polypeptide includes substitutions of C214S, R409K, H435R and Y436F (9) a heterodimer protein, in which the first polypeptide includes substitutions of C131S, R133K, S228P and R409K of the EU index and the second polypeptide includes substitutions of C214S, S228P, R409K, H435R and Y436F

(10) a heterodimer protein, in which the first polypeptide includes substitutions of C131S, R133K, S228P, L235E and R409K of the EU index and the second polypeptide includes substitutions of C214S, S228P, L235E, R409K, H435R and Y436F (2) Control of Binding Activity of Heterodimer Protein The heterodimer protein of the present invention can be prepared into a heterodimer protein having a monovalent to tetravalent binding activity by connecting a molecule-specific binding protein to the N-terminus and C-terminus of each polypeptide of CH and CL-Fc (hereinafter, heterodimer scaffold protein; referred to as HSP in some cases) constituting the heterodimer molecule.

Figure 1:
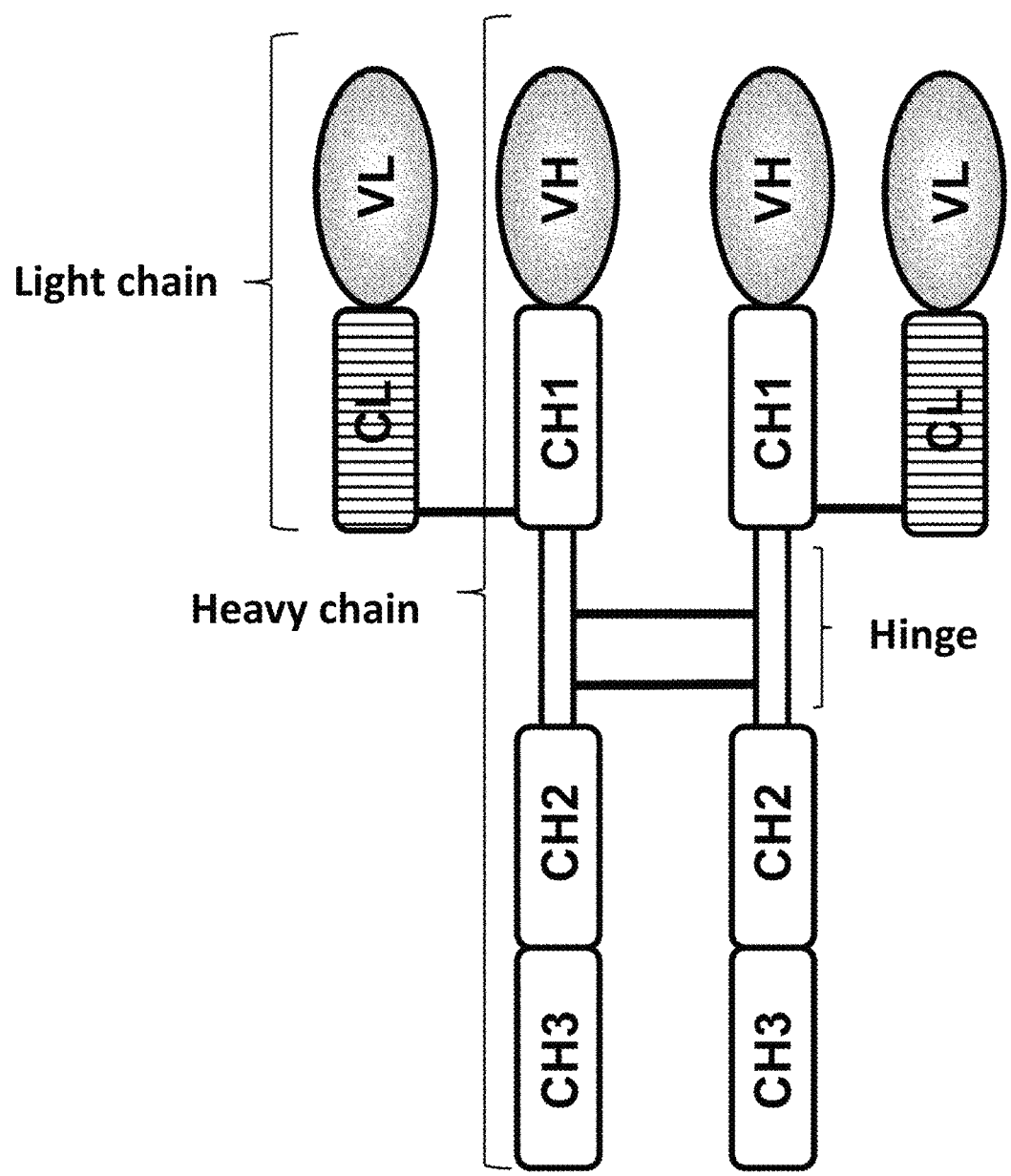
FIG. 1 is a diagram of IgG antibody.
Figure 2A:
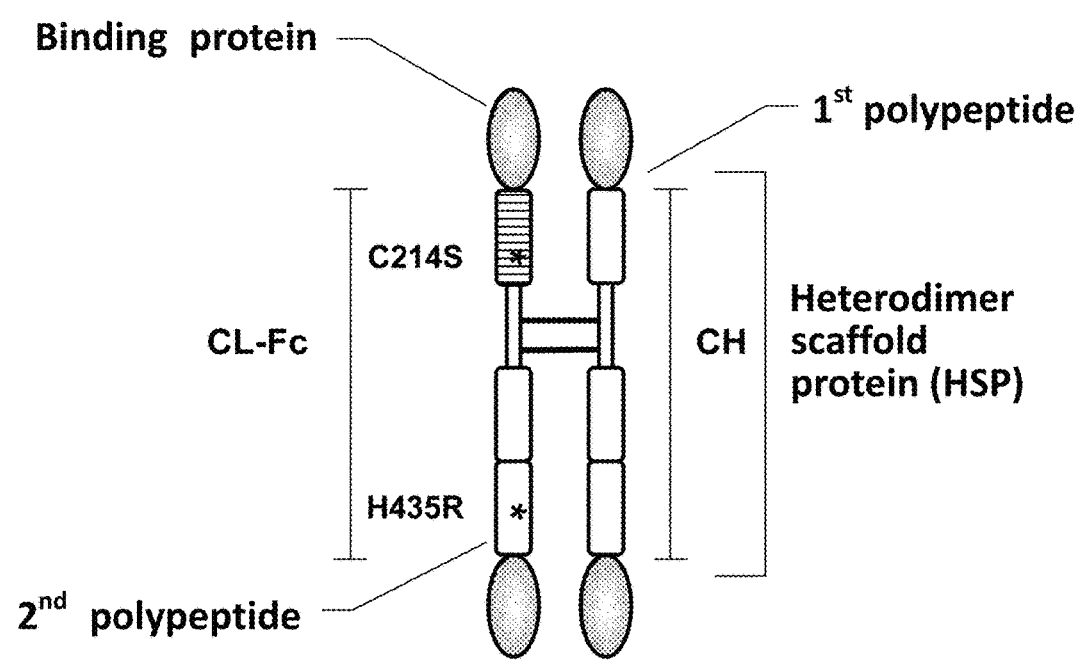
FIG. 2A is a diagram showing the structure of the heterodimer protein of the present invention.
Figure 2B:
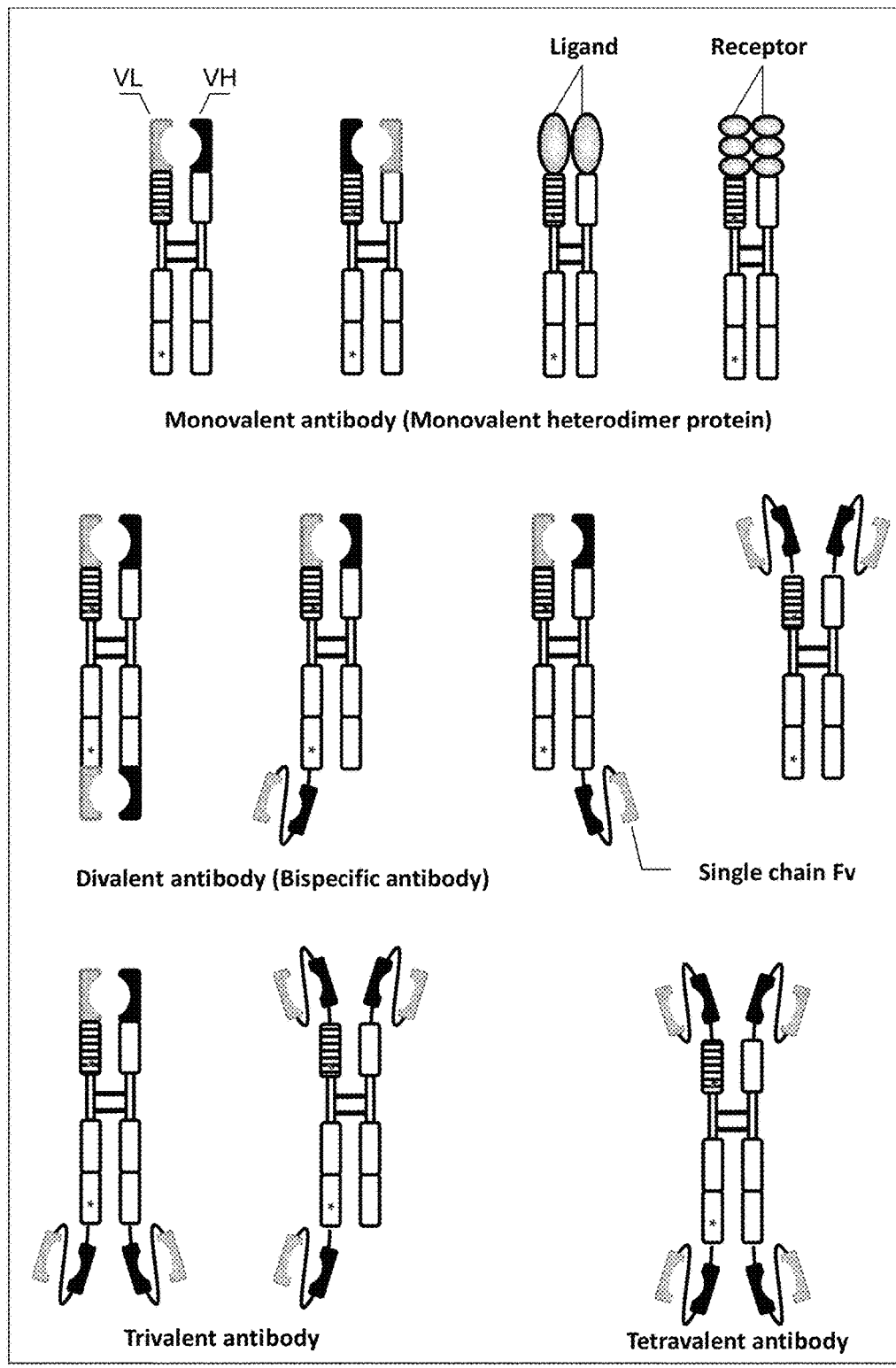
FIG. 2B is a diagram showing the structures of typical monovalent to tetravalent antibodies that can prepared based on the heterodimer scaffold protein (HSP) structure of the present invention.

Therefore, the heterodimer protein of the present invention can be a heterodimer protein comprising HSP composed of CH and CL-Fc, in which at least one binding protein is bound to HSP (FIGS. 2A and 2B).

The heterodimer protein having a monovalent binding domain of the present invention (hereinafter, referred to as monovalent antibody or monomeric antibody in some cases) can include a monovalent antibody composed of a first polypeptide and a second polypeptide, in which VH and VL are bound to the N-terminus of CH and CL-Fc, respectively, and a monovalent antibody composed of a first polypeptide in which scFv is bound to the N-terminus of CH and a second polypeptide of CL-Fc.

The heterodimer protein having a divalent binding domain of the present invention (hereinafter, referred to as bispecific antibody or divalent antibody in some cases) can include a bispecific antibody composed of a first polypeptide and a second polypeptide, in which a first scFv and a second scFv are bound to the N-terminus of CH and CL-Fc, respectively, and a bispecific antibody composed of a first polypeptide in which VH is bound to the N-terminus of CH and scFv is bound to the C-terminus thereof, and a second polypeptide in which VL is bound to the N-terminus of CL-Fc (FIG. 2B). Further, it can include a heterodimer protein having a divalent binding activity in which scFv is bound to the N-terminus of the above described monovalent antibody.

The heterodimer protein having a trivalent or tetravalent binding domain of the present invention (hereinafter, referred to as trivalent or tetravalent antibody in some cases) can include a trivalent or tetravalent antibody in which three to four scFvs are bound to the N-terminus and C-terminus of CH and CL-Fc. Further, it can include a heterodimer protein having a trivalent binding activity in which the first scFv and the second scFv are bound to the N-terminus of the above described monovalent antibody.

Because the monovalent antibody of the present invention binds to one epitope, it does not cause the effect such as cross-linkage of antigens and does not cause unnecessary activities related to antigen cross-linkage.

Hereinafter, the preparation method of the heterodimer protein composition of the present invention will be described in detail.

4. Preparation Method of Heterodimer Protein Composition

The preparation method of the heterodimer protein of the present invention can be a preparation method comprising the following processes of (i) to (iii).

(i) a process of introducing into cells a vector including DNA encoding the first polypeptide comprising CH and a vector including DNA encoding the second polypeptide comprising CL-Fc having a reduced binding activity for the CH binder.

(ii) a process of culturing the cells and recovering the culture supernatant.

(iii) a process of binding the heterodimer protein to the CH binder for purification.

More specifically, for example, in the process of preparing the production cells for preparing the heterodimer protein of (1) described above, a process of adding a substitution of C131S of the EU index to the first polypeptide and adding any one selected from a substitution of C214S, a substitution of C220S, and substitutions of H435R and Y436F, of the EU index to the second polypeptide is properly performed according to the subclass of the antibody constant region included in the heterodimer protein.

More specifically, a process of adding a substitution of C131S of the EU index to the first polypeptide and a substitution of H435R of the EU index to the second polypeptide, adding substitutions of C214S and H435R of the EU index, substitutions of C220S and H435R of the EU index, or substitutions of C214S, H435R and Y436F of the EU index to the second polypeptide can be exemplified.

Further, the preparation method of the heterodimer protein of the present invention can include the following processes of (i) to (v).

(i) a process of reducing or deleting the binding activity of the second polypeptide for the CH binder in the heterodimer protein composed of the first polypeptide comprising CH and the second polypeptide comprising CL-Fc.

(ii) a process of deleting or substituting the Cys residues involved in disulfide bonds between CH and CL of the heterodimer protein.

(iii) a process of introducing into cells the vector including DNA encoding the first polypeptide comprising CH and the vector including DNA encoding the second polypeptide comprising CL-Fc having a reduced binding activity for the CH binder.

(iv) a process of culturing the cells and recovering the culture supernatant.

(v) a process of binding the heterodimer protein to the CH binder for purification.

The heterodimer protein composition of the present invention can be obtained by expressing it in a host cell using the methods described in Molecular Cloning, Second Edition Current protocols in molecular biology, Antibodies, A Laboratory manual, Cold Spring Harbor Laboratory, 1988, Monoclonal Antibodies: principles and practice, Third Edition, Acad. Press, 1993, Antibody Engineering, A Practical Approach, IRL Press at Oxford University Press, 1996 or the like, for example, in the following manner.

(1) Construction of Expression Vector for Heterodimer Protein Composition of the Present Invention The expression vector for heterodimer protein composition of the present invention is an expression vector for animal cells into which genes encoding the first polypeptide and the second polypeptide of the heterodimer protein molecule included in the heterodimer protein composition of the present invention are introduced.

The vector for expressing the heterodimer protein composition can be constructed by cloning each of the genes encoding the first and second polypeptides of the heterodimer protein molecule included in the heterodimer protein composition into an expression vector for animal cells.

The gene encoding the first polypeptide constituting the heterodimer protein molecule included in the heterodimer protein composition of the present invention can be prepared by preparing an amino acid sequence in which an amino acid sequence of the desired binding protein is linked to the N-terminus or C-terminus of antibody H chain constant region (CH).

In the same manner, the gene encoding the second polypeptide can be prepared by preparing an amino acid sequence in which an amino acid sequence of the desired binding protein is linked to the N-terminus or C-terminus of CL-Fc prepared by fusion of antibody L chain constant region (CL) and Fc.

Also, the total DNA can be synthesized by using synthetic DNAs and synthesis using polymerase chain reaction (PCR) is also possible (Molecular Cloning, Second Edition). Furthermore, the gene encoding the heterodimer protein can be produced in combinations of plural these techniques.

Specifically, when an IgG4-type monovalent antibody having a monovalent binding domain is prepared as the heterodimer protein of the present invention, an amino acid sequence is designed by adding amino acid substitutions of C131S/R133K/S228P/L235E/R409K to the amino acid sequence of CH of human IgG4 antibody, and the amino acid sequence of VH is linked to the N-terminus of the amino acid sequence of IgG4-CH to prepare an amino acid sequence of the first polypeptide.

Meanwhile, an amino acid sequence is designed by adding amino acid substitutions of C214S/S228P/L235E/R409K/H435R/Y436F to IgG4-CL-Fc that is prepared by linking the amino acid sequence of human CLκ and the amino acid sequences of hinge domain, CH2 domain and CH3 domain of human IgG4 antibody, and an amino acid sequence of the second polypeptide in which the amino acid sequence of VL is linked to the N-terminus of the amino acid sequence thereof, is prepared. Nucleotide sequences of DNA encoding the prepared amino acid sequences of the first and second polypeptides are prepared and inserted into an expression vector for animal cells, thereby preparing an expression vector for the monovalent antibody of the present invention.

When an animal cell is used as a host, any expression vector can be used as long as it exhibits its functions in animal cells, and examples thereof can include pcDNAI, pAGE107 [Japanese Patent Publication No. H3-22979; Cytotechnology, 3, 133 (1990)], pAS3-3 (Japanese Patent Publication No. H2-227075), pCDM8 [Nature, 329, 840 (1987)], pcDNAI/Amp (manufactured by Invitrogen), pcDNA 3.1 (manufactured by Invitrogen), pREP4 (manufactured by Invitrogen), pAGE103 [J. Biochemistry, 101, 1307 (1987)], pAGE210, pME18SFL3, pKANTEX93 (WO 97/10354), N5KG1val (U.S. Pat. No. 6,001,358), Tol2 transposon vector (WO 2010/143698) or the like.

As a promoter, any promoter can be used as long as it exhibits its functions in animal cells, and examples thereof may include the promoter of immediate early (IE) gene of cytomegalovirus (CMV), the SV40 early promoter, the promoter of a retrovirus, the metallothionein promoter, the heat shock promoter, the SRα promoter, the promoter or enhancer of Moloney murine leukemia virus. The enhancer of IE gene of human CMV may be also used in combination with the promoter.

The expression vector for the heterodimer protein composition of the present invention can be either of a type in which the gene encoding the antibody H chain and L chain exist on separate vectors or a type in which they exist on the same vector (hereinafter, referred to as tandem type).

(2) Acquisition of cDNA Encoding Variable Region of Antibody cDNAs encoding VH and VL of any antibody can be obtained in the following manner.

A cDNA is synthesized by using mRNA as a template, which is extracted from a hybridoma cell producing any antibody. The synthesized cDNA is inserted into a vector such as a phage or a plasmid to obtain a cDNA library.

Each of a recombinant phage or recombinant plasmid having a cDNA encoding VH and a recombinant phage or recombinant plasmid having a cDNA encoding VL is isolated from the above library by using DNA encoding the constant region or variable region of a known antibody as the probe. Full length nucleotide sequences of VH and VL of the desired antibody on the recombinant phage or recombinant plasmid are determined, and full length amino acid sequences of VH and VL are deduced from the nucleotide sequences.

Hybridoma cells producing any non-human animal antibody can be obtained by immunizing a non-human animal with an antigen to be bound by the antibody and hybridomas are prepared from antibody-producing cells of the immunized animal and myeloma cells according to a known method [Molecular Cloning, Second Edition Current protocols in molecular biology, Antibodies, A Laboratory manual, Cold Spring Harbor Laboratory, 1988, Monoclonal Antibodies: principles and practice, Third Edition, Acad. Press, 1993, Antibody Engineering, A Practical Approach, IRL Press at Oxford University Press, 1996]. Subsequently, single cell cloned hybridomas are selected, cultured and the antibody is purified from the culture supernatant.

As the non-human animal, any animal can be used as long as hybridoma cells can be prepared from the animal such as mouse, rat, hamster, rabbit or the like.

The methods for preparing total RNA from a hybridoma cell may include, for example, the guanidine thiocyanate-cesium trifluoroacetate method [Methods in Enzymol., 154, 3 (1987)] and an RNeasy kit (manufactured by QIAGEN). The methods for preparing mRNA from the total RNA may include the oligo (dT) immobilized cellulose column method [Molecular Cloning: A Laboratory Manual, Cold Spring Harbor Lab. Press New York, 1989] or the like.

Further, examples of the kits for preparing mRNA from a hybridoma cell may include a Fast Track mRNA Isolation Kit (manufactured by Invitrogen), a Quick Prep mRNA Purification Kit (manufactured by Pharmacia) or the like.

The methods for synthesizing the cDNA and preparing the cDNA library may include conventional methods (Molecular Cloning: A Laboratory Manual, Cold Spring Harbor Lab. Press New York, 1989; Current Protocols in Molecular Biology, Supplement 1-34], or methods using commercially available kits, for example, SuperScript (registered trade name) Plasmid System for cDNA Synthesis and Plasmid Cloning (manufactured by GIBCO BRL), ZAP-cDNA Synthesis Kit (manufactured by Stratagene) or the like.

In preparation of the cDNA library, the vector for integrating the cDNA that is synthesized using the mRNA extracted from a hybridoma cell as a template may be any vector as long as the cDNA can be integrated.

For example, ZAP Express (Strategies, 5, 58, 1992), pBluescript II SK(+) (Nucleic Acids Research, 17, 9494, 1989), λZAP II (manufactured by Stratagene), λgt10, λgt11 (DNA Cloning: A Practical Approach, I, 49, 1985), Lambda BlueMid (manufactured by Clontech), λExCell, pT7T3 18U (manufactured by Pharmacia), pcD2 (Mol. Cell. Biol., 3, 280, 1983), pUC18 (Gene, 33, 103, 1985) or the like may be used.

As *Escherichia coli* for introducing the cDNA library constructed with a phage or plasmid vector, any one can be used as long as the cDNA library can be introduced, expressed and maintained.

For example, XL1-Blue MRF (Strategies, 5, 81, 1992), C600 (Genetics, 39, 440, 1954), Y1088, Y1090 (Science, 222, 778, 1983), NM522 (Journal of Molecular Biology; J. Mol. Biol., 166, 1, 1983), K802 (J. Mol. Biol., 16, 118, 1966), JM105 (Gene, 38, 275, 1985) or the like may be used.

The methods for selecting the cDNA clones encoding VH and VL of a non-human animal antibody from the cDNA library can include colony hybridization or plaque hybridization (Molecular Cloning: A Laboratory Manual, Cold Spring Harbor Lab. Press New York, 1989) using an isotope- or fluorescence-labeled probe.

It is also possible to prepare the cDNAs encoding VH and VL by preparing primers and carrying out PCR (Molecular Cloning: A Laboratory Manual, Cold Spring Harbor Lab. Press New York, 1989; Current Protocols in Molecular Biology, Supplement 1-34) using the cDNA or cDNA library as a template.

The nucleotide sequences of the cDNAs selected by the above methods can be determined by cleaving the cDNAs with appropriate restriction enzymes, cloning it into a plasmid such as pBluescript II SK(-) (manufactured by Stratagene), and then analyzing it by generally employed nucleotide sequence analyzing methods, for example, the dideoxy method of Sanger, et al. (Proc. Natl. Acad. Sci., U.S.A., 74, 5463, 1977) or by use of nucleotide sequence autoanalyzers, for example, ABI PRISM 377 DNA Sequencer (manufactured by Applied Biosystems).

The full length of amino acid sequences of VH and VL are deduced from the determined nucleotide sequences and compared with the full length of amino acid sequences of VH and VL of a known antibody (Sequences of Proteins of Immunological Interest, US Dept. Health and Human Services, 1991), whereby it can be confirmed whether the obtained cDNAs encode amino acid sequences which completely include VH and VL of the antibody comprising secretory signal sequences.

Further, when the amino acid sequence of an antibody variable region or the nucleotide sequence of DNA encoding the variable region is already known, it can be obtained by the following methods.

When the amino acid sequence is known, the DNA can be obtained by designing a nucleotide sequence of DNA encoding the variable region taking into consideration the frequency of codon usage (Sequences of Proteins of Immunological Interest, US Dept. Health and Human Services, 1991), synthesizing several synthetic DNAs composed of approximately 100 to 150 bases based on the designed nucleotide sequence of DNA, and carrying out PCR using them or synthesizing complete length of DNA sequence. When the nucleotide sequence is known, the DNA can be obtained by the same method described above based on the information.

(3) Analysis of Amino Acid Sequence of Variable Region of Antibody

By comparing the full length of amino acid sequences of VH and VL of the antibody comprising secretory signal sequences with the amino acid sequences of VH and VL of a known antibody (Sequences of Proteins of Immunological Interest, US Dept. Health and Human Services, 1991), it is possible to deduce the length of the secretory signal sequences and the N-terminus amino acid sequences and further to know the subgroup to which the antibody belongs. In addition, the amino acid sequences of CDRs of VH and VL can be determined in a similar manner.

(4) Construction of cDNA Encoding Variable Region of Humanized Antibody cDNAs encoding VH and VL of the humanized antibody can be constructed in the following manner. First, amino acid sequences of framework regions (hereinafter, referred to as FR) of VH and VL of the human antibody for grafting CDRs of VH and VL of the desired non-human animal antibody are selected. The amino acid sequences of FRs of VH and VL of the human antibody can be any of those from human antibodies.

Examples thereof can include the amino acid sequences of FRs of VHs and VLs of human antibodies registered at databases such as Protein Data Bank, the amino acid sequences common to subgroups of FRs of VHs and VLs of human antibodies (Sequences of Proteins of Immunological Interest, US Dept. Health and Human Services, 1991) or the like.

In order to prepare the humanized antibody having a sufficient activity among them, it is preferred to select amino acid sequences having a homology as high as possible (at least 60% or more) with the amino acid sequences of FRs of VH and VL of the desired non-human animal antibody.

Next, the amino acid sequences of CDRs of VH and VL of the desired non-human animal antibody are grafted to the selected amino acid sequences of FRs of VH and VL of the human antibody to design amino acid sequences of VH and VL of the humanized antibody. The designed amino acid sequences are converted into nucleotide sequences of DNA taking into consideration the codon usage in the nucleotide sequences of antibody genes (Sequences of Proteins of Immunological Interest, US Dept. Health and Human Services, 1991), and nucleotide sequences of DNA encoding the amino acid sequences of VH and VL of the humanized antibody are designed. The designed DNA sequences are fully synthesized.

Cloning into the expression vector for the heterodimer protein composition of the present invention constructed in the above 3(1) can be easily carried out by introducing recognition sequences for appropriate restriction enzymes to the 5'-terminals of synthetic DNAs present on both ends. After PCR, the amplification products are cloned into a plasmid such as pBluescript II SK(−) (manufactured by Stratagene) and the nucleotide sequences are determined by the method described in the above 3(2) to obtain a plasmid having the nucleotide sequences of DNA that encode the amino acid sequences of VH and VL of the desired humanized antibody.

(5) Modification of Amino Acid Sequence of Variable Region of Humanized Antibody It is known that a humanized antibody prepared merely by grafting only CDRs of VH and VL of a non-human animal antibody to FRs of VH and VL of a human antibody has a reduced antigen-binding activity, compared with the original non-human animal antibody (BIO/TECHNOLOGY, 9, 266, 1991).

This is probably because in VH and VL of the original non-human animal antibody, not only CDRs but also some of the amino acid residues in FRs are involved directly or indirectly in the antigen-binding activity, and such amino acid residues are changed to different amino acid residues of FRs of VH and VL of the human antibody by CDR grafting.

In order to solve this problem, attempts have been made with regard to a humanized antibody to raise the lowered antigen-binding activity by identifying the amino acid residues in the amino acid sequences of FRs of VH and VL of the human antibody which are directly relating to the binding to an antigen or which are indirectly relating to it through interaction with amino acid residues of CDRs or maintenance of the conformation of the antibody, and modifying such amino acid residues to those derived from the original non-human animal antibody (BIO/TECHNOLOGY, 9, 266, 1991).

In the preparation of the humanized antibody, it is most important to efficiently identify the amino acid residues of FR which are relating to the antigen-binding activity. The conformations of antibodies have been generated and analyzed by X ray crystallography (J. Mol. Biol., 112, 535, 1977), computer modeling (Protein Engineering, 7, 1501, 1994) or the like.

Such information of the conformations of antibodies have provided much useful information for the preparation of humanized antibodies. However, there is no established method for preparing a humanized antibody that is adaptable to any type of antibodies. At present, it is still necessary to make trial-and-error approaches, e.g., preparation of several variants for each antibody and examination of the correlation with the antigen-binding activity among antibody variants.

Modification of the amino acid residues in FRs of VH and VL of a human antibody can be achieved by PCR as described in the above 3(4) using synthetic DNAs for modification. The nucleotide sequence of the PCR amplification product is determined by the method described in the above 3(2) to confirm that the desired modification has been achieved.

(6) Expression of Heterodimer Protein

Transformants capable of transiently or stably producing the heterodimer protein can be obtained by introducing the heterodimer protein expression vectors of the above 3(1) into appropriate animal cells.

The heterodimer protein of the present invention is a protein composed of the first polypeptide comprising CH and the second polypeptide comprising CL-Fc, in which Cys residues involved in disulfide bonds between CL and CH1 are deleted or substituted, and the amount of the multimers of the heterodimer protein is remarkably reduced in the host cells introduced with the expression vector. Therefore, the heterodimer protein of the present invention is a molecule that can efficiently form a heterodimeric structure composed of the first polypeptide comprising CH and the second polypeptide comprising CL-Fc.

Further, the present invention includes a method for reducing multimers of heterodimer protein by deleting or substituting Cys residues involved in disulfide bonds between CL and CH1 in the heterodimer protein composed of the first polypeptide comprising CH and the second polypeptide comprising CL-Fc.

(6-a) Transient Expression of Heterodimer Protein

The heterodimer protein expression vectors obtained in (3) and (6) or expression vectors obtained by modifying those vectors are used for transient expression of the heterodimer protein. In this manner, it is possible to efficiently evaluate the antigen binding activity of the various types of prepared heterodimer proteins.

Any type of cell can be used as the host cell to which the expression vector is introduced, as long as it is a host cell which can express the heterodimer protein, and for example, COS-7 cell [American Type Culture Collection (ATCC) No. CRL1651] can be used (Methods in Nucleic Acids Res., CRC press, 283, 1991).

For introducing an expression vector to COS-7 cell, a DEAE dextran method (Methods in Nucleic Acids Res., CRC press, 1991), a lipofection method [Proc. Natl. Acad. Sci. USA, 84, 7413 (1987)], or the like is used.

After the introduction of the expression vector, the expression amount and the antigen binding activity of the heterodimer protein in the culture supernatant are measured by ELISA (Monoclonal Antibodies-Principles and practice, Third edition, Academic Press (1996), Antibodies-A Laboratory Manual, Cold Spring Harbor Laboratory (1988), Manual for Monoclonal Antibody Experiment, Kodansha Scientific Ltd. (1987) or the like.

(6-b) Stable Expression of Heterodimer Protein

Transformants capable of stably expressing the heterodimer protein can be obtained by introducing the heterodimer protein expression vectors obtained in (1) into appropriate host cells.

Any method can be used as the method of introducing the expression vector into the host cell as long as it is the method of introducing a DNA into host cells. Examples thereof can include electroporation (Cytotechnology, 3, 133 (1990)), a calcium phosphate method (Japanese Patent Publication No. H2-227075), a lipofection method (Proc. Natl. Acad. Sci. U.S.A., 84, 7413, 1987), an injection method [Manipulating the Mouse Embryo A Laboratory Manual], a method using a particle gun (gene gun) (Japanese Patent Nos. 2606856 and 2517813), a DEAE-dextran method [Biomanual Series 4-Methods of Gene Transfer, Expression and Analysis (Yodosha), edited by Takashi Yokota and Kenichi Arai (1994)] and a virus vector method (Manipulating Mouse Embryo, Second Edition) or the like.

The host cells introduced with the heterodimer protein expression vector can be any cells as long as they are able to express the heterodimer protein. Human leukemia cell Namalwa cells, monkey COS cells, Chinese hamster CHO cells, HBT5637 (Japanese Patent Publication No. S63-299), rat myeloma cells, mouse myeloma cells, cells derived from Syrian hamster kidney, embryonic stem cells, fertilized egg cells, or the like can be used.

Specific examples thereof can include PER.C6, CHO-K1 (ATCC CCL-61), DUKXB11 (ATCC CCL-9096), Pro-5 (ATCC CCL-1781), CHO-S (Life Technologies, Cat #11619), Lec13 cell, rat myeloma cell YB2/

3HL.P2.G11.16Ag. 20 (ATCC NO. CRL1662, or also called YB2/0), mouse myeloma cell NS0, mouse myeloma cell SP2/0-Ag14 (ATCC NO. CRL1581), mouse P3X63-Ag8.653 cell (ATCC NO. CRL1580), dihydroforate reductase gene (hereinafter, referred to as dhfr)-deficient CHO cell (CHO/DG44) [Proc. Natl. Acad. Sci. USA, 77, 4216 (1980)], Syrian Hamster cell BHK, HBT563 cell, substrains of the above cell lines and cells prepared by adapting the above cell lines, in serum free medium or under non-adhesion culture conditions, or the like.

In the present invention, as a cell used for the production of the heterodimer protein, a cell reducing or deleting the amount of core fucose of the sugar chain bound to Asn at position 297 of the EU index in the Fc region can be used. Specifically, cells in which an enzyme relating to the synthesis of GDP-L-fucose, an enzyme relating to transport of GDP-L-fucose to Golgi body, or an enzyme relating to the binding of a core fucose is reduced or deleted can be selected, or cells obtained by various artificial methods can be used as host cells.

Specifically, a cell in which a core fucose is controlled can be prepared by a method for decreasing or deleting an enzyme activity relating to the sugar chain modification of a core fucose, a method for increasing an activity of a core fucose cleavage enzyme, or the like.

Examples of the enzyme relating to the sugar chain modification of a core fucose can include an enzyme relating to the synthesis or transport of GDP-L-fucose, and an enzyme relating to the binding of a core fucose to a complex type N-glycoside-linked sugar chain.

Specific examples of the enzyme relating to the synthesis of GDP-L-fucose or the transport to Golgi body can include GDP-mannose 4,6-dehydratase (hereinafter referred to as GMD), GDP-4-keto-6-deoxy-D-mannose-3,5-epimerase (hereinafter referred to as Fx), GDP-beta-L-fucose pyrophosphorylase (GFPP), fucokinase, GDP-L-fucose transporter or the like.

Examples of the enzymes relating to the binding of core fucose can include α1,6-fucosyltransferase (hereinafter referred to as FUT8), or the like.

The cell for producing the heterodimer protein of the present invention can include a cell in which one of the above enzyme activities is decreased or deleted or a cell in which plural enzyme activities in the above are decreased or deleted.

The method for decreasing or deleting the above enzyme activity can include (a) technique of gene disruption targeting a gene of the enzyme;

(b) technique of introducing a dominant-negative mutant of the gene of the enzyme;

(c) technique of introducing a mutation into the enzyme;

(d) technique of suppressing transcription or translation of the gene of the enzyme;

(e) technique of electing a cell line resistant to a lectin which recognizes a sugar chain structure in which 1-position of fucose is bound to 6-position of N-acetylglucosamine at the reducing end of a N-glycoside-linked sugar chain through α-bond; or the like.

The lectin can include lectin binding to α1,6 fucose, such as lentil lectin LCA (lentil agglutinin derived from *Lens culinaris*), pea lectin PSA (pea lectin derived from *Pisum sativum*), broad bean lectin VFA (agglutinin derived from *Vicia faba*), Aleuria aurantia lectin AAL (lectin derived from *Aleuria aurantia*) or the like.

Specific examples of the cell can include FUT8 gene-deficient CHO cell (WO 2005/035586, WO 2002/31140, WO 2000/061739), lectin resistance-acquired Lec13 (Somatic Cell and Molecular genetics, 12, 55, 1986), GDP-fucose transporter gene-deficient cell (WO 2003/085102), GDP-mannose 4,6-dehydratase (GMD) gene-deficient cell (WO 2002/31140), WGA lectin resistant cell, LCA lectin resistant cell (WO 2002/31140) or the like.

In addition to the above described method, the heterodimer protein composition in which high mannose type N-linked sugar chain binds and the amount of core fucose is reduced can be expressed by inhibiting an enzyme relating to N-linked sugar chain synthesis system, such as mannosidase I, mannosidase II or the like.

Further, by using a host cell overexpressing N-acetylglucosamine transferase III (GnTIII), the heterodimer protein composition to which a bisecting GlcNAc-binding complex and hybrid sugar chains bind, and in which the amount of core fucose is reduced, can be produced.

After introduction of the expression vector, transformants that stably express the heterodimer protein are selected by culturing them in a medium for animal cell culture containing an agent such as G418 sulfate (hereinafter, referred to as G418), cycloheximide (hereinafter, abbreviated to CHX), methotrexate (hereinafter, abbreviated to MTX) or the like (Japanese Patent Publication No. H2-257891).

The medium for animal cell culture can include RPMI1640 medium (manufactured by Invitrogen), GIT medium (manufactured by NIHON PHARMACEUTICAL CO.), EX-CELL301 medium, EX-CELL302, EX-CELL325 medium (manufactured by JRH), IMDM medium (manufactured by Invitrogen), Hybridoma-SFM medium (manufactured by Invitrogen), media obtained by adding various additives such as fetal bovine serum (hereinafter abbreviated to FBS) to these media, or the like.

The heterodimer protein can be expressed and accumulated in a culture supernatant by culturing the obtained transformants in a medium. The expression amount and antigen binding activity of the heterodimer protein in the culture supernatant can be measured by ELISA or the like. Also, the expression amount of the heterodimer protein produced by the transformant can be increased by using a dhfr gene amplification system or the like (Japanese Patent Publication No. H2-257891).

The method for expressing the heterodimer protein composition using an animal cell as the host has been described, but the heterodimer protein composition can also be produced in yeast, an insect cell, a plant cell, an animal individual or a plant individual in the same manner as in the animal cell based on the known technology.

When yeast is used as the host cell, a microorganism belonging to *Saccharomyces, Schizosaccharomyces, Kluyveromyces, Trichosporon, Schwanniomyces* or the like, for example, *Saccharomyces cerevisiae, Schizosaccharomyces pombe, Kluyveromyces lactis, Trichosporon pullulans, Schwanniomyces alluvius* or the like can be exemplified.

Introduction of the recombinant vector can be carried out by any of the methods for introducing DNA into yeast, for example, electroporation (Methods Enzymol., 194, 182 (1990)), the spheroplast method (Proc. Natl. Acad. Sci. USA, 84, 1929 (1978)), the lithium acetate method (J. Bacteriology, 153, 163 (1983)), the method described in Proc. Natl. Acad. Sci. USA, 75, 1929 (1978) or the like.

When an insect cell is used as the host cell, the heterodimer protein can be expressed by, for example, the methods described in current Protocols in Molecular Biology; Baculovirus Expression Vectors, A Laboratory Manual, W.H. Freeman and Company, New York, 1992), Bio/Technology, 6, 47, 1988 or the like.

Therefore, if the host cell has an ability to express the heterodimer protein molecule, the heterodimer protein composition of the present invention can be produced by introducing the gene of the heterodimer protein into the host cells described below, culturing the cells and then purifying the desired heterodimer protein composition from the culture.

Further, the heterodimer protein composition can be produced using an animal individual into which a gene is introduced (non-human transgenic animal) or a plant individual into which a gene is introduced (transgenic plant), which is constructed by redifferentiating the animal or plant cells into which genes are introduced.

When the transformant is an animal individual or a plant individual, the heterodimer protein composition can be produced by rearing or cultivating them in a usual manner, allowing the heterodimer protein composition to form and accumulate therein, and collecting the heterodimer protein composition from the animal individual or plant individual.

Examples of the production method of the heterodimer protein composition using an animal individual can include a method of producing the desired heterodimer protein composition in an animal constructed by introducing the gene according to known methods [American Journal of Clinical Nutrition, 63, 639S, 1996; American Journal of Clinical Nutrition, 63, 627S, 1996; Bio/Technology, 9, 830, 1991].

In the case of an animal individual, the heterodimer protein composition can be produced, for example, by raising a non-human transgenic animal into which DNA encoding the heterodimer protein molecule is introduced, allowing the heterodimer protein composition to form and accumulate in the animal, and collecting the heterodimer protein composition from the animal.

The places for formation and accumulation in the animal can include, for example, milk (Japanese Patent Publication No. S63-309192), egg or the like of the animal. As the promoter in this process, any promoters capable of expressing it in an animal can be used. For example, mammary gland cell-specific promoters such as a casein promoter, β casein promoter, β lactoglobulin promoter, whey acidic protein promoter or the like are preferably used.

Examples of the production method of the heterodimer protein composition using a plant individual can include a method of cultivating a transgenic plant into which DNA encoding the heterodimer protein molecule is introduced according to known methods [Tissue Culture, 20 (1994); Tissue Culture, 21 (1995); Trends in Biotechnology, 15, 45 (1997)], allowing the heterodimer protein composition to form and accumulate in the plant, and collecting the heterodimer protein composition from the plant.

(7) Purification of Heterodimer Protein

When the host cells introduced with the heterodimer protein expression vector are cultured, homodimer proteins composed of the two second polypeptides and heterodimer proteins composed of the first polypeptide and the second polypeptide are produced. The heterodimer protein of the present invention is a protein composed of the first polypeptide comprising CH and the second polypeptide comprising CL-Fc, in which the second polypeptide is also a polypeptide having a reduced or no binding activity for the CH-binder, and therefore, the heterodimer protein including the first polypeptide binding to the CH binder can be only specifically separated and purified.

Therefore, the purification method used in the present invention includes a process of binding the heterodimer protein to the CH binder and a process of eluting the heterodimer protein. That is, the purification method of the heterodimer protein of the present invention can be a purification method comprising the following processes of (i) to (iii).

(i) a process of reducing or deleting the binding activity of the second polypeptide for the CH binder in the heterodimer protein composed of the first polypeptide comprising CH and the second polypeptide comprising CL-Fc.

(ii) a process of binding the heterodimer protein to the CH binder.

(iii) a process of eluting the heterodimer protein.

More specifically, for example, in the process of preparing the cells for production of the heterodimer protein of (i) described above, a process of adding any one selected from a substitution of C214S, a substitution of C220S, a substitution of H435R and a substitution of Y436F, of the EU index to the second polypeptide can be properly performed according to the subclass of the antibody constant region included in the heterodimer protein.

Specific examples thereof can include a process of adding substitutions of C214S and H435R of the EU index, substitutions of C220S and H435R of the EU index, or substitutions of C214S, H435R and Y436F of the EU index to the second polypeptide, or the like.

Further, the purification method of the heterodimer protein of the present invention can be a purification method comprising the following processes of (i) to (iv).

(i) a process of reducing or deleting the binding activity of the second polypeptide for the CH binder in the heterodimer protein composed of the first polypeptide comprising CH and the second polypeptide comprising CL-Fc.

(ii) a process of deleting or substituting Cys residues involved in disulfide bonds between CH and CL of the heterodimer protein.

(iii) a process of binding the heterodimer protein to the CH binder.

(iv) a process of eluting the heterodimer protein.

In the present invention, the formation of halfmers and/or multimers of the heterodimer protein of the present invention can be reduced by deleting or substituting Cys residues involved in disulfide bonds between CH and CL during the above described production process (i).

The method for reducing the formation of halfmers of the heterodimer protein of the present invention can be a method for reducing the formation of halfmers of the heterodimer protein comprising the following processes of (i) to (iii).

(i) a process of introducing a substitution of R409K of the EU index in the heterodimer protein composed of the first polypeptide comprising CH and the second polypeptide comprising CL-Fc.

(ii) a process of binding the heterodimer protein to the CH binder.

(iii) a process of purifying the heterodimer protein.

The present invention can include a method for reducing the formation of multimers of the heterodimer protein comprising the following processes of (i) to (iii).

(i) a process of deleting or substituting Cys residues involved in disulfide bonds between CH and CL in the heterodimer protein composed of the first polypeptide comprising CH and the second polypeptide comprising CL-Fc.

(ii) a process of binding the heterodimer protein to the CH binder.

(iii) a process of purifying the heterodimer protein.

The method for reducing the formation of halfmers and multimers of the heterodimer protein of the present invention may be a method for reducing the formation of halfmers of the heterodimer protein comprising the following processes of (i) to (iv).

(i) a process of deleting or substituting Cys residues involved in disulfide bonds between CH and CL of the heterodimer protein composed of the first polypeptide comprising CH and the second polypeptide comprising CL-Fc.

(ii) a process of introducing a substitution of R409K of the EU index.

(iii) a process of binding the heterodimer protein to the CH binder.

(iv) a process of purifying the heterodimer protein.

More specifically, for example, in the process of preparing the cells for production of the heterodimer protein of (i) or (ii) described above, a process of adding any one selected from substitution of C214S of the EU index, substitution of C220S, substitution of R409K, and substitution of H435R to the second polypeptide can be properly performed according to the subclass of the antibody constant region included in the heterodimer protein.

More specifically, for example, a process of adding substitutions of C214S, R409K and H435R of the EU index, substitutions of C220S, R409K and H435R of the EU index, or substitutions of C214S, R409K, H435R and Y436F of the EU index to the second polypeptide can be performed.

The heterodimer protein of the present invention can be purified in the following manner. The heterodimer protein composition that is prepared by the transformant introduced with the gene encoding the heterodimer protein molecule can be obtained as follows. For example, when the heterodimer protein composition is expressed as a soluble protein within the cells, the cells are recovered by centrifugation after culturing is completed, suspended in an aqueous buffer and then disrupted using a ultrasonicator, a French press, a Manton Gaulin homogenizer, a dynomill or the like to obtain a cell-free extract.

From the supernatant that is obtained by centrifugation of the cell-free extract, a purified product of the heterodimer protein composition can be obtained by general enzyme isolation and purification techniques such as solvent extraction, salting-out using ammonium sulfate or the like, desalting, precipitation using an organic solvent, anion exchange chromatography using a resin such as diethylaminoethyl (DEAE) sepharose or DIAION HPA-75 (manufactured by Mitsubishi Chemical Corporation), cation exchange chromatography using a resin such as S-Sepharose FF (manufactured by Pharmacia), hydrophobic chromatography using a resin such as butyl-sepharose or phenyl-sepharose, gel filtration using a molecular sieve, affinity chromatography, chromatofocusing, electrophoresis such as isoelectric focusing electrophoresis, or the like which can be used alone or used in combination.

In the present invention, as the affinity chromatography, affinity chromatography using a CH binder is used (Monoclonal Antibodies-Principles and practice, Third edition, Academic Press (1996), Antibodies-A Laboratory Manual, Cold Spring Harbor Laboratory, 1988).

Further, when the heterodimer protein composition is expressed within cells by forming an inclusion body, the cells are recovered, disrupted and centrifuged in the same manner, and the inclusion body of the heterodimer protein composition is recovered as a precipitation fraction. The recovered inclusion body of the heterodimer protein composition is solubilized with a protein denaturing agent. The heterodimer protein composition is made into a normal conformation by diluting or dialyzing the solubilized solution, and then a purified product of the heterodimer protein composition is obtained by the same isolation and purification method as above.

When the heterodimer protein composition is secreted extracellularly, the heterodimer protein composition or the derivative thereof can be recovered from the culture supernatant. That is, the culture is treated by a method such as centrifugation in the same manner as above to obtain a culture supernatant, a purified product of the heterodimer protein composition can be obtained from the culture supernatant by the same isolation and purification method as above.

Specifically, the CH binder or Fc binder can be any one as long as it binds to CH or Fc, such as proteins, resins or the like, and examples thereof can include Fc-binding proteins, antibodies bound to H chain constant region (CH) of an antibody or the like.

Specific example of the Fc-binding protein can include *Staphylococcus Aureus*-derived Protein A, hemolytic *Streptococcus*-derived Protein G, Fc receptor, the subclasses (FcγRI, IIA, IIB, IIIA, IIIB), binding fragments thereof, or the like.

Examples of the CH-binding antibody can include antibodies binding to CH1 domain, hinge domain, CH2 domain or CH3 domain.

In the present invention, the CH binder can include more preferably Protein A, Protein G, anti-CH1 antibody and binding fragments thereof.

As the purification method of the heterodimer protein of the present invention, for example, the supernatant obtained by culturing the transformed cell line prepared in 3(6) is loaded on Protein A column or Protein G column, and then this column is washed with phosphate buffer saline, (hereinafter, abbreviated to PBS).

Thereafter, the heterodimer protein is eluted from the column using a citrate buffer of low pH (pH 2.0 to 6.0) or the like, the eluate was neutralized with alkaline Tris buffer or the like. The neutralized eluate was subjected to dialysis using a sufficient amount of PBS, or the like. to obtain the purified heterodimer protein.

The molecular weight of the purified heterodimer protein molecule can be measured by polyacrylamide gel electrophoresis [Nature, 227, 680 (1970)], Western blotting [Monoclonal Antibodies—Principles and practice, Third edition, Academic Press (1996), Antibodies-A Laboratory Manual, Cold Spring Harbor Laboratory (1988)] or the like.

5. Evaluation of Activity of Heterodimer Protein Composition

The protein amount, FcR binding activity, C1q binding activity, antigen binding activity or cytotoxic activity, such as ADCC activity and CDC activity of the purified heterodimer protein composition can be measured using the known methods, for example, described in Molecular Cloning 2nd Edition, Current Protocols in Molecular Biology, Antibodies, A Laboratory manual, Cold Spring Harbor Laboratory, 1988, Monoclonal Antibodies: principles and practice, Third Edition, Acad. Press, 1993, Antibody Engineering, A Practical Approach, IRL Press at Oxford University Press, 1996 or the like.

Specifically, the binding activity of the heterodimer protein composition to an antigen or an antigen-positive cultured cell line can be measured by ELISA, the fluorescent antibody technique (Cancer Immunol. Immunother, 36, 373, 1993) or the like. The cytotoxic activity to the cultured cell line which is antigen-positive can be evaluated by measuring CDC activity, ADCC activity, or the like [Cancer Immunol. Immunother, 36, 373, 1993, US Patent Application Publication No. 2004/0259150].

The FcR binding activity of the heterodimer protein composition of the present invention can be confirmed by producing a recombinant FcγRIIIA protein or a recombinant neonatal Fc receptor (FcRn) and then measuring a binding activity (US Patent Application Publication No. 2004/0259150).

Example of the method for measuring ADCC activity can include a method in which a target cell labeled with a radioisotope, a fluorescent substance, a dye or the like is allowed to contact with the heterodimer protein and an effector cell, and then the activity of the labeled substance released from the injured target cell is measured or the biological activity of an enzyme released therefrom is measured.

Example of the method for measuring CDC activity can include a method in which a target cell labeled with a radioisotope, a fluorescent substance, a dye or the like is allowed to contact with the heterodimer protein and a biological sample such as serum containing a complement component, and then the activity of the labeled substance released from the injured target cell or the biological activity of an enzyme released therefrom is measured.

6. Sugar Chain Analysis of Heterodimer Protein Composition

The sugar chain structure of the heterodimer protein molecule expressed in various cells can be analyzed according to general methods of analyzing the sugar chain structure of glycoprotein. For example, a sugar chain bound to an IgG molecule consists of neutral sugars such as galactose (Gal), mannose (Man), or fucose (Fuc), amino sugars such as N-acetylglucosamine (GlcNAc), and acidic sugars such as sialic acid (Sial), and can be analyzed by techniques such as sugar chain structure analysis using sugar composition analysis and two-dimensional sugar chain mapping.

(1) Analysis of Neutral Sugar and Amino Sugar Compositions

The sugar chain composition of the heterodimer protein composition can be analyzed by carrying out acid hydrolysis of sugar chains with trifluoroacetic acid or the like to release neutral sugars or amino sugars and by analyzing the composition ratio.

Specifically, the analysis can be carried out, for example, by a method using a sugar composition analysis device manufactured by Dionex. BioLC is a device for analyzing the sugar composition by HPAEC-PAD (high performance anion-exchange chromatography-pulsed amperometric detection) (J. Liq. Chromatogr., 6, 1577 (1983)].

Further, the composition ratio can also be analyzed by the fluorescence labeling method using 2-aminopyridine. Specifically, the composition ratio can be calculated by fluorescence labeling an acid-hydrolyzed sample by 2-aminopyridylation according to a known method [Agric. Biol. Chem., 55(1), 283-284 (1991)] and then analyzing the composition by HPLC.

(2) Analysis of Sugar Chain Structures

The sugar chain structures of the heterodimer protein composition can be analyzed by two-dimensional sugar chain mapping [Anal. Biochem., 171,73, 1988, Biochemical Experimentation Methods 23—Methods of Studies on Glycoprotein Sugar Chains (Japan Scientific Societies Press) Reiko Takahashi (1989)]. The two-dimensional sugar chain mapping is a method of deducing a sugar chain structure, for example, by plotting the retention time or elution position of a sugar chain by reversed phase chromatography as the X axis and the retention time or elution position of the sugar chain by normal phase chromatography as the Y axis, respectively, and comparing them with the results of known sugar chains.

Specifically, a sugar chain is released from the heterodimer protein by hydrazinolysis of the heterodimer protein and subjected to fluorescence labeling with 2-aminopyridine (hereinafter, abbreviated to PA) (J. Biochem., 95, 197, 1984). After being separated from an extra PA-treating reagent by gel filtration, the sugar chain is subjected to reversed phase chromatography. Then, each peak of the fractionated sugar chain is subjected to normal phase chromatography. The sugar chain structure can be deduced by plotting the obtained results on a two-dimensional sugar chain map and comparing them with the spots of a sugar chain standard (manufactured by TaKaRa) or those in the document (Anal. Biochem., 171, 73, 1988).

Further, the structure deduced by the two-dimensional sugar chain mapping can be confirmed by carrying out mass spectrometry, e.g., MALDI-TOF-MS, of each sugar chain.

The portion to which a sugar chain is bound in Fc region of the heterodimer protein can be confirmed by treating the heterodimer protein that is subjected to reductive alkylation with endoprotease such as trypsin, pepsin, Lys-C or Asp-N, and separating it using reverse phase chromatography (LC) to analyze them using a mass spectrometer (MS).

Namely, it can be confirmed whether a sugar chain is actually bound or not by checking if the molecular weights of obtainable peptides by protease treatment and the molecular weight of peptide to which a sugar chain is bound correspond to analysis values of MS based on the amino acid sequence of the objective Fc region of the heterodimer protein.

7. Method for Determining Sugar Chain Structure of Heterodimer Protein Molecule

The heterodimer protein composition is composed of heterodimer protein molecules that are different in sugar chain structures bound to Asn at position 297 in the Fc region of the heterodimer protein. The heterodimer protein composition in which the ratio of sugar chains with no core fucose among the total complex-type N-glycoside-linked sugar chains which bind to Fc of the heterodimer protein composition of the present invention is 20% or more, shows high ADCC activity. Such a heterodimer protein composition can be determined using the method for analyzing the sugar chain structure of the heterodimer protein molecule described in the above 5. Further, it can also be determined by an immunological quantitative method using lectins.

Determination of the sugar chain structure of the heterodimer protein molecule by an immunological quantitative method using lectins can be made according to the immunological quantitative method such as Western staining, RIA (radioimmunoassay), VIA (viroimmunoassay), EIA (enzyme immunoassay), FIA (fluoroimmunoassay) and MIA (metalloimmunoassay) described in the document [Monoclonal Antibodies: Principles and Applications, Wiley-Liss, Inc. (1995); Enzyme Immunoassay, 3rd Ed., IGAKU-SHOIN Ltd. (1987); Enzyme Antibody Technique, Revised Edition, Gakusai Kikaku (1985)], for example, in the following manner.

A lectin recognizing the sugar chain structure of the heterodimer protein molecule included in the heterodimer protein composition is labeled, and the labeled lectin is subjected to the reaction with the sample heterodimer protein composition, followed by measurement of the amount of a complex of the labeled lectin with the heterodimer protein molecule.

Examples of the lectin used for identifying the sugar chain structure of the heterodimer protein molecule can include WGA (*T. vulgaris*-derived wheat-germ agglutinin), ConA (*C. ensiformis*-derived concanavalin A), RIC (*R. communis*- derived toxin), L-PHA (*P. vulgaris*-derived leukoagglutinin), LCA (*L. culinaris*-derived lentil agglutinin), PSA (*P. sativum*-derived Pea lectin), AAL (*Aleuria aurantia* Lectin), ACL (*Amaranthus caudatus* Lectin), BPL (*Bauhinia purpurea* Lectin), DSL (*Datura stramonium* Lectin), DBA (*Dolichos biflorus* Agglutinin), EBL (Elderberry Balk Lectin), ECL (*Erythrina cristagalli* Lectin), EEL (*Euonymus europaeus* Lectin), GNL (*Galanthus nivalis* Lectin), GSL (*Griffonia simplicifolia* Lectin), HPA (*Helix pomatia* Agglutinin), HHL (*Hippeastrum* Hybrid Lectin), Jacalin, LTL (*Lotus tetragonolobus* Lectin), LEL (*Lycopersicon esculentum* Lectin), MAL (*Maackia amurensis* Lectin), MPL (*Maclura pomifera* Lectin), NPL (*Narcissus pseudonarcissus* Lectin), PNA (Peanut Agglutinin), E-PHA (*Phaseolus vulgaris* Erythroagglutinin), PTL (*Psophocarpus tetragonolobus* Lectin), RCA (*Ricinus communis* Agglutinin), STL (*Solanum tuberosum* Lectin), SJA (*Sophora japonica* Agglutinin), SBA (Soybean Agglutinin), UEA (*Ulex europaeus* Agglutinin), VVL (*Vicia villosa* Lectin), WFA (*Wisteria floribunda* Agglutinin).

Lectin specifically recognizing the core fucose is preferably used, and specific examples thereof can include lentil lectin LCA (lentil agglutinin derived from *Lens culinaris*), pea lectin PSA (pea lectin derived from *Pisum sativum*), broad bean lectin VFA (agglutinin derived from *Vicia faba*), *Aleuria aurantia* lectin AAL (lectin derived from *Aleuria aurantia*) or the like.

8. Use of Heterodimer Protein Composition of the Present Invention

With respect to the heterodimer protein composition of the present invention, the heterodimer proteins having monovalent to tetravalent binding activity can be prepared by connecting a molecule-specific binding protein to the N-terminus and the C-terminus of the CH and CL-Fc (heterodimer scaffold protein; HSP) constituting the heterodimer protein molecule.

Therefore, the heterodimer protein composition of the present invention can be used as a heterodimer protein drug, because it can be tailored to have a molecular shape for the target antigen.

For example, if the heterodimer protein of the present invention is a monovalent antibody having a monovalent binding domain, it binds to one epitope of the target at 1:1, and thus does not cause cross-linkage of the antigen and is able to inhibit antigen activation and antigen activity.

Further, if the heterodimer protein of the present invention is a divalent antibody (also called bispecific antibody) having a divalent binding activity, it binds to two epitopes, thereby causing cross-linkage of two antigens or it binds to two antigens expressed on different cells, thereby causing cell-cell cross-linkage.

Further, when the heterodimer protein of the present invention causes cell-cell cross-linkage, immune cells can be collected around the target cells and activated by cross-linking an antigen on the target cell with an antigen on the surface of cells such as cytotoxic T cells (CTL), B cells, NK cells, macrophages, neutrophils, eosinophils, basophilis, and mast cells.

The antigen binding to the heterodimer protein of the present invention may be any antigen, and preferably include antigen molecules associated with cancer, immune diseases, allergic diseases or cardiovascular diseases. Examples thereof may include cytokines, chemokines, growth factors and receptors thereof, CD antigens or the like.

Examples of the cytokines or the growth factors can include interferon (hereinafter, referred to as IFN)-α, IFN-β, IFN-γ, interleukin (hereinafter, referred to as IL)-2, IL-3, IL-4, IL-5, IL-6, IL-7, IL-8, IL-9, IL-10, IL-12, IL-13, IL-15, IL-17, IL-18, IL-21, IL-23, IL-27, granulocyte colony-stimulating factor (G-CSF), granulocyte/macrophage colony stimulating factor (GM-CSF), macrophage colony stimulating factor (M-CSF), receptors thereof, or the like.

Examples of the chemokines can include SLC, ELC, I-309, TARC, MDC, MP-3α, CTACK and receptors of these chemokines.

Examples of growth factors can include Epidermal Growth Factor (EGF), vascular endothelial growth factor (VEGF), angiopoietin, fibroblast growth factor (FGF), hepatocyte growth factor (HGF), platelet-derived growth factor (PDGF), insulin-like growth factor (IGF), erythropoietin (EPO), TGFβ, ephrin, angiopoietin, Frizzled ligand, SDF-1, receptors thereof, or the like.

Examples of cluster of differentiation (hereinafter, referred to as CD) antigens can include CD2, CD3, CD4, CD7, CD10, CD14, CD16, CD19, CD20, CD21, CD22, CD23, CD24, CD28, CD32, CD37, CD40, CD44, CD52, CD64, CD53, CD56, CD72, CD73, CD74, CDw75, CDw76, CD77, CDw78, CD79a, CD79b, CD80 (B7.1), CD81, CD82, CD83, CDw84, CD85, CD86 (B7.2), CD98, human leukocyte antigen (HLA)-Class II, HLA-I, or the like.

Further, examples of the antigen involved in formation of pathologic state of tumor or the antigen for the antibody which regulates immunological function can include ganglioside GM1, GM2, GD2, GD3, Lewis X, Lewis Y, CD3, CD4, CD40, CD40 ligand, B7 family molecules (e.g., CD80, CD86, CD274, B7-DC, B7-H2, B7-H3, or B7-H4), ligand of B7 family molecules (e.g., CD28, CTLA-4, ICOS, PD-1, or BTLA), OX-40, OX-40 ligand, CD137, tumor necrosis factor (TNF) receptor family molecules (e.g., DR3, DR4, DR5, TNFR1, or TNFR2), TNF-related apoptosis-inducing ligand receptor (TRAIL) family molecules, receptor family of TRAIL family molecule (e.g., TRAIL-R1, TRAIL-R2, TRAIL-R3, or TRAIL-R4), receptor activator of nuclear factor kappa B ligand (RANK), RANK ligand, CD25, folate receptors, Mesothelin, cytokines [e.g., IL-1α, IL-1β, IL-4, IL-5, IL-6, IL-10, IL-13, transforming growth factor (TGF) β, or TNFα, or the like.], receptors of these cytokines, chemokines (e.g., SLC, ELC, I-309, TARC, MDC, or CTACK, or the like.), or receptors of these chemokines.

The proper target molecule of the monovalent antibody is exemplified by antigens that can be activated by dimerization or agglutination. Examples of the molecule having this property can include enzyme-linked receptors, cell adhesion molecules or the like. The enzyme-linked receptors can include receptor tyrosine-kinase, tyrosine-kinase-associated receptor, receptor serine-threonine kinase, and receptor guanylate cyclase.

Examples of the receptor tyrosine-kinase can include EGF receptor, insulin receptor, IGF-1 receptor, NGF receptor, PDGF receptor, M-CSF receptor, FGF receptor, VEGF receptor, Eph receptor or the like. Examples of the tyrosine-kinase-associated receptor can include cytokine receptor, Fc receptor or the like. Further, examples of the cell adhesion molecules can include cadherin, integrin or the like.

Specific examples thereof can include interleukin-1 receptor 1 (IL-1R1), interleukin-1 receptor accessory protein (IL-1RAP), hepatocyte growth factor receptor (c-Met), macrophage stimulating 1 receptor (RON), platelet-derived growth factor receptor (PDGFR), junctional adhesion molecule-like (JAML), nectin-like protein 5 (Necl-5), tumor necrosis factor receptor 1 (TNF-R1), tumor necrosis factor receptor 2 (TNF-R2), TNF-related apoptosis-inducing ligand receptor 1 (TRAIL-R1), TNF-related apoptosis-inducing ligand receptor 2 (TRAIL-R2), death receptor 3 (DR3), death receptor 6 (DR6), receptor activator of NF-kB (RANK), nerve growth factor receptor (NGFR), lymphotoxin-beta receptor (LTβR), OX40 (TNFRSF4), Fas (TNFRSF6), 4-1BB (TNFRSF9), Fn14 (TNFRSF12A), TACI (TNFRSF13B), BAFF-R (TNFRSF13C), HVEM (TNFRSF14), BCMA (TNFRSF17), GITR (TNFRSF18), TROY (TNFRSF19), ectodysplasin A1 receptor (EDAR), ectodysplasin A2 receptor (XEDAR), receptor expressed in lymphoid tissues (RELT), CD3, CD27, CD30, CD40, FcαRI, FcγRIII, FcεRI, or the like.

A drug comprising the heterodimer protein composition of the present invention can be administered alone as a therapeutic agent. However, it is preferably mixed with one or more pharmaceutically acceptable carriers and provided as a pharmaceutical preparation produced by an arbitrary method well known in the technical field of pharmaceutics.

It is preferable to use the administration route that is most effective for the treatment. Examples thereof can include oral administration and parenteral administration such as intraoral administration, intratracheal administration, intrarectal administration, subcutaneous administration, intramuscular administration and intravenous administration. In the case of a heterodimer protein preparation, intravenous administration is preferred.

Examples of the administration form can include spray, capsules, tablets, granules, syrup, emulsion, suppository, injection, ointment, tape, or the like.

Examples of the preparations suitable for oral administration can include emulsions, syrups, capsules, tablets, powders, granules or the like.

Liquid preparations such as emulsions and syrups can be prepared using, as additives, water, sugars such as sucrose, sorbitol, fructose, glycols such as polyethylene glycol, propylene glycol, oils such as sesame oil, olive oil, soybean oil, antiseptics such as p-hydroxybenzoate esters, flavors such as strawberry flavor, peppermint, or the like.

Capsules, tablets, powders, granules or the like can be prepared using, as additives, excipients such as lactose, glucose, sucrose, mannitol, disintegrating agents such as starch, sodium alginate, lubricants such as magnesium stearate, talc, binders such as polyvinyl alcohol, hydroxypropyl cellulose, gelatin, surfactants such as fatty acid esters, plasticizers such as glycerin, or the like.

Examples of the preparations suitable for parenteral administration can include injections, suppositories, sprays or the like.

Injections can be prepared using carriers comprising a salt solution, a glucose solution, or a mixture thereof, or the like. Alternatively, it is also possible to prepare powder injections by freeze-drying the heterodimer protein composition according to a conventional method and adding sodium chloride thereto.

Suppositories can be prepared using carriers such as cacao butter, hydrogenated fat, carboxylic acid or the like.

Sprays can be prepared using the heterodimer protein composition as it is, or using a carrier which does not stimulate the buccal or airway mucous membrane of the recipient and can facilitate absorption of the heterodimer protein composition by dispersing it as fine particles, or the like.

Specific examples of the carriers can include lactose, glycerin or the like. It is also possible to prepare aerosols, dry powders, or the like according to the properties of the heterodimer protein composition and the carriers used. For these parenteral preparations, the above-mentioned additives for the oral preparations can also be added.

The dose and administration frequency will vary depending on the desired therapeutic effect, the administration route, the period of treatment, age, body weight, or the like. However, a dose of the active ingredient for an adult person is generally 10 µg/kg to 20 mg/kg per day.

Furthermore, the anti-tumor effect of the heterodimer protein composition against various tumor cells can be examined by in vitro tests such as CDC activity measurement and ADCC activity measurement. In addition, examples of in vivo tests can include anti-tumor experiments using tumor systems in an experimental animal such as mice.

EXAMPLES

Figure 3A:
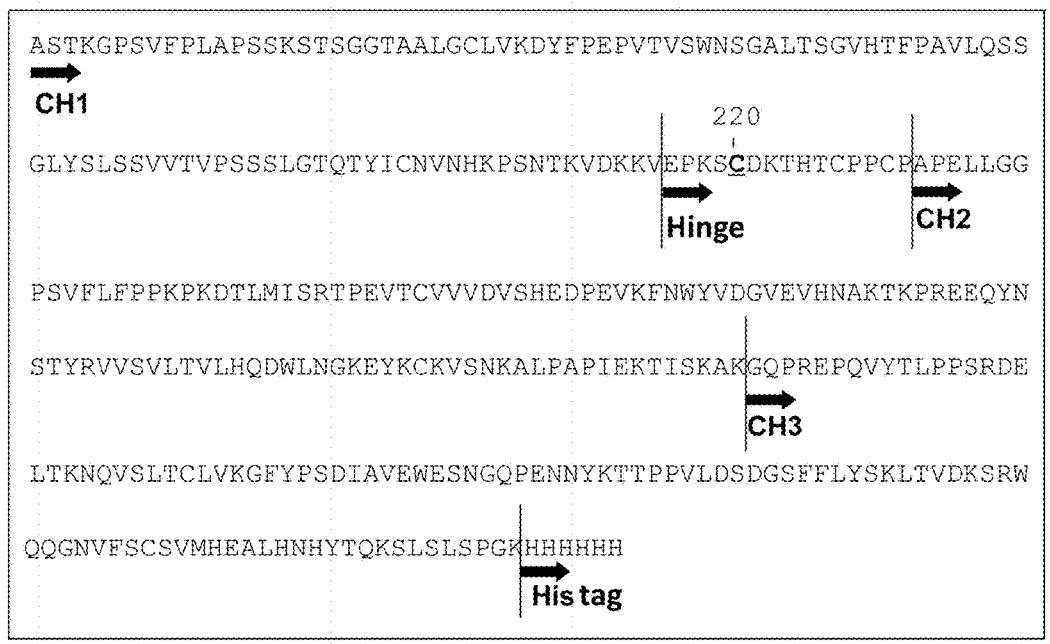
FIG. 3A shows the amino acid sequence (IgG1-CH) of the H chain constant region of IgG1 type monovalent antibody (SEQ ID NO: 6). The amino acid residues underlined represent amino acid residue substitution-introduced region (Table 1), and the numbers represent those defined by the EU index.
Figure 3B:
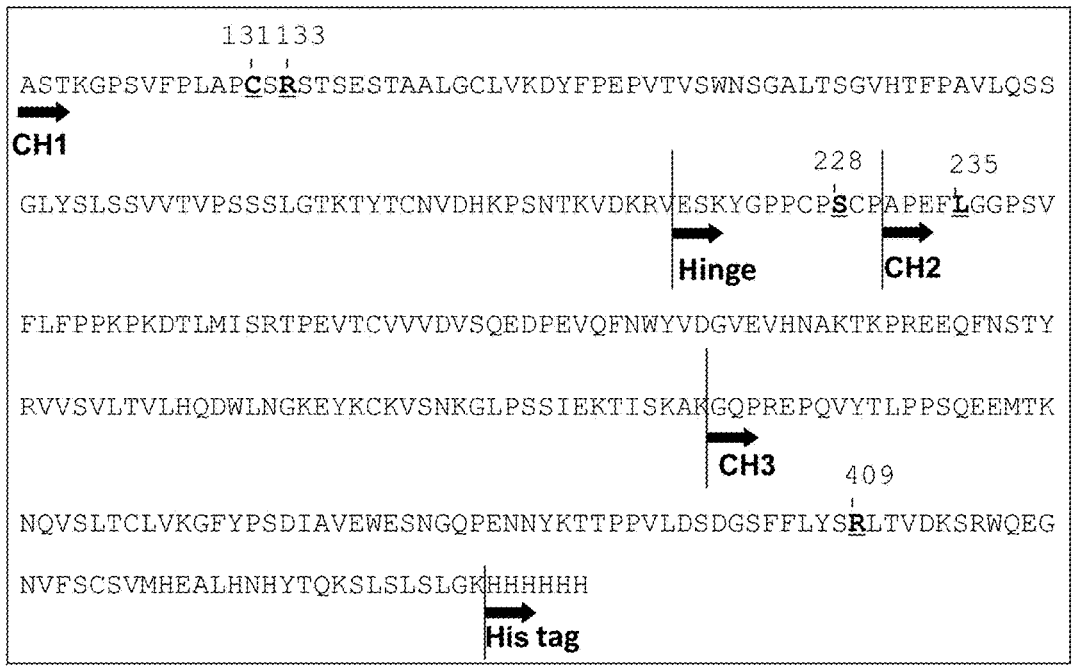
FIG. 3B shows the amino acid sequence (IgG4-CH) of the H chain constant region of IgG4 type monovalent antibody (SEQ ID NO: 8). The amino acid residues underlined represent amino acid residue substitution-introduced region (Table 1), and the numbers represent those defined by the EU index.

[Example 1] Construction of Heterodimer Protein Expression Vector (1) Introduction of Amino Acid Modification into H Chain Constant Region The amino acid sequences, IgG1-CH and IgG4-CH (SEQ ID NOs: 6 and 8) (FIGS. 3A and 3B) were respectively designed by connecting 6 histidine residues (hereinafter, referred to as His tag) to the C-terminus of the amino acid sequences (SEQ ID NOs: 2 and 4) (nucleotide sequence of DNA: SEQ ID NOs: 1 and 3) of human IgG1 CH (Mol. Immunol., 2000; 37: 1035) and human IgG4 CH (J. Immunol. Methods, 2005; 306: 151), and the nucleotide sequences of DNA (SEQ ID NOs: 5 and 7) encoding the amino acid sequences were prepared. The recognition sequences for the restriction enzymes ApaI and BamHI were introduced into the 5'- and 3'-terminals of the nucleotide sequences of DNA so as to prepare DNA fragments of IgG1-CH and IgG4-CH.

The prepared IgG1-CH fragment and IgG4-CH fragment and a plasmid pBluescript SK-(manufactured by Stratagene) were treated with the restriction enzymes, ApaI and BamHI, and then ligation was performed, respectively. Each fragment was inserted into the pBluescript SK-vector to prepare an IgG1-CH vector and an IgG4-CH vector.

CH comprising an amino acid residue substitution was prepared by using the prepared IgG1-CH and IgG4-CH vectors as templates and a QuikChange (registered trade name) II XL Site-Directed Mutagenesis Kit (manufactured by Stratagene). Thus, IgG1-CH vectors and IgG4-CH vectors, each including the amino acid residue substitutions shown in Table 1, were prepared. Cys residue at position 220 present in the hinge domain of IgG1 is known to form an intermolecular disulfide bond with Cys residues of L chain. Thus, it was substituted with Ser to remove the disulfide bond.

Meanwhile, Cys residue at position 131 present in the CH1 domain of IgG4 is known to form an intermolecular disulfide bond with Cys residue of L chain. On the basis of this fact that Ser and Lys residues are located at positions 131 and 133 of IgG1, the partial sequences of C131/R133 including Cys residue involved in the disulfide bond between CH1-CL were substituted with C131S/R133K in the IgG4-type monovalent antibody to be made for IgG1-type sequence, in order to remove the disulfide bond and to reduce antigenicity.

Further, Ser residue at position 228 of the hinge domain of IgG4 and Arg residue at position 409 of the CH3 domain of IgG4 are known to be involved in IgG4-specific Fab-arm exchange. Because Pro and Lys are located at positions 228 and 409 of IgG1, respectively, amino acid residue substitutions of S228P and R409K were added to H chain of the IgG4-type monovalent antibody, in order to inhibit Fab-arm exchange. Further, amino acid residue substitution of L235E in IgG4 can reduce the effector activity.

Hereinafter, unless otherwise particularly mentioned, the amino acid sequence was represented as 1 letter based on the EU index of Kabat et al. [Sequences of Proteins of Immunological Interest, US Dept. Health and Human Services (1991)]. In addition, the amino acid residue before substitution was described before a number, and the amino acid residue after substitution was described after the number. The nucleotide sequences of DNA of IgG H chain are represented by SEQ ID NOs: 9, 11, 13, 15, 17 and 19, respectively.

Subsequently, a gene sequences was prepared by linking 3'-untranslated region (UTR) of L light chain included in pKANTEX93 vector (J. Immunol. Methods, 2005; 306: 151) and a recognition sequence for the restriction enzyme KpnI to the 3'-terminus of the CL-Fc, and linking a recognition sequence for the restriction enzyme BsiWI to the 5'-terminus thereof.

The prepared BsiWI-KpnI gene fragment was cloned into a pTA2 vector (manufactured by TOYOBO) included in a Target Clone-Plus-kit (manufactured by TOYOBO) so as to prepare an IgG1-L vector and an IgG4-L vector.

Because the Cys residue at position 214 of human κ chain is known to form an intermolecular disulfide bond with Cys residue of H chain, it was substituted with Ser, thereby

TABLE 1

Amino acid substitution introduced in CH

| Sequence name | DNA SEQ ID NO: | Protein SEQ ID NO: | Subclass | CH1 | Hinge | CH2 | CH3 |
|---|---|---|---|---|---|---|---|
| 1H0 | 9 | 10 | IgG1 | — | — | — | — |
| 1H1 | 11 | 12 | IgG1 | — | C220S | — | — |
| 4H0 | 13 | 14 | IgG4 | — | — | — | — |
| 4H1 | 15 | 16 | IgG4 | C131S/R133K | — | — | — |
| 4H2 | 17 | 18 | IgG4 | C131S/R133K | S228P | — | R409K |
| 4H3 | 19 | 20 | IgG4 | C131S/R133K | S228P | L235E | R409K |

(2) Introduction of Amino Acid Modification into Artificial Constant Region Prepared by Fusion of Human κ Chain Constant Region (CL) and IgG Antibody Fc The C-terminus of the human κ chain constant region (SEQ ID NOs: 57 and 58) was bound with the hinge domain, CH2 domain and CH3 domain of the constant region of human IgG1 or human IgG4 in this order to design the amino acid sequence of CL-Fc (hereinafter, referred to as IgG1-L and IgG4-L) (SEQ ID NO: 22 and SEQ ID NO: 26) (FIGS. 4A and 4B). Then, nucleotide sequences of DNA (SEQ ID NO: 21 and SEQ ID NO: 25) encoding the amino acid sequences were prepared. Hereinafter, the second polypeptide comprising CL-Fc is referred to as L chain in some cases.

Meanwhile, a hinge domain having a deletion of the amino acid residues EPKSC at positions from 216 to 220 of the EU index corresponding to 5 amino acid residues from the N-terminus of the hinge domain was used in the IgG1-L (FIG. 4A). As described above, Cys residues involved in intermolecular disulfide bond with L chain exist in the hinge domain of IgG1. To remove this, EPKSC was deleted.

removing the disulfide bond. Further, His residue at position 435 and Tyr residue at position 436 of the CH3 domain of IgG1 and IgG4 are known to be involved in Protein A binding of an antibody.

Arg and Phe exist at positions 435 and 436 of IgG3 having no Protein A-binding activity. Thus, amino acid residue substitutions of H435R and Y436F were introduced into the L chain to reduce the Protein A-binding activity of the CL-Fc chain of the monovalent antibody.

CL-Fc including the amino acid substitution shown in Table 2 was prepared by using the IgG1-L vector and IgG4-L vector as templates and the QuikChange (registered trade name) IIXL Site-Directed Mutagenesis Kit (manufactured by Stratagene). The nucleotide sequences of DNA of each CL-Fc were represented by SEQ ID NOs: 21, 23, 25, 27, 29, 31 and 33, respectively.

TABLE 2

Amino acid substitution introduced in CL-Fc

| Sequence name | DNA SEQ ID NO: | Protein SEQ ID NO: | Subclass | CH1 | Hinge | CH2 | CH3 |
|---|---|---|---|---|---|---|---|
| 1L0 | 21 | 22 | IgG1 | — | Deletion (216-220) | — | — |
| 1L1 | 23 | 24 | IgG1 | C214S | Deletion (216-220) | — | H435R/Y436F |
| 4L0 | 25 | 26 | IgG4 | — | — | — | — |
| 4L1 | 27 | 28 | IgG4 | C214S | — | — | — |
| 4L2 | 29 | 30 | IgG4 | C214S | — | — | H435R/Y436F |
| 4L3 | 31 | 32 | IgG4 | C214S | S228P | — | R409K/H435R/Y436F |
| 4L4 | 33 | 34 | IgG4 | C214S | S228P | L235E | R409K/H435R/Y436F |

(3) Construction of Monovalent Antibody Expression Vector

A heterodimer protein having a monovalent binding domain (hereinafter, abbreviated to monovalent antibody) in which the H chain variable region (VH) and L chain variable region (VL) of IgG antibody were linked to CH and CL-Fc prepared in Example 1(1) and (2) was prepared in the following manner. Hereinafter, the first polypeptide is referred to as H chain and the second polypeptide is referred to as L chain in some cases.

As the binding proteins to be bound with CH and CL-Fc, the variable regions of anti-CD20 antibody humanized B-Ly1 (B-HH2 and B-KV1, hereinafter, referred to as GA101) (Japanese Patent Publication No. 2010-81940) and anti-HER2 antibody humAb4D5-8 (hereinafter, referred to as 4D5) (Proc. Natl. Acad. Sci. U.S.A., 1992; 89: 4285) were used. As the nucleotide sequences of DNA and amino acid sequences, GA101-VH (SEQ ID NOs: 35 and 36), GA101-VL (SEQ ID NOs: 37 and 38), 4D5-VH (SEQ ID NOs: 39 and 40) and 4D5-VL (SEQ ID NOs: 41 and 42) were used.

The recognition sequence for the restriction enzyme NotI was introduced into the 5'-terminals of the nucleotide sequences of DNA encoding the amino acid sequences of VHs of GA101 antibody and 4D5 antibody, and the recognition sequence for the restriction enzyme ApaI was introduced into the 3'-terminals thereof so as to prepare nucleotide sequences of DNA, which were inserted into the NotI-ApaI site of a pKANTEX93 vector (J. Immunol. Methods, 2005; 306: 151).

Consequently, an expression vector pKANTEX93/GA101-VH including anti-CD20 humanized antibody VH and an expression vector pKANTEX93/4D5-VH including anti-HER2 humanized antibody VH were prepared.

Subsequently, the recognition sequence for the restriction enzyme BsiWI was introduced into the 5'-terminals of the nucleotide sequences of DNA encoding the amino acid sequences of VLs of GA101 antibody and 4D5 antibody and the recognition sequence for the restriction enzyme KpnI was introduced into the 3'-terminals thereof so as to prepare nucleotide sequences of DNA, each was inserted into the NotI-ApaI site of the pKANTEX93/GA101-VH vector or the pKANTEX93/4D5-VH vector, respectively.

Consequently, an anti-CD20 humanized antibody GA101 expression vector pKANTEX93/GA101, and an anti-HER2 humanized antibody expression vector pKANTEX93/humAb4D5-8 were obtained.

CHs included in the ApaI-BamHI site of anti-CD20 humanized antibody GA101 expression vector pKANTEX93/GA101 and anti-HER2 humanized antibody expression vector pKANTEX93/humAb4D5-8 were substituted with a variety of IgG1-CH or IgG4-CH prepared in Example 1 (1) above.

Subsequently, CL included in the BsiWI-KpnI site of the expression vectors was substituted with a variety of CL-Fc that was prepared by fusion of hinge domain, CH2 domain and CH3 domain with the CL prepared in Example 1(2) above.

Figure 5:
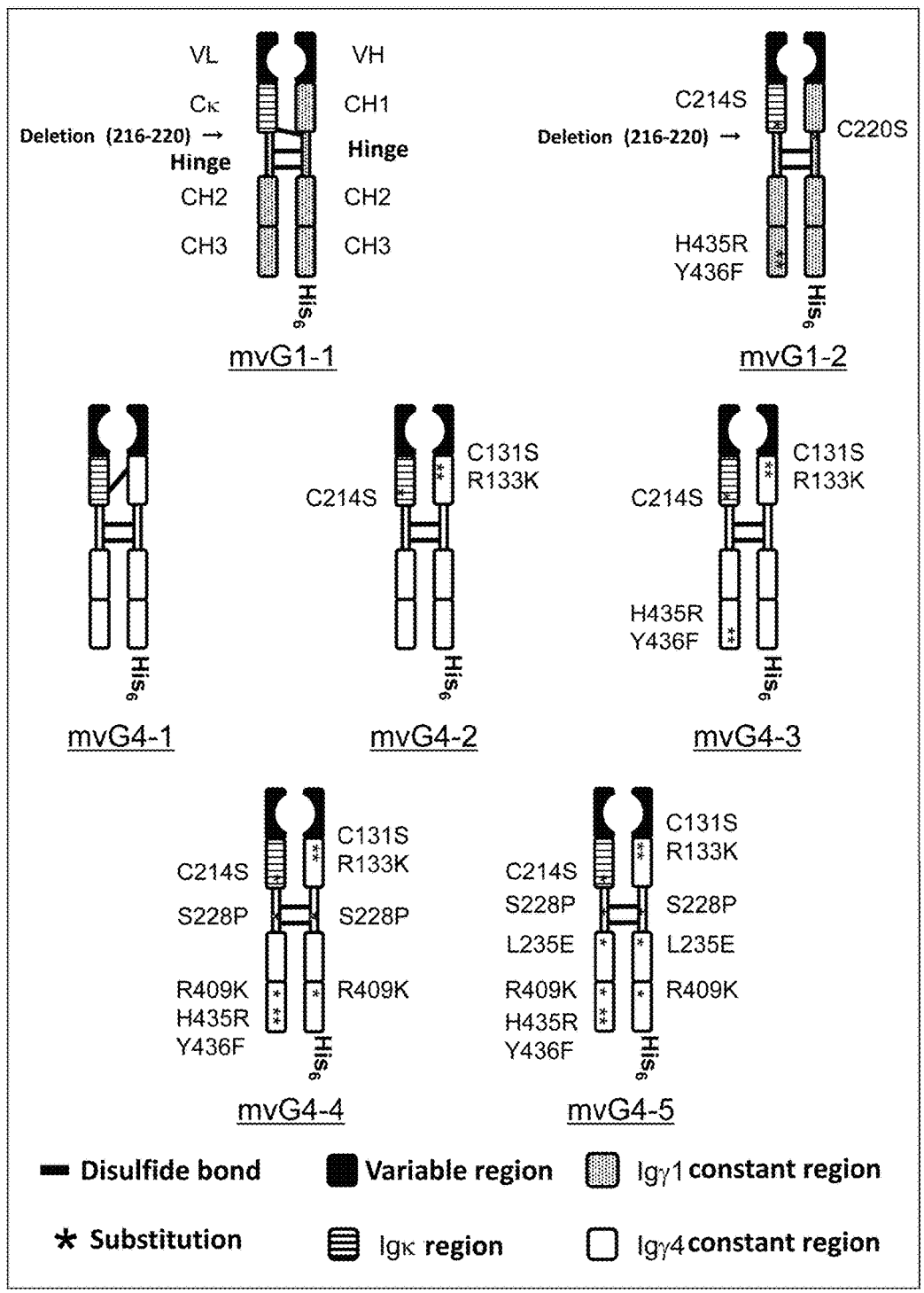
FIG. 5 shows the structures of various monovalent antibodies.

Consequently, a variety of monovalent antibody expression vectors composed of the first polypeptide comprising VH-CH and the second polypeptide comprising VL-CL-Fc were prepared (Table 3). Further, the structures of various monovalent antibody molecules are shown in FIG. 5.

TABLE 3

Combination list of variable region, CH and CL-Fc of various monovalent antibodies

| Variable region | CH | CL-Fc | Expression vector |
| --- | --- | --- | --- |
| humAb4D5-8 | 1H0 | 1L0 | pKANTEX93/mvG1-1 |
| GA101 | 1H1 | 1L1 | pKANTEX93/mvG1-2 |
| humAb4D5-8 | 4H0 | 4L0 | pKANTEX93/mvG4-1 |
| humAb4D5-8 | 4H1 | 4L1 | pKANTEX93/mvG4-2 |

TABLE 3-continued

Combination list of variable region, CH and CL-Fc of various monovalent antibodies

| Variable region | CH | CL-Fc | Expression vector |
| --- | --- | --- | --- |
| humAb4D5-8 | 4H1 | 4L2 | pKANTEX93/mvG4-3 |
| humAb4D5-8 | 4H2 | 4L3 | pKANTEX93/mvG4-4 |
| humAb4D5-8 | 4H3 | 4L4 | pKANTEX93/mvG4-5 |

[Example 2] Construction of Bispecific Heterodimer Protein Expression Vector

Figure 6:
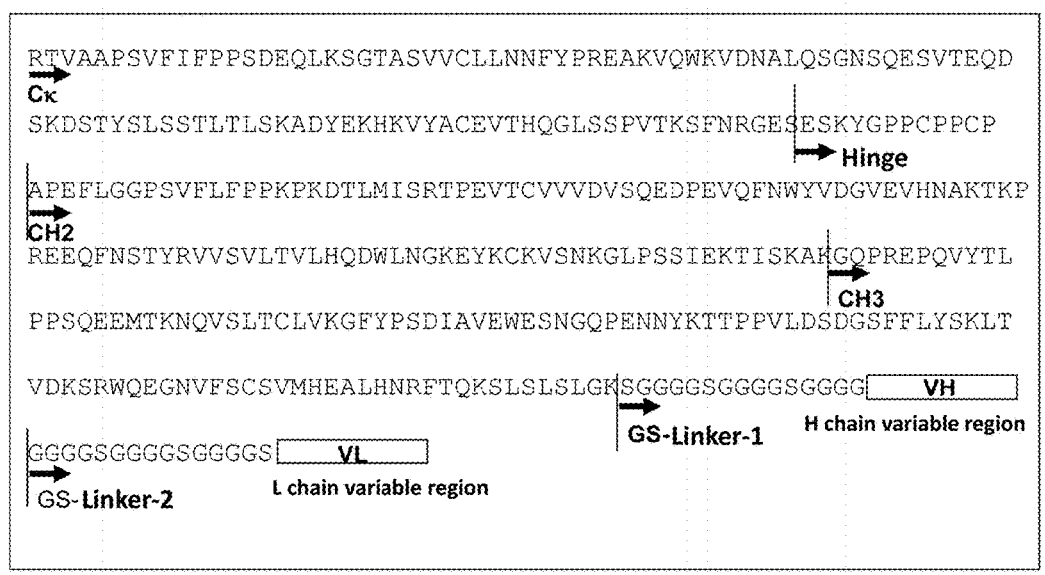
FIG. 6 shows the amino acid sequence of the second polypeptide of bispecific antibody. For example, the amino acid sequence of amino acid residues 13 to 707 of SEQ ID NO: 54 (SEQ ID NO: 61) corresponds to an amino acid sequence of FIG. 6 in which VH and VL are those derived from the 2F2 antibody. The amino acid sequence of amino acid residues 113 to 705 of SEQ ID NO: 56 corresponds to the amino acid sequence of FIG. 6 in which VH and VL are those of the 4D5 antibody.
Figure 7:
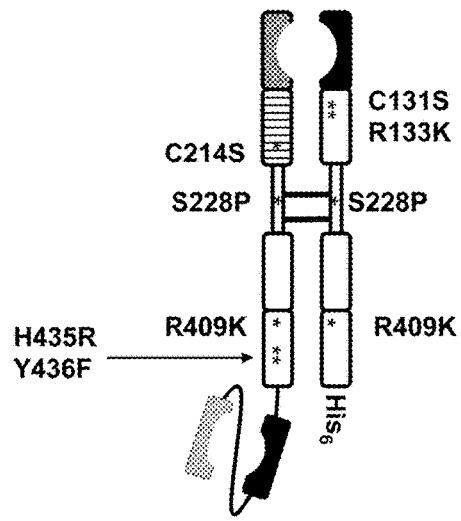
FIG. 7 shows the structure of bispecific antibody.

In order to construct a heterodimer protein having a divalent binding domain (hereinafter, referred to as bispecific antibody), a bispecific antibody was designed to be composed of the first polypeptide having VH linked at the N-terminus of CH and the second polypeptide having VL linked at the N-terminus of CL-Fc and a single chain Fv (scFv)-type variable region linked at the C-terminus thereof (FIGS. 6 and 7).

The bispecific antibody has a divalent binding activity, in which the binding domain composed of VH-VL specifically binds to CD74 and the scFv linked at the C-terminus of the second polypeptide specifically binds to Her2 or CD20. The bispecific antibody was prepared in the following manner.

(1) Construction of Anti-CD74 Antibody Expression Vector

As the anti-CD74 antibody, the known anti-CD74 humanized antibody hLL1 (U.S. Pat. No. 7,312,318) (SEQ ID NOs: 43 to 46) was used. The recognition sequence for a restriction enzyme was linked at the 5'- and 3'-terminals of VH and VL of the anti-CD74 humanized antibody hLL1 in the same manner as in Example 1(3) above, which was inserted into a pKANTEX93 vector, thereby preparing an anti-CD74 humanized antibody expression vector, pKANTEX93/hLL1.

(2) Construction of Anti-CD74 IgG4-Type Monovalent Antibody Expression Vector

In the same manner as in Example 2(1), DNA fragments of VH and VL of the anti-CD74 humanized antibody hLL1 antibody were prepared, and inserted into the NotI-ApaI site and the EcoRI-BsiWI site of the pKANTEX93/mvG4-4 vector prepared in Example 1(3). Consequently, an anti-CD74 IgG4-type monovalent antibody expression vector, pKANTEX93/G4-4/hLL1 was prepared.

(3) Construction of CD74-HER2 Bispecific Antibody and CD74-CD20 Bispecific Antibody Expression Vectors In order to prepare CD74-HER2 bispecific antibody and CD74-CD20 bispecific antibody which was prepared by fusion of anti-HER2scFv or anti-CD20 scFv at the C-terminus of the second polypeptide of the anti-CD74 IgG4-type monovalent antibody prepared in Example 2(2) above, CL-Fc and scFv were linked to each other via a linker composed of 15 amino acid residues of [Ser-Gly-Gly-Gly-Gly]×3 (hereinafter, referred to as GS linker) (SEQ ID NOs: 47 and 48) so as to design CL-Fc-linker-VH-linker-VL (FIGS. 6 and 7). Further, each scFv was prepared in the following manner.

The VH and VL sequences of anti-HER2 humanized antibody 4D5-8 described in Example 1(3) above were used in the anti-HER2 antibody, and the VH and VL sequences (SEQ ID NOs:49-52) of anti-CD20 antibody 2F2 (US Patent Application Publication No. 2004/0167319) was used for the anti-CD20 antibody.

A stop codon of CL-Fc of the anti-CD74 IgG4-type monovalent antibody expression vector pKANTEX93/G4-4/hLL1 was deleted, and subsequently, the nucleotide sequences of DNA of CD74VL-CL-Fc-2F2scFv and CD74VL-CL-Fc-4D5scFv which were prepared by linking the nucleotide sequence of DNA encoding the GS linker, DNA encoding VH, DNA encoding the linker composed of 15 amino acid residues of [Gly-Gly-Gly-Gly-Ser]×3, and DNA encoding VL were designed (SEQ ID NOs: 53 to 56).

Subsequently, anti-HER2 4D5-8scFv or anti-CD20 2F2scFv was inserted into the anti-CD74 IgG4-type monovalent antibody expression vector, pKANTEX93/G4-4/hLL1 to prepare pKANTEX93/G4-4/hLL1-4D5-8scFv and pKANTEX93/G4-4/hLL1-2F2scFv, respectively.

[Example 3] Production of Heterodimer Protein (1) Expression of Heterodimer Protein Cell culture was performed at 37° C. in a 5% $CO_2$ incubator. In order to express a variety of monovalent antibodies and bispecific antibodies, introduction of the expression vectors was performed in the following manner.

8 μg of various monovalent antibody expression vectors or bispecific antibody expression vectors were added to $4 \times 10^6$ of Chinese hamster ovary cell CHO/DG44 cell (Somatic Cell Mol. Genet., 12, 555, 1986) or α1,6-fucosyltransferase gene (FUT8)-knockout CHO/DG44 cell (hereinafter, abbreviated to CHO/FUT8KOcell) (U.S. Pat. No. 6,946,292), and gene was introduced by electroporation method [Cytotechnology, 3, 133(1990)]. The names of the host cells, expression vectors, and heterodimer proteins to be produced are summarized in Table 4.

The heterodimer protein composition prepared by CHO cells has fucose binding to N-acetylglucosamine included in the reducing end of the N-glycoside sugar chain bound to Fc, but the heterodimer protein composition prepared by CHO/FUT8KO cells has no fucose binding thereto at the sugar chain. Hereinafter, F (fucosylated) and DF (defucosylated) were added to the sample name of the heterodimer protein composition prepared by each cell.

After gene introduction, each cell was cultured in an IMDM medium (manufactured by GIBCO) [hereinafter, abbreviated to IMDM-(10)] containing 10% dialyzed fetal bovine serum (hereinafter, abbreviated to dFBS) for 2 days, and then the medium was replaced with IMDM-(10) [hereinafter, abbreviated to IMDM-(10G)] containing 0.5 mg/mL G418 sulfate (NACALAI TESQUE, INC.) to continue the culture, thereby obtaining a G418 resistant cell line.

$3 \times 10^5$ cell/mL of G418 resistant cell line was suspended in IMDM-(10G) and cultured for 3 days, and then the medium was replaced with Excell302 (manufactured by SAFC Biosciences) to perform the culture for 7 to 11 days and then culture supernatant was recovered.

TABLE 4

List of combination and sample name of vector and host cell

| Expression vector | Host cell | |
|---|---|---|
| | CHO/DG44 | CHO/FUT8KO |
| pKANTEX93/humAb4D5-8 | — | 4D5/IgG1 DF |
| pKANTEX93/GA101 | GA101/IgG1 F | GA101/IgG1 DF |
| pKANTEX93/mvG1-1 | — | 4D5/mvG1-1 DF |
| pKANTEX93/mvG1-2 | GA101/mvG1-2 F | GA101/mvG1-2 DF |
| pKANTEX93/mvG4-1 | — | 4D5/mvG4-1 DF |

TABLE 4-continued

List of combination and sample name of vector and host cell

| Expression vector | Host cell | |
|---|---|---|
| | CHO/DG44 | CHO/FUT8KO |
| pKANTEX93/mvG4-2 | — | 4D5/mvG4-2 DF |
| pKANTEX93/mvG4-3 | — | 4D5/mvG4-3 DF |
| pKANTEX93/mvG4-4 | 4D5/mvG4-4 F | 4D5/mvG4-4 DF |
| pKANTEX93/mvG4-5 | 4D5/mvG4-5 F | — |
| pKANTEX93/hLL1 | hLL1/IgG1 F | |
| pKANTEX93/G4-4/hLL1 | hLL1/mvG4-4 F | — |
| pKANTEX93/G4-4/hLL1-4D5-8scFv | hLL1-4D5/mvG4-4 F | — |
| pKANTEX93/G4-4/hLL1-2F2scFv | hLL1-2F2/mvG4-4 F | — |

(2) Purification of Heterodimer Protein

The culture supernatants of the various monovalent antibodies and bispecific antibodies obtained in Example 3(1) above were passed through a column packed with ProSep-vA High Capacity (manufactured by MILLIPORE) carrier at a flow rate of 0.5 to 1.0 mL/min. The column was washed with phosphate buffer saline (PBS), and then proteins were eluted using 0.1 M citrate buffer of pH 5.0 to pH 3.0, and immediately neutralized with 2 M Tris-hydrochloric acid buffer (pH 8.0).

Purification of 4D5/mvG4-3 DF and 4D5/mvG4-4 DF was also performed using a Protein G carrier. The culture supernatant was passed through the column packed with ProSep-G (manufactured by MILLIPORE) carrier at a flow rate of 0.5 to 1.0 mL/min. The column was washed with PBS, and then protein was eluted using 0.1 M citrate buffer of pH 5.0 to pH 2.5, and immediately neutralized with 2 M Tris-hydrochloric acid buffer (pH 8.0).

The elution fraction showing a high protein concentration was dialyzed against a buffer (hereinafter, abbreviated to citrate buffer) containing 10 mM citric acid, of which pH was adjusted to 6.0 with sodium hydroxide, and 150 mM sodium chloride. The sample was recovered, and a low-concentration sample was concentrated by an ultrafiltration filter (manufactured by MILLIPORE), and sterilized using a 0.22 μm filter (manufactured by MILLIPORE). The protein concentration was calculated from absorbance at 280 nm ($OD_{280}$).

The sample was further purified by gel filtration chromatography, and used in the in vitro activity test. A Superdex 200 10/300 GL column (GE Healthcare) was connected to a High speed liquid chromatography system AKTA explore 10S (GE Healthcare), and the citrate buffer was used as a running buffer, and the sample was passed through the column at a flow rate of 0.5 mL/min. The fractions detected as peaks around 25 to 30 minutes were recovered, and used for analysis.

(3) SDS-PAGE Analysis of Heterodimer Protein

The various monovalent antibodies purified using Protein A were subjected to SDS-PAGE analysis. The samples were adjusted with a buffer (hereinafter, abbreviated to sample buffer) containing 10% sodium dodecyl sulfate, 50% glycerol, and 0.3 M Tris hydrochloric acid (pH 6.8) containing 0 mM dithiothreitol (DTT) (non-reducing conditions) or 10 mM DTT (reducing conditions), and treated at 100° C. for 5 minutes, and 1 μg/lane thereof was loaded in a polyacrylamide gel (ATTO catalog No. E-T520L) for electrophoresis. As a molecular weight marker, Precision plus protein all blue standards (Bio-Rad Laboratories Inc.) were used and added in an amount of 5 μL/lane. After gel recovery, staining was performed using Quick CBB (Wako Pure Chemical Industries, Ltd.) according to the product procedure manual.

Figure 8A:
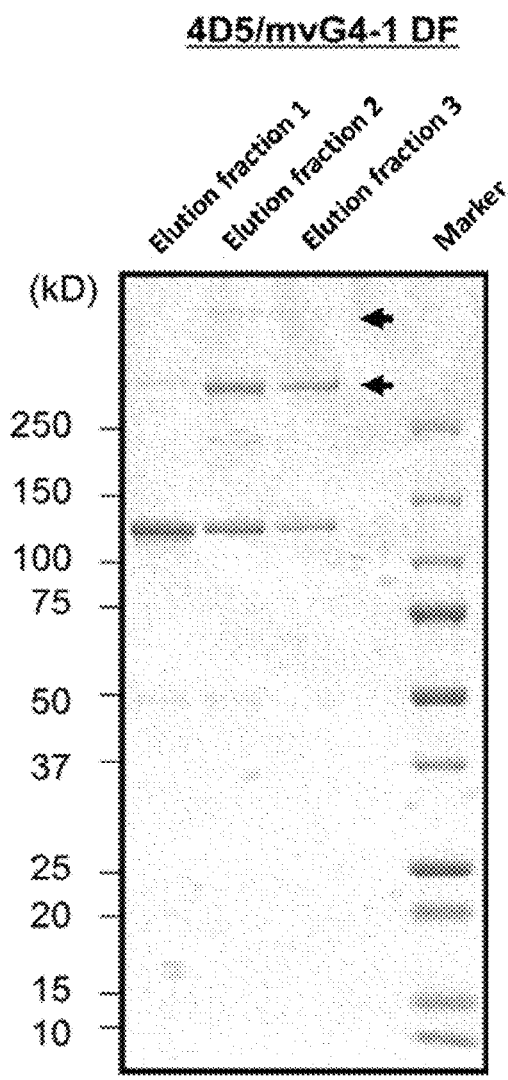
FIGS. 8A (a) and (b) show the results of SDS-PAGE analysis of anti-HER2 IgG4 type monovalent antibodies, 4D5/mvG4-1 DF and 4D5/mvG4-2 DF under non-reducing conditions.
In the SDS-PAGE analysis, elution fractions 1 to 3 eluted at each pH in Protein A purification were used. Arrows in the figure represent multimer bands.
Figure 8B:
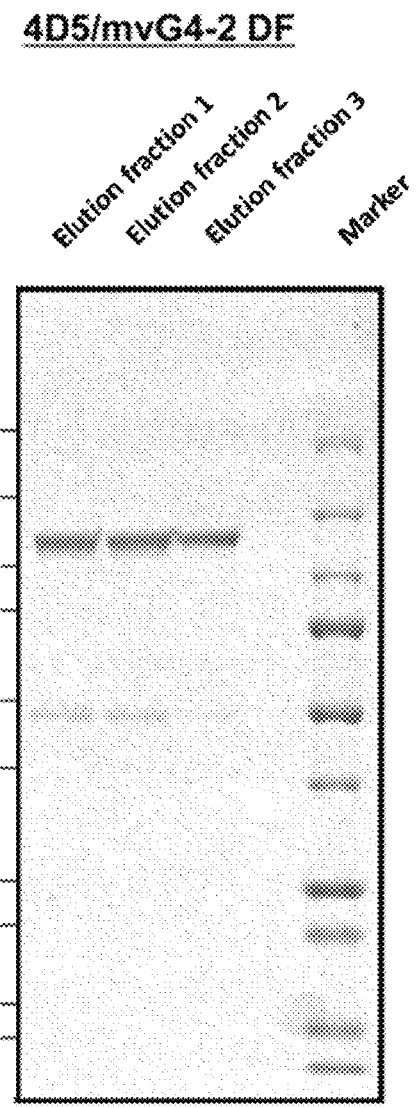
FIG. 8B shows the results of SDS-PAGE analysis of anti-HER2 IgG4 type monovalent antibodies, 4D5/mvG4-3 DF and 4D5/mvG4-4 DF under non-reducing conditions. In the SDS-PAGE analysis, purified proteins collectively eluted at pH 3.0 in Protein A purification were used. Arrows in the figure represent halfmer bands.
Figure 8C:
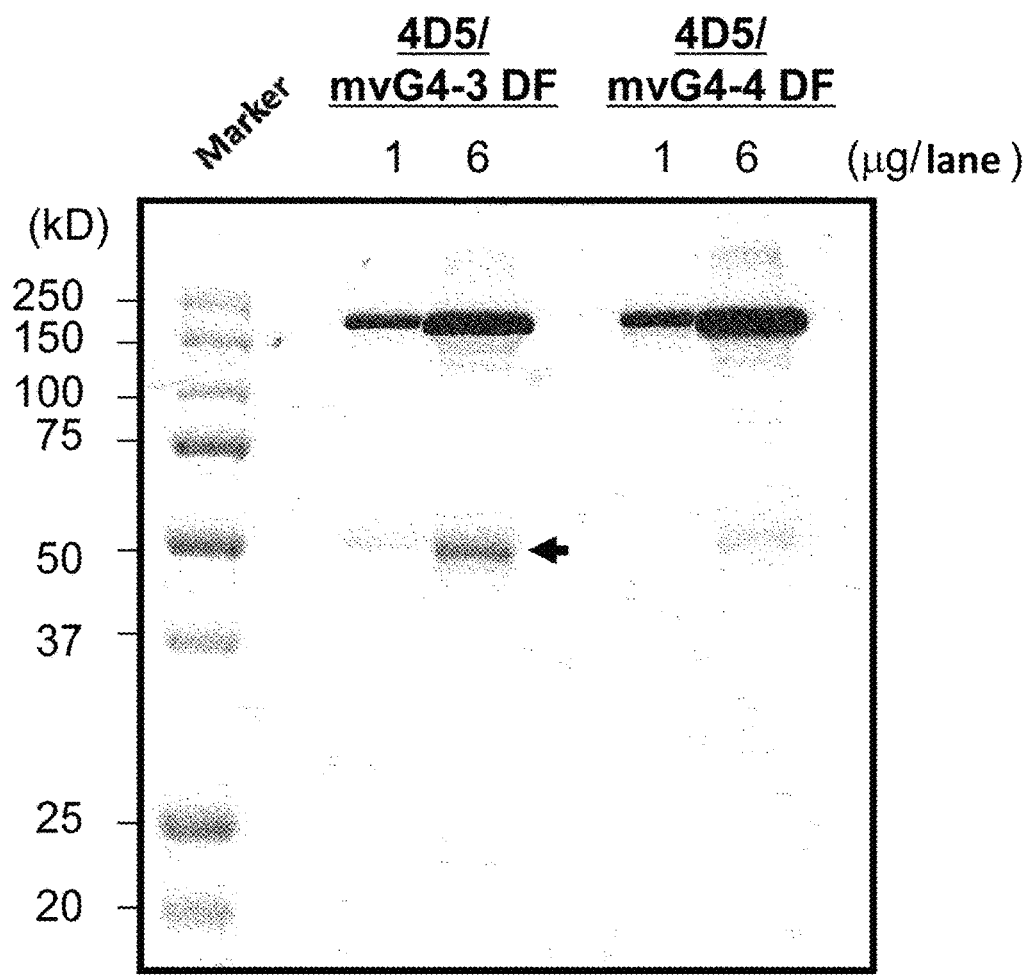

As a result, both H chain and L chain of the monovalent antibody had a molecular weight of approximately 50 kDa. In the SDS-PAGE under the non-reducing conditions, plural bands at 250 kDa or greater which were predicted as a multimer, a band around approximately 100 kDa which was predicted as a monomer composed of two polypeptide chains, and a band around approximately 50 kDa which was predicted as a halfmer composed of one polypeptide chain were recognized (FIGS. 8A, 8B and 8C).

In anti-HER2 IgG4-type monovalent antibody 4D5/mvG4-1 DF, plural bands of 250 kDa or greater which were predicted as a multimer were detected, it was indicated that plural multimers were formed. However, in 4D5/mvG4-2 DF composed of H chain including C131S/R133K substitutions and L chain including C214S substitution, multimers were hardly detected (FIGS. 8A and 8B).

Therefore, it was found that in the heterodimer protein composed of the first polypeptide comprising IgG4-CH and the second polypeptide comprising IgG4-L, substitution of H chain C131S/R133K, substitution of L chain C214S, and substitutions of H chain C131S/R133K and L chain C214S deleting Cys residue involved in disulfide bonds between IgG4-CH and Cκ are able to inhibit multimer formation caused by intermolecular disulfide bonds.

Similarly, bands of multimers were not detected in 4D5/mvG4-3 DF, 4D5/mvG4-4 DF, 4D5/mvG4-4 F, and 4D5/mvG4-5 F having substitutions of H chain C131S/R133K and L chain C214S. Further, the multimers were clearly detected in 4D5/mvG1-1 DF, but not detected in GA101/mvG1-2 DF and GA101/mvG1-2 F including substitutions of H chain C220S and L chain C214S.

Therefore, it was found that in the heterodimer protein composed of the first polypeptide comprising IgG1-CH and the second polypeptide comprising IgG1-L, substitution of H chain C220S, substitution of L chain C214S, and substitutions of H chain C220S and L chain C214S deleting Cys residues involved in disulfide bonds between IgG1-CH and Cκ are able to inhibit multimer formation.

On the other hand, in 4D5/mvG4-1 DF, 4D5/mvG4-2 DF and 4D5/mvG4-3 DF, bands around approximately 50 kDa which was predicted as a halfmer were detected. However, in 4D5/mvG4-4 DF, 4D5/mvG4-4 F and 4D5/mvG4-5 F including substitutions of S228P/R409K in both H chain and L chain, halfmer bands were not recognized. Therefore it was indicated that substitution of S228P, substitution of R409K and substitutions of S228P/R409K in H chain and L chain are able to inhibit halfmer formation (FIG. 8C).

These results suggest that the heterodimer protein composition of the present invention is a composition having reduced amounts of multimer, halfmer, and multimer/halfmer generated during production of the heterodimer protein.

[Example 4] Component Analysis of Monovalent Antibody (1) Component Separation by Cation Exchange Chromatography In order to perform a detailed component analysis of anti-HER2 IgG4 type monovalent antibody 4D5/mvG4-2 DF that was purified by affinity purification using the Protein A column in Example 3 described above, cation exchange chromatography was performed. 4D5/mvG4-2 DF is an IgG4 type monovalent antibody including amino acid residue substitution of C214S in CL and amino acid residue substitutions of C131S/R133K in CH1 and having no fucose that is bound to N-acetylglucosamine included in the reducing end of N-glycoside sugar chain bound to Fc.

A WCX-10 (manufactured by DIONEX) column was connected to High Performance Liquid Chromatography (HPLC) analysis equipment (LC-10Avp series, SHIMADZU Corporation), and a buffer of 10 mM sodium phosphate at pH 6.2 (hereinafter, abbreviated to Buffer A) was used as a staring buffer, and a buffer of 10 mM sodium phosphate and 500 mM sodium chloride at pH 6.2 (hereinafter, abbreviated to Buffer B) was used as an elution buffer.

After applying the sample, buffer A was applied at a flow rate of 1 mL/min, and analysis was performed for 30 minutes with 1% increase of the ratio of buffer B per minute. Then, the running buffer was replaced with buffer B, and analysis was performed for 10 minutes.

Figure 9:
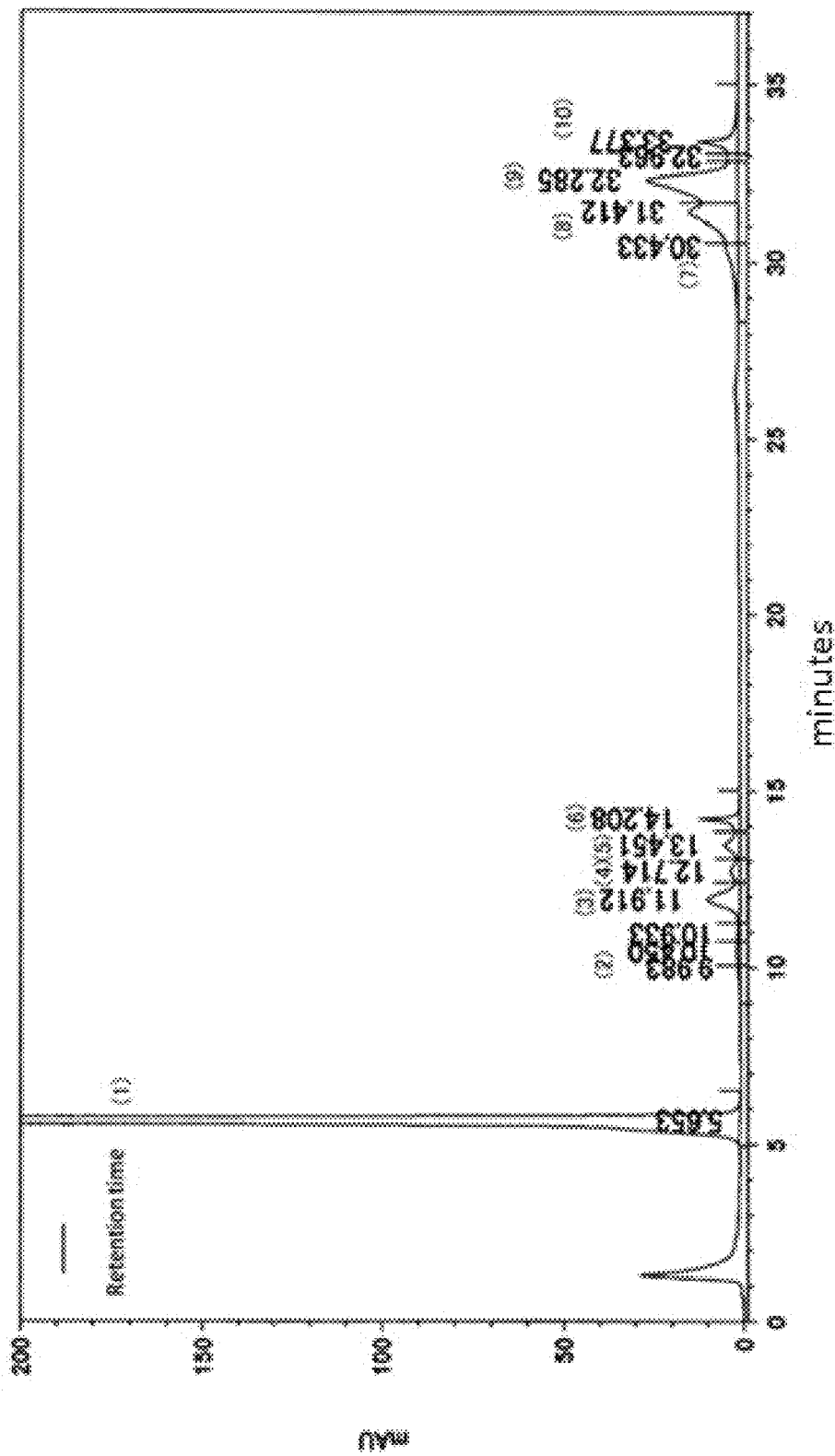
FIG. 9 shows the results of cation exchange chromatography of anti-HER2 IgG4 type monovalent antibody 4D5/mvG4-2 DF. Peaks (1) to (10) in the figure represent fractionated fractions.

The results of cation exchange chromatography of 4D5/mvG4-2 DF showed that three peak groups of (1), (2) to (6) and (7) to (10) were separated as shown in FIG. 9, indicating that plural components are included in the Protein A-purified protein. Therefore, the peaks (1) to (10) were further fractionated and analysis of each peak was performed.

(2) Classification of Components by Western Blot Analysis

In the same manner as in Example 3(3) above, 40 ng was added per lane under non-reducing conditions to perform SDS-PAGE electrophoresis, and a PVDF membrane and a gel were put between filter papers soaked in a transfer buffer containing 0.1 M Tris, 0.2 M glycine and 20% methanol, and proteins were blotted on the PVDF membrane (2.5 mA/cm$^2$, for 40 minutes). Thereafter, PBS containing 1% bovine serum albumin (BSA) (hereinafter, abbreviated to BSA-PBS) was used to block the protein-transferred PVDF membrane.

As a detection antibody, 1000-fold diluted peroxidase (hereinafter, abbreviated to HRP)-labeled anti-His tag antibody (NACALAI TESQUE, INC., Cat. No. 04546-34) for H chain detection, 5000-fold diluted peroxidase-labeled anti-human κ chain antibody (SIGMA, Cat. No. 7164) for L chain detection, and 5000-fold diluted peroxidase-labeled anti-human IgG antibody (American Qualex, Cat. No. A 110PD) for IgG detection were used, and reacted at room temperature for 1 hour.

Thereafter, the PVDF membrane was washed with PBS containing 0.1% Tween 20 (hereinafter, abbreviated to Tween-PBS), and reacted with a SuperSignal West Dura Extended Duration Substrate (manufactured by Thermo Scientific), followed by detection using an image analyzer (manufactured by FUJI FILM).

The results of Western blot analysis (FIG. 10) of the peaks (1) to (10) detected in the cation exchange chromatography (FIG. 9) of 4D5/mvG4-2 DF showed that bands around 100 kDa predicted as a monomer composed of two polypeptide chains were detected in the peaks (1) and (3). It reacted with both anti-human κ chain antibody and anti-hIgG antibody but did not react with anti-His tag antibody, indicating L chain-L chain homodimer monomer (hereafter, abbreviated to LL form) comprising only L chain and no H chain including His tag.

Figure 10:
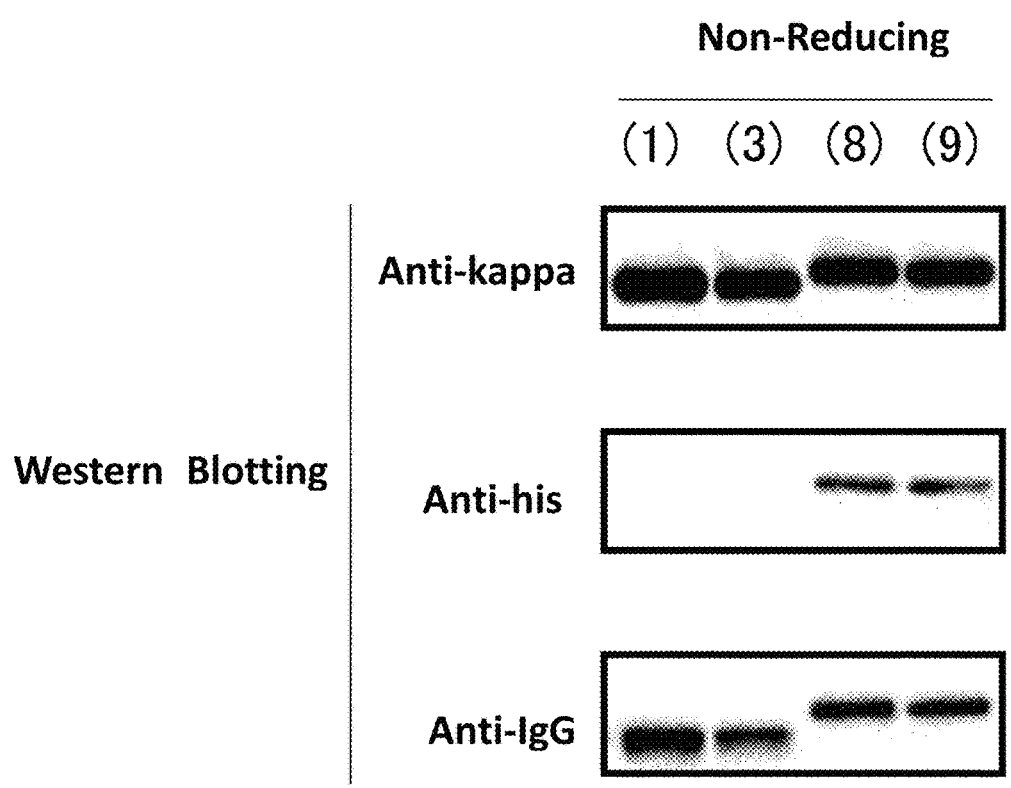
FIG. 10 shows the results of Western blot analysis of anti-HER2 IgG4 type monovalent antibody 4D5/mvG4-2

Further, bands around 100 kDa predicted as a monomer were detected in the peaks (8) and (9). It reacted with all detection antibodies of anti-human κ chain antibody, anti-His tag antibody, and anti-hIgG antibody, indicating HL heterodimer monomer (hereafter, abbreviated to HL form) comprising L chain and H chain including His tag (FIG. 10).

Further, the detection results by peroxidase-labeled anti-hIgG antibody showed that components of peaks (1), (3) and peaks (8), (9) were different in the molecular weight, and can be separated by SDS-PAGE. The samples of other peaks (2), (4) to (7) and (10) were below the detection limits of Western blot analysis, and thus their components could not be identified.

(3) Separation of Heterodimer and Homodimer from Mixture

In the above section, it was suggested that HL and LL forms were included in 4D5/mvG4-2 DF purified by Protein A. Subsequently, in order to obtain standard products of HL and LL forms, each of the fractions obtained by changing elution pH during the protein A purification was analyzed by cation exchange chromatography. As a result, fraction X, which was one of the fractions eluted at pH 3.5 during the Protein A purification, was identified to have peaks (8) and (9) as a main component. Fraction Y, which was eluted at pH 5.0 during the Protein A purification, was identified to have peak (1) as a main component.

As shown in Table 5, the content of HL form in fraction X was 74.9% or more, and the content of LL form in fraction Y was 93.8% or more. In the subsequent analysis, fraction X was used as a control of the sample including HL form as the main component, and fraction Y was used as a control of the sample including LL form as the main component. Further, the values of Table 5 represent an area ratio (%), and [n.d.] represents "unanalyzed".

TABLE 5

Component analysis of each fractions of mvG4-2 DF by cation exchange chromatography

| | | mvG4-2 DF | |
|---|---|---|---|
| Peak no. | Component | Fraction X | Fraction Y |
| (1) | LL | 1 | 88.6 |
| (2) | unidentified | n.d. | 1.5 |
| (3) | LL | n.d. | 5.2 |
| (4) | unidentified | n.d. | 1.3 |
| (5) | unidentified | n.d. | 2.1 |
| (6) | unidentified | 5.7 | 1.3 |
| (7) | unidentified | 10.3 | n.d. |
| (8) | HL | 24.2 | n.d. |
| (9) | HL | 49.9 | n.d. |
| (10) | unidentified | 8.8 | n.d. |
| Total (%) | LL | 1 | 93.8 |
| | HL | 74.1 | n.d. |
| | unidentified | 24.9 | 6.2 |

(4) Specific Purification of Heterodimer Protein

In order to confirm specific separation and purification of the heterodimer protein that includes the second polypeptide comprising CL-Fc having a reduced binding activity for the CH binder, Protein G and Protein A were used to perform purification, and purified proteins were compared.

Protein G is known to bind to any subclass of human IgG, and human IgG3 having no Protein A-binding activity is able to bind to Protein G. In the purification using Protein G, therefore, it is suggested that all antibody molecules can be purified irrespective of the presence or absence of amino acid residue substitution in this Example in the Protein A-binding site.

In this Example, a heterodimer protein (4D5/mvG4-3 DF) including CL-Fc having a reduced Protein A-binding activity was prepared by substituting His at position 435 and Tyr at position 436 of the EU index of IgG1, which are known to be involved in the protein A binding, with Arg and Phe that are amino acid residues of human IgG3 having no Protein A-binding activity, followed by analysis.

In the same manner as in Example 3(3) and Example 4(2) above, SDS-PAGE analysis under non-reducing conditions and Western blotting were performed.

In SDS-PAGE under non-reducing conditions, the results of performing the electrophoresis for a long time showed that X fraction of 4D5/mvG4-2 mainly including HL form had a band in the higher molecular weight region than Y fraction of 4D5/mvG4-2 DF mainly including LL form. Therefore it was found that the band in the high molecular weight region is the HL form and a band in the low molecular weight region is LL form. Further, as the electrophoresis time was prolonged, HL heteromonomer and LL homomonomer could be separated (FIG. 11).

Similarly, the results of Western blotting using anti-κ chain antibody also showed that X fraction of 4D5/mvG4-2 had a band in the higher molecular weight region than Y fraction of 4D5/mvG4-2 (FIG. 11).

Further, with respect to 4D5/mvG4-3 DF purified using Protein G or Protein A, each of the purified products was subjected to SDS-PAGE, and a comparison was performed.

First, the conditions for purifying 4D5/mvG4-3 DF using each carrier were examined, and as a result, all proteins were found to be eluted by Protein G at pH 2.5 and by Protein A at pH 3.0.

In 4D5/mvG4-3 DF (Protein G purified product) obtained by performing elution using Protein G at pH 2.5, both bands of HL and LL forms were observed, indicating that 4D5/mvG4-3 DF purified by Protein G includes both HL and LL forms, like 4D5/mvG4-2 DF (FIG. 11, SDS-PAGE). Therefore, it was found that both molecules of HL and LL are expressed in 4D5/mvG4-3 DF prepared by adding amino acid residue substitutions of H435R and Y436F to 4D5/mvG4-2.

Meanwhile, the results of SDS-PAGE of 4D5/mvG4-3 DF (Protein A purified product) obtained by eluting the same culture supernatant as in the Protein G purification at pH 3.0 using Protein A showed that the band of HL was observed, but the band of LL was hardly observed, and the results of Western blot analysis by anti-κ chain antibody also showed that the band of HL of the high molecular weight region was only observed (FIG. 11).

Therefore, it was found that cells expressing 4D5/mvG4-3 DF express HL heterodimer and LL homodimer in the culture supernatant, but HL heterodimer protein of 4D5/mvG4-3 DF can be selectively purified by Protein A purification (FIG. 11).

Meanwhile, LL form as well as HL form can be purified by Protein A from 4D5/mvG4-2 DF having no amino acid residue substitutions of H435R and Y436F in L chain. It was indicated that only HL form can be specifically purified from LL form having no Protein A-binding activity and HL form having Protein A-binding activity by adding amino acid substitutions of H435R and Y436F to L chain.

[Example 5] Heterodimer Protein-detection ELISA (1) Sandwich ELISA of IgG4 Type Monovalent Antibody For the detection of HL form, establishment of a sandwich enzyme-linked immunosorbent assay (ELISA) system was examined. The monovalent antibody prepared in this Example is a heterodimer protein that is composed of H chain having His tag at the C-terminus of CH and L chain prepared by fusion of Fc and Cκ chain, as shown in the structure of FIG. 5, and thus, anti-His tag antibody could be used as the H chain-specific binding antibody and anti-human κ chain antibody could be used as the L chain-specific binding antibody.

The anti-His tag antibody (QIAGEN, Cat. No. 34670) was immobilized on an ELISA plate (2 μg/mL, 50 μL/well, 4° C., 16 hours), and washed with PBS, followed by blocking with BSA-PBS (100 μL/well, room temperature, 1 hour).

After the blocking solution was discarded, various concentrations of monovalent antibody 4D5/mvG4-2 DF fraction X, 4D5/mvG4-2 DF fraction Y, and 4D5/mvG4-3 DF, 4D5/mvG4-4 F and 4D5/mvG4-5 F purified by Protein A were reacted (50 μL/well, room temperature, 2 hours).

Subsequently, after washing with 0.05% Tween 20-containing PBS (hereinafter, abbreviated to Tween-PBS), 5000-fold diluted horseradish peroxidase (hereinafter, abbreviated to HRP)-labeled anti-human κ chain antibody (SIGMA, Cat. No. A7164) was reacted (50 μL/well, 2 hours).

Subsequently, after washing with Tween-PBS, 50 μL/well of ABTS chromogenic substrate [2.2-azinobis(3-ethylbenzothiazole-6-sulfonic acid)ammonium] solution [1 mmoL/L ABTS/0.1 moL/L citrate buffer (pH 4.2), 0.1% $H_2O_2$] was added to develop a color at room temperature for 15 minutes. The color development was terminated by addition of 50 μL/well of 5% SDS aqueous solution. Absorbance was determined on a plate reader at 415 nm with a reference at 490 nm. SoftMax Pro(Molecular Devices) was used for data analysis. The experiment was repeated three times.

In the binding ELISA system, fraction X composed of HL heterodimer of 4D5/mvG4-2 DF was used as a positive control, and fraction Y composed of LL homodimer of 4D5/mvG4-2 DF was used as a negative control.

As a result, 4D5/mvG4-3 DF, 4D5/mvG4-4 F and 4D5/mvG4-5 F obtained by Protein A purification equivalently bound to 4D5/mvG4-2 DF fraction X, but hardly bound to 4D5/mvG4-2 DF fraction Y (FIG. 12).

Therefore, it was found that all of the IgG4 type monovalent antibodies, 4D5/mvG4-3 DF, 4D5/mvG4-4 F and 4D5/mvG4-5 F are HL heterodimer proteins composed of the first polypeptide comprising CH-His tag and the second polypeptide comprising CL-Fc (FIG. 12).

Further, it was found that the HL heterodimer can be specifically purified from all of IgG4 type monovalent antibody 4D5/mvG4-3 DF prepared by further adding amino acid substitutions of H435Y and R436F to L chain in the HL heterodimer protein of IgG4 type monovalent antibody 4D5/mvG4-2 DF, 4D5/mvG4-4 F prepared by further adding amino acid substitutions of S228P/R409K, and 4D5/mvG4-5 F prepared by further adding amino acid substitution of L235E to 4D5/mvG4-4 F, by Protein A purification (FIG. 12).

Therefore, the effect that the HL heterodimer form can be specifically purified using Protein A by adding amino acid substitutions of H435Y and R436F to L chain is maintained, even though the amino acid substitutions of S228P/R409K and L235E are included.

(2) Sandwich ELISA of IgG1 Type Monovalent Antibody

In the same manner as in Example 5(1) described above, Protein A purified fractions of IgG1 type monovalent antibody 4D5/mvG1-1 DF were subjected to sandwich ELISA.

As a result, the fractions 1 to 4 that were eluted at each pH by Protein A purification showed different reactivities in sandwich ELISA, indicating that the contents of HL heterodimer in the fractions differ from each other (FIG. 13A).

Therefore, fraction showing the highest reactivity was used as 4D5/mvG1-1 DF in the subsequent in vitro activity test.

Meanwhile, IgG1 type monovalent antibody GA101/mvG1-2 F and GA101/mvG1-2 DF including amino acid residue substitutions of H435R and Y436F showed reactivity equivalent to that of the 4D5/mvG4-2 DF fraction X including HL heterodimer as a main component (FIG. 13B).

Therefore, it was shown that in the IgG1 type monovalent antibodies GA101/mvG1-2 F and GA101/mvG1-2 DF that were purified by use of Protein A, HL heterodimers were specifically purified (FIG. 13B).

These results suggest that in IgG1 type monovalent antibody as well as IgG4 type monovalent antibody, heterodimer proteins including amino acid residue substitutions of H435R/Y436F in L chain can be specifically purified by Protein A.

[Example 6] Binding Activity of Heterodimer Protein for Cancer Cells

Binding activities of IgG1 type and IgG4 type monovalent antibodies for cancer cells were confirmed by binding inhibition experiment of each IgG1 antibody. First, as a control antibody, anti-CD20 IgG1 antibody GA101/IgG1 F, anti-HER2 IgG1 antibody Herceptin (Proc. Natl. Acad. Sci. U.S.A., 1992; 89: 4285) and human IgG1 (manufactured by Millipore, AG502) were labeled with Alexa488 using an Alexa488 labeling kit (Invitrogen, A20181) to prepare GA101_Alx, Herceptin_Alx and hIgG1_Alx.

CD20-positive human lymphoma cell line Raji (JCRB9012) and HER2-positive human breast cancer cell line SK-BR-3 (ATCC: HTB-30) were used to perform flow cytometry. The experiment was repeated twice. $1\times10^5$ cells were suspended in a PBS buffer containing 1% BSA, 0.02% ethylene diamine tetracetate (EDTA), and 0.05% sodium azide (hereinafter, abbreviated to FACS buffer), and 2.0 μg/mL of Alexa-labeled antibody and 210 nM to 1.68 nM of non-labeled IgG1 antibody or various monovalent antibodies were added to the suspension at the same time, and reacted at 4° C. under shading conditions for 1.5 hours.

Further, hIgG1_Alx was used as a negative control. After washing with FACS buffer, a flow cytometer Cytomics FC 500 MPL (Beckman Coulter) was used for measurement.

As a result, the negative control hIgG1 antibody did not inhibit the binding of anti-HER2 antibody Herceptin_Alx to SK-BR-3 cells, but anti-HER2 IgG1 antibody Herceptin, anti-HER2 IgG1 defucosylated antibody 4D5/IgG1 DF, anti-HER2 IgG1 type monovalent antibody 4D5/mvG1-1 DF, anti-HER2 IgG4 type monovalent antibody 4D5/mvG4-4 F and 4D5/mvG4-5 F inhibited the binding of Herceptin_Alx to SK-BR-3 in an antibody concentration dependent manner (FIG. 14A).

Therefore, anti-HER2 monovalent antibody was found to specifically bind to HER2. It was indicated that the heterodimer protein prepared on the basis of the heterodimer scaffold protein (HSP) composed of CH and CL-Fc is a heterodimer protein having a monovalent binding activity.

However, the inhibitory effect of the binding by the monovalent antibody per unit mol concentration was lower than those of anti-HER2 IgG1 antibody Herceptin and 4D5/IgG1 DF (FIG. 14A).

Meanwhile, in CD20-positive lymphoma cell line Raji, similarly, the negative control hIgG1 antibody did not inhibit the binding of GA101_Alx to Raji cells, but anti-CD20 IgG1 antibody GA101, anti-CD20 IgG1 defucosylated antibody GA101/IgG1 DF, anti-CD20 IgG1 type monovalent antibodies, GA101/mvG1-2 F and GA101/mvG1-2 DF inhibited the binding of GA101_Alx to Raji cells in an antibody concentration dependent manner (FIG. 14B).

Therefore, anti-CD20 monovalent antibody was found to specifically bind to CD20. Like HER2 antibody, the inhibitory effect of the binding by the monovalent antibody per unit mol concentration was lower than those of anti-CD20 IgG1 antibodies, GA101/IgG1 F and GA101/IgG1 DF (FIG. 14B).

[Example 7] Antibody-dependent Cytotoxicity of Heterodimer Protein (1) Antibody-Dependent Cytotoxicity of Anti-HER2 Monovalent Antibody ADCC activity of antibody was measured by the method described in WO 2007/011041, and repeated three times.

HER2-positive human breast cancer cell SK-BR-3 (ATCC: HTB-30), human breast cancer BT-20 (ATCC: HTB-19), CD20-positive human lymphoma cell Raji (JCRB9012), Burkitt lymphoma cell ST-486 (ATCC: CRL-1647) and chronic B cell leukemia cell MEC-1 (DSMZ: ACC-497) were used as target cells and peripheral blood mononuclear cells (PBMC) prepared from a healthy donor was used as an effector cell.

The experiment was performed at a ratio of the effector cell to the target cell of 1:25, and cytotoxicity (%) was calculated by the following Equation.

$$\text{Cytotoxicity (\%)}=100\times(S-Ab)/(\text{Max}-T)$$

S=absorbance of sample reaction well-absorbance of medium well

Ab=absorbance of non-antibody added well-absorbance of medium well

T=absorbance of target well-absorbance of medium well

Max=absorbance of 100% reaction well-absorbance of 100% reaction control well hIgG1 was used as a negative control and anti-HER2 IgG1 antibody Herceptin and anti-HER2 IgG1 defucosylated antibody 4D5/IgG1 DF were used as positive controls, and PBMC prepared from another volunteer donor was used as effector cells. The well including target cells lysed in Triton X-100 was used as the 100% reaction well.

As a result, anti-HER2 monovalent antibody 4D5/mvG1-1 DF (Protein A purified fraction) showed high ADCC activity in an antibody concentration dependent manner, equivalent to that of anti-HER2 IgG1 antibody 4D5/IgG1 DF (FIGS. 15A and 15B). In contrast, both of the anti-HER2 IgG4 type monovalent antibodies, mvG4-4F and mvG4-5F showed no ADCC activity (FIGS. 15C and 15D).

Therefore, it was found that the heterodimer protein composed of the first polypeptide comprising IgG1-CH and the second polypeptide comprising CL(IgG1-L) prepared by fusion of IgG1-Fc is able to impart ADCC activity and the heterodimer protein composed of the first polypeptide comprising IgG4-CH and the second polypeptide comprising CL(IgG4-L) prepared by fusion of IgG4-Fc is able to exclude ADCC activity.

Further, although IgG1 type monovalent antibody has an antigen binding site reduced from divalent to monovalent, compared to IgG1 antibody, it showed equivalent effects to that of IgG1 antibody under the same conditions, indicating that a monovalent antibody having the reduced unnecessary bivalent binding activity while retaining ADCC activity can be prepared.

(2) Antibody-dependent Cytotoxicity of Anti-CD20 Monovalent Antibody

In the same manner as in Example 7(1) described above, hIgG1 was used as the negative control, and anti-CD20 IgG1 antibody GA101/IgG1 F and anti-CD20 IgG1 defucosylated antibody GA101/IgG1 DF were used as positive controls. All experiments were performed using PBMC prepared from one healthy donor.

As a result, anti-CD20 IgG1 type defucosylated monovalent antibody GA101/mvG1-2 DF showed a remarkably increased ADCC activity, compared to anti-CD20 IgG1 type monovalent antibody GA101/mvG1-2 F [FIGS. 16A to 16C].

It was known that removal of core fucose from human IgG increases ADCC activity. Removal of core fucose from IgG1 type monovalent antibody composed of the first polypeptide comprising CH and the second polypeptide comprising CL-Fc was also found to increase ADCC activity. That is, the ADCC activity of the heterodimer protein composed of the first polypeptide including CH and the second polypeptide comprising CL-Fc was found to be increased or decreased by changing the content of core fucose binding to Fc.

Further, induced potency of ADCC activity per unit mol concentration of anti-CD20 IgG1 type defucosylated monovalent antibody GA101/mvG1-2 DF was reduced, compared to anti-CD20 IgG1 defucosylated antibody GA101/IgG1 DF, but the maximum efficacy was almost equivalent. That is, although anti-CD20 IgG1 type monovalent antibody has an antigen binding site reduced from divalent to monovalent, compared to anti-CD20 IgG1 antibody, equivalent effects to that of IgG1 antibody can be obtained by increasing the number of monovalent antibody molecule under the same conditions.

[Example 8] Preparation of Divalent Heterodimer Protein (1) Preparation of Bispecific Antibody As a divalent heterodimer protein, a bispecific antibody that is composed of a first polypeptide comprising CD74 antibody H chain and a second polypeptide comprising anti-CD20 scFv antibody or anti-HER2 scFv antibody bound to the C-terminus of CD74 antibody VLCL-Fc, and anti-CD74 IgG4 type monovalent antibody hLL1/mvG4-4 F were prepared.

The bispecific antibody expression vector of Example 2(3) was used to express and purify the bispecific antibodies in the same manner as in Example 3, thereby obtaining CD74-HER2 bispecific antibody, CD74-CD20 bispecific antibody and anti-CD74 IgG4 type monovalent antibody hLL1/mvG4-4 F.

The results of SDS-PAGE showed that hLL1/mvG4-4 F, hLL1-4D5/mvG4-4 F and hLL1-2 F2/mvG4-4 F compositions showed high purity, and included little impurities, degradation products and aggregates (FIG. 17).

(2) Evaluation of Binding Activity for Recombinant Human HER2 and CD74 by ELISA

In the assay, a 96-well plate for ELISA (Greiner) was used. 2 µg/mL of recombinant human HER2-Fc (R&D Systems) or 2 µg/mL of CD74 (Santa Cruz Biotechnology) was dispensed in an amount of 50 µL/well, and left at 4° C. overnight for adsorption. The plate was washed with PBS, and then 100 µL/well of BSA-PBS was added and left at room temperature for 1 hour to block the remaining active groups.

Thereafter, BSA-PBS was discarded, and various concentrations of anti-HER2 IgG1 antibody Herceptin F, anti-CD74 IgG1 antibody hLL1 F or CD74-HER2 bispecific antibody hLL1-4D5/mvG4-4 F were dispensed as primary antibodies in the plate at an amount of 50 µL/well, and left at room temperature for 1 hour.

The plate was washed with Tween-PBS, and then peroxidase-labeled goat anti-human κ chain antibody (Southern Biotech) was dispensed as a secondary antibody at an amount of 50 μL/well, and left at room temperature for 1 hour. The plate was washed with Tween-PBS, and 50 μL/well of ABTS colorimetric substrate [2.2-azinobis(3-ethylbenzothiazole-6-sulfonic acid)ammonium] solution [1 mmoL/L ABTS/0.1 moL/L citrate buffer (pH 4.2), 0.1% $H_2O_2$] was added for color development.

The reaction was terminated by addition of 50 μL/well of 5% sodium dodecyl sulfate (SDS) solution. Absorbance (0D415-490) was determined using a plate reader (SPECTRA Max 340PC, Molecular Devices) at a sample wavelength of 415 nm and a reference wavelength of 490 nm.

Figure 18B:
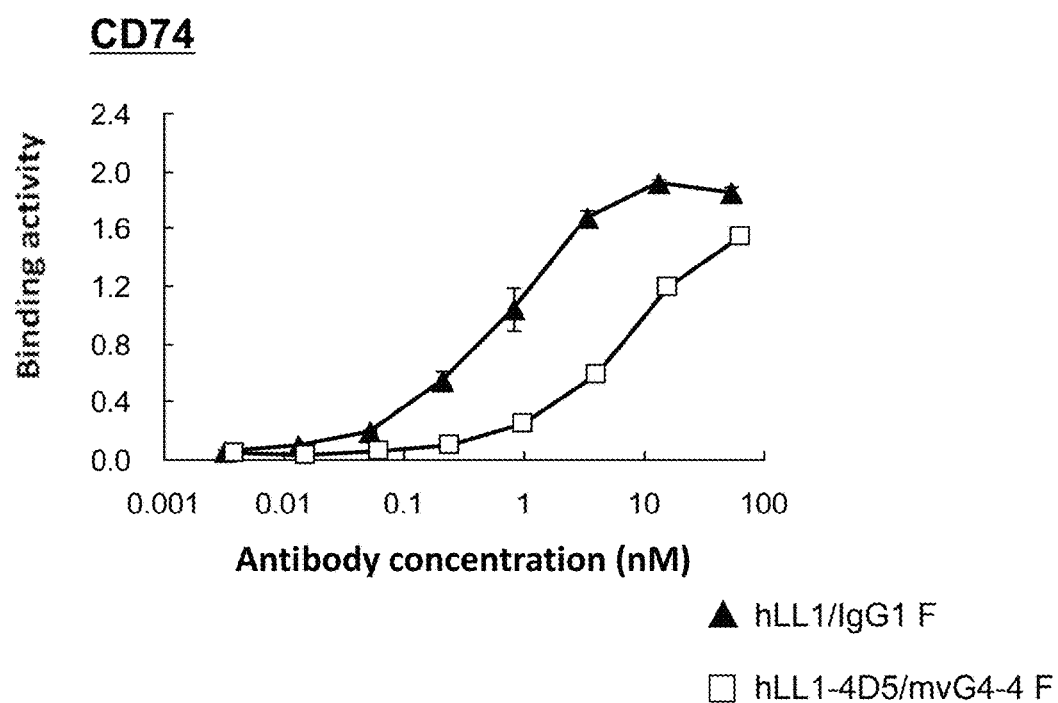

As a result, CD74-HER2 bispecific antibody hLL1-4D5/mvG4-4 F bound to HER2 protein, like anti-HER2 IgG1 antibody Herceptin F. Further, hLL1-4D5/mvG4-4 F bound to CD74 protein, like anti-CD74 IgG1 antibody hLL1 F [FIGS. 18A to 18B].

Therefore, CD74-HER2 bispecific antibody hLL1-4D5/mvG4-4 F prepared on the basis of the heterodimer scaffold protein (HSP) composed of CH and CL-Fc was found to be a heterodimer protein having a divalent binding activity.

[Example 9] Complement-dependent Cytotoxicity (CDC Activity) of Heterodimer Protein CDC activity of the monovalent antibody composed of two polypeptides of H chain and CL-Fc chain prepared in Example 3 was measured according to the method described in WO 2011/108502. The experiment was repeated three times. CD20-positive Burkitt lymphoma cell line ST-486 (ATCC: CRL-1647) was used as a target cell.

50 μL of the target cells diluted by $1.0 \times 10^6$/mL using RPMI1640 (Wako Pure Chemical Industries, Ltd.) containing 10% FBS (JRH), 50 μL of the antibody solution adjusted to 3-fold of the final concentration, and 50 μL of 2-fold diluted human complement (SIGMA) were dispensed in each well of 96-well flat-bottom plate (Sumitomo Bakelite Co., Ltd.). hIgG1 was used as a negative control and anti-CD20 antibody GA101/IgG1 F and anti-CD20 defucosylated antibody GA101/IgG1 DF were used as positive controls.

Further, the well containing no antibody was prepared as a 0% reaction well, and the well containing no target cell was prepared as a 100% reaction well. The cells were cultured at 37° C. (5% $CO_2$) for 2 hours, and then 15 μL of WST-1 (ROCHE) was added to each reaction well, and cultured at 37° C. (5% $CO_2$) for 3 hours.

After completing the reaction, OD450 of each well was measured and cytotoxicity (%) was calculated using the following Equation.

Cytotoxicity (%)=100×{1−(absorbance of reaction well−absorbance of 100% reaction well)/(absorbance of 0% reaction well−absorbance of 100% reaction well)}

CDC activity per mol concentration of anti-CD20 IgG1 type monovalent antibody was shown in FIG. 19. As a result, the anti-CD20 IgG1 type monovalent antibody GA101/mvG1-2 F and anti-CD20 IgG1 type defucosylated monovalent antibody GA101/mvG1-2 DF showed increased CDC activity, compared to anti-CD20 antibody GA101/IgG1 F and GA101/IgG1 DF.

[Example 10] C1q Binding Activity of Heterodimer Protein

Binding of IgG antibody, monovalent antibody and C1q bound to thereof on cell surface were measured by flow cytometry. CD20-positive tumor cell line Raji (JCRB9012) and ST-486 (ATCC: CRL-1647) were used as target cells. The target cells were adjusted to $4 \times 10^6$/mL using BSA-PBS (NACALAI TESQUE, INC.), and 1/20-diluted mouse serum (CEDARLANE) was further added, and left at room temperature for 5 minutes.

50 μL of this cell suspension was dispensed in each well of 96-well U plate (FALCON) and each 50 μL of 3-fold concentration antibody solution (GA101/IgG1 F, GA101/mvG1-2 F, hIgG1) in BSA-PBS and 3-fold concentration of purified C1q (SIGMA, C1740) were added. Buffer was added as a negative control.

Each well was suspended, and left on ice for 1 hour. Then, the supernatant was discarded by centrifugation. 180 μL of BSA-PBS was added to each well, and the supernatant was also discarded by centrifugation. This manipulation was repeated twice for washing.

Thereafter, 30 μL of 10 μg/mL FITC-labeled anti-human IgG-Fc antibody (Abcam, ab99763) or FITC-labeled anti-C1q antibody (Dako, F0254) was added to each well, and left on ice under shading conditions for 30 minutes. Thereafter, the above described washing manipulation was repeated twice, and they were suspended in 180 μL of BSA-PBS to use as a measurement sample.

Mean Fluorescent Intensity (MFI) of each measurement sample was determined by flow cytometry. A ratio of MFI of the sample well to that of the negative control well was calculated as Relative Fluorescent Intensity (RFI). With respect to antibody concentration and RFI value, the binding amount of antibody to Raji cell and the binding amount of C1q to Raji cell are shown in FIGS. 20A and 20B, respectively, and the binding amount of antibody to ST-486 cell and the binding amount of C1q to ST-486 cell are shown in FIGS. 21A and 21B, respectively.

In both Raji [FIGS. 20A and 20B] and ST-486 [FIGS. 21A and 21B], the binding amount of anti-IgG-Fc antibody was increased in monovalent antibody GA101/mvG1-2 F, compared to IgG1 antibody GA101/IgG1 F [FIGS. 20A and 21A], and the binding amount of anti-C1q antibody was increased in monovalent antibody GA101/mvG1-2 F, compared to IgG1 antibody GA101/IgG1 F [FIGS. 20B and 21B].

Meanwhile, it was already confirmed that affinities of anti-IgG-Fc antibody for GA101/IgG1 F and GA101/mvG1-2 F used in this experiment were equivalent (data not shown). These results suggest that the antigen binding activity of anti-CD20 IgG1 type monovalent antibody GA101/mvG1-2 F was reduced, compared to that of anti-CD20 IgG antibody GA101/IgG1 F, but the C1q binding activity of anti-CD20 IgG1 type monovalent antibody GA101/mvG1-2 F was increased compared to anti-CD20 IgG antibody GA101/IgG1 F.

[Example 11] Preparation of CDC Enhanced-heterodimer Protein

In order to prepare a CDC enhanced-monovalent antibody as a CDC enhanced-heterodimer protein, a monovalent antibody expression vector including a CDC enhanced-Fc region (WO 2011/108502) was prepared in the following manner.

(1) Preparation of H Chain Vector

The amino acid sequence of Fc region of H chain constant region 1H1 described in Example 1 was substituted with the amino acid sequence of Fc region of the high CDC constant region represented by SEQ ID NO: 3, described in WO 2011/108502. The fragments of CH2 and CH3 regions of IgG1-CH vector 1H1 were digested with the restriction enzymes, BmgBI and EcoT22I.

In the same manner, the pKTX93/113 F-N392K vector (WO 2011/108502) containing CDC enhanced-Fc region was treated with the restriction enzymes, BmgBI and EcoT22I, and the digested BmgBI-EcoT22I fragment was inserted into the IgG1-CH vector 1H1. Consequently, a monovalent antibody H chain vector including CDC enhanced-Fc region (hereinafter, abbreviated to HCVcom) was obtained.

(2) Preparation of L Chain Vector

In the same manner as in (1), the amino acid sequence of Fc region of CL-Fc (1L1) described in Example 1 was substituted with the amino acid sequence of Fc region of the high CDC constant region represented by SEQ ID NO: 3, described in WO 2011/108502, so as to obtain a monovalent antibody L chain vector including CDC enhanced-Fc (hereinafter, abbreviated to LCVcom).

(3) Preparation of CDC Enhanced-Monovalent Antibody Expression Vector

HCVcom and LCVcom obtained in (1) and (2) above were introduced into CH and CL regions of pKANTEX93/mvG1-2 described in Table 3 of Example 1 in the following manner. The ApaI site present at the 5'-terminus of CH1 region and the BamHI site present at the 3'-terminus of CH3 region of HCVcom were cleaved with each restriction enzyme and inserted into the corresponding site of pKANTEX93/mvG1-2, and subsequently, the BsiWI site present at the 5'-terminus of Cκ region and the PmaCI site present at the 3'-terminus of CH3 region of LCVcom were cleaved with each restriction enzyme and inserted into the corresponding site.

Consequently, a monovalent antibody expression vector including CDC enhanced-Fc (hereinafter, referred to as pKANTEX93/mvCom) was obtained. The amino acid sequences of the constant regions of H chain and L chain of the prepared pKANTEX93/mvCom are shown in FIGS. 22A and 22B.

Further, in order to prepare CDC enhanced anti-CD20 antibody GA101, DNAs encoding the amino acid sequences (SEQ ID NOs: 36 and 38) of GA101-VH and VL were inserted into the appropriate sites of pKTX93/113 F-N392K vector (WO 2011/108502) to prepare CDC enhanced anti-CD20 divalent antibody GA101/IgG1-Com expression vector.

(4) Production of CDC Enhanced-monovalent Antibody

Production of CDC enhanced-monovalent and divalent antibodies was performed in the same manner as in Example 3, and anti-CD20 monovalent antibody expression vector pKANTEX93/mvG1-2 and CDC enhanced anti-CD20 monovalent antibody expression vector pKANTEX93/mvCom were introduced into CHO/FUT8KO cell, and the monovalent antibodies having no α1,6-fucose at the N-linked sugar chain, GA101/mvG1-2 DF and GA101/mvCom DF, or the divalent antibody GA101/IgG1-Com DF were expressed.

The purification of monovalent antibodies was performed in the same manner as in Example 2(2), except that Protein A purification was performed using a MabSelectSuRe (GE Healthcare) carrier, and 0.1 M citrate buffer of pH 3.9 was used as an elution buffer. The purified proteins were subjected to SDS-PAGE analysis in the same manner as in Example 2(3).

As shown in FIG. 23, the molecular weights of both of CL-Fc chain and H chain of the monovalent antibody were approximately 50 kDa, and a single band around 50 kDa was found under reducing conditions, and a single band around 100 kDa predicted as the heterodimer composed of two polypeptide chains of H chain and CL-Fc chain was recognized under non-reducing conditions. Therefore, the uniform monovalent antibodies, GA101/mvG1-2 DF and GA101/mvCom DF were purified.

These results suggest that not only IgG1 and IgG4 type monovalent antibodies, but also the CDC enhanced-monovalent antibodies including plural amino acid residue substitutions in the constant region can be specifically purified as heterodimer protein by Protein A with adding amino acid substitutions of H435Y/Y436F to CL-Fc chain.

That is, it was revealed that it is possible to prepare a heterodimer protein including plural amino acid residue substitutions in the first polypeptide and/or the second polypeptide.

[Example 12] CDC Activity of CDC Enhanced-heterodimer Protein

CDC activity of the monovalent antibody composed of two polypeptides of H chain and CL-Fc chain prepared in Example 11 was measured by the method described in WO 2011/108502. The experiment was performed three times. CD20-positive human lymphoma cell Raji (JCRB9012) and chronic B cell leukemia cell MEC-1 (DSMZ: ACC-497) were used as target cells. Hereinafter, CDC activity was measured in the same manner as in Example 9.

Figure 24B:
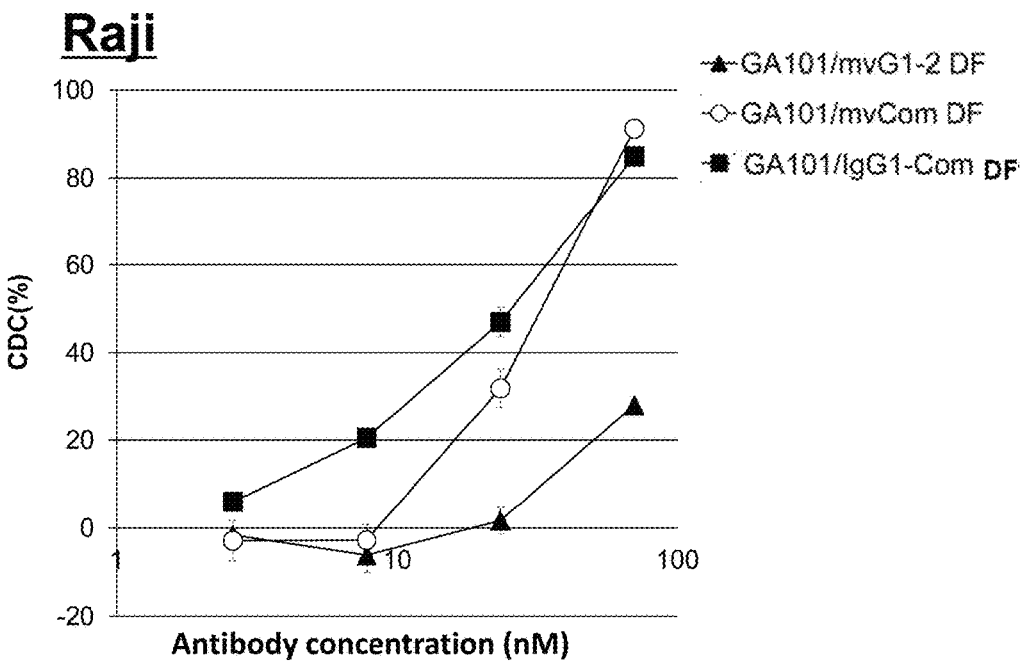

The results are shown in FIGS. 24A and 24B. The CDC enhanced anti-CD20 monovalent antibody GA101/mvCom DF showed enhanced CDC activity, compared to anti-CD20 IgG1 type monovalent antibody GA101/mvG1-2 DF. Further, the CDC enhanced anti-CD20 high monovalent antibody GA101/mvCom DF showed equivalent CDC activity to the CDC enhanced divalent anti-CD20 antibody GA101/IgG1-Com DF in the high concentration range.

Therefore, it was also revealed that the CDC activity of monovalent antibody was increased by plural amino acid residue substitutions of the antibody constant region in the monovalent antibody which is a heterodimer protein composed of H chain and CL-Fc, like in the divalent IgG antibody.

[Example 13] ADCC Activity of Heterodimer Protein

The ADCC activity of CDC enhanced anti-CD20 monovalent antibody GA101/mvCom DF which is the CDC enhanced-heterodimer protein prepared in Example 11 was measured in the same manner as in Example 7(2). CD20-positive human lymphoma cell Raji (JCRB9012) and chronic B cell leukemia cell MEC-1 (DSMZ: ACC-497) were used as target cells.

hIgG1 (Millipore, AG-502) was used as a negative control, anti-CD20 IgG1 type defucosylated monovalent antibody GA101/mvG1-2 DF was used as a positive control, and anti-CD20 IgG1 type fucosylated monovalent antibody GA101/mvG1-2 F was used as a comparison control.

Figure 25B:
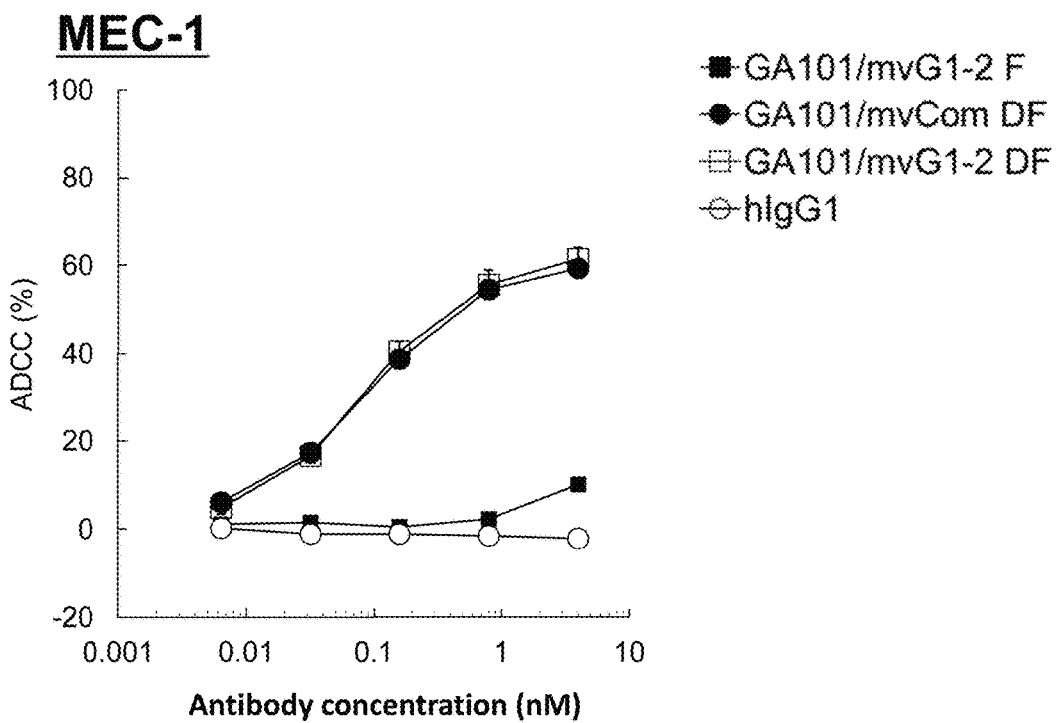

The results are shown in FIGS. 25A and 25B. It was found that the CDC enhanced anti-CD20 defucosylated monovalent antibody GA101/mvCom DF showed high ADCC activity, equivalent to that of anti-CD20 IgG1 type defucosylated monovalent antibody GA101/mvG1-2 DF.

Though the present invention has been described in detail by using specific embodiments, a person skilled in the art knows clearly that the various changes and modifications can be made within a range which does not depart from the spirit and scope of the present invention. The present application is based on U.S. provisional application (No. 61/710, 221) filed on Oct. 5, 2012, the entire content of which is incorporated herein as reference.

SEQ ID NO: 1—Nucleotide sequence of DNA of human IgG1CH
SEQ ID NO: 2—Amino acid sequence of human IgG1CH
SEQ ID NO: 3—Nucleotide sequence of DNA of human IgG4CH
SEQ ID NO: 4—Amino acid sequence of human IgG4CH
SEQ ID NO: 5—Nucleotide sequence of DNA of human IgG1CH-His
SEQ ID NO: 6—Amino acid sequence of human IgG1CH-His
SEQ ID NO: 7—Nucleotide sequence of DNA of human IgG4CH-His
SEQ ID NO: 8—Amino acid sequence of human IgG4CH-His
SEQ ID NO: 9—Nucleotide sequence of DNA of 1H0
SEQ ID NO: 10—Amino acid sequence of 1H0
SEQ ID NO: 11—Nucleotide sequence of DNA of 1H1
SEQ ID NO: 12—Amino acid sequence of 1H1
SEQ ID NO: 13—Nucleotide sequence of DNA of 4H0
SEQ ID NO: 14—Amino acid sequence of 4H0
SEQ ID NO: 15—Nucleotide sequence of DNA of 4H1
SEQ ID NO: 16—Amino acid sequence of 4H1
SEQ ID NO: 17—Nucleotide sequence of DNA of 4H2
SEQ ID NO: 18—Amino acid sequence of 4H2
SEQ ID NO: 19—Nucleotide sequence of DNA of 4H3
SEQ ID NO: 20—Amino acid sequence of 4H3
SEQ ID NO: 21—Nucleotide sequence of DNA of 1L0
SEQ ID NO: 22—Amino acid sequence of 1L0
SEQ ID NO: 23—Nucleotide sequence of DNA of 1L1
SEQ ID NO: 24—Amino acid sequence of 1L1
SEQ ID NO: 25—Nucleotide sequence of DNA of 4L0
SEQ ID NO: 26—Amino acid sequence of 4L0
SEQ ID NO: 27—Nucleotide sequence of DNA of 4L1
SEQ ID NO: 28—Amino acid sequence of 4L1
SEQ ID NO: 29—Nucleotide sequence of DNA of 4L2
SEQ ID NO: 30—Amino acid sequence of 4L2
SEQ ID NO: 31—Nucleotide sequence of DNA of 4L3
SEQ ID NO: 32—Amino acid sequence of 4L3
SEQ ID NO: 33—Nucleotide sequence of DNA of 4L4
SEQ ID NO: 34—Amino acid sequence of 4L4
SEQ ID NO: 35—Nucleotide sequence of DNA of GA101 VH
SEQ ID NO: 36—Amino acid sequence of GA101 VH
SEQ ID NO: 37—Nucleotide sequence of DNA of GA101 VL
SEQ ID NO: 38—Amino acid sequence of GA101 VL
SEQ ID NO: 39—Nucleotide sequence of DNA of 4D5 VH
SEQ ID NO: 40—Amino acid sequence of 4D5 VH
SEQ ID NO: 41—Nucleotide sequence of DNA of 4D5 VL
SEQ ID NO: 42—Amino acid sequence of 4D5 VL
SEQ ID NO: 43—Nucleotide sequence of DNA of CD74 VH
SEQ ID NO: 44—Amino acid sequence of CD74 VH
SEQ ID NO: 45—Nucleotide sequence of DNA of CD74 VL
SEQ ID NO: 46—Amino acid sequence of CD74 VL
SEQ ID NO: 47—Nucleotide sequence of DNA of GS linker
SEQ ID NO: 48—Amino acid sequence of GS linker
SEQ ID NO: 49—Nucleotide sequence of DNA of 2F2 VH
SEQ ID NO: 50—Amino acid sequence of 2F2 VH
SEQ ID NO: 51—Nucleotide sequence of DNA of 2F2 VL
SEQ ID NO: 52—Amino acid sequence of 2F2 VL
SEQ ID NO: 53—Nucleotide sequence of DNA of CD74VL-CL-Fc-2F2scFv
SEQ ID NO: 54—Amino acid sequence of CD74VL-CL-Fc-2F2scFv
SEQ ID NO: 55—Nucleotide sequence of DNA of CD74VL-CL-Fc-4D5scFv
SEQ ID NO: 56—Amino acid sequence of CD74VL-CL-Fc-4D5scFv
SEQ ID NO: 57—Nucleotide sequence of DNA of human Cκ
SEQ ID NO: 58—Amino acid sequence of human Cκ

What is claimed is:

1. A DNA encoding a heterodimer protein, the heterodimer protein being (i) a heterodimer protein composed of a first polypeptide comprising a heavy chain variable region (VH) and an immunoglobulin G (IgG)1 heavy chain constant region (CH), and a second polypeptide comprising a light chain variable region (VL) and a fusion polypeptide (CL-Fc) prepared by fusion of a light chain constant region (CL) and an Fc region of IgG1, wherein the heterodimer protein has a modification selected from the group consisting of:

(a-i) substitutions of C220S in the first polypeptide and H435R in the second polypeptide, (b-i) substitutions of C214S and H435R in the second polypeptide, (c-i) substitutions of C220S in the first polypeptide and C214S and H435R in the second polypeptide, (d-i) substitutions of C220S in the first polypeptide and C220S, C214S and H435R in the second polypeptide, (e-i) substitutions of C220S in the first polypeptide and C214S and H435R in the second polypeptide and a deletion of positions 216-220 in the second polypeptide, (f-i) substitutions of C220S in the first polypeptide and C214S, H435R and Y436F in the second polypeptide, (g-i) substitutions of C220S in the first polypeptide and C214S, H435R and Y436F in the second polypeptide and a deletion of positions 216-220 in the second polypeptide, (h-i) substitutions of C220S, K332A and P331S in the first polypeptide, and C214S, K322A, P331S, H435R and Y436F in the second polypeptide and a deletion of positions 216-220 in the second polypeptide, and (j-i) substitutions of C220S and I332E in the first polypeptide and C214S, I332E, H435R and Y436F in the second polypeptide and a deletion of positions 216-220 in the second polypeptide, numbering according to the EU index of Kabat ("the EU index"), or (ii) a heterodimer protein composed of a first polypeptide comprising a VH and an IgG4 CH, and a second polypeptide comprising a VL and a CL-Fc prepared by fusion of a CL and an Fc region of IgG4, wherein the heterodimer protein has a modification selected from the group consisting of:

(a-ii) substitutions of C131S in the first polypeptide and C214S and H435R in the second polypeptide, (b-ii) substitutions of C131S in the first polypeptide and C214S, H435R and Y436F in the second polypeptide, (c-ii) substitutions of C131S and R409K in the first polypeptide and C214S, R409K, H435R and Y436F in the second polypeptide, (d-ii) substitutions of C131S, S228P and R409K in the first polypeptide and C214S, S228P, R409K, H435R and Y436F in the second polypeptide, (e-ii) substitutions of C131S, S228P, L235E and R409K in the first polypeptide and C214S, S228P, L235E, R409K, H435R and Y436F in the second polypeptide, (f-ii) substitutions of C131S and R133K in the first polypeptide and C214S and H435R in the second polypeptide, (g-ii) substitutions of C131S and R133K in the first polypeptide and C214S, H435R and Y436F in the second polypeptide, (h-ii) substitutions of C131S, R133K and R409K in the first polypeptide and C214S, R409K, H435R and Y436F in the second polypeptide, (j-ii) substitutions of C131S, R133K, S228P and R409K in the first polypeptide and C214S, S228P, R409K, H435R and Y436F in the second polypeptide, and (k-ii) substitutions of C131S, R133K, S228P, L235E and R409K in the first polypeptide and C214S, S228P, L235E, R409K, H435R and Y436F in the second polypeptide, numbering according to the EU index of Kabat, wherein in (i) and (ii), the VH of the first polypeptide and the VL of the second polypeptide forms a binding domain.

2. A transformant host cell expressing a heterodimer protein, comprising a protein expression vector including the DNA of claim 1.

3. A method for producing a heterodimer protein, comprising
  (a) culturing the transformant host cell of claim 2 in a culture medium to express the heterodimer protein; and
  (b) purifying the heterodimer protein from a culture supernatant obtained in (a).

4. The DNA according to claim 1, wherein the heterodimer protein is the heterodimer protein of (ii).

5. The DNA according to claim 1, wherein the heterodimer protein of (ii) has a modification selected from the group consisting of (d-ii), (e-ii), (j-ii) and (k-ii).

6. The DNA according to claim 1, wherein the heterodimer protein of (ii) has a modification selected from the group consisting of (c-ii), (d-ii), (e-ii), (h-ii), (j-ii) and (k-ii).

7. The DNA according to claim 1, wherein the heterodimer protein of (ii) has a modification selected from the group consisting of (e-ii) and (k-ii).

8. The DNA according to claim 1, wherein the heterodimer protein is the heterodimer protein of (i).

9. The DNA according to claim 1, wherein the heterodimer protein of (i) has a modification selected from the group consisting of (e-i), (g-i), (h-i) and (j-i).

10. The DNA according to claim 1, wherein the Fc region in (i) and (ii) have N-glycoside linked sugar chains bound thereto, and a content of fucose-free sugar chains is 20% or more based on the total N-glycoside linked sugar chains of the heterodimer protein.

11. The DNA according to claim 1, wherein the first polypeptide in (i) or (ii) and/or the second polypeptide (i) or (ii) has one or more additional amino acid residue substitutions selected from the group consisting of P247I, F243L, R292P, Y300L, Y300F, P396L, T393A, H433P, S239D, S298A, A330L, 332E, E333A, K334A, L235E, P238A, N297A, K322A, P331S, K326A, S267E, H268F, S324T, K274Q, N276K, Y296F, K326W, K326Y, E333A, E333S, A339T, A339D, D356E, L358M, N384S, K392N, T394F, T394Y, V397M and V422I, numbering according to the EU Index.

12. The DNA according to claim 1, which further comprises one or more binding proteins bound at the N-terminus and/or the C-terminus of the CH of the first polypeptide in (i) or (ii) and the CL-Fc of the second polypeptide in (i) or (ii).

13. The DNA according to claim 12, wherein the one or more binding proteins are selected from the group consisting of an antibody variable region, a single chain Fv and a single variable domain.

14. The DNA according to claim 1, which further comprises an immunoglobulin heavy chain variable region bound at the N-terminus and/or C-terminus of the CH of the first polypeptide in (i) and/or (ii), and an immunoglobulin light chain variable region bound at the N-terminus and/or C-terminus of the CL-Fc of the second polypeptide in (i) and/or (ii).

15. The DNA according to claim 1, which further comprises an immunoglobulin light chain variable region bound at the N-terminus and/or C-terminus of the CH of the first polypeptide in (i) and/or (ii), and an immunoglobulin heavy chain variable region bound at the N-terminus and/or C-terminus of the CL-Fc of the second polypeptide in (i) and/or (ii).

16. The DNA according to claim 13, wherein the heterodimer protein is selected from the group consisting of a monovalent antibody, a divalent antibody, a trivalent antibody and a tetravalent antibody.

17. The DNA according to claim 1, which further comprises a light chain variable region or a heavy chain variable region at the N-terminus and/or the C-terminus of the first polypeptide in (i) or (ii) and/or the second polypeptide in (i) or (ii).

18. The DNA according to claim 17, wherein the heterodimer protein is bispecific and binds to CD74 and Her2 or CD74 and CD20.

19. A DNA encoding a heterodimer protein, the heterodimer protein being
  (i) a heterodimer protein composed of
  a first polypeptide comprising a light chain variable region (VL) and an IgG1 heavy chain constant region (CH), and
  a second polypeptide comprising a heavy chain variable region (VH) and a fusion polypeptide (CL-Fc) prepared by fusion of a light chain constant region (CL) and an Fc region of IgG1,
  wherein the heterodimer protein has a modification selected from the group consisting of:
    (a-i) substitutions of C220S in the first polypeptide and H35R in the second polypeptide,
    (b-i) substitutions of C214S and H435R in the second polypeptide,
    (c-i) substitutions of C220S in the first polypeptide and C214S and H435R in the second polypeptide,
    (d-i) substitutions of C220S in the first polypeptide and C220S, C214S and H435R in the second polypeptide,
    (e-i) substitutions of C220S in the first polypeptide and C214S and H435R in the second polypeptide and a deletion of positions 216-220 in the second polypeptide,
    (f-i) substitutions of C220S in the first polypeptide and C214S, H435R and Y436F in the second polypeptide,
    (g-i) substitutions of C220S in the first polypeptide and C214S, H435R and Y436F in the second polypeptide and a deletion of positions 216-220 in the second polypeptide,
    (h-i) substitutions of C220S, K332A and P331S in the first polypeptide, and C214S, K322A, P31S, H35R and Y436F in the second polypeptide and a deletion of positions 216-220 in the second polypeptide, and
    (j-i) substitutions of C220S and I332E in the first polypeptide and C214S, I332E, H435R and Y436F in the second polypeptide and a deletion of positions 16-220 in the second polypeptide, numbering according to the EU index of Kabat ("the EU index"), or
  (ii) a heterodimer protein composed of
  a first polypeptide comprising a VL and an IgG4 CH, and
  a second polypeptide comprising a VH and a CL-Fc prepared by fusion of a CL and an Fc region of IgG4,
  wherein the heterodimer protein has a modification selected from the group consisting of:
    (a-ii) substitutions of C131S in the first polypeptide and C214S and H435R in the second polypeptide,
    (b-ii) substitutions of C131S in the first polypeptide and C214S, H435R and Y436F in the second polypeptide,
    (c-ii) substitutions of C131S in the first polypeptide and C214S, R409K, H435R and Y436F in the second polypeptide,
    (d-ii) substitutions of C131S, S228P and R409K in the first polypeptide and C214S, S228P, R409K, H435R and Y436F in the second polypeptide, (e-ii) substitutions of C131S, S228P, L235E and R409K in the first polypeptide and C214S, S228P, L235E, R409K, H435R and Y436F in the second polypeptide, (f-ii) substitutions of C131S and R133K in the first polypeptide and C214S and H435R in the second polypeptide, (g-ii) substitutions of C131S and R133K in the first polypeptide and C214S, H435R and Y436F in the second polypeptide, (h-ii) substitutions of C131S, R133K and R409K in the first polypeptide and C214S, R409K, H435R and Y436F in the second polypeptide, (j-ii) substitutions of C131S, R133K, S228P and R409K in the first polypeptide and C214S, S228P, R409K, H435R and Y436F in the second polypeptide and (k-ii) substitutions of C131S, R133K, S228P, L235E and R409K in the first polypeptide and C214S, S228P, L235E, R409K, H435R and Y436F in the second polypeptide, numbering according to the EU index of Kabat, wherein in (i) and (ii), the VL of the first polypeptide and the VH of the second polypeptide forms a binding domain.

* * * * *

SEQUENCE LISTING

```
<160> NUMBER OF SEQ ID NOS: 61

<210> SEQ ID NO 1
<211> LENGTH: 993
<212> TYPE: DNA
<213> ORGANISM: Homo sapiens
<220> FEATURE:
<221> NAME/KEY: CDS
<222> LOCATION: (1)..(993)

<400> SEQUENCE: 1 gcc tcc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60
```

-continued

| | |
|---|---|
| ctc agc agc gtg gtg acc gtg ccc tcc agc agc ttg ggc acc cag acc<br>Leu Ser Ser Val Val Thr Val Pro Ser Ser Ser Leu Gly Thr Gln Thr<br>65                             70                         75                    80 | 240 |
| tac atc tgc aac gtg aat cac aag ccc agc aac acc aag gtg gac aag<br>Tyr Ile Cys Asn Val Asn His Lys Pro Ser Asn Thr Lys Val Asp Lys<br>85                           90                         95 | 288 |
| aaa gtt gag ccc aaa tct tgt gac aaa act cac aca tgc cca ccg tgc<br>Lys Val Glu Pro Lys Ser Cys Asp Lys Thr His Thr Cys Pro Pro Cys<br>                100                      105                      110 | 336 |
| cca gca cct gaa ctc ctg ggg gga ccg tca gtc ttc ctc ttc ccc cca<br>Pro Ala Pro Glu Leu Leu Gly Gly Pro Ser Val Phe Leu Phe Pro Pro<br>        115                      120                      125 | 384 |
| aaa ccc aag gac acc ctc atg atc tcc cgg acc cct gag gtc aca tgc<br>Lys Pro Lys Asp Thr Leu Met Ile Ser Arg Thr Pro Glu Val Thr Cys<br>130                           135                      140 | 432 |
| gtg gtg gtg gac gtg agc cac gaa gac cct gag gtc aag ttc aac tgg<br>Val Val Val Asp Val Ser His Glu Asp Pro Glu Val Lys Phe Asn Trp<br>145                         150                      155                  160 | 480 |
| tac gtg gac ggc gtg gag gtg cat aat gcc aag aca aag ccg cgg gag<br>Tyr Val Asp Gly Val Glu Val His Asn Ala Lys Thr Lys Pro Arg Glu<br>                  165                      170                      175 | 528 |
| gag cag tac aac agc acg tac cgt gtg gtc agc gtc ctc acc gtc ctg<br>Glu Gln Tyr Asn Ser Thr Tyr Arg Val Val Ser Val Leu Thr Val Leu<br>        180                      185                      190 | 576 |
| cac cag gac tgg ctg aat ggc aag gag tac aag tgc aag gtc tcc aac<br>His Gln Asp Trp Leu Asn Gly Lys Glu Tyr Lys Cys Lys Val Ser Asn<br>                195                      200                      205 | 624 |
| aaa gcc ctc cca gcc ccc atc gag aaa acc atc tcc aaa gcc aaa ggg<br>Lys Ala Leu Pro Ala Pro Ile Glu Lys Thr Ile Ser Lys Ala Lys Gly<br>210                         215                      220 | 672 |
| cag ccc cga gaa cca cag gtg tac acc ctg ccc cca tcc cgg gat gag<br>Gln Pro Arg Glu Pro Gln Val Tyr Thr Leu Pro Pro Ser Arg Asp Glu<br>225                         230                      235                  240 | 720 |
| ctg acc aag aac cag gtc agc ctg acc tgc ctg gtc aaa ggc ttc tat<br>Leu Thr Lys Asn Gln Val Ser Leu Thr Cys Leu Val Lys Gly Phe Tyr<br>        245                      250                      255 | 768 |
| ccc agc gac atc gcc gtg gag tgg gag agc aat ggg cag ccg gag aac<br>Pro Ser Asp Ile Ala Val Glu Trp Glu Ser Asn Gly Gln Pro Glu Asn<br>                260                      265                      270 | 816 |
| aac tac aag acc acg cct ccc gtg ctg gac tcc gac ggc tcc ttc ttc<br>Asn Tyr Lys Thr Thr Pro Pro Val Leu Asp Ser Asp Gly Ser Phe Phe<br>        275                      280                      285 | 864 |
| ctc tac agc aag ctc acc gtg gac aag agc agg tgg cag cag ggg aac<br>Leu Tyr Ser Lys Leu Thr Val Asp Lys Ser Arg Trp Gln Gln Gly Asn<br>        290                      295                      300 | 912 |
| gtc ttc tca tgc tcc gtg atg cat gag gct ctg cac aac cac tac acg<br>Val Phe Ser Cys Ser Val Met His Glu Ala Leu His Asn His Tyr Thr<br>305                         310                      315                  320 | 960 |
| cag aag agc ctc tcc ctg tct ccg ggt aaa tga<br>Gln Lys Ser Leu Ser Leu Ser Pro Gly Lys<br>        325                      330 | 993 |

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                    10                  15

```
Ser Thr Ser Gly Gly Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 984
<212> TYPE: DNA
<213> ORGANISM: Homo sapiens
<220> FEATURE:
<221> NAME/KEY: CDS
<222> LOCATION: (1)..(984)

<400> SEQUENCE: 3 gcc tcc acc aag ggc cca tcc gtc ttc ccc ctg gcg ccc tgc tcc agg    48
Ala Ser Thr Lys Gly Pro Ser Val Phe Pro Leu Ala Pro Cys Ser Arg
 1               5                  10                  15 agc acc tcc gag agc aca gcc gcc ctg ggc tgc ctg gtc aag gac tac    96
Ser Thr Ser Glu Ser Thr Ala Ala Leu Gly Cys Leu Val Lys Asp Tyr
             20                  25                  30
```

```
ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acg aag acc      240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag      288
Tyr Thr Cys Asn Val Asp His Lys Pro Ser Asn Thr Lys Val Asp Lys
                     85                  90                  95 aga gtt gag tcc aaa tat ggt ccc cca tgc cca tca tgc cca gca cct      336
Arg Val Glu Ser Lys Tyr Gly Pro Pro Cys Pro Ser Cys Pro Ala Pro
                100                 105                 110 gag ttc ctg ggg gga cca tca gtc ttc ctg ttc ccc cca aaa ccc aag      384
Glu Phe Leu Gly Gly Pro Ser Val Phe Leu Phe Pro Pro Lys Pro Lys
            115                 120                 125 gac act ctc atg atc tcc cgg acc cct gag gtc acc tgc gtg gtg gtg      432
Asp Thr Leu Met Ile Ser Arg Thr Pro Glu Val Thr Cys Val Val Val
130                 135                 140 gac gtg agc cag gaa gac ccc gag gtc cag ttc aac tgg tac gtg gat      480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc      528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac      576
Asn Ser Thr Tyr Arg Val Val Ser Val Leu Thr Val Leu His Gln Asp
            180                 185                 190 tgg ctg aac ggc aag gag tac aag tgc aag gtc tcc aac aaa ggc ctc      624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga      672
Pro Ser Ser Ile Glu Lys Thr Ile Ser Lys Ala Lys Gly Gln Pro Arg
210                 215                 220 gag cca cag gtg tac acc ctg ccc cca tcc cag gag gag atg acc aag      720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac      768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag      816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc      864
Thr Thr Pro Pro Val Leu Asp Ser Asp Gly Ser Phe Phe Leu Tyr Ser
        275                 280                 285 agg cta acc gtg gac aag agc agg tgg cag gag ggg aat gtc ttc tca      912
Arg Leu Thr Val Asp Lys Ser Arg Trp Gln Glu Gly Asn Val Phe Ser
290                 295                 300 tgc tcc gtg atg cat gag gct ctg cac aac cac tac aca cag aag agc      960
Cys Ser Val Met His Glu Ala Leu His Asn His Tyr Thr Gln Lys Ser
305                 310                 315                 320 ctc tcc ctg tct ctg ggt aaa tga                                      984
Leu Ser Leu Ser Leu Gly Lys
                325
```

<210> SEQ ID NO 4

```
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 1011
<212> TYPE: DNA
<213> ORGANISM: Artificial
<220> FEATURE:
<223> OTHER INFORMATION: Description of artificial sequence: IgG1-CH-His
<220> FEATURE:
<221> NAME/KEY: CDS
<222> LOCATION: (1)..(1011)
```

<400> SEQUENCE: 5

```
gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag     720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat     768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac     816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc     864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac     912
Leu Tyr Ser Lys Leu Thr Val Asp Lys Ser Arg Trp Gln Gln Gly Asn
    290                 295                 300
```

| | | | | | | | | | | | | |
|---|---|---|---|---|---|---|---|---|---|---|---|---|
| gtc | ttc | tca | tgc | tcc | gtg | atg | cat | gag | gct | ctg | cac | aac | cac | tac | acg | 960 |
| Val | Phe | Ser | Cys | Ser | Val | Met | His | Glu | Ala | Leu | His | Asn | His | Tyr | Thr | |
| 305 | | | | 310 | | | | | 315 | | | | | 320 | | |

| | | | | | | | | | | | | |
|---|---|---|---|---|---|---|---|---|---|---|---|---|
| cag | aag | agc | ctc | tcc | ctg | tct | ccg | ggt | aaa | cat | cac | cat | cac | cat | cac | 1008 |
| Gln | Lys | Ser | Leu | Ser | Leu | Ser | Pro | Gly | Lys | His | His | His | His | His | His | |
| | | | 325 | | | | | 330 | | | | 335 | | | | | tga                                                              1011

<210> SEQ ID NO 6
<211> LENGTH: 336
<212> TYPE: PRT
<213> ORGANISM: Artificial
<220> FEATURE:
<223> OTHER INFORMATION: Synthetic Construct

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

<210> SEQ ID NO 7
<211> LENGTH: 1002
<212> TYPE: DNA
<213> ORGANISM: Artificial
<220> FEATURE:
<223> OTHER INFORMATION: Description of artificial sequence: IgG4-CH-His
<220> FEATURE:
<221> NAME/KEY: CDS
<222> LOCATION: (1)..(1002)

<400> SEQUENCE: 7

```
gcc tcc acc aag ggc cca tcc gtc ttc ccc ctg gcg ccc tgc tcc agg        48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac        96
Ser Thr Ser Glu Ser Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acg aag acc       240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag       288
Tyr Thr Cys Asn Val Asp His Lys Pro Ser Asn Thr Lys Val Asp Lys
                85                  90                  95 aga gtt gag tcc aaa tat ggt ccc cca tgc cca tca tgc cca gca cct       336
Arg Val Glu Ser Lys Tyr Gly Pro Pro Cys Pro Ser Cys Pro Ala Pro
            100                 105                 110 gag ttc ctg ggg gga cca tca gtc ttc ctg ttc ccc cca aaa ccc aag       384
Glu Phe Leu Gly Gly Pro Ser Val Phe Leu Phe Pro Pro Lys Pro Lys
        115                 120                 125 gac act ctc atg atc tcc cgg acc cct gag gtc acc tgc gtg gtg gtg       432
Asp Thr Leu Met Ile Ser Arg Thr Pro Glu Val Thr Cys Val Val Val
    130                 135                 140 gac gtg agc cag gaa gac ccc gag gtc cag ttc aac tgg tac gtg gat       480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc       528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac       576
Asn Ser Thr Tyr Arg Val Val Ser Val Leu Thr Val Leu His Gln Asp
            180                 185                 190 tgg ctg aac ggc aag gag tac aag tgc aag gtc tcc aac aaa ggc ctc       624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga       672
Pro Ser Ser Ile Glu Lys Thr Ile Ser Lys Ala Lys Gly Gln Pro Arg
    210                 215                 220 gag cca cag gtg tac acc ctg ccc cca tcc cag gag gag atg acc aag       720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac       768
Asn Gln Val Ser Leu Thr Cys Leu Val Lys Gly Phe Tyr Pro Ser Asp
```

```
                         245                 250                 255
atc gcc gtg gag tgg gag agc aat ggg cag ccg gag aac aac tac aag      816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc      864
Thr Thr Pro Pro Val Leu Asp Ser Asp Gly Ser Phe Phe Leu Tyr Ser
        275                 280                 285 agg cta acc gtg gac aag agc agg tgg cag gag ggg aat gtc ttc tca      912
Arg Leu Thr Val Asp Lys Ser Arg Trp Gln Glu Gly Asn Val Phe Ser
    290                 295                 300 tgc tcc gtg atg cat gag gct ctg cac aac cac tac aca cag aag agc      960
Cys Ser Val Met His Glu Ala Leu His Asn His Tyr Thr Gln Lys Ser
305                 310                 315                 320 ctc tcc ctg tct ctg ggt aaa cat cac cat cac cat cac tga              1002
Leu Ser Leu Ser Leu Gly Lys His His His His His His
                325                 330

<210> SEQ ID NO 8
<211> LENGTH: 333
<212> TYPE: PRT
<213> ORGANISM: Artificial
<220> FEATURE:
<223> OTHER INFORMATION: Synthetic Construct

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys His His His His His
                325                 330

<210> SEQ ID NO 9
<211> LENGTH: 993
<212> TYPE: DNA
<213> ORGANISM: Artificial
<220> FEATURE:
<223> OTHER INFORMATION: Description of artificial sequence: 1H0
<220> FEATURE:
<221> NAME/KEY: CDS
<222> LOCATION: (1)..(993)

<400> SEQUENCE: 9
```

| | |
|---|---:|
| gcc tcc acc aag ggc cca tcg gtc ttc ccc ctg gca ccc tcc tcc aag<br>Ala Ser Thr Lys Gly Pro Ser Val Phe Pro Leu Ala Pro Ser Ser Lys<br>1               5                   10                  15 | 48 |
| agc acc tct ggg ggc aca gcg gcc ctg ggc tgc ctg gtc aag gac tac<br>Ser Thr Ser Gly Gly Thr Ala Ala Leu Gly Cys Leu Val Lys Asp Tyr<br>                20                  25                  30 | 96 |
| ttc ccc gaa ccg gtg acg gtg tcg tgg aac tca ggc gcc ctg acc agc<br>Phe Pro Glu Pro Val Thr Val Ser Trp Asn Ser Gly Ala Leu Thr Ser<br>            35                  40                  45 | 144 |
| ggc gtg cac acc ttc ccg gct gtc cta cag tcc tca gga ctc tac tcc<br>Gly Val His Thr Phe Pro Ala Val Leu Gln Ser Ser Gly Leu Tyr Ser<br>        50                  55                  60 | 192 |
| ctc agc agc gtg gtg acc gtg ccc tcc agc agc ttg ggc acc cag acc<br>Leu Ser Ser Val Val Thr Val Pro Ser Ser Ser Leu Gly Thr Gln Thr<br>65                  70                  75                  80 | 240 |
| tac atc tgc aac gtg aat cac aag ccc agc aac acc aag gtg gac aag<br>Tyr Ile Cys Asn Val Asn His Lys Pro Ser Asn Thr Lys Val Asp Lys<br>                85                  90                  95 | 288 |
| aaa gtt gag ccc aaa tct tgt gac aaa act cac aca tgc cca ccg tgc<br>Lys Val Glu Pro Lys Ser Cys Asp Lys Thr His Thr Cys Pro Pro Cys<br>            100                 105                 110 | 336 |
| cca gca cct gaa ctc ctg ggg gga ccg tca gtc ttc ctc ttc ccc cca<br>Pro Ala Pro Glu Leu Leu Gly Gly Pro Ser Val Phe Leu Phe Pro Pro<br>        115                 120                 125 | 384 |
| aaa ccc aag gac acc ctc atg atc tcc cgg acc cct gag gtc aca tgc<br>Lys Pro Lys Asp Thr Leu Met Ile Ser Arg Thr Pro Glu Val Thr Cys<br>    130                 135                 140 | 432 |
| gtg gtg gtg gac gtg agc cac gaa gac cct gag gtc aag ttc aac tgg<br>Val Val Val Asp Val Ser His Glu Asp Pro Glu Val Lys Phe Asn Trp<br>145                 150                 155                 160 | 480 |
| tac gtg gac ggc gtg gag gtg cat aat gcc aag aca aag ccg cgg gag<br>Tyr Val Asp Gly Val Glu Val His Asn Ala Lys Thr Lys Pro Arg Glu<br>                165                 170                 175 | 528 |
| gag cag tac aac agc acg tac cgt gtg gtc agc gtc ctc acc gtc ctg<br>Glu Gln Tyr Asn Ser Thr Tyr Arg Val Val Ser Val Leu Thr Val Leu<br>            180                 185                 190 | 576 |
| cac cag gac tgg ctg aat ggc aag gag tac aag tgc aag gtc tcc aac<br>His Gln Asp Trp Leu Asn Gly Lys Glu Tyr Lys Cys Lys Val Ser Asn | 624 |

```
            195                 200                 205
aaa gcc ctc cca gcc ccc atc gag aaa acc atc tcc aaa gcc aaa ggg        672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag        720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat        768
Leu Thr Lys Asn Gln Val Ser Leu Thr Cys Leu Val Lys Gly Phe Tyr
            245                 250                 255 ccc agc gac atc gcc gtg gag tgg gag agc aat ggg cag ccg gag aac        816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc        864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac        912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg        960
Val Phe Ser Cys Ser Val Met His Glu Ala Leu His Asn His Tyr Thr
305                 310                 315                 320 cag aag agc ctc tcc ctg tct ccg ggt aaa tga                            993
Gln Lys Ser Leu Ser Leu Ser Pro Gly Lys
            325                 330

<210> SEQ ID NO 10
<211> LENGTH: 330
<212> TYPE: PRT
<213> ORGANISM: Artificial
<220> FEATURE:
<223> OTHER INFORMATION: Synthetic Construct

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 993
<212> TYPE: DNA
<213> ORGANISM: Artificial
<220> FEATURE:
<223> OTHER INFORMATION: Description of artificial sequence: 1H1
<220> FEATURE:
<221> NAME/KEY: CDS
<222> LOCATION: (1)..(993)

<400> SEQUENCE: 11 gcc tcc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc       240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95 aaa gtt gag ccc aaa tct agc gac aaa act cac aca tgc cca ccg tgc       336
Lys Val Glu Pro Lys Ser Ser Asp Lys Thr His Thr Cys Pro Pro Cys
            100                 105                 110 cca gca cct gaa ctc ctg ggg gga ccg tca gtc ttc ctc ttc ccc cca       384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc       432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg       480
Val Val Val Asp Val Ser His Glu Asp Pro Glu Val Lys Phe Asn Trp
```

```
tac gtg gac ggc gtg gag gtg cat aat gcc aag aca aag ccg cgg gag      528
Tyr Val Asp Gly Val Glu Val His Asn Ala Lys Thr Lys Pro Arg Glu
            165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
        180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
    195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
210                 215                 220 cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
        245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
        260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
    275                 280                 285 ctc tac agc aag ctc acc gtg gac aag agc agg tgg cag cag ggg aac      912
Leu Tyr Ser Lys Leu Thr Val Asp Lys Ser Arg Trp Gln Gln Gly Asn
290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa tga                          993
Gln Lys Ser Leu Ser Leu Ser Pro Gly Lys
                325                 330

<210> SEQ ID NO 12
<211> LENGTH: 330
<212> TYPE: PRT
<213> ORGANISM: Artificial
<220> FEATURE:
<223> OTHER INFORMATION: Synthetic Construct

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 13
<211> LENGTH: 984
<212> TYPE: DNA
<213> ORGANISM: Artificial
<220> FEATURE:
<223> OTHER INFORMATION: Description of artificial sequence: 4H0
<220> FEATURE:
<221> NAME/KEY: CDS
<222> LOCATION: (1)..(984)

<400> SEQUENCE: 13 gcc tcc acc aag ggc cca tcc gtc ttc ccc ctg gcg ccc tgc tcc agg     48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac     96
Ser Thr Ser Glu Ser Thr Ala Ala Leu Gly Cys Leu Val Lys Asp Tyr
            20                  25                  30 ttc ccc gaa ccg gtg acg gtg tcg tgg aac tca ggc gcc ctg acc agc    144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc    192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acg aag acc    240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag    288
Tyr Thr Cys Asn Val Asp His Lys Pro Ser Asn Thr Lys Val Asp Lys
                85                  90                  95 aga gtt gag tcc aaa tat ggt ccc cca tgc cca tca tgc cca gca cct    336
Arg Val Glu Ser Lys Tyr Gly Pro Pro Cys Pro Ser Cys Pro Ala Pro
```

```
                   100                 105                 110
gag ttc ctg ggg gga cca tca gtc ttc ctg ttc ccc cca aaa ccc aag       384
Glu Phe Leu Gly Gly Pro Ser Val Phe Leu Phe Pro Pro Lys Pro Lys
            115                 120                 125 gac act ctc atg atc tcc cgg acc cct gag gtc acc tgc gtg gtg gtg       432
Asp Thr Leu Met Ile Ser Arg Thr Pro Glu Val Thr Cys Val Val Val
130                 135                 140 gac gtg agc cag gaa gac ccc gag gtc cag ttc aac tgg tac gtg gat       480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc       528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac       576
Asn Ser Thr Tyr Arg Val Val Ser Val Leu Thr Val Leu His Gln Asp
            180                 185                 190 tgg ctg aac ggc aag gag tac aag tgc aag gtc tcc aac aaa ggc ctc       624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga       672
Pro Ser Ser Ile Glu Lys Thr Ile Ser Lys Ala Lys Gly Gln Pro Arg
    210                 215                 220 gag cca cag gtg tac acc ctg ccc cca tcc cag gag gag atg acc aag       720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac       768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag       816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc       864
Thr Thr Pro Pro Val Leu Asp Ser Asp Gly Ser Phe Phe Leu Tyr Ser
        275                 280                 285 agg cta acc gtg gac aag agc agg tgg cag gag ggg aat gtc ttc tca       912
Arg Leu Thr Val Asp Lys Ser Arg Trp Gln Glu Gly Asn Val Phe Ser
    290                 295                 300 tgc tcc gtg atg cat gag gct ctg cac aac cac tac aca cag aag agc       960
Cys Ser Val Met His Glu Ala Leu His Asn His Tyr Thr Gln Lys Ser
305                 310                 315                 320 ctc tcc ctg tct ctg ggt aaa tga                                       984
Leu Ser Leu Ser Leu Gly Lys
                325

<210> SEQ ID NO 14
<211> LENGTH: 327
<212> TYPE: PRT
<213> ORGANISM: Artificial
<220> FEATURE:
<223> OTHER INFORMATION: Synthetic Construct

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 15
<211> LENGTH: 984
<212> TYPE: DNA
<213> ORGANISM: Artificial
<220> FEATURE:
<223> OTHER INFORMATION: Description of artificial sequence: 4H1
<220> FEATURE:
<221> NAME/KEY: CDS
<222> LOCATION: (1)..(984)

<400> SEQUENCE: 15

```
gcc tcc acc aag ggc cca tcc gtc ttc ccc ctg gcg ccc tcc tcc aag      48
Ala Ser Thr Lys Gly Pro Ser Val Phe Pro Leu Ala Pro Ser Ser Lys
  1               5                  10                  15 agc acc tcc gag agc aca gcc gcc ctg ggc tgc ctg gtc aag gac tac      96
Ser Thr Ser Glu Ser Thr Ala Ala Leu Gly Cys Leu Val Lys Asp Tyr
                 20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
             35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
```

```
ctc agc agc gtg gtg acc gtg ccc tcc agc agc ttg ggc acg aag acc      240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag      288
Tyr Thr Cys Asn Val Asp His Lys Pro Ser Asn Thr Lys Val Asp Lys
                    85                  90                  95 aga gtt gag tcc aaa tat ggt ccc cca tgc cca tca tgc cca gca cct      336
Arg Val Glu Ser Lys Tyr Gly Pro Pro Cys Pro Ser Cys Pro Ala Pro
                100                 105                 110 gag ttc ctg ggg gga cca tca gtc ttc ctg ttc ccc cca aaa ccc aag      384
Glu Phe Leu Gly Gly Pro Ser Val Phe Leu Phe Pro Pro Lys Pro Lys
            115                 120                 125 gac act ctc atg atc tcc cgg acc cct gag gtc acc tgc gtg gtg gtg      432
Asp Thr Leu Met Ile Ser Arg Thr Pro Glu Val Thr Cys Val Val Val
130                 135                 140 gac gtg agc cag gaa gac ccc gag gtc cag ttc aac tgg tac gtg gat      480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc      528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac      576
Asn Ser Thr Tyr Arg Val Val Ser Val Leu Thr Val Leu His Gln Asp
                180                 185                 190 tgg ctg aac ggc aag gag tac aag tgc aag gtc tcc aac aaa ggc ctc      624
Trp Leu Asn Gly Lys Glu Tyr Lys Cys Lys Val Ser Asn Lys Gly Leu
            195                 200                 205 ccg tcc tcc atc gag aaa acc atc tcc aaa gcc aaa ggg cag ccc cga      672
Pro Ser Ser Ile Glu Lys Thr Ile Ser Lys Ala Lys Gly Gln Pro Arg
210                 215                 220 gag cca cag gtg tac acc ctg ccc cca tcc cag gag gag atg acc aag      720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac      768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag      816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc      864
Thr Thr Pro Pro Val Leu Asp Ser Asp Gly Ser Phe Phe Leu Tyr Ser
        275                 280                 285 agg cta acc gtg gac aag agc agg tgg cag gag ggg aat gtc ttc tca      912
Arg Leu Thr Val Asp Lys Ser Arg Trp Gln Glu Gly Asn Val Phe Ser
290                 295                 300 tgc tcc gtg atg cat gag gct ctg cac aac cac tac aca cag aag agc      960
Cys Ser Val Met His Glu Ala Leu His Asn His Tyr Thr Gln Lys Ser
305                 310                 315                 320 ctc tcc ctg tct ctg ggt aaa tga                                      984
Leu Ser Leu Ser Leu Gly Lys
                325
```

<210> SEQ ID NO 16
<211> LENGTH: 327
<212> TYPE: PRT
<213> ORGANISM: Artificial
<220> FEATURE:
<223> OTHER INFORMATION: Synthetic Construct

<400> SEQUENCE: 16

```
Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 17
<211> LENGTH: 984
<212> TYPE: DNA
<213> ORGANISM: Artificial
<220> FEATURE:
<223> OTHER INFORMATION: Description of artificial sequence: 4H2
<220> FEATURE:
<221> NAME/KEY: CDS
<222> LOCATION: (1)..(984)

<400> SEQUENCE: 17 gcc tcc acc aag ggc cca tcc gtc ttc ccc ctg gcg ccc tcc tcc aag    48
Ala Ser Thr Lys Gly Pro Ser Val Phe Pro Leu Ala Pro Ser Ser Lys
```

```
          1                5                    10                        15
    agc acc tcc gag agc aca gcc gcc ctg ggc tgc ctg gtc aag gac tac         96
    Ser Thr Ser Glu Ser Thr Ala Ala Leu Gly Cys Leu Val Lys Asp Tyr
                     20                  25                  30 ttc ccc gaa ccg gtg acg gtg tcg tgg aac tca ggc gcc ctg acc agc        144
    Phe Pro Glu Pro Val Thr Val Ser Trp Asn Ser Gly Ala Leu Thr Ser
                35                  40                  45 ggc gtg cac acc ttc ccg gct gtc cta cag tcc tca gga ctc tac tcc        192
    Gly Val His Thr Phe Pro Ala Val Leu Gln Ser Ser Gly Leu Tyr Ser
            50                  55                  60 ctc agc agc gtg gtg acc gtg ccc tcc agc agc ttg ggc acg aag acc        240
    Leu Ser Ser Val Val Thr Val Pro Ser Ser Ser Leu Gly Thr Lys Thr
    65                  70                  75                  80 tac acc tgc aac gta gat cac aag ccc agc aac acc aag gtg gac aag        288
    Tyr Thr Cys Asn Val Asp His Lys Pro Ser Asn Thr Lys Val Asp Lys
                        85                  90                  95 aga gtt gag tcc aaa tat ggt ccc cca tgc cca ccg tgc cca gca cct        336
    Arg Val Glu Ser Lys Tyr Gly Pro Pro Cys Pro Pro Cys Pro Ala Pro
                    100                 105                 110 gag ttc ctg ggg gga cca tca gtc ttc ctg ttc ccc cca aaa ccc aag        384
    Glu Phe Leu Gly Gly Pro Ser Val Phe Leu Phe Pro Pro Lys Pro Lys
                115                 120                 125 gac act ctc atg atc tcc cgg acc cct gag gtc acc tgc gtg gtg gtg        432
    Asp Thr Leu Met Ile Ser Arg Thr Pro Glu Val Thr Cys Val Val Val
            130                 135                 140 gac gtg agc cag gaa gac ccc gag gtc cag ttc aac tgg tac gtg gat        480
    Asp Val Ser Gln Glu Asp Pro Glu Val Gln Phe Asn Trp Tyr Val Asp
    145                 150                 155                 160 ggc gtg gag gtg cat aat gcc aag aca aag ccg cgg gag gag cag ttc        528
    Gly Val Glu Val His Asn Ala Lys Thr Lys Pro Arg Glu Glu Gln Phe
                        165                 170                 175 aac agc acg tac cgt gtg gtc agc gtc ctc acc gtc ctg cac cag gac        576
    Asn Ser Thr Tyr Arg Val Val Ser Val Leu Thr Val Leu His Gln Asp
                    180                 185                 190 tgg ctg aac ggc aag gag tac aag tgc aag gtc tcc aac aaa ggc ctc        624
    Trp Leu Asn Gly Lys Glu Tyr Lys Cys Lys Val Ser Asn Lys Gly Leu
                195                 200                 205 ccg tcc tcc atc gag aaa acc atc tcc aaa gcc aaa ggg cag ccc cga        672
    Pro Ser Ser Ile Glu Lys Thr Ile Ser Lys Ala Lys Gly Gln Pro Arg
            210                 215                 220 gag cca cag gtg tac acc ctg ccc cca tcc cag gag gag atg acc aag        720
    Glu Pro Gln Val Tyr Thr Leu Pro Pro Ser Gln Glu Glu Met Thr Lys
    225                 230                 235                 240 aac cag gtc agc ctg acc tgc ctg gtc aaa ggc ttc tac ccc agc gac        768
    Asn Gln Val Ser Leu Thr Cys Leu Val Lys Gly Phe Tyr Pro Ser Asp
                        245                 250                 255 atc gcc gtg gag tgg gag agc aat ggg cag ccg gag aac aac tac aag        816
    Ile Ala Val Glu Trp Glu Ser Asn Gly Gln Pro Glu Asn Asn Tyr Lys
                    260                 265                 270 acc acg cct ccc gtg ctg gac tcc gac ggc tcc ttc ttc ctc tac agc        864
    Thr Thr Pro Pro Val Leu Asp Ser Asp Gly Ser Phe Phe Leu Tyr Ser
                275                 280                 285 aag cta acc gtg gac aag agc agg tgg cag gag ggg aat gtc ttc tca        912
    Lys Leu Thr Val Asp Lys Ser Arg Trp Gln Glu Gly Asn Val Phe Ser
            290                 295                 300 tgc tcc gtg atg cat gag gct ctg cac aac cac tac aca cag aag agc        960
    Cys Ser Val Met His Glu Ala Leu His Asn His Tyr Thr Gln Lys Ser
    305                 310                 315                 320 ctc tcc ctg tct ctg ggt aaa tga                                        984
```

Leu Ser Leu Ser Leu Gly Lys
            325

<210> SEQ ID NO 18
<211> LENGTH: 327
<212> TYPE: PRT
<213> ORGANISM: Artificial
<220> FEATURE:
<223> OTHER INFORMATION: Synthetic Construct

<400> SEQUENCE: 18

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 19
<211> LENGTH: 984

-continued

```
<212> TYPE: DNA
<213> ORGANISM: Artificial
<220> FEATURE:
<223> OTHER INFORMATION: Description of artificial sequence: 4H3
<220> FEATURE:
<221> NAME/KEY: CDS
<222> LOCATION: (1)..(984)

<400> SEQUENCE: 19 gcc tcc acc aag ggc cca tcc gtc ttc ccc ctg gcg ccc tcc tcc aag       48
Ala Ser Thr Lys Gly Pro Ser Val Phe Pro Leu Ala Pro Ser Ser Lys
1               5                   10                  15 agc acc tcc gag agc aca gcc gcc ctg ggc tgc ctg gtc aag gac tac       96
Ser Thr Ser Glu Ser Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acg aag acc      240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag      288
Tyr Thr Cys Asn Val Asp His Lys Pro Ser Asn Thr Lys Val Asp Lys
                85                  90                  95 aga gtt gag tcc aaa tat ggt ccc cca tgc cca ccg tgc cca gca cct      336
Arg Val Glu Ser Lys Tyr Gly Pro Pro Cys Pro Pro Cys Pro Ala Pro
            100                 105                 110 gag ttc gag ggg gga cca tca gtc ttc ctg ttc ccc cca aaa ccc aag      384
Glu Phe Glu Gly Gly Pro Ser Val Phe Leu Phe Pro Pro Lys Pro Lys
        115                 120                 125 gac act ctc atg atc tcc cgg acc cct gag gtc acc tgc gtg gtg gtg      432
Asp Thr Leu Met Ile Ser Arg Thr Pro Glu Val Thr Cys Val Val Val
    130                 135                 140 gac gtg agc cag gaa gac ccc gag gtc cag ttc aac tgg tac gtg gat      480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc      528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac      576
Asn Ser Thr Tyr Arg Val Val Ser Val Leu Thr Val Leu His Gln Asp
            180                 185                 190 tgg ctg aac ggc aag gag tac aag tgc aag gtc tcc aac aaa ggc ctc      624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga      672
Pro Ser Ser Ile Glu Lys Thr Ile Ser Lys Ala Lys Gly Gln Pro Arg
    210                 215                 220 gag cca cag gtg tac acc ctg ccc cca tcc cag gag gag atg acc aag      720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac      768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag      816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc      864
```

```
Thr Thr Pro Pro Val Leu Asp Ser Asp Gly Ser Phe Phe Leu Tyr Ser
            275                 280                 285 aag cta acc gtg gac aag agc agg tgg cag gag ggg aat gtc ttc tca    912
Lys Leu Thr Val Asp Lys Ser Arg Trp Gln Glu Gly Asn Val Phe Ser
        290                 295                 300 tgc tcc gtg atg cat gag gct ctg cac aac cac tac aca cag aag agc    960
Cys Ser Val Met His Glu Ala Leu His Asn His Tyr Thr Gln Lys Ser
305                 310                 315                 320 ctc tcc ctg tct ctg ggt aaa tga                                    984
Leu Ser Leu Ser Leu Gly Lys
                325

<210> SEQ ID NO 20
<211> LENGTH: 327
<212> TYPE: PRT
<213> ORGANISM: Artificial
<220> FEATURE:
<223> OTHER INFORMATION: Synthetic Construct

<400> SEQUENCE: 20

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
            Lys Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
            305                 310                 315                 320

Leu Ser Leu Ser Leu Gly Lys
                            325

<210> SEQ ID NO 21
<211> LENGTH: 1005
<212> TYPE: DNA
<213> ORGANISM: Artificial
<220> FEATURE:
<223> OTHER INFORMATION: Description of artificial sequence: 1L0
<220> FEATURE:
<221> NAME/KEY: CDS
<222> LOCATION: (1)..(1005)

<400> SEQUENCE: 21 cgt acg gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc        96
Gln Leu Lys Ser Gly Thr Ala Ser Val Val Cys Leu Leu Asn Asn Phe
                20                  25                  30 tat ccc aga gag gcc aaa gta cag tgg aag gtg gat aac gcc ctc caa       144
Tyr Pro Arg Glu Ala Lys Val Gln Trp Lys Val Asp Asn Ala Leu Gln
            35                  40                  45 tcg ggt aac tcc cag gag agt gtc aca gag cag gac agc aag gac agc       192
Ser Gly Asn Ser Gln Glu Ser Val Thr Glu Gln Asp Ser Lys Asp Ser
        50                  55                  60 acc tac agc ctc agc agc acc ctg acg ctg agc aaa gca gac tac gag       240
Thr Tyr Ser Leu Ser Ser Thr Leu Thr Leu Ser Lys Ala Asp Tyr Glu
65                  70                  75                  80 aaa cac aaa gtc tac gcc tgc gaa gtc aca cat cag ggc ctc agc tcg       288
Lys His Lys Val Tyr Ala Cys Glu Val Thr His Gln Gly Leu Ser Ser
                85                  90                  95 ccc gtc aca aag agc ttc aac agg gga gag tgt gac aaa act cac aca       336
Pro Val Thr Lys Ser Phe Asn Arg Gly Glu Cys Asp Lys Thr His Thr
                100                 105                 110 tgc cca ccg tgc cca gca cct gaa ctc ctg ggg gga ccg tca gtc ttc       384
Cys Pro Pro Cys Pro Ala Pro Glu Leu Leu Gly Gly Pro Ser Val Phe
            115                 120                 125 ctc ttc ccc cca aaa ccc aag gac acc ctc atg atc tcc cgg acc cct       432
Leu Phe Pro Pro Lys Pro Lys Asp Thr Leu Met Ile Ser Arg Thr Pro
        130                 135                 140 gag gtc aca tgc gtg gtg gtg gac gtg agc cac gaa gac cct gag gtc       480
Glu Val Thr Cys Val Val Val Asp Val Ser His Glu Asp Pro Glu Val
145                 150                 155                 160 aag ttc aac tgg tac gtg gac ggc gtg gag gtg cat aat gcc aag aca       528
Lys Phe Asn Trp Tyr Val Asp Gly Val Glu Val His Asn Ala Lys Thr
                165                 170                 175 aag ccg cgg gag gag cag tac aac agc acg tac cgt gtg gtc agc gtc       576
Lys Pro Arg Glu Glu Gln Tyr Asn Ser Thr Tyr Arg Val Val Ser Val
            180                 185                 190 ctc acc gtc ctg cac cag gac tgg ctg aat ggc aag gag tac aag tgc       624
Leu Thr Val Leu His Gln Asp Trp Leu Asn Gly Lys Glu Tyr Lys Cys
        195                 200                 205 aag gtc tcc aac aaa gcc ctc cca gcc ccc atc gag aaa acc atc tcc       672
Lys Val Ser Asn Lys Ala Leu Pro Ala Pro Ile Glu Lys Thr Ile Ser
    210                 215                 220 aaa gcc aaa ggg cag ccc cga gaa cca cag gtg tac acc ctg ccc cca       720
```

```
Lys Ala Lys Gly Gln Pro Arg Glu Pro Gln Val Tyr Thr Leu Pro Pro
225                 230                 235                 240 tcc cgg gat gag ctg acc aag aac cag gtc agc ctg acc tgc ctg gtc      768
Ser Arg Asp Glu Leu Thr Lys Asn Gln Val Ser Leu Thr Cys Leu Val
                        245                 250                 255 aaa ggc ttc tat ccc agc gac atc gcc gtg gag tgg gag agc aat ggg      816
Lys Gly Phe Tyr Pro Ser Asp Ile Ala Val Glu Trp Glu Ser Asn Gly
                260                 265                 270 cag ccg gag aac aac tac aag acc acg cct ccc gtg ctg gac tcc gac      864
Gln Pro Glu Asn Asn Tyr Lys Thr Thr Pro Pro Val Leu Asp Ser Asp
            275                 280                 285 ggc tcc ttc ttc ctc tac agc aag ctc acc gtg gac aag agc agg tgg      912
Gly Ser Phe Phe Leu Tyr Ser Lys Leu Thr Val Asp Lys Ser Arg Trp
    290                 295                 300 cag cag ggg aac gtc ttc tca tgc tcc gtg atg cat gag gct ctg cac      960
Gln Gln Gly Asn Val Phe Ser Cys Ser Val Met His Glu Ala Leu His
305                 310                 315                 320 aac cac tac acg cag aag agc ctc tcc ctg tct ccg ggc aag tag         1005
Asn His Tyr Thr Gln Lys Ser Leu Ser Leu Ser Pro Gly Lys
                325                 330

<210> SEQ ID NO 22
<211> LENGTH: 334
<212> TYPE: PRT
<213> ORGANISM: Artificial
<220> FEATURE:
<223> OTHER INFORMATION: Synthetic Construct

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220
```

| | | | | | | | | | | | | |
|---|---|---|---|---|---|---|---|---|---|---|---|---|
| Lys | Ala | Lys | Gly | Gln | Pro | Arg | Glu | Pro | Gln | Val | Tyr | Thr | Leu | Pro | Pro |
| 225 | | | | 230 | | | | 235 | | | | 240 |

Ser Arg Asp Glu Leu Thr Lys Asn Gln Val Ser Leu Thr Cys Leu Val
            245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330

<210> SEQ ID NO 23
<211> LENGTH: 1005
<212> TYPE: DNA
<213> ORGANISM: Artificial
<220> FEATURE:
<223> OTHER INFORMATION: Description of artificial sequence: 1L1
<220> FEATURE:
<221> NAME/KEY: CDS
<222> LOCATION: (1)..(1005)

<400> SEQUENCE: 23

```
cgt acg gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
                20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
            35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
        50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc aca cat cag ggc ctc agc tcg     288
Lys His Lys Val Tyr Ala Cys Glu Val Thr His Gln Gly Leu Ser Ser
                85                  90                  95 ccc gtc aca aag agc ttc aac agg gga gag agc gac aaa act cac aca     336
Pro Val Thr Lys Ser Phe Asn Arg Gly Glu Ser Asp Lys Thr His Thr
                100                 105                 110 tgc cca ccg tgc cca gca cct gaa ctc ctg ggg gga ccg tca gtc ttc     384
Cys Pro Pro Cys Pro Ala Pro Glu Leu Leu Gly Gly Pro Ser Val Phe
            115                 120                 125 ctc ttc ccc cca aaa ccc aag gac acc ctc atg atc tcc cgg acc cct     432
Leu Phe Pro Pro Lys Pro Lys Asp Thr Leu Met Ile Ser Arg Thr Pro
        130                 135                 140 gag gtc aca tgc gtg gtg gtg gac gtg agc cac gaa gac cct gag gtc     480
Glu Val Thr Cys Val Val Val Asp Val Ser His Glu Asp Pro Glu Val
145                 150                 155                 160 aag ttc aac tgg tac gtg gac ggc gtg gag gtg cat aat gcc aag aca     528
Lys Phe Asn Trp Tyr Val Asp Gly Val Glu Val His Asn Ala Lys Thr
                165                 170                 175 aag ccg cgg gag gag cag tac aac agc acg tac cgt gtg gtc agc gtc     576
Lys Pro Arg Glu Glu Gln Tyr Asn Ser Thr Tyr Arg Val Val Ser Val
```

```
                Lys Pro Arg Glu Glu Gln Tyr Asn Ser Thr Tyr Arg Val Val Ser Val
                            180                 185                 190 ctc acc gtc ctg cac cag gac tgg ctg aat ggc aag gag tac aag tgc         624
Leu Thr Val Leu His Gln Asp Trp Leu Asn Gly Lys Glu Tyr Lys Cys
        195                 200                 205 aag gtc tcc aac aaa gcc ctc cca gcc ccc atc gag aaa acc atc tcc         672
Lys Val Ser Asn Lys Ala Leu Pro Ala Pro Ile Glu Lys Thr Ile Ser
210                 215                 220 aaa gcc aaa ggg cag ccc cga gaa cca cag gtg tac acc ctg ccc cca         720
Lys Ala Lys Gly Gln Pro Arg Glu Pro Gln Val Tyr Thr Leu Pro Pro
225                 230                 235                 240 tcc cgg gat gag ctg acc aag aac cag gtc agc ctg acc tgc ctg gtc         768
Ser Arg Asp Glu Leu Thr Lys Asn Gln Val Ser Leu Thr Cys Leu Val
                245                 250                 255 aaa ggc ttc tat ccc agc gac atc gcc gtg gag tgg gag agc aat ggg         816
Lys Gly Phe Tyr Pro Ser Asp Ile Ala Val Glu Trp Glu Ser Asn Gly
        260                 265                 270 cag ccg gag aac aac tac aag acc acg cct ccc gtg ctg gac tcc gac         864
Gln Pro Glu Asn Asn Tyr Lys Thr Thr Pro Pro Val Leu Asp Ser Asp
    275                 280                 285 ggc tcc ttc ttc ctc tac agc aag ctc acc gtg gac aag agc agg tgg         912
Gly Ser Phe Phe Leu Tyr Ser Lys Leu Thr Val Asp Lys Ser Arg Trp
290                 295                 300 cag cag ggg aac gtc ttc tca tgc tcc gtg atg cat gag gct ctg cac         960
Gln Gln Gly Asn Val Phe Ser Cys Ser Val Met His Glu Ala Leu His
305                 310                 315                 320 aac cgc ttc acg cag aag agc ctc tcc ctg tct ccg ggc aag tag            1005
Asn Arg Phe Thr Gln Lys Ser Leu Ser Leu Ser Pro Gly Lys
                325                 330

<210> SEQ ID NO 24
<211> LENGTH: 334
<212> TYPE: PRT
<213> ORGANISM: Artificial
<220> FEATURE:
<223> OTHER INFORMATION: Synthetic Construct

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160
```

```
Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn Arg Phe Thr Gln Lys Ser Leu Ser Leu Ser Pro Gly Lys
                325                 330

<210> SEQ ID NO 25
<211> LENGTH: 1011
<212> TYPE: DNA
<213> ORGANISM: Artificial
<220> FEATURE:
<223> OTHER INFORMATION: Description of artificial sequence: 4L0
<220> FEATURE:
<221> NAME/KEY: CDS
<222> LOCATION: (1)..(1011)

<400> SEQUENCE: 25 cgt acg gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc aca cat cag ggc ctc agc tcg     288
Lys His Lys Val Tyr Ala Cys Glu Val Thr His Gln Gly Leu Ser Ser
                85                  90                  95 ccc gtc aca aag agc ttc aac agg gga gag tgt gag tcc aaa tat ggt     336
Pro Val Thr Lys Ser Phe Asn Arg Gly Glu Cys Glu Ser Lys Tyr Gly
            100                 105                 110 ccc cca tgc cca tca tgc cca gca cct gag ttc ctg ggg gga cca tca     384
Pro Pro Cys Pro Ser Cys Pro Ala Pro Glu Phe Leu Gly Gly Pro Ser
        115                 120                 125 gtc ttc ctg ttc ccc cca aaa ccc aag gac act ctc atg atc tcc cgg     432
```

| | | |
|---|---|---|
| Val Phe Leu Phe Pro Pro Lys Pro Lys Asp Thr Leu Met Ile Ser Arg<br>     130                      135                      140 | |
| acc cct gag gtc acc tgc gtg gtg gtg gac gtg agc cag gaa gac ccc<br>Thr Pro Glu Val Thr Cys Val Val Val Asp Val Ser Gln Glu Asp Pro<br>145                     150                      155                  160 | 480 |
| gag gtc cag ttc aac tgg tac gtg gat ggc gtg gag gtg cat aat gcc<br>Glu Val Gln Phe Asn Trp Tyr Val Asp Gly Val Glu Val His Asn Ala<br>                 165                      170                      175 | 528 |
| aag aca aag ccg cgg gag gag cag ttc aac agc acg tac cgt gtg gtc<br>Lys Thr Lys Pro Arg Glu Glu Gln Phe Asn Ser Thr Tyr Arg Val Val<br>               180                      185                      190 | 576 |
| agc gtc ctc acc gtc ctg cac cag gac tgg ctg aac ggc aag gag tac<br>Ser Val Leu Thr Val Leu His Gln Asp Trp Leu Asn Gly Lys Glu Tyr<br>    195                      200                      205 | 624 |
| aag tgc aag gtc tcc aac aaa ggc ctc ccg tcc tcc atc gag aaa acc<br>Lys Cys Lys Val Ser Asn Lys Gly Leu Pro Ser Ser Ile Glu Lys Thr<br>210                     215                      220 | 672 |
| atc tcc aaa gcc aaa ggg cag ccc cga gag cca cag gtg tac acc ctg<br>Ile Ser Lys Ala Lys Gly Gln Pro Arg Glu Pro Gln Val Tyr Thr Leu<br>225                     230                      235                  240 | 720 |
| ccc cca tcc cag gag gag atg acc aag aac cag gtc agc ctg acc tgc<br>Pro Pro Ser Gln Glu Glu Met Thr Lys Asn Gln Val Ser Leu Thr Cys<br>                 245                      250                      255 | 768 |
| ctg gtc aaa ggc ttc tac ccc agc gac atc gcc gtg gag tgg gag agc<br>Leu Val Lys Gly Phe Tyr Pro Ser Asp Ile Ala Val Glu Trp Glu Ser<br>              260                      265                      270 | 816 |
| aat ggg cag ccg gag aac aac tac aag acc acg cct ccc gtg ctg gac<br>Asn Gly Gln Pro Glu Asn Asn Tyr Lys Thr Thr Pro Pro Val Leu Asp<br>    275                      280                      285 | 864 |
| tcc gac ggc tcc ttc ttc ctc tac agc agg cta acc gtg gac aag agc<br>Ser Asp Gly Ser Phe Phe Leu Tyr Ser Arg Leu Thr Val Asp Lys Ser<br>290                     295                      300 | 912 |
| agg tgg cag gag ggg aat gtc ttc tca tgc tcc gtg atg cat gag gct<br>Arg Trp Gln Glu Gly Asn Val Phe Ser Cys Ser Val Met His Glu Ala<br>305                     310                      315                  320 | 960 |
| ctg cac aac cac tac aca cag aag agc ctc tcc ctg tct ctg ggt aaa<br>Leu His Asn His Tyr Thr Gln Lys Ser Leu Ser Leu Ser Leu Gly Lys<br>                 325                      330                      335 | 1008 |
| tag | 1011 |

<210> SEQ ID NO 26
<211> LENGTH: 336
<212> TYPE: PRT
<213> ORGANISM: Artificial
<220> FEATURE:
<223> OTHER INFORMATION: Synthetic Construct

<400> SEQUENCE: 26

Arg Thr Val Ala Ala Pro Ser Val Phe Ile Phe Pro Pro Ser Asp Glu
1                 5                     10                    15

Gln Leu Lys Ser Gly Thr Ala Ser Val Val Cys Leu Leu Asn Asn Phe
                 20                     25                     30

Tyr Pro Arg Glu Ala Lys Val Gln Trp Lys Val Asp Asn Ala Leu Gln
               35                     40                    45

Ser Gly Asn Ser Gln Glu Ser Val Thr Glu Gln Asp Ser Lys Asp Ser
    50                     55                     60

Thr Tyr Ser Leu Ser Ser Thr Leu Thr Leu Ser Lys Ala Asp Tyr Glu
65                 70                     75                    80

Lys His Lys Val Tyr Ala Cys Glu Val Thr His Gln Gly Leu Ser Ser

```
                    85                  90                  95
Pro Val Thr Lys Ser Phe Asn Arg Gly Glu Cys Glu Ser Lys Tyr Gly
                100                 105                 110

Pro Pro Cys Pro Ser Cys Pro Ala Pro Glu Phe Leu Gly Gly Pro Ser
            115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Gly Leu Pro Ser Ser Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285

Ser Asp Gly Ser Phe Phe Leu Tyr Ser Arg Leu Thr Val Asp Lys Ser
    290                 295                 300

Arg Trp Gln Glu Gly Asn Val Phe Ser Cys Ser Val Met His Glu Ala
305                 310                 315                 320

Leu His Asn His Tyr Thr Gln Lys Ser Leu Ser Leu Ser Leu Gly Lys
                325                 330                 335

<210> SEQ ID NO 27
<211> LENGTH: 1011
<212> TYPE: DNA
<213> ORGANISM: Artificial
<220> FEATURE:
<223> OTHER INFORMATION: Description of artificial sequence: 4L1
<220> FEATURE:
<221> NAME/KEY: CDS
<222> LOCATION: (1)..(1011)

<400> SEQUENCE: 27 cgt acg gtg gct gca cca tct gtc ttc atc ttc ccg cca tct gat gag     48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc     96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa    144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc    192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag    240
Thr Tyr Ser Leu Ser Ser Thr Leu Thr Leu Ser Lys Ala Asp Tyr Glu
65                  70                  75                  80
```

```
aaa cac aaa gtc tac gcc tgc gaa gtc aca cat cag ggc ctc agc tcg    288
Lys His Lys Val Tyr Ala Cys Glu Val Thr His Gln Gly Leu Ser Ser
                85                  90                  95 ccc gtc aca aag agc ttc aac agg gga gag agt gag tcc aaa tat ggt    336
Pro Val Thr Lys Ser Phe Asn Arg Gly Glu Ser Glu Ser Lys Tyr Gly
            100                 105                 110 ccc cca tgc cca tca tgc cca gca cct gag ttc ctg ggg gga cca tca    384
Pro Pro Cys Pro Ser Cys Pro Ala Pro Glu Phe Leu Gly Gly Pro Ser
        115                 120                 125 gtc ttc ctg ttc ccc cca aaa ccc aag gac act ctc atg atc tcc cgg    432
Val Phe Leu Phe Pro Pro Lys Pro Lys Asp Thr Leu Met Ile Ser Arg
    130                 135                 140 acc cct gag gtc acc tgc gtg gtg gtg gac gtg agc cag gaa gac ccc    480
Thr Pro Glu Val Thr Cys Val Val Val Asp Val Ser Gln Glu Asp Pro
145                 150                 155                 160 gag gtc cag ttc aac tgg tac gtg gat ggc gtg gag gtg cat aat gcc    528
Glu Val Gln Phe Asn Trp Tyr Val Asp Gly Val Glu Val His Asn Ala
                165                 170                 175 aag aca aag ccg cgg gag gag cag ttc aac agc acg tac cgt gtg gtc    576
Lys Thr Lys Pro Arg Glu Glu Gln Phe Asn Ser Thr Tyr Arg Val Val
            180                 185                 190 agc gtc ctc acc gtc ctg cac cag gac tgg ctg aac ggc aag gag tac    624
Ser Val Leu Thr Val Leu His Gln Asp Trp Leu Asn Gly Lys Glu Tyr
        195                 200                 205 aag tgc aag gtc tcc aac aaa ggc ctc ccg tcc tcc atc gag aaa acc    672
Lys Cys Lys Val Ser Asn Lys Gly Leu Pro Ser Ser Ile Glu Lys Thr
    210                 215                 220 atc tcc aaa gcc aaa ggg cag ccc cga gag cca cag gtg tac acc ctg    720
Ile Ser Lys Ala Lys Gly Gln Pro Arg Glu Pro Gln Val Tyr Thr Leu
225                 230                 235                 240 ccc cca tcc cag gag gag atg acc aag aac cag gtc agc ctg acc tgc    768
Pro Pro Ser Gln Glu Glu Met Thr Lys Asn Gln Val Ser Leu Thr Cys
                245                 250                 255 ctg gtc aaa ggc ttc tac ccc agc gac atc gcc gtg gag tgg gag agc    816
Leu Val Lys Gly Phe Tyr Pro Ser Asp Ile Ala Val Glu Trp Glu Ser
            260                 265                 270 aat ggg cag ccg gag aac aac tac aag acc acg cct ccc gtg ctg gac    864
Asn Gly Gln Pro Glu Asn Asn Tyr Lys Thr Thr Pro Pro Val Leu Asp
        275                 280                 285 tcc gac ggc tcc ttc ttc ctc tac agc agg cta acc gtg gac aag agc    912
Ser Asp Gly Ser Phe Phe Leu Tyr Ser Arg Leu Thr Val Asp Lys Ser
    290                 295                 300 agg tgg cag gag ggg aat gtc ttc tca tgc tcc gtg atg cat gag gct    960
Arg Trp Gln Glu Gly Asn Val Phe Ser Cys Ser Val Met His Glu Ala
305                 310                 315                 320 ctg cac aac cac tac aca cag aag agc ctc tcc ctg tct ctg ggt aaa   1008
Leu His Asn His Tyr Thr Gln Lys Ser Leu Ser Leu Ser Leu Gly Lys
                325                 330                 335 tag                                                               1011
```

<210> SEQ ID NO 28
<211> LENGTH: 336
<212> TYPE: PRT
<213> ORGANISM: Artificial
<220> FEATURE:
<223> OTHER INFORMATION: Synthetic Construct

<400> SEQUENCE: 28

```
Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
         20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Ser Glu Ser Lys Tyr Gly
            100                 105                 110

Pro Pro Cys Pro Ser Cys Pro Ala Pro Glu Phe Leu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Gly Leu Pro Ser Ser Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285

Ser Asp Gly Ser Phe Phe Leu Tyr Ser Arg Leu Thr Val Asp Lys Ser
    290                 295                 300

Arg Trp Gln Glu Gly Asn Val Phe Ser Cys Ser Val Met His Glu Ala
305                 310                 315                 320

Leu His Asn His Tyr Thr Gln Lys Ser Leu Ser Leu Ser Leu Gly Lys
                325                 330                 335

<210> SEQ ID NO 29
<211> LENGTH: 1011
<212> TYPE: DNA
<213> ORGANISM: Artificial
<220> FEATURE:
<223> OTHER INFORMATION: Description of artificial sequence: 4L2
<220> FEATURE:
<221> NAME/KEY: CDS
<222> LOCATION: (1)..(1011)

<400> SEQUENCE: 29 cgt acg gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
```

```
                Gln Leu Lys Ser Gly Thr Ala Ser Val Val Cys Leu Leu Asn Asn Phe
                         20                  25                  30 tat ccc aga gag gcc aaa gta cag tgg aag gtg gat aac gcc ctc caa        144
Tyr Pro Arg Glu Ala Lys Val Gln Trp Lys Val Asp Asn Ala Leu Gln
         35                  40                  45 tcg ggt aac tcc cag gag agt gtc aca gag cag gac agc aag gac agc        192
Ser Gly Asn Ser Gln Glu Ser Val Thr Glu Gln Asp Ser Lys Asp Ser
 50                  55                  60 acc tac agc ctc agc agc acc ctg acg ctg agc aaa gca gac tac gag        240
Thr Tyr Ser Leu Ser Ser Thr Leu Thr Leu Ser Lys Ala Asp Tyr Glu
 65                  70                  75                  80 aaa cac aaa gtc tac gcc tgc gaa gtc aca cat cag ggc ctc agc tcg        288
Lys His Lys Val Tyr Ala Cys Glu Val Thr His Gln Gly Leu Ser Ser
                 85                  90                  95 ccc gtc aca aag agc ttc aac agg gga gag agt gag tcc aaa tat ggt        336
Pro Val Thr Lys Ser Phe Asn Arg Gly Glu Ser Glu Ser Lys Tyr Gly
            100                 105                 110 ccc cca tgc cca tca tgc cca gca cct gag ttc ctg ggg gga cca tca        384
Pro Pro Cys Pro Ser Cys Pro Ala Pro Glu Phe Leu Gly Gly Pro Ser
        115                 120                 125 gtc ttc ctg ttc ccc cca aaa ccc aag gac act ctc atg atc tcc cgg        432
Val Phe Leu Phe Pro Pro Lys Pro Lys Asp Thr Leu Met Ile Ser Arg
    130                 135                 140 acc cct gag gtc acc tgc gtg gtg gtg gac gtg agc cag gaa gac ccc        480
Thr Pro Glu Val Thr Cys Val Val Val Asp Val Ser Gln Glu Asp Pro
145                 150                 155                 160 gag gtc cag ttc aac tgg tac gtg gat ggc gtg gag gtg cat aat gcc        528
Glu Val Gln Phe Asn Trp Tyr Val Asp Gly Val Glu Val His Asn Ala
                165                 170                 175 aag aca aag ccg cgg gag gag cag ttc aac agc acg tac cgt gtg gtc        576
Lys Thr Lys Pro Arg Glu Glu Gln Phe Asn Ser Thr Tyr Arg Val Val
            180                 185                 190 agc gtc ctc acc gtc ctg cac cag gac tgg ctg aac ggc aag gag tac        624
Ser Val Leu Thr Val Leu His Gln Asp Trp Leu Asn Gly Lys Glu Tyr
        195                 200                 205 aag tgc aag gtc tcc aac aaa ggc ctc ccg tcc tcc atc gag aaa acc        672
Lys Cys Lys Val Ser Asn Lys Gly Leu Pro Ser Ser Ile Glu Lys Thr
    210                 215                 220 atc tcc aaa gcc aaa ggg cag ccc cga gag cca cag gtg tac acc ctg        720
Ile Ser Lys Ala Lys Gly Gln Pro Arg Glu Pro Gln Val Tyr Thr Leu
225                 230                 235                 240 ccc cca tcc cag gag gag atg acc aag aac cag gtc agc ctg acc tgc        768
Pro Pro Ser Gln Glu Glu Met Thr Lys Asn Gln Val Ser Leu Thr Cys
                245                 250                 255 ctg gtc aaa ggc ttc tac ccc agc gac atc gcc gtg gag tgg gag agc        816
Leu Val Lys Gly Phe Tyr Pro Ser Asp Ile Ala Val Glu Trp Glu Ser
            260                 265                 270 aat ggg cag ccg gag aac aac tac aag acc acg cct ccc gtg ctg gac        864
Asn Gly Gln Pro Glu Asn Asn Tyr Lys Thr Thr Pro Pro Val Leu Asp
        275                 280                 285 tcc gac ggc tcc ttc ttc ctc tac agc agg cta acc gtg gac aag agc        912
Ser Asp Gly Ser Phe Phe Leu Tyr Ser Arg Leu Thr Val Asp Lys Ser
    290                 295                 300 agg tgg cag gag ggg aat gtc ttc tca tgc tcc gtg atg cat gag gct        960
Arg Trp Gln Glu Gly Asn Val Phe Ser Cys Ser Val Met His Glu Ala
305                 310                 315                 320 ctg cac aac cgc ttc aca cag aag agc ctc tcc ctg tct ctg ggt aaa       1008
Leu His Asn Arg Phe Thr Gln Lys Ser Leu Ser Leu Ser Leu Gly Lys
                325                 330                 335
``` tag                                                                  1011

<210> SEQ ID NO 30
<211> LENGTH: 336
<212> TYPE: PRT
<213> ORGANISM: Artificial
<220> FEATURE:
<223> OTHER INFORMATION: Synthetic Construct

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Glu Ser Lys Tyr Gly
            100                 105                 110

Pro Pro Cys Pro Ser Cys Pro Ala Pro Glu Phe Leu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Gly Leu Pro Ser Ser Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285

Ser Asp Gly Ser Phe Phe Leu Tyr Ser Arg Leu Thr Val Asp Lys Ser
    290                 295                 300

Arg Trp Gln Glu Gly Asn Val Phe Ser Cys Ser Val Met His Glu Ala
305                 310                 315                 320

Leu His Asn Arg Phe Thr Gln Lys Ser Leu Ser Leu Ser Leu Gly Lys
                325                 330                 335

<210> SEQ ID NO 31
<211> LENGTH: 1011
<212> TYPE: DNA

```
<213> ORGANISM: Artificial
<220> FEATURE:
<223> OTHER INFORMATION: Description of artificial sequence: 4L3
<220> FEATURE:
<221> NAME/KEY: CDS
<222> LOCATION: (1)..(1011)

<400> SEQUENCE: 31 cgt acg gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc        96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa       144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc       192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag       240
Thr Tyr Ser Leu Ser Ser Thr Leu Thr Leu Ser Lys Ala Asp Tyr Glu
65                  70                  75                  80 aaa cac aaa gtc tac gcc tgc gaa gtc aca cat cag ggc ctc agc tcg       288
Lys His Lys Val Tyr Ala Cys Glu Val Thr His Gln Gly Leu Ser Ser
                85                  90                  95 ccc gtc aca aag agc ttc aac agg gga gag agt gag tcc aaa tat ggt       336
Pro Val Thr Lys Ser Phe Asn Arg Gly Glu Ser Glu Ser Lys Tyr Gly
            100                 105                 110 ccc cca tgc cca ccg tgc cca gca cct gag ttc ctg ggg gga cca tca       384
Pro Pro Cys Pro Pro Cys Pro Ala Pro Glu Phe Leu Gly Gly Pro Ser
        115                 120                 125 gtc ttc ctg ttc ccc cca aaa ccc aag gac act ctc atg atc tcc cgg       432
Val Phe Leu Phe Pro Pro Lys Pro Lys Asp Thr Leu Met Ile Ser Arg
    130                 135                 140 acc cct gag gtc acc tgc gtg gtg gtg gac gtg agc cag gaa gac ccc       480
Thr Pro Glu Val Thr Cys Val Val Val Asp Val Ser Gln Glu Asp Pro
145                 150                 155                 160 gag gtc cag ttc aac tgg tac gtg gat ggc gtg gag gtg cat aat gcc       528
Glu Val Gln Phe Asn Trp Tyr Val Asp Gly Val Glu Val His Asn Ala
                165                 170                 175 aag aca aag ccg cgg gag gag cag ttc aac agc acg tac cgt gtg gtc       576
Lys Thr Lys Pro Arg Glu Glu Gln Phe Asn Ser Thr Tyr Arg Val Val
            180                 185                 190 agc gtc ctc acc gtc ctg cac cag gac tgg ctg aac ggc aag gag tac       624
Ser Val Leu Thr Val Leu His Gln Asp Trp Leu Asn Gly Lys Glu Tyr
        195                 200                 205 aag tgc aag gtc tcc aac aaa ggc ctc ccg tcc tcc atc gag aaa acc       672
Lys Cys Lys Val Ser Asn Lys Gly Leu Pro Ser Ser Ile Glu Lys Thr
    210                 215                 220 atc tcc aaa gcc aaa ggg cag ccc cga gag cca cag gtg tac acc ctg       720
Ile Ser Lys Ala Lys Gly Gln Pro Arg Glu Pro Gln Val Tyr Thr Leu
225                 230                 235                 240 ccc cca tcc cag gag gag atg acc aag aac cag gtc agc ctg acc tgc       768
Pro Pro Ser Gln Glu Glu Met Thr Lys Asn Gln Val Ser Leu Thr Cys
                245                 250                 255 ctg gtc aaa ggc ttc tac ccc agc gac atc gcc gtg gag tgg gag agc       816
Leu Val Lys Gly Phe Tyr Pro Ser Asp Ile Ala Val Glu Trp Glu Ser
            260                 265                 270 aat ggg cag ccg gag aac aac tac aag acc acg cct ccc gtg ctg gac       864
Asn Gly Gln Pro Glu Asn Asn Tyr Lys Thr Thr Pro Pro Val Leu Asp
```

-continued

```
                275                 280                 285
tcc gac ggc tcc ttc ttc ctc tac agc aag cta acc gtg gac aag agc     912
Ser Asp Gly Ser Phe Phe Leu Tyr Ser Lys Leu Thr Val Asp Lys Ser
    290                 295                 300 agg tgg cag gag ggg aat gtc ttc tca tgc tcc gtg atg cat gag gct     960
Arg Trp Gln Glu Gly Asn Val Phe Ser Cys Ser Val Met His Glu Ala
305                 310                 315                 320 ctg cac aac cgc ttc aca cag aag agc ctc tcc ctg tct ctg ggt aaa    1008
Leu His Asn Arg Phe Thr Gln Lys Ser Leu Ser Leu Ser Leu Gly Lys
                325                 330                 335 tag                                                                 1011
```

<210> SEQ ID NO 32
<211> LENGTH: 336
<212> TYPE: PRT
<213> ORGANISM: Artificial
<220> FEATURE:
<223> OTHER INFORMATION: Synthetic Construct

<400> SEQUENCE: 32

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Glu Ser Lys Tyr Gly
            100                 105                 110

Pro Pro Cys Pro Pro Cys Pro Ala Pro Glu Phe Leu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
        195                 200                 205

Lys Cys Lys Val Ser Asn Lys Gly Leu Pro Ser Ser Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285
```

```
Ser Asp Gly Ser Phe Phe Leu Tyr Ser Lys Leu Thr Val Asp Lys Ser
    290                 295                 300
Arg Trp Gln Glu Gly Asn Val Phe Ser Cys Ser Val Met His Glu Ala
305                 310                 315                 320
Leu His Asn Arg Phe Thr Gln Lys Ser Leu Ser Leu Ser Leu Gly Lys
                325                 330                 335

<210> SEQ ID NO 33
<211> LENGTH: 1011
<212> TYPE: DNA
<213> ORGANISM: Artificial
<220> FEATURE:
<223> OTHER INFORMATION: Description of artificial sequence: 4L4
<220> FEATURE:
<221> NAME/KEY: CDS
<222> LOCATION: (1)..(1011)

<400> SEQUENCE: 33 cgt acg gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc aca cat cag ggc ctc agc tcg     288
Lys His Lys Val Tyr Ala Cys Glu Val Thr His Gln Gly Leu Ser Ser
                85                  90                  95 ccc gtc aca aag agc ttc aac agg gga gag agt gag tcc aaa tat ggt     336
Pro Val Thr Lys Ser Phe Asn Arg Gly Glu Ser Glu Ser Lys Tyr Gly
            100                 105                 110 ccc cca tgc cca ccg tgc cca gca cct gag ttc gag ggg gga cca tca     384
Pro Pro Cys Pro Pro Cys Pro Ala Pro Glu Phe Glu Gly Gly Pro Ser
        115                 120                 125 gtc ttc ctg ttc ccc cca aaa ccc aag gac act ctc atg atc tcc cgg     432
Val Phe Leu Phe Pro Pro Lys Pro Lys Asp Thr Leu Met Ile Ser Arg
130                 135                 140 acc cct gag gtc acc tgc gtg gtg gtg gac gtg agc cag gaa gac ccc     480
Thr Pro Glu Val Thr Cys Val Val Val Asp Val Ser Gln Glu Asp Pro
145                 150                 155                 160 gag gtc cag ttc aac tgg tac gtg gat ggc gtg gag gtg cat aat gcc     528
Glu Val Gln Phe Asn Trp Tyr Val Asp Gly Val Glu Val His Asn Ala
                165                 170                 175 aag aca aag ccg cgg gag gag cag ttc aac agc acg tac cgt gtg gtc     576
Lys Thr Lys Pro Arg Glu Glu Gln Phe Asn Ser Thr Tyr Arg Val Val
            180                 185                 190 agc gtc ctc acc gtc ctg cac cag gac tgg ctg aac ggc aag gag tac     624
Ser Val Leu Thr Val Leu His Gln Asp Trp Leu Asn Gly Lys Glu Tyr
        195                 200                 205 aag tgc aag gtc tcc aac aaa ggc ctc ccg tcc tcc atc gag aaa acc     672
Lys Cys Lys Val Ser Asn Lys Gly Leu Pro Ser Ser Ile Glu Lys Thr
210                 215                 220
```

-continued

| | |
|---|---|
| atc tcc aaa gcc aaa ggg cag ccc cga gag cca cag gtg tac acc ctg<br>Ile Ser Lys Ala Lys Gly Gln Pro Arg Glu Pro Gln Val Tyr Thr Leu<br>225                            230                            235                            240 | 720 |
| ccc cca tcc cag gag gag atg acc aag aac cag gtc agc ctg acc tgc<br>Pro Pro Ser Gln Glu Glu Met Thr Lys Asn Gln Val Ser Leu Thr Cys<br>                      245                            250                            255 | 768 |
| ctg gtc aaa ggc ttc tac ccc agc gac atc gcc gtg gag tgg gag agc<br>Leu Val Lys Gly Phe Tyr Pro Ser Asp Ile Ala Val Glu Trp Glu Ser<br>260                            265                            270 | 816 |
| aat ggg cag ccg gag aac aac tac aag acc acg cct ccc gtg ctg gac<br>Asn Gly Gln Pro Glu Asn Asn Tyr Lys Thr Thr Pro Pro Val Leu Asp<br>               275                            280                            285 | 864 |
| tcc gac ggc tcc ttc ttc ctc tac agc aag cta acc gtg gac aag agc<br>Ser Asp Gly Ser Phe Phe Leu Tyr Ser Lys Leu Thr Val Asp Lys Ser<br>290                            295                            300 | 912 |
| agg tgg cag gag ggg aat gtc ttc tca tgc tcc gtg atg cat gag gct<br>Arg Trp Gln Glu Gly Asn Val Phe Ser Cys Ser Val Met His Glu Ala<br>305                            310                            315                            320 | 960 |
| ctg cac aac cgc ttc aca cag aag agc ctc tcc ctg tct ctg ggt aaa<br>Leu His Asn Arg Phe Thr Gln Lys Ser Leu Ser Leu Ser Leu Gly Lys<br>               325                            330                            335 | 1008 |
| tag | 1011 |

<210> SEQ ID NO 34
<211> LENGTH: 336
<212> TYPE: PRT
<213> ORGANISM: Artificial
<220> FEATURE:
<223> OTHER INFORMATION: Synthetic Construct

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Glu Ser Lys Tyr Gly
            100                 105                 110

Pro Pro Cys Pro Pro Cys Pro Ala Pro Glu Phe Glu Gly Gly Pro Ser
        115                 120                 125

Val Phe Leu Phe Pro Pro Lys Pro Lys Asp Thr Leu Met Ile Ser Arg
    130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
        195                 200                 205

```
Lys Cys Lys Val Ser Asn Lys Gly Leu Pro Ser Ser Ile Glu Lys Thr
    210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
        275                 280                 285

Ser Asp Gly Ser Phe Phe Leu Tyr Ser Lys Leu Thr Val Asp Lys Ser
290                 295                 300

Arg Trp Gln Gln Gly Asn Val Phe Ser Cys Ser Val Met His Glu Ala
305                 310                 315                 320

Leu His Asn Arg Phe Thr Gln Lys Ser Leu Ser Leu Ser Leu Gly Lys
                325                 330                 335

<210> SEQ ID NO 35
<211> LENGTH: 357
<212> TYPE: DNA
<213> ORGANISM: Artificial
<220> FEATURE:
<223> OTHER INFORMATION: Description of artificial sequence: GA101VH
<220> FEATURE:
<221> NAME/KEY: CDS
<222> LOCATION: (1)..(357)

<400> SEQUENCE: 35 cag gtg caa ttg gtg cag tct ggc gct gaa gtt aag aag cct ggg agt      48
Gln Val Gln Leu Val Gln Ser Gly Ala Glu Val Lys Lys Pro Gly Ser
1               5                   10                  15 tca gtg aag gtc tcc tgc aag gct tcc gga tac gcc ttc agc tat tct     96
Ser Val Lys Val Ser Cys Lys Ala Ser Gly Tyr Ala Phe Ser Tyr Ser
                20                  25                  30 tgg atg aac tgg gtg cgg cag gcc cct gga caa ggg ctc gag tgg atg    144
Trp Met Asn Trp Val Arg Gln Ala Pro Gly Gln Gly Leu Glu Trp Met
            35                  40                  45 gga cgg atc ttt ccc ggc gat ggg gat act gac tac aat ggg aaa ttc    192
Gly Arg Ile Phe Pro Gly Asp Gly Asp Thr Asp Tyr Asn Gly Lys Phe
        50                  55                  60 aag ggc aga gtc aca att acc gcc gac aaa tcc act agc aca gcc tat    240
Lys Gly Arg Val Thr Ile Thr Ala Asp Lys Ser Thr Ser Thr Ala Tyr
65                  70                  75                  80 atg gag ctg agc agc ctg aga tcc gag gac acg gcc gtg tat tac tgt    288
Met Glu Leu Ser Ser Leu Arg Ser Glu Asp Thr Ala Val Tyr Tyr Cys
                85                  90                  95 gca aga aat gtc ttt gat ggt tac tgg ctt gtt tac tgg ggc cag gga    336
Ala Arg Asn Val Phe Asp Gly Tyr Trp Leu Val Tyr Trp Gly Gln Gly
            100                 105                 110 acc ctg gtc acc gtc tcc tca                                        357
Thr Leu Val Thr Val Ser Ser
        115

<210> SEQ ID NO 36
<211> LENGTH: 119
<212> TYPE: PRT
<213> ORGANISM: Artificial
<220> FEATURE:
<223> OTHER INFORMATION: Synthetic Construct

<400> SEQUENCE: 36
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
            115
```

```
<210> SEQ ID NO 37
<211> LENGTH: 336
<212> TYPE: DNA
<213> ORGANISM: Artificial
<220> FEATURE:
<223> OTHER INFORMATION: Description of artificial sequence: GA101VL
<220> FEATURE:
<221> NAME/KEY: CDS
<222> LOCATION: (1)..(336)

<400> SEQUENCE: 37 gat atc gtg atg acc cag act cca ctc tcc ctg ccc gtc acc cct gga     48
Asp Ile Val Met Thr Gln Thr Pro Leu Ser Leu Pro Val Thr Pro Gly
1               5                   10                  15 gag ccc gcc agc att agc tgc agg tct agc aag agc ctc ttg cac agc     96
Glu Pro Ala Ser Ile Ser Cys Arg Ser Ser Lys Ser Leu Leu His Ser
            20                  25                  30 aat ggc atc act tat ttg tat tgg tac ctg caa aag cca ggg cag tct    144
Asn Gly Ile Thr Tyr Leu Tyr Trp Tyr Leu Gln Lys Pro Gly Gln Ser
        35                  40                  45 cca cag ctc ctg att tat caa atg tcc aac ctt gtc tct ggc gtc cct    192
Pro Gln Leu Leu Ile Tyr Gln Met Ser Asn Leu Val Ser Gly Val Pro
    50                  55                  60 gac cgg ttc tcc ggc tcc ggg tca ggc act gat ttc aca ctg aaa atc    240
Asp Arg Phe Ser Gly Ser Gly Ser Gly Thr Asp Phe Thr Leu Lys Ile
65                  70                  75                  80 agc agg gtg gag gct gag gat gtt gga gtt tat tac tgc gct cag aat    288
Ser Arg Val Glu Ala Glu Asp Val Gly Val Tyr Tyr Cys Ala Gln Asn
                85                  90                  95 cta gaa ctt cct tac acc ttc ggc gga ggg acc aag gtg gag atc aaa    336
Leu Glu Leu Pro Tyr Thr Phe Gly Gly Gly Thr Lys Val Glu Ile Lys
            100                 105                 110
```

```
<210> SEQ ID NO 38
<211> LENGTH: 112
<212> TYPE: PRT
<213> ORGANISM: Artificial
<220> FEATURE:
<223> OTHER INFORMATION: Synthetic Construct

<400> SEQUENCE: 38

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
```

```
              20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

<210> SEQ ID NO 39
<211> LENGTH: 360
<212> TYPE: DNA
<213> ORGANISM: Artificial
<220> FEATURE:
<223> OTHER INFORMATION: Description of artificial sequence: 4D5VH
<220> FEATURE:
<221> NAME/KEY: CDS
<222> LOCATION: (1)..(360)

<400> SEQUENCE: 39 gag gtt cag ctg gtg gag tct ggc ggt ggc ctg gtg cag cca ggg ggc      48
Glu Val Gln Leu Val Glu Ser Gly Gly Gly Leu Val Gln Pro Gly Gly
 1               5                  10                  15 tca ctc cgt ttg tcc tgt gca gct tct ggc ttc aac att aaa gac acc      96
Ser Leu Arg Leu Ser Cys Ala Ala Ser Gly Phe Asn Ile Lys Asp Thr
            20                  25                  30 tat ata cac tgg gtg cgt cag gcc ccg ggt aag ggc ctg gaa tgg gtt     144
Tyr Ile His Trp Val Arg Gln Ala Pro Gly Lys Gly Leu Glu Trp Val
        35                  40                  45 gca agg att tat cct acg aat ggt tat act aga tat gcc gat agc gtc     192
Ala Arg Ile Tyr Pro Thr Asn Gly Tyr Thr Arg Tyr Ala Asp Ser Val
    50                  55                  60 aag ggc cgt ttc act ata agc gca gac aca tcc aaa aac aca gcc tac     240
Lys Gly Arg Phe Thr Ile Ser Ala Asp Thr Ser Lys Asn Thr Ala Tyr
 65                  70                  75                  80 ctg cag atg aac agc ctg cgt gct gag gac act gcc gtc tat tat tgt     288
Leu Gln Met Asn Ser Leu Arg Ala Glu Asp Thr Ala Val Tyr Tyr Cys
                85                  90                  95 tct aga tgg gga ggg gac ggc ttc tat gct atg gac tac tgg ggt caa     336
Ser Arg Trp Gly Gly Asp Gly Phe Tyr Ala Met Asp Tyr Trp Gly Gln
            100                 105                 110 gga acc ctg gtc acc gtc tcc tcg                                     360
Gly Thr Leu Val Thr Val Ser Ser
        115                 120

<210> SEQ ID NO 40
<211> LENGTH: 120
<212> TYPE: PRT
<213> ORGANISM: Artificial
<220> FEATURE:
<223> OTHER INFORMATION: Synthetic Construct

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                35                  40                  45
Ala Arg Ile Tyr Pro Thr Asn Gly Tyr Thr Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser
            115                 120

<210> SEQ ID NO 41
<211> LENGTH: 321
<212> TYPE: DNA
<213> ORGANISM: Artificial
<220> FEATURE:
<223> OTHER INFORMATION: Description of artificial sequence: 4D5VL
<220> FEATURE:
<221> NAME/KEY: CDS
<222> LOCATION: (1)..(321)

<400> SEQUENCE: 41 gat atc cag atg acc cag tcc ccg agc tcc ctg tcc gcc tct gtg ggc      48
Asp Ile Gln Met Thr Gln Ser Pro Ser Ser Leu Ser Ala Ser Val Gly
  1               5                  10                  15 gat agg gtc acc atc acc tgc cgt gcc agt cag gat gtg aat act gct      96
Asp Arg Val Thr Ile Thr Cys Arg Ala Ser Gln Asp Val Asn Thr Ala
                 20                  25                  30 gta gcc tgg tat caa cag aaa cca gga aaa gct ccg aaa cta ctg att     144
Val Ala Trp Tyr Gln Gln Lys Pro Gly Lys Ala Pro Lys Leu Leu Ile
             35                  40                  45 tac tcg gca tcc ttc ctc tac tct gga gtc cct tct cgc ttc tct gga     192
Tyr Ser Ala Ser Phe Leu Tyr Ser Gly Val Pro Ser Arg Phe Ser Gly
 50                  55                  60 tcc aga tct ggg acg gat ttc act ctg acc atc agc agt ctg cag ccg     240
Ser Arg Ser Gly Thr Asp Phe Thr Leu Thr Ile Ser Ser Leu Gln Pro
 65                  70                  75                  80 gaa gac ttc gca act tat tac tgt cag caa cat tat act act cct ccc     288
Glu Asp Phe Ala Thr Tyr Tyr Cys Gln Gln His Tyr Thr Thr Pro Pro
                 85                  90                  95 acg ttc gga cag ggt acc aag gtg gag atc aaa                         321
Thr Phe Gly Gln Gly Thr Lys Val Glu Ile Lys
            100                 105

<210> SEQ ID NO 42
<211> LENGTH: 107
<212> TYPE: PRT
<213> ORGANISM: Artificial
<220> FEATURE:
<223> OTHER INFORMATION: Synthetic Construct

<400> SEQUENCE: 42

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60
```

-continued

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 43
<211> LENGTH: 360
<212> TYPE: DNA
<213> ORGANISM: Artificial
<220> FEATURE:
<223> OTHER INFORMATION: Description of artificial sequence: CD74VH
<220> FEATURE:
<221> NAME/KEY: CDS
<222> LOCATION: (1)..(360)

<400> SEQUENCE: 43

```
cag gtc caa ctg cag caa tct ggg tct gag ttg aag aag cct ggg gcc      48
Gln Val Gln Leu Gln Gln Ser Gly Ser Glu Leu Lys Lys Pro Gly Ala
1               5                   10                  15 tca gtg aag gtt tcc tgc aag gct tct gga tac acc ttc act aac tat      96
Ser Val Lys Val Ser Cys Lys Ala Ser Gly Tyr Thr Phe Thr Asn Tyr
            20                  25                  30 gga gtg aac tgg ata aag cag gcc cct gga caa ggg ctt cag tgg atg     144
Gly Val Asn Trp Ile Lys Gln Ala Pro Gly Gln Gly Leu Gln Trp Met
        35                  40                  45 ggc tgg ata aac ccc aac act gga gag cca aca ttt gat gat gac ttc     192
Gly Trp Ile Asn Pro Asn Thr Gly Glu Pro Thr Phe Asp Asp Asp Phe
    50                  55                  60 aag gga cga ttt gcc ttc tcc ttg gac acc tct gtc agc acg gca tat     240
Lys Gly Arg Phe Ala Phe Ser Leu Asp Thr Ser Val Ser Thr Ala Tyr
65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                85                  90                  95 tca aga tcg agg ggt aaa aac gaa gcc tgg ttt gct tat tgg ggc caa     336
Ser Arg Ser Arg Gly Lys Asn Glu Ala Trp Phe Ala Tyr Trp Gly Gln
            100                 105                 110 ggg acc ctg gtc acc gtc tcc tca                                     360
Gly Thr Leu Val Thr Val Ser Ser
        115                 120
```

<210> SEQ ID NO 44
<211> LENGTH: 120
<212> TYPE: PRT
<213> ORGANISM: Artificial
<220> FEATURE:
<223> OTHER INFORMATION: Synthetic Construct

<400> SEQUENCE: 44

```
Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80
```

```
Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser
        115                 120

<210> SEQ ID NO 45
<211> LENGTH: 336
<212> TYPE: DNA
<213> ORGANISM: Artificial
<220> FEATURE:
<223> OTHER INFORMATION: Description of artificial sequence: CD74VL
<220> FEATURE:
<221> NAME/KEY: CDS
<222> LOCATION: (1)..(336)

<400> SEQUENCE: 45 gac atc cag ctg act cag tct cca ctc tcc ctg ccc gtc acc ctt gga        48
Asp Ile Gln Leu Thr Gln Ser Pro Leu Ser Leu Pro Val Thr Leu Gly
1               5                   10                  15 cag ccg gcc tcc atc tcc tgc aga tca agt cag agc ctt gta cac aga        96
Gln Pro Ala Ser Ile Ser Cys Arg Ser Ser Gln Ser Leu Val His Arg
            20                  25                  30 aat gga aac acc tat tta cat tgg ttt cag cag agg cca ggc caa tct       144
Asn Gly Asn Thr Tyr Leu His Trp Phe Gln Gln Arg Pro Gly Gln Ser
        35                  40                  45 cca agg ctc ctg atc tac aca gtt tcc aac cga ttt tct ggg gtc cca       192
Pro Arg Leu Leu Ile Tyr Thr Val Ser Asn Arg Phe Ser Gly Val Pro
    50                  55                  60 gac aga ttc agc ggc agt ggg tca ggc act gat ttc aca ctg aaa atc       240
Asp Arg Phe Ser Gly Ser Gly Ser Gly Thr Asp Phe Thr Leu Lys Ile
65                  70                  75                  80 agc agg gtg gag gct gag gat gtt ggg gtt tat ttc tgc tct caa agt       288
Ser Arg Val Glu Ala Glu Asp Val Gly Val Tyr Phe Cys Ser Gln Ser
                85                  90                  95 tca cat gtt cct ccc acg ttc ggt gct ggg aca cga ctg gag atc aaa       336
Ser His Val Pro Pro Thr Phe Gly Ala Gly Thr Arg Leu Glu Ile Lys
            100                 105                 110

<210> SEQ ID NO 46
<211> LENGTH: 112
<212> TYPE: PRT
<213> ORGANISM: Artificial
<220> FEATURE:
<223> OTHER INFORMATION: Synthetic Construct

<400> SEQUENCE: 46

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95
```

```
Ser His Val Pro Pro Thr Phe Gly Ala Gly Thr Arg Leu Glu Ile Lys
            100                 105                 110
```

<210> SEQ ID NO 47
<211> LENGTH: 45
<212> TYPE: DNA
<213> ORGANISM: Artificial
<220> FEATURE:
<223> OTHER INFORMATION: Description of artificial sequence: GS-linker
<220> FEATURE:
<221> NAME/KEY: CDS
<222> LOCATION: (1)..(45)

<400> SEQUENCE: 47

```
tcc ggc gga ggg ggt tcc gga gga ggg ggt tcc ggc gga ggg ggt         45
Ser Gly Gly Gly Gly Ser Gly Gly Gly Gly Ser Gly Gly Gly Gly
1               5                   10                  15
```

<210> SEQ ID NO 48
<211> LENGTH: 15
<212> TYPE: PRT
<213> ORGANISM: Artificial
<220> FEATURE:
<223> OTHER INFORMATION: Synthetic Construct

<400> SEQUENCE: 48

```
Ser Gly Gly Gly Gly Ser Gly Gly Gly Gly Ser Gly Gly Gly Gly
1               5                   10                  15
```

<210> SEQ ID NO 49
<211> LENGTH: 366
<212> TYPE: DNA
<213> ORGANISM: Artificial
<220> FEATURE:
<223> OTHER INFORMATION: Description of artificial sequence: CD20-2F2-VH
<220> FEATURE:
<221> NAME/KEY: CDS
<222> LOCATION: (1)..(366)

<400> SEQUENCE: 49

```
gaa gtg cag ctg gtg gag tct ggg gga ggc ttg gta cag cct ggc agg      48
Glu Val Gln Leu Val Glu Ser Gly Gly Gly Leu Val Gln Pro Gly Arg
1               5                   10                  15 tcc ctg aga ctc tcc tgt gca gcc tct gga ttc acc ttt aat gat tat      96
Ser Leu Arg Leu Ser Cys Ala Ala Ser Gly Phe Thr Phe Asn Asp Tyr
                20                  25                  30 gcc atg cac tgg gtc cgg caa gct cca ggg aag ggc ctg gag tgg gtc     144
Ala Met His Trp Val Arg Gln Ala Pro Gly Lys Gly Leu Glu Trp Val
            35                  40                  45 tca act att agt tgg aat agt ggt tcc ata ggc tat gcg gac tct gtg     192
Ser Thr Ile Ser Trp Asn Ser Gly Ser Ile Gly Tyr Ala Asp Ser Val
        50                  55                  60 aag ggc cga ttc acc atc tcc aga gac aac gcc aag aag tcc ctg tat     240
Lys Gly Arg Phe Thr Ile Ser Arg Asp Asn Ala Lys Lys Ser Leu Tyr
65                  70                  75                  80 ctg caa atg aac agt ctg aga gct gag gac acg gcc ttg tat tac tgt     288
Leu Gln Met Asn Ser Leu Arg Ala Glu Asp Thr Ala Leu Tyr Tyr Cys
                85                  90                  95 gca aaa gat ata cag tac ggc aac tac tac tac ggt atg gac gtc tgg     336
Ala Lys Asp Ile Gln Tyr Gly Asn Tyr Tyr Tyr Gly Met Asp Val Trp
            100                 105                 110 ggc caa ggg acc acg gtc acc gtc tcc tca                             366
Gly Gln Gly Thr Thr Val Thr Val Ser Ser
        115                 120
```

<210> SEQ ID NO 50
<211> LENGTH: 122
<212> TYPE: PRT
<213> ORGANISM: Artificial
<220> FEATURE:
<223> OTHER INFORMATION: Synthetic Construct

<400> SEQUENCE: 50

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120
```

<210> SEQ ID NO 51
<211> LENGTH: 321
<212> TYPE: DNA
<213> ORGANISM: Artificial
<220> FEATURE:
<223> OTHER INFORMATION: Description of artificial sequence: CD20-2F2-VL
<220> FEATURE:
<221> NAME/KEY: CDS
<222> LOCATION: (1)..(321)

<400> SEQUENCE: 51

```
gaa att gtg ttg aca cag tct cca gcc acc ctg tct ttg tct cca ggg     48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac     96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg ccg atc    288
Glu Asp Phe Ala Val Tyr Tyr Cys Gln Gln Arg Ser Asn Trp Pro Ile
                85                  90                  95 acc ttc ggc caa ggg aca cga ctg gag att aaa                        321
Thr Phe Gly Gln Gly Thr Arg Leu Glu Ile Lys
            100                 105
```

<210> SEQ ID NO 52
<211> LENGTH: 107
<212> TYPE: PRT
<213> ORGANISM: Artificial

```
<220> FEATURE:
<223> OTHER INFORMATION: Synthetic Construct

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 53
<211> LENGTH: 2121
<212> TYPE: DNA
<213> ORGANISM: Artificial
<220> FEATURE:
<223> OTHER INFORMATION: Description of the artificial sequence: CD74VL-
      CL-Fc-2F2scFv
<220> FEATURE:
<221> NAME/KEY: CDS
<222> LOCATION: (1)..(2121)

<400> SEQUENCE: 53 gac atc cag ctg act cag tct cca ctc tcc ctg ccc gtc acc ctt gga        48
Asp Ile Gln Leu Thr Gln Ser Pro Leu Ser Leu Pro Val Thr Leu Gly
1               5                   10                  15 cag ccg gcc tcc atc tcc tgc aga tca agt cag agc ctt gta cac aga        96
Gln Pro Ala Ser Ile Ser Cys Arg Ser Ser Gln Ser Leu Val His Arg
                20                  25                  30 aat gga aac acc tat tta cat tgg ttt cag cag agg cca ggc caa tct       144
Asn Gly Asn Thr Tyr Leu His Trp Phe Gln Gln Arg Pro Gly Gln Ser
            35                  40                  45 cca agg ctc ctg atc tac aca gtt tcc aac cga ttt tct ggg gtc cca       192
Pro Arg Leu Leu Ile Tyr Thr Val Ser Asn Arg Phe Ser Gly Val Pro
    50                  55                  60 gac aga ttc agc ggc agt ggg tca ggc act gat ttc aca ctg aaa atc       240
Asp Arg Phe Ser Gly Ser Gly Ser Gly Thr Asp Phe Thr Leu Lys Ile
65                  70                  75                  80 agc agg gtg gag gct gag gat gtt ggg gtt tat ttc tgc tct caa agt       288
Ser Arg Val Glu Ala Glu Asp Val Gly Val Tyr Phe Cys Ser Gln Ser
                85                  90                  95 tca cat gtt cct ccc acg ttc ggt gct ggg aca cga ctg gag atc aaa       336
Ser His Val Pro Pro Thr Phe Gly Ala Gly Thr Arg Leu Glu Ile Lys
            100                 105                 110 cgt acg gtg gct gca cca tct gtc ttc atc ttc ccg cca tct gat gag       384
Arg Thr Val Ala Ala Pro Ser Val Phe Ile Phe Pro Pro Ser Asp Glu
        115                 120                 125 cag ttg aaa tct gga act gcc tct gtt gtg tgc ctg ctg aat aac ttc       432
Gln Leu Lys Ser Gly Thr Ala Ser Val Val Cys Leu Leu Asn Asn Phe
    130                 135                 140 tat ccc aga gag gcc aaa gta cag tgg aag gtg gat aac gcc ctc caa       480
Tyr Pro Arg Glu Ala Lys Val Gln Trp Lys Val Asp Asn Ala Leu Gln
145                 150                 155                 160
```

```
tcg ggt aac tcc cag gag agt gtc aca gag cag gac agc aag gac agc    528
Ser Gly Asn Ser Gln Glu Ser Val Thr Glu Gln Asp Ser Lys Asp Ser
                165                 170                 175 acc tac agc ctc agc agc acc ctg acg ctg agc aaa gca gac tac gag    576
Thr Tyr Ser Leu Ser Ser Thr Leu Thr Leu Ser Lys Ala Asp Tyr Glu
                180                 185                 190 aaa cac aaa gtc tac gcc tgc gaa gtc aca cat cag ggc ctc agc tcg    624
Lys His Lys Val Tyr Ala Cys Glu Val Thr His Gln Gly Leu Ser Ser
                195                 200                 205 ccc gtc aca aag agc ttc aac agg gga gag agt gag tcc aaa tat ggt    672
Pro Val Thr Lys Ser Phe Asn Arg Gly Glu Ser Glu Ser Lys Tyr Gly
                210                 215                 220 ccc cca tgc cca ccg tgc cca gca cct gag ttc ctg ggg gga cca tca    720
Pro Pro Cys Pro Pro Cys Pro Ala Pro Glu Phe Leu Gly Gly Pro Ser
225                 230                 235                 240 gtc ttc ctg ttc ccc cca aaa ccc aag gac act ctc atg atc tcc cgg    768
Val Phe Leu Phe Pro Pro Lys Pro Lys Asp Thr Leu Met Ile Ser Arg
                245                 250                 255 acc cct gag gtc acc tgc gtg gtg gtg gac gtg agc cag gaa gac ccc    816
Thr Pro Glu Val Thr Cys Val Val Val Asp Val Ser Gln Glu Asp Pro
                260                 265                 270 gag gtc cag ttc aac tgg tac gtg gat ggc gtg gag gtg cat aat gcc    864
Glu Val Gln Phe Asn Trp Tyr Val Asp Gly Val Glu Val His Asn Ala
                275                 280                 285 aag aca aag ccg cgg gag gag cag ttc aac agc acg tac cgt gtg gtc    912
Lys Thr Lys Pro Arg Glu Glu Gln Phe Asn Ser Thr Tyr Arg Val Val
                290                 295                 300 agc gtc ctc acc gtc ctg cac cag gac tgg ctg aac ggc aag gag tac    960
Ser Val Leu Thr Val Leu His Gln Asp Trp Leu Asn Gly Lys Glu Tyr
305                 310                 315                 320 aag tgc aag gtc tcc aac aaa ggc ctc ccg tcc tcc atc gag aaa acc   1008
Lys Cys Lys Val Ser Asn Lys Gly Leu Pro Ser Ser Ile Glu Lys Thr
                325                 330                 335 atc tcc aaa gcc aaa ggg cag ccc cga gag cca cag gtg tac acc ctg   1056
Ile Ser Lys Ala Lys Gly Gln Pro Arg Glu Pro Gln Val Tyr Thr Leu
                340                 345                 350 ccc cca tcc cag gag gag atg acc aag aac cag gtc agc ctg acc tgc   1104
Pro Pro Ser Gln Glu Glu Met Thr Lys Asn Gln Val Ser Leu Thr Cys
                355                 360                 365 ctg gtc aaa ggc ttc tac ccc agc gac atc gcc gtg gag tgg gag agc   1152
Leu Val Lys Gly Phe Tyr Pro Ser Asp Ile Ala Val Glu Trp Glu Ser
                370                 375                 380 aat ggg cag ccg gag aac aac tac aag acc acg cct ccc gtg ctg gac   1200
Asn Gly Gln Pro Glu Asn Asn Tyr Lys Thr Thr Pro Pro Val Leu Asp
385                 390                 395                 400 tcc gac ggc tcc ttc ttc ctc tac agc aag cta acc gtg gac aag agc   1248
Ser Asp Gly Ser Phe Phe Leu Tyr Ser Lys Leu Thr Val Asp Lys Ser
                405                 410                 415 agg tgg cag gag ggg aat gtc ttc tca tgc tcc gtg atg cat gag gct   1296
Arg Trp Gln Glu Gly Asn Val Phe Ser Cys Ser Val Met His Glu Ala
                420                 425                 430 ctg cac aac cgc ttc aca cag aag agc ctc tcc ctg tct ctg ggt aaa   1344
Leu His Asn Arg Phe Thr Gln Lys Ser Leu Ser Leu Ser Leu Gly Lys
                435                 440                 445 tcc ggc gga ggg ggt tcc gga gga ggg ggt tcc ggc gga ggg ggt gaa   1392
Ser Gly Gly Gly Gly Ser Gly Gly Gly Gly Ser Gly Gly Gly Gly Glu
                450                 455                 460 gtg cag ctg gtg gag tct ggg gga ggc ttg gta cag cct ggc agg tcc   1440
Val Gln Leu Val Glu Ser Gly Gly Gly Leu Val Gln Pro Gly Arg Ser
```

```
                465                 470                 475                 480
ctg aga ctc tcc tgt gca gcc tct gga ttc acc ttt aat gat tat gcc      1488
Leu Arg Leu Ser Cys Ala Ala Ser Gly Phe Thr Phe Asn Asp Tyr Ala
                485                 490                 495 atg cac tgg gtc cgg caa gct cca ggg aag ggc ctg gag tgg gtc tca      1536
Met His Trp Val Arg Gln Ala Pro Gly Lys Gly Leu Glu Trp Val Ser
            500                 505                 510 act att agt tgg aat agt ggt tcc ata ggc tat gcg gac tct gtg aag      1584
Thr Ile Ser Trp Asn Ser Gly Ser Ile Gly Tyr Ala Asp Ser Val Lys
        515                 520                 525 ggc cga ttc acc atc tcc aga gac aac gcc aag aag tcc ctg tat ctg      1632
Gly Arg Phe Thr Ile Ser Arg Asp Asn Ala Lys Lys Ser Leu Tyr Leu
    530                 535                 540 caa atg aac agt ctg aga gct gag gac acg gcc ttg tat tac tgt gca      1680
Gln Met Asn Ser Leu Arg Ala Glu Asp Thr Ala Leu Tyr Tyr Cys Ala
545                 550                 555                 560 aaa gat ata cag tac ggc aac tac tac tac ggt atg gac gtc tgg ggc      1728
Lys Asp Ile Gln Tyr Gly Asn Tyr Tyr Tyr Gly Met Asp Val Trp Gly
                565                 570                 575 caa ggg acc acg gtc acc gtc tcc tca ggt ggt gga ggt agt gga ggt      1776
Gln Gly Thr Thr Val Thr Val Ser Ser Gly Gly Gly Gly Ser Gly Gly
            580                 585                 590 ggt gga tct ggt gga ggt gga agt gaa att gtg ttg aca cag tct cca      1824
Gly Gly Ser Gly Gly Gly Gly Ser Glu Ile Val Leu Thr Gln Ser Pro
        595                 600                 605 gcc acc ctg tct ttg tct cca ggg gaa aga gcc acc ctc tcc tgc agg      1872
Ala Thr Leu Ser Leu Ser Pro Gly Glu Arg Ala Thr Leu Ser Cys Arg
    610                 615                 620 gcc agt cag agt gtt agc agc tac tta gcc tgg tac caa cag aaa cct      1920
Ala Ser Gln Ser Val Ser Ser Tyr Leu Ala Trp Tyr Gln Gln Lys Pro
625                 630                 635                 640 ggc cag gct ccc agg ctc ctc atc tat gat gca tcc aac agg gcc act      1968
Gly Gln Ala Pro Arg Leu Leu Ile Tyr Asp Ala Ser Asn Arg Ala Thr
                645                 650                 655 ggc atc cca gcc agg ttc agt ggc agt ggg tct ggg aca gac ttc act      2016
Gly Ile Pro Ala Arg Phe Ser Gly Ser Gly Ser Gly Thr Asp Phe Thr
            660                 665                 670 ctc acc atc agc agc cta gag cct gaa gat ttt gca gtt tat tac tgt      2064
Leu Thr Ile Ser Ser Leu Glu Pro Glu Asp Phe Ala Val Tyr Tyr Cys
        675                 680                 685 cag cag cgt agc aac tgg ccg atc acc ttc ggc caa ggg aca cga ctg      2112
Gln Gln Arg Ser Asn Trp Pro Ile Thr Phe Gly Gln Gly Thr Arg Leu
    690                 695                 700 gag att aaa                                                          2121
Glu Ile Lys
705

<210> SEQ ID NO 54
<211> LENGTH: 707
<212> TYPE: PRT
<213> ORGANISM: Artificial
<220> FEATURE:
<223> OTHER INFORMATION: Synthetic Construct

<400> SEQUENCE: 54

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
```

```
            35                  40                  45
Pro Arg Leu Leu Ile Tyr Thr Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Phe Cys Ser Gln Ser
                 85                  90                  95
Ser His Val Pro Pro Thr Phe Gly Ala Gly Thr Arg Leu Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Ser Glu Ser Lys Tyr Gly
210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
                260                 265                 270
Glu Val Gln Phe Asn Trp Tyr Val Asp Gly Val Glu Val His Asn Ala
                275                 280                 285
Lys Thr Lys Pro Arg Glu Glu Gln Phe Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Gln Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Glu Gly Asn Val Phe Ser Cys Ser Val Met His Glu Ala
                420                 425                 430
Leu His Asn Arg Phe Thr Gln Lys Ser Leu Ser Leu Ser Leu Gly Lys
                435                 440                 445
Ser Gly Gly Gly Gly Ser Gly Gly Gly Gly Ser Gly Gly Gly Gly Glu
450                 455                 460
```

```
Val Gln Leu Val Glu Ser Gly Gly Leu Val Gln Pro Gly Arg Ser
465                 470                 475                 480

Leu Arg Leu Ser Cys Ala Ala Ser Gly Phe Thr Phe Asn Asp Tyr Ala
                485                 490                 495

Met His Trp Val Arg Gln Ala Pro Gly Lys Gly Leu Glu Trp Val Ser
            500                 505                 510

Thr Ile Ser Trp Asn Ser Gly Ser Ile Gly Tyr Ala Asp Ser Val Lys
            515                 520                 525

Gly Arg Phe Thr Ile Ser Arg Asp Asn Ala Lys Lys Ser Leu Tyr Leu
530                 535                 540

Gln Met Asn Ser Leu Arg Ala Glu Asp Thr Ala Leu Tyr Tyr Cys Ala
545                 550                 555                 560

Lys Asp Ile Gln Tyr Gly Asn Tyr Tyr Tyr Gly Met Asp Val Trp Gly
                565                 570                 575

Gln Gly Thr Thr Val Thr Val Ser Ser Gly Gly Gly Ser Gly Gly
            580                 585                 590

Gly Gly Ser Gly Gly Gly Ser Glu Ile Val Leu Thr Gln Ser Pro
    595                 600                 605

Ala Thr Leu Ser Leu Ser Pro Gly Glu Arg Ala Thr Leu Ser Cys Arg
    610                 615                 620

Ala Ser Gln Ser Val Ser Ser Tyr Leu Ala Trp Tyr Gln Gln Lys Pro
625                 630                 635                 640

Gly Gln Ala Pro Arg Leu Leu Ile Tyr Asp Ala Ser Asn Arg Ala Thr
                645                 650                 655

Gly Ile Pro Ala Arg Phe Ser Gly Ser Gly Ser Gly Thr Asp Phe Thr
                660                 665                 670

Leu Thr Ile Ser Ser Leu Glu Pro Glu Asp Phe Ala Val Tyr Tyr Cys
            675                 680                 685

Gln Gln Arg Ser Asn Trp Pro Ile Thr Phe Gly Gln Gly Thr Arg Leu
        690                 695                 700

Glu Ile Lys
705

<210> SEQ ID NO 55
<211> LENGTH: 2115
<212> TYPE: DNA
<213> ORGANISM: Artificial
<220> FEATURE:
<223> OTHER INFORMATION: Description of the artificial sequence: CD74VL-
      CL-Fc-4D5scFv
<220> FEATURE:
<221> NAME/KEY: CDS
<222> LOCATION: (1)..(2115)

<400> SEQUENCE: 55 gac atc cag ctg act cag tct cca ctc tcc ctg ccc gtc acc ctt gga      48
Asp Ile Gln Leu Thr Gln Ser Pro Leu Ser Leu Pro Val Thr Leu Gly
1               5                   10                  15 cag ccg gcc tcc atc tcc tgc aga tca agt cag agc ctt gta cac aga      96
Gln Pro Ala Ser Ile Ser Cys Arg Ser Ser Gln Ser Leu Val His Arg
            20                  25                  30 aat gga aac acc tat tta cat tgg ttt cag cag agg cca ggc caa tct     144
Asn Gly Asn Thr Tyr Leu His Trp Phe Gln Gln Arg Pro Gly Gln Ser
        35                  40                  45 cca agg ctc ctg atc tac aca gtt tcc aac cga ttt tct ggg gtc cca     192
Pro Arg Leu Leu Ile Tyr Thr Val Ser Asn Arg Phe Ser Gly Val Pro
    50                  55                  60
```

```
gac aga ttc agc ggc agt ggg tca ggc act gat ttc aca ctg aaa atc      240
Asp Arg Phe Ser Gly Ser Gly Ser Gly Thr Asp Phe Thr Leu Lys Ile
 65                  70                  75                  80 agc agg gtg gag gct gag gat gtt ggg gtt tat ttc tgc tct caa agt      288
Ser Arg Val Glu Ala Glu Asp Val Gly Val Tyr Phe Cys Ser Gln Ser
                 85                  90                  95 tca cat gtt cct ccc acg ttc ggt gct ggg aca cga ctg gag atc aaa      336
Ser His Val Pro Pro Thr Phe Gly Ala Gly Thr Arg Leu Glu Ile Lys
            100                 105                 110 cgt acg gtg gct gca cca tct gtc ttc atc ttc ccg cca tct gat gag      384
Arg Thr Val Ala Ala Pro Ser Val Phe Ile Phe Pro Pro Ser Asp Glu
        115                 120                 125 cag ttg aaa tct gga act gcc tct gtt gtg tgc ctg ctg aat aac ttc      432
Gln Leu Lys Ser Gly Thr Ala Ser Val Val Cys Leu Leu Asn Asn Phe
    130                 135                 140 tat ccc aga gag gcc aaa gta cag tgg aag gtg gat aac gcc ctc caa      480
Tyr Pro Arg Glu Ala Lys Val Gln Trp Lys Val Asp Asn Ala Leu Gln
145                 150                 155                 160 tcg ggt aac tcc cag gag agt gtc aca gag cag gac agc aag gac agc      528
Ser Gly Asn Ser Gln Glu Ser Val Thr Glu Gln Asp Ser Lys Asp Ser
                165                 170                 175 acc tac agc ctc agc agc acc ctg acg ctg agc aaa gca gac tac gag      576
Thr Tyr Ser Leu Ser Ser Thr Leu Thr Leu Ser Lys Ala Asp Tyr Glu
            180                 185                 190 aaa cac aaa gtc tac gcc tgc gaa gtc aca cat cag ggc ctc agc tcg      624
Lys His Lys Val Tyr Ala Cys Glu Val Thr His Gln Gly Leu Ser Ser
        195                 200                 205 ccc gtc aca aag agc ttc aac agg gga gag agt gag tcc aaa tat ggt      672
Pro Val Thr Lys Ser Phe Asn Arg Gly Glu Ser Glu Ser Lys Tyr Gly
    210                 215                 220 ccc cca tgc cca ccg tgc cca gca cct gag ttc ctg ggg gga cca tca      720
Pro Pro Cys Pro Pro Cys Pro Ala Pro Glu Phe Leu Gly Gly Pro Ser
225                 230                 235                 240 gtc ttc ctg ttc ccc cca aaa ccc aag gac act ctc atg atc tcc cgg      768
Val Phe Leu Phe Pro Pro Lys Pro Lys Asp Thr Leu Met Ile Ser Arg
                245                 250                 255 acc cct gag gtc acc tgc gtg gtg gtg gac gtg agc cag gaa gac ccc      816
Thr Pro Glu Val Thr Cys Val Val Val Asp Val Ser Gln Glu Asp Pro
            260                 265                 270 gag gtc cag ttc aac tgg tac gtg gat ggc gtg gag gtg cat aat gcc      864
Glu Val Gln Phe Asn Trp Tyr Val Asp Gly Val Glu Val His Asn Ala
        275                 280                 285 aag aca aag ccg cgg gag gag cag ttc aac agc acg tac cgt gtg gtc      912
Lys Thr Lys Pro Arg Glu Glu Gln Phe Asn Ser Thr Tyr Arg Val Val
    290                 295                 300 agc gtc ctc acc gtc ctg cac cag gac tgg ctg aac ggc aag gag tac      960
Ser Val Leu Thr Val Leu His Gln Asp Trp Leu Asn Gly Lys Glu Tyr
305                 310                 315                 320 aag tgc aag gtc tcc aac aaa ggc ctc ccg tcc tcc atc gag aaa acc     1008
Lys Cys Lys Val Ser Asn Lys Gly Leu Pro Ser Ser Ile Glu Lys Thr
                325                 330                 335 atc tcc aaa gcc aaa ggg cag ccc cga gag cca cag gtg tac acc ctg     1056
Ile Ser Lys Ala Lys Gly Gln Pro Arg Glu Pro Gln Val Tyr Thr Leu
            340                 345                 350 ccc cca tcc cag gag gag atg acc aag aac cag gtc agc ctg acc tgc     1104
Pro Pro Ser Gln Glu Glu Met Thr Lys Asn Gln Val Ser Leu Thr Cys
        355                 360                 365 ctg gtc aaa ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380
```

```
aat ggg cag ccg gag aac aac tac aag acc acg cct ccc gtg ctg gac       1200
Asn Gly Gln Pro Glu Asn Asn Tyr Lys Thr Thr Pro Pro Val Leu Asp
385                 390                 395                 400 tcc gac ggc tcc ttc ttc ctc tac agc aag cta acc gtg gac aag agc       1248
Ser Asp Gly Ser Phe Phe Leu Tyr Ser Lys Leu Thr Val Asp Lys Ser
                405                 410                 415 agg tgg cag gag ggg aat gtc ttc tca tgc tcc gtg atg cat gag gct       1296
Arg Trp Gln Glu Gly Asn Val Phe Ser Cys Ser Val Met His Glu Ala
        420                 425                 430 ctg cac aac cgc ttc aca cag aag agc ctc tcc ctg tct ctg ggt aaa       1344
Leu His Asn Arg Phe Thr Gln Lys Ser Leu Ser Leu Ser Leu Gly Lys
            435                 440                 445 tcc ggc gga ggg ggt tcc gga gga ggg ggt tcc ggc gga ggg ggt gag       1392
Ser Gly Gly Gly Gly Ser Gly Gly Gly Gly Ser Gly Gly Gly Gly Glu
        450                 455                 460 gtt cag ctg gtg gag tct ggc ggt ggc ctg gtg cag cca ggg ggc tca       1440
Val Gln Leu Val Glu Ser Gly Gly Gly Leu Val Gln Pro Gly Gly Ser
465                 470                 475                 480 ctc cgt ttg tcc tgt gca gct tct ggc ttc aac att aaa gac acc tat       1488
Leu Arg Leu Ser Cys Ala Ala Ser Gly Phe Asn Ile Lys Asp Thr Tyr
                485                 490                 495 ata cac tgg gtg cgt cag gcc ccg ggt aag ggc ctg gaa tgg gtt gca       1536
Ile His Trp Val Arg Gln Ala Pro Gly Lys Gly Leu Glu Trp Val Ala
        500                 505                 510 agg att tat cct acg aat ggt tat act aga tat gcc gat agc gtc aag       1584
Arg Ile Tyr Pro Thr Asn Gly Tyr Thr Arg Tyr Ala Asp Ser Val Lys
            515                 520                 525 ggc cgt ttc act ata agc gca gac aca tcc aaa aac aca gcc tac ctg       1632
Gly Arg Phe Thr Ile Ser Ala Asp Thr Ser Lys Asn Thr Ala Tyr Leu
        530                 535                 540 cag atg aac agc ctg cgt gct gag gac act gcc gtc tat tat tgt tct       1680
Gln Met Asn Ser Leu Arg Ala Glu Asp Thr Ala Val Tyr Tyr Cys Ser
545                 550                 555                 560 aga tgg gga ggg gac ggc ttc tat gct atg gac tac tgg ggt caa gga       1728
Arg Trp Gly Gly Asp Gly Phe Tyr Ala Met Asp Tyr Trp Gly Gln Gly
                565                 570                 575 acc ctg gtc acc gtc tcc tcg ggt ggt gga ggt agt gga ggt ggt gga       1776
Thr Leu Val Thr Val Ser Ser Gly Gly Gly Gly Ser Gly Gly Gly Gly
        580                 585                 590 tct ggt gga ggt gga agt gat atc cag atg acc cag tcc ccg agc tcc       1824
Ser Gly Gly Gly Gly Ser Asp Ile Gln Met Thr Gln Ser Pro Ser Ser
            595                 600                 605 ctg tcc gcc tct gtg ggc gat agg gtc acc atc acc tgc cgt gcc agt       1872
Leu Ser Ala Ser Val Gly Asp Arg Val Thr Ile Thr Cys Arg Ala Ser
        610                 615                 620 cag gat gtg aat act gct gta gcc tgg tat caa cag aaa cca gga aaa       1920
Gln Asp Val Asn Thr Ala Val Ala Trp Tyr Gln Gln Lys Pro Gly Lys
625                 630                 635                 640 gct ccg aaa cta ctg att tac tcg gca tcc ttc ctc tac tct gga gtc       1968
Ala Pro Lys Leu Leu Ile Tyr Ser Ala Ser Phe Leu Tyr Ser Gly Val
                645                 650                 655 cct tct cgc ttc tct gga tct aga tcc ggg acg gat ttc act ctg acc       2016
Pro Ser Arg Phe Ser Gly Ser Arg Ser Gly Thr Asp Phe Thr Leu Thr
        660                 665                 670 atc agc agt ctg cag ccg gaa gac ttc gca act tat tac tgt cag caa       2064
Ile Ser Ser Leu Gln Pro Glu Asp Phe Ala Thr Tyr Tyr Cys Gln Gln
            675                 680                 685 cat tat act act cct ccc acg ttc gga cag ggt acc aag gtg gag atc       2112
His Tyr Thr Thr Pro Pro Thr Phe Gly Gln Gly Thr Lys Val Glu Ile
```

```
                690               695               700
aaa                                                                    2115
Lys
705

<210> SEQ ID NO 56
<211> LENGTH: 705
<212> TYPE: PRT
<213> ORGANISM: Artificial
<220> FEATURE:
<223> OTHER INFORMATION: Synthetic Construct

<400> SEQUENCE: 56

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn Arg Phe Thr Gln Lys Ser Leu Ser Leu Ser Leu Gly Lys
            435                 440                 445

Ser Gly Gly Gly Gly Ser Gly Gly Gly Gly Ser Gly Gly Gly Gly Glu
            450                 455                 460

Val Gln Leu Val Glu Ser Gly Gly Gly Leu Val Gln Pro Gly Gly Ser
465                 470                 475                 480

Leu Arg Leu Ser Cys Ala Ala Ser Gly Phe Asn Ile Lys Asp Thr Tyr
                485                 490                 495

Ile His Trp Val Arg Gln Ala Pro Gly Lys Gly Leu Glu Trp Val Ala
            500                 505                 510

Arg Ile Tyr Pro Thr Asn Gly Tyr Thr Arg Tyr Ala Asp Ser Val Lys
            515                 520                 525

Gly Arg Phe Thr Ile Ser Ala Asp Thr Ser Lys Asn Thr Ala Tyr Leu
            530                 535                 540

Gln Met Asn Ser Leu Arg Ala Glu Asp Thr Ala Val Tyr Tyr Cys Ser
545                 550                 555                 560

Arg Trp Gly Gly Asp Gly Phe Tyr Ala Met Asp Tyr Trp Gly Gln Gly
                565                 570                 575

Thr Leu Val Thr Val Ser Ser Gly Gly Gly Gly Ser Gly Gly Gly Gly
            580                 585                 590

Ser Gly Gly Gly Gly Ser Asp Ile Gln Met Thr Gln Ser Pro Ser Ser
            595                 600                 605

Leu Ser Ala Ser Val Gly Asp Arg Val Thr Ile Thr Cys Arg Ala Ser
610                 615                 620

Gln Asp Val Asn Thr Ala Val Ala Trp Tyr Gln Gln Lys Pro Gly Lys
625                 630                 635                 640

Ala Pro Lys Leu Leu Ile Tyr Ser Ala Ser Phe Leu Tyr Ser Gly Val
                645                 650                 655

Pro Ser Arg Phe Ser Gly Ser Arg Ser Gly Thr Asp Phe Thr Leu Thr
            660                 665                 670

Ile Ser Ser Leu Gln Pro Glu Asp Phe Ala Thr Tyr Tyr Cys Gln Gln
            675                 680                 685

His Tyr Thr Thr Pro Pro Thr Phe Gly Gln Gly Thr Lys Val Glu Ile
            690                 695                 700

Lys
705

<210> SEQ ID NO 57
<211> LENGTH: 321
<212> TYPE: DNA
<213> ORGANISM: Artificial Sequence
<220> FEATURE:
<223> OTHER INFORMATION: Description of the artificial sequence: human
```

```
        IgG-k
<220> FEATURE:
<221> NAME/KEY: CDS
<222> LOCATION: (1)..(321)

<400> SEQUENCE: 57 cgt acg gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc        96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa       144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc       192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag       240
Thr Tyr Ser Leu Ser Ser Thr Leu Thr Leu Ser Lys Ala Asp Tyr Glu
65                  70                  75                  80 aaa cac aaa gtc tac gcc tgc gaa gtc aca cat cag ggc ctc agc tcg       288
Lys His Lys Val Tyr Ala Cys Glu Val Thr His Gln Gly Leu Ser Ser
                85                  90                  95 ccc gtc aca aag agc ttc aac agg gga gag tgt                           321
Pro Val Thr Lys Ser Phe Asn Arg Gly Glu Cys
            100                 105

<210> SEQ ID NO 58
<211> LENGTH: 107
<212> TYPE: PRT
<213> ORGANISM: Artificial Sequence
<220> FEATURE:
<223> OTHER INFORMATION: Synthetic Construct

<400> SEQUENCE: 58

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 59
<211> LENGTH: 336
<212> TYPE: PRT
<213> ORGANISM: Artificial Sequence
<220> FEATURE:
<223> OTHER INFORMATION: Synthetic Construct

<400> SEQUENCE: 59

Ala Ser Thr Lys Gly Pro Ser Val Phe Pro Leu Ala Pro Ser Ser Lys
1               5                   10                  15
```

-continued

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys His His His His His His
                325                 330                 335

<210> SEQ ID NO 60
<211> LENGTH: 334
<212> TYPE: PRT
<213> ORGANISM: Artificial Sequence
<220> FEATURE:
<223> OTHER INFORMATION: Synthetic Construct

<400> SEQUENCE: 60

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

-continued

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
130                 135                 140

Glu Val Thr Cys Val Val Val Asp Val Ser His Glu Asp Pro Glu Val
145                 150                 155                 160

Gln Phe Lys Trp Tyr Val Asp Gly Val Glu Val His Asn Ala Lys Thr
                165                 170                 175

Lys Pro Arg Glu Glu Gln Phe Asn Ser Thr Phe Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Thr Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Ser Gly
            260                 265                 270

Gln Pro Glu Asn Asn Tyr Lys Thr Thr Pro Pro Met Leu Asp Ser Asp
        275                 280                 285

Gly Ser Phe Phe Leu Tyr Ser Lys Leu Thr Val Asp Lys Ser Arg Trp
290                 295                 300

Gln Gln Gly Asn Ile Phe Ser Cys Ser Val Met His Glu Ala Leu His
305                 310                 315                 320

Asn Arg Phe Thr Gln Lys Ser Leu Ser Leu Ser Pro Gly Lys
                325                 330

<210> SEQ ID NO 61
<211> LENGTH: 595
<212> TYPE: PRT
<213> ORGANISM: Artificial Sequence
<220> FEATURE:
<223> OTHER INFORMATION: Synthetic Construct

<400> SEQUENCE: 61

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

```
Lys His Lys Val Tyr Ala Cys Glu Val Thr His Gln Gly Leu Ser Ser
                 85                  90                  95

Pro Val Thr Lys Ser Phe Asn Arg Gly Glu Ser Glu Ser Lys Tyr Gly
            100                 105                 110

Pro Pro Cys Pro Pro Cys Pro Ala Pro Glu Phe Leu Gly Gly Pro Ser
            115                 120                 125

Val Phe Leu Phe Pro Pro Lys Pro Lys Asp Thr Leu Met Ile Ser Arg
130                 135                 140

Thr Pro Glu Val Thr Cys Val Val Val Asp Val Ser Gln Glu Asp Pro
145                 150                 155                 160

Glu Val Gln Phe Asn Trp Tyr Val Asp Gly Val Glu Val His Asn Ala
                165                 170                 175

Lys Thr Lys Pro Arg Glu Glu Gln Phe Asn Ser Thr Tyr Arg Val Val
            180                 185                 190

Ser Val Leu Thr Val Leu His Gln Asp Trp Leu Asn Gly Lys Glu Tyr
            195                 200                 205

Lys Cys Lys Val Ser Asn Lys Gly Leu Pro Ser Ser Ile Glu Lys Thr
210                 215                 220

Ile Ser Lys Ala Lys Gly Gln Pro Arg Glu Pro Gln Val Tyr Thr Leu
225                 230                 235                 240

Pro Pro Ser Gln Glu Glu Met Thr Lys Asn Gln Val Ser Leu Thr Cys
                245                 250                 255

Leu Val Lys Gly Phe Tyr Pro Ser Asp Ile Ala Val Glu Trp Glu Ser
            260                 265                 270

Asn Gly Gln Pro Glu Asn Asn Tyr Lys Thr Thr Pro Pro Val Leu Asp
            275                 280                 285

Ser Asp Gly Ser Phe Phe Leu Tyr Ser Lys Leu Thr Val Asp Lys Ser
290                 295                 300

Arg Trp Gln Glu Gly Asn Val Phe Ser Cys Ser Val Met His Glu Ala
305                 310                 315                 320

Leu His Asn Arg Phe Thr Gln Lys Ser Leu Ser Leu Ser Leu Gly Lys
                325                 330                 335

Ser Gly Gly Gly Gly Ser Gly Gly Gly Ser Gly Gly Gly Gly Glu
            340                 345                 350

Val Gln Leu Val Glu Ser Gly Gly Gly Leu Val Gln Pro Gly Arg Ser
            355                 360                 365

Leu Arg Leu Ser Cys Ala Ala Ser Gly Phe Thr Phe Asn Asp Tyr Ala
370                 375                 380

Met His Trp Val Arg Gln Ala Pro Gly Lys Gly Leu Glu Trp Val Ser
385                 390                 395                 400

Thr Ile Ser Trp Asn Ser Gly Ser Ile Gly Tyr Ala Asp Ser Val Lys
                405                 410                 415

Gly Arg Phe Thr Ile Ser Arg Asp Asn Ala Lys Lys Ser Leu Tyr Leu
            420                 425                 430

Gln Met Asn Ser Leu Arg Ala Glu Asp Thr Ala Leu Tyr Tyr Cys Ala
            435                 440                 445

Lys Asp Ile Gln Tyr Gly Asn Tyr Tyr Tyr Gly Met Asp Val Trp Gly
450                 455                 460

Gln Gly Thr Thr Val Thr Val Ser Ser Gly Gly Gly Ser Gly Gly
465                 470                 475                 480

Gly Gly Ser Gly Gly Gly Gly Ser Glu Ile Val Leu Thr Gln Ser Pro
                485                 490                 495

Ala Thr Leu Ser Leu Ser Pro Gly Glu Arg Ala Thr Leu Ser Cys Arg
```

-continued

```
                    500                 505                 510
Ala Ser Gln Ser Val Ser Ser Tyr Leu Ala Trp Tyr Gln Gln Lys Pro
            515                 520                 525

Gly Gln Ala Pro Arg Leu Leu Ile Tyr Asp Ala Ser Asn Arg Ala Thr
            530                 535                 540

Gly Ile Pro Ala Arg Phe Ser Gly Ser Gly Ser Gly Thr Asp Phe Thr
545                 550                 555                 560

Leu Thr Ile Ser Ser Leu Glu Pro Glu Asp Phe Ala Val Tyr Tyr Cys
                565                 570                 575

Gln Gln Arg Ser Asn Trp Pro Ile Thr Phe Gly Gln Gly Thr Arg Leu
            580                 585                 590

Glu Ile Lys
            595
```